(12) United States Patent
Dubcovsky et al.

(10) Patent No.: US 9,464,299 B2
(45) Date of Patent: Oct. 11, 2016

(54) KINASE-START GENE CONFERRING RESISTANCE TO PLANT DISEASE AND TRANSGENIC PLANTS COMPRISING IT

(75) Inventors: Jorge Dubcovsky, Davis, CA (US); Tzion Fahima, Kiryat Tivon (IL); Assaf Distelfeld, Kiryat-Tivon (IL); Cristobal Uauy, Norwich (GB); Ann E. Blechl, Richmond, CA (US); Daolin Fu, Woodland, CA (US)

(73) Assignees: Carmel—Haifa University Economic Corporation Ltd., Haifa (IL); The Regents of The University of California, Oakland, CA (US); The United States of America as represented by the Secretary of Agriculture, Washington, DC (US)

( * ) Notice: Subject to any disclaimer, the term of this patent is extended or adjusted under 35 U.S.C. 154(b) by 1218 days.

(21) Appl. No.: 13/202,273

(22) PCT Filed: Feb. 21, 2010

(86) PCT No.: PCT/IL2010/000147
§ 371 (c)(1),
(2), (4) Date: Nov. 2, 2011

(87) PCT Pub. No.: WO2010/095138
PCT Pub. Date: Aug. 26, 2010

(65) Prior Publication Data
US 2012/0047604 A1 Feb. 23, 2012

Related U.S. Application Data

(60) Provisional application No. 61/153,773, filed on Feb. 19, 2009.

(51) Int. Cl.
C12N 15/82 (2006.01)
C07K 14/415 (2006.01)
A01H 5/10 (2006.01)
C12N 9/12 (2006.01)

(52) U.S. Cl.
CPC .......... *C12N 15/8282* (2013.01); *C12N 9/1205* (2013.01); *C12N 15/8237* (2013.01)

(58) Field of Classification Search
CPC combination set(s) only.
See application file for complete search history.

(56) References Cited

FOREIGN PATENT DOCUMENTS

WO WO 2010/095138 8/2010

OTHER PUBLICATIONS

GenBank. Wheat kinase-START domain protein [Triticum dicoccoides]. 2009. Accession ACF33182.*
GenBank. Wheat kinase-START domain protein [Triticum dicoccoides]. 2009. Accession ACF33182 Revision History.*
Raya et al., 1999, The Journal of Biological Chemistry 274(18):12642.*
Alpy et al., 2005, Journal of Cell Science 118:2791-2801.*
Li et al (2009, Plant Molecular Biology, 69(3): 337-346.*

(Continued)

*Primary Examiner* — Russell Kallis
*Assistant Examiner* — Weihua Fan

(57) ABSTRACT

An isolated nucleic acid molecule comprising a nucleotide sequence which encodes a polypeptide comprising both a steroidogenic acute regulatory protein-related lipid transfer (START) domain and a kinase domain is provided, as well as plant cells and transgenic plants comprising said nucleic acid molecule, said transgenic plants being resistant to plant diseases.

Figure 1:
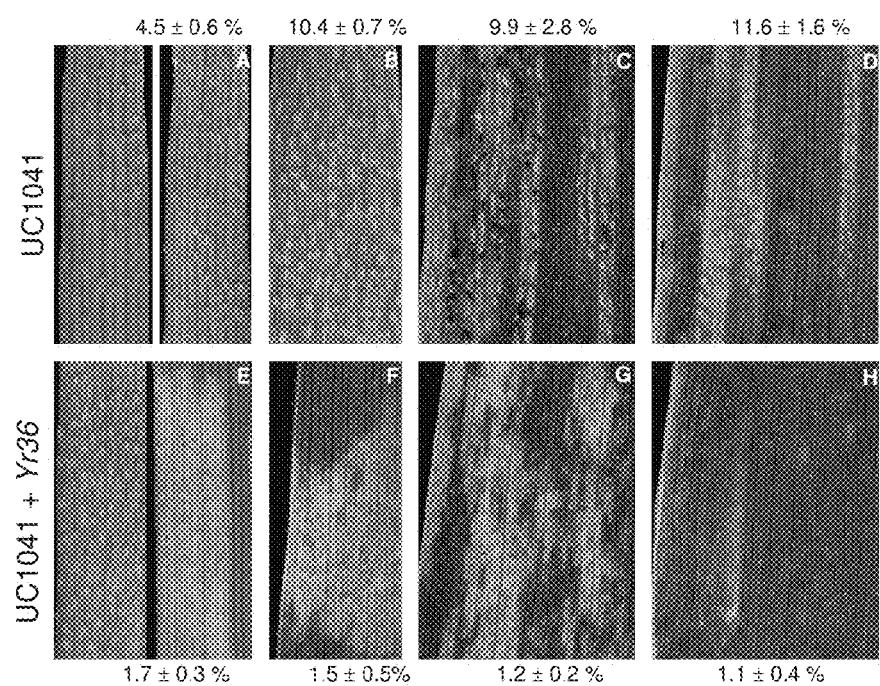

22 Claims, 19 Drawing Sheets
(17 of 19 Drawing Sheet(s) Filed in Color)

(56) References Cited

OTHER PUBLICATIONS

Uauy, et al., 2005, Theoretical and Applied Genetics 112.1: 97-105.*
Faris et al., 2003. Genetics 164(1): 311-321.*
Venkata and Schrick, 2006, Proceedings of the 17th International Symposium on Plant Lipids, Michigan State University Press.*
Oldach et al (2001. Molecular Plant-Microbe Interactions 14(7):832-838.*
Wu, 2011, Characterization of resistance gene WKSI and identification of downstream interactors, Wu, Kati C . . . University of California, Davis, ProQuest, UMI Dissertations Publishing, 2011. 1493710.*
Fu, Daolin, et al. "A kinase-START gene confers temperature-dependent resistance to wheat stripe rust." science 323.5919 (2009): 1357-1360.*
International Preliminary Report on Patentability Dated Sep. 1, 2012 From the International Bureau of WIPO Re. Application No. PCT/IL2010/000147.
International Search Report and the Written Opinion Dated Jun. 8, 2010 From the International Searching Authority Re. Application No. PCT/IL2010/000147.
Office Action and Search Report (Chinese) Dated Aug. 31, 2012 From the State Intellectual Property Office of the People's Republic of China Re. Application No. 201080017333.5 and Its Translation Into English.
Chicaiza et al. "Registration of Five Wheat Isogenic Lines for Leaf Rust and Stripe Rust Resistance Genes", Crop Science, XP002580305, 46(1): 485-487, Jan. 24, 2006.
Fu et al. "A Kinase-START Gene Confers Temperature-Dependent Resistance to Wheat Stripe Rust", Science, XP002580306, 323(5919): 1357-1360, Mar. 2009.
Fu et al. "Triticum Turgidum Supsp. Dicoccoides Wheat Kinase-START Domain Protein (WKS1) Gene, Complete Cds, Alternatively Spliced", Database Nucleotide [Online], XP002580304, Retrieved From NCBI, Database Accession No. EU835199, Feb. 6, 2009. [A Novel Kinase-START Gene Confers Temperature-Dependent Resistance to Wheat Stripe Rust].
Uauy et al. "High-Temperature Adult-Plant (HTAP) Stripe Rust Resistance Gene Yr36 From *Triticum turgidum* Ssp. *dicoccoides* Is Closely Linked to the Grain Protein Content Locus Gpc-Bl", Theoretical and Applied Genetics, XP019322120, 112(1): 97-105, Dec. 1, 2005.

Notification of Transmittal of the International Search Report and the Written Opinion of the International Searching Authority, or the Declaration, including an International Search Report and Written Opinion of the International Searching Authority, mailed Jun. 8, 2010 in connection with PCT International Application No. PCT/IL2010/000147, filed Feb. 21, 2010.
Fu, D., Uauy, C., Distelfeld, A., Blechl, A. Epstein, L., Chen, X., . . . Dubcovsky, J. (2009). A novel kinase-START gene confers temperature-dependent resistance to wheat stripe rust. XP002580304 retrieved from NCBI. Database accession No. EU835199 [Sequence].
Uauy, C., Brevis, J. C., Chen, X., Khan, I., Jackson, L., Chicaiza, O., . . . Dubcovsky, J. (2005). High-temperature adult-plant (HTAP) stripe rust resistance gene Yr36 from *Triticum turgidum* ssp. *dicoccoides* is closely linked to the grain protein content locus Gpc-B1. *Theoretical and Applied Genetics*, 112(1), 97-105.
Chicaiza, O., Khan, I. A., Zhang, X., Brevis, J. C., Jackson, L., Chen, X., & Dubcovsky, J. (2006). Registration of five wheat isogenic lines for leaf rust and stripe rust resistance genes. *Crop Science*, 46(1), 485-487.
Fu, D., Uauy, C., Distelfeld, A., Blechl, A. Epstein, L., Chen, X., . . . Dubcovsky, J. (2009). A kinase-START gene confers temperature-dependent resistance to wheat stripe rust. *Science*, 323(5919), 1357-1360.
Li et al. "Research Advance in Molecular Biology and Transgene Breeding on Wheat Resistance to Puccinia Striiformis", Southwest China Journal of Agricultural Sciences, 15(4): 96-100, Dec. 2002.
Liu et al. "Puccinia Striiformis West—Induced Gene Expression of Wheat Germplasm With Stripe Rust Resistance", Acta Botanica Boreali-Occidentalia Sinica, 26(3): 521-526, Mar. 2006.
Liu et al. The Cloning and Sequencing of Resistance Gene Analogues in Wheat, Chinese Agricultural Science Bulletin, 23(3): 83-88, Mar. 2007.
Qin et al. "Isolation of Resistance Gene Analogs From Wheat Based on Conserved Domains of Resistance Genes", Acta Botanica Sinica, 45(3): 340-345, Dec. 31, 2003.
International Preliminary Report on Patentability (Chapter I of the Patent Cooperation Treat), including Written Opinion of the International Searching Authority, issued Aug. 23, 2011 in connection with PCT International Application No. PCT/IL2010/000147, filed Feb. 21, 2010.

* cited by examiner

Fig. 8A

KINASE-START GENE CONFERRING RESISTANCE TO PLANT DISEASE AND TRANSGENIC PLANTS COMPRISING IT

This application is a §371 national stage of PCT International Application No. PCT/IL2010/000147, filed Feb. 21, 2010, claiming benefit of U.S. Provisional Application No. 61/153,773, filed Feb. 19, 2009, the entire contents of which are hereby incorporated by reference into this application.

GOVERNMENT RIGHTS

This invention was made in part with the United States Government support under grants USDA/NRI20053530115906 and USDA/NRI20065560616629 awarded by the US Department of Agriculture, and with the support of the United States Israel Binational Agricultural Research and Development Fund (BARD) under grant US402407. The U.S. Government has certain rights in this invention.

REFERENCE TO SEQUENCE LISTING

This application incorporates-by-reference nucleotide and/or amino acid sequence which are present in the file named "110818_0031_83220_PCT_US_Substitute_Sequence_Listing_WS.txt", which is 71.5 kilobytes in size, and which was created Aug. 8, 2011 in the IBM-PC machine format, having an operating system compatibility with MS-Windows, which is contained in the text file filed Aug. 18, 2011 as part of this application.

TECHNICAL FIELD

The present invention relates to a novel kinase-START gene conferring resistance to plant disease, and transgenic plants comprising it for use in methods to control plant disease, such as stripe rust in cereal crop plants.

BACKGROUND ART

Bread wheat (*Triticum aestivum* L.) provides approximately 20% of the calories consumed by humankind. The increasing world demand for cereals requires improved strategies to reduce yield losses due to pathogens. Wheat stripe rust, caused by the fungus *Puccinia striiformis* f. sp. *tritici* (PST, Table 1) affects millions of hectares of wheat and virulent races that appeared within the last decade are causing large yield losses (Singh et al., 2004). Historically, resistant varieties have provided an economical and "environmentally friendly" method to control stripe rust. Numerous race-specific resistance genes have been deployed by breeders, but each had limited durability presumably because of rapid pathogen evolution. In contrast, broad-race resistance genes (i.e. "slow-rusting") have a broader spectrum of resistance and are generally more effective at adult plant stages, provide partial resistance, and usually confer more durable resistance than race-specific genes (Singh et al., 2004). Unfortunately, our understanding of broad-race resistance is limited because none of these genes has yet been cloned.

SUMMARY OF INVENTION

The gene Yr36, which confers non race-specific resistance to stripe rust at relatively high temperatures (above about 15° C.), has been cloned and sequenced in accordance with the present invention. The cloned gene, referred to herein as WKS1, is shown herein to be equivalent to Yr36.

The present invention is directed, in one aspect, to an isolated nucleic acid molecule comprising a nucleotide sequence which encodes a polypeptide comprising both a steroidogenic acute regulatory protein-related lipid transfer (START) domain and a kinase domain. In some embodiments, the isolated nucleic acid molecule encodes a WSK1 polypeptide.

In some aspects, the present invention relates to an isolated nucleic acid molecule that is a complementary to the above isolated nucleic acid molecule comprising a START domain and/or a kinase domain.

In further aspects, the present invention relates to an isolated nucleic acid molecule comprising a nucleotide sequence having promoter function or a variant or a fragment thereof, wherein said promoter is a temperature-sensitive promoter. This temperature-sensitive promoter nucleotide sequence may be operably linked to the above isolated nucleic acid molecule comprising a START domain and a kinase domain.

In further aspects, the present invention provides a vector comprising the isolated nucleic acid molecule comprising a START domain and a kinase domain of the invention that may be operably linked to the above isolated nucleic acid molecule comprising a nucleotide sequence having promoter function.

In additional aspects, the present invention provides a host cell, in particular a plant cell, and a transformed seed, that contain the vector or the isolated nucleic acid molecule comprising a START domain and a kinase domain of the present invention.

In additional aspects, the present invention provides a transgenic plant comprising the host cell, wherein the polypeptide encoded by the nucleic acid molecule confers to the transgenic plant resistance to diseases caused by specific pathogen races or they may confer non-race specific broad-spectrum resistance.

In additional aspects, the present invention is directed to a method for conferring resistance to stripe rust in a cereal crop plant, said method comprising transforming said plant with a vector or a nucleic acid molecule as defined herein above. In some embodiments, the cereal crop plant is wheat.

BRIEF DESCRIPTION OF DRAWINGS

The file of this patent contains at least one drawing executed in color photograph. Copies of this patent with color photograph(s) will be provided by the Patent and Trademark Office upon request and payment of necessary fee.

FIG. 1 shows the effect of plant age on Yr36 resistance response (10/25° C.). UC1041 near isogenic plants with and without Yr36 at different developmental stages were inoculated on the same day with race PST-113 and the percent leaf area covered with pustules was evaluated three weeks later using the pd program (FIG. 3). (panels A and E) Inoculated at 1st leaf and scored at 3rd-4th leaf. (panels B and F) Inoculated at 4th leaf and scored at 6-7th leaf (panels C and G) Inoculated at elongation stage and scored at flag leaf emergence. (panels D and H) Inoculated at heading and scored at anthesis. Plants at the first two developmental stages are classified as juvenile plants, whereas those at the two later stages are classified as adult plants. The black areas in panel C are teliospores. Values are averages of four plants±SEM of the percentage area covered with PST pustules. Bar=2 mm.

FIG. 2 Map-based cloning of Yr36. (panel A and panel B) Phenotype of susceptible parent Langdon with PST sporulation (A) and partially resistant parent RSL65 (B). Bar=1 mm. (panel C and panel D) Genetic maps of colinear regions of rice chromosome 2 (C) and wheat chromosome 6B (D). (panel E) Physical map of the Yr36 region. Genes are represented by colored arrows and the deleted region in Langdon by a light blue line. The left-pointing black arrow points in the direction of the telomere. The yellow rectangle delineates the Yr36 region (panel F) Structure of the WKS genes. Exons are represented by rectangles and the kinase and START domains are shown in blue and red, respectively. The green hatched box represents the LINE retrotransposon.

Figure 3:
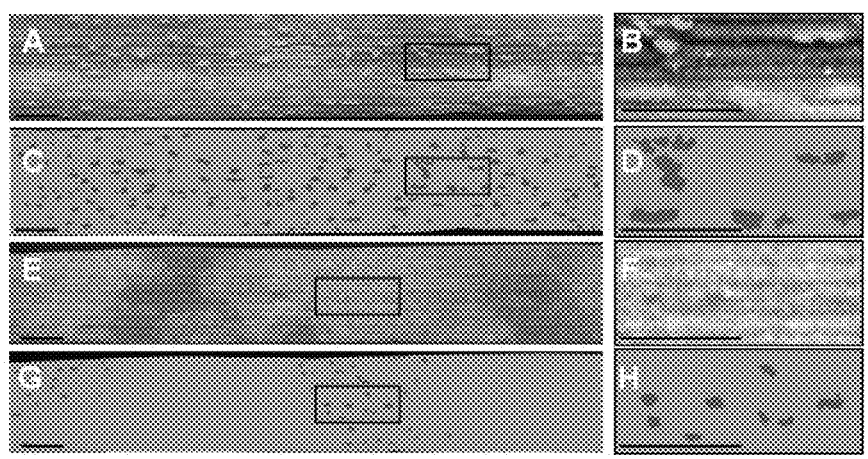

FIG. 3 shows examples of leaves used for quantification of the percentage of leaf area covered with PST pustules. (panel A and panel E) Scanned images of 5-cm segments of wheat leaves. (panel C and panel G) Each pixel in (A) and (E) was categorized by the pd program as either leaf (green), *Puccinia striiformis* f. sp. *tritici* (PST) (red) or background (black). Images in the right column are an enlargement of the image in the rectangle in the left column. (A to D) Susceptible RSL 11-19 with pustules covering 6.9% of the surface area in the segment shown in (A). (E to H) Resistant RSL3-28 with pustules only on 0.9% of the segment shown in (E). Contrast and brightness were manipulated in (B) and (F) to better show pustules. The white areas in (E) are necrotic patches. Bar=5 mm. The pd program is freely available at plantpathology (dot) ucdavis (dot) edu/faculty/epstein/.

Figure 4A:
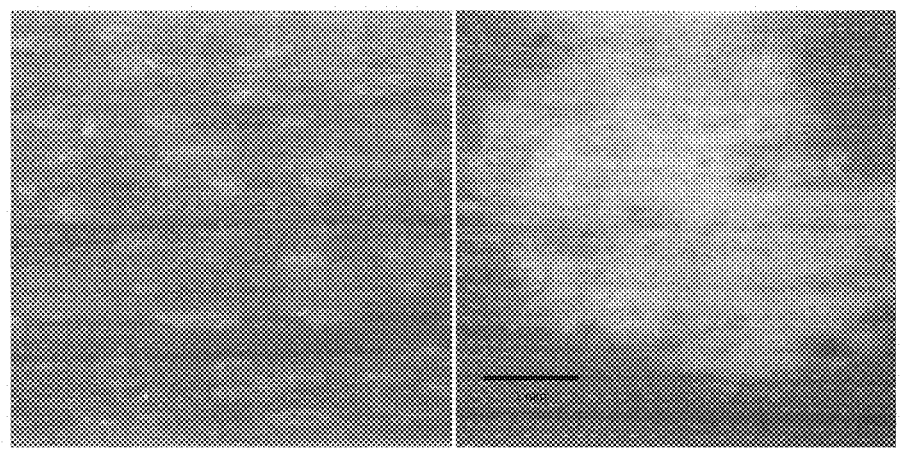
Figure 4B:
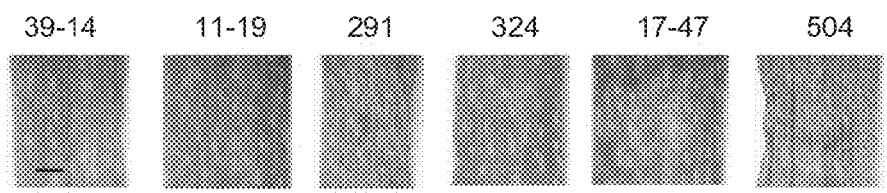
Figure 4C:
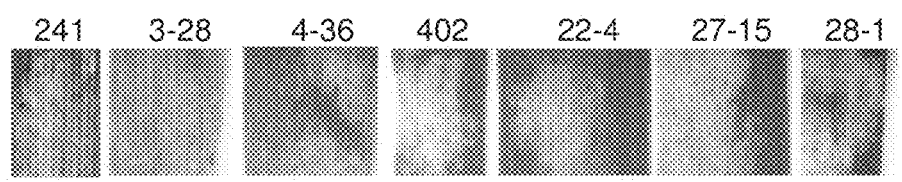

FIGS. 4A-C show the reaction to *Puccinia striiformis* f. sp. *tritici* (PST) in parental and 13 critical recombinant substitution lines (RSLs) used to map Yr36. (A) Left panel, susceptible parent LDN; Right panel, resistant parent RSL65. Plants at the 3-leaf stage were inoculated with PST-100 and then incubated in a growth chamber with a daily 10/25° C. cycle. (B) Leaves of susceptible recombinant progeny have prodigious sporulation in the orange pustules. (C) Leaves of resistant recombinant progeny have necrotic regions with reduced sporulation. Images of the progeny leaves are perpendicular to the parental leaves. Bars=1 mm.

Figure 5:
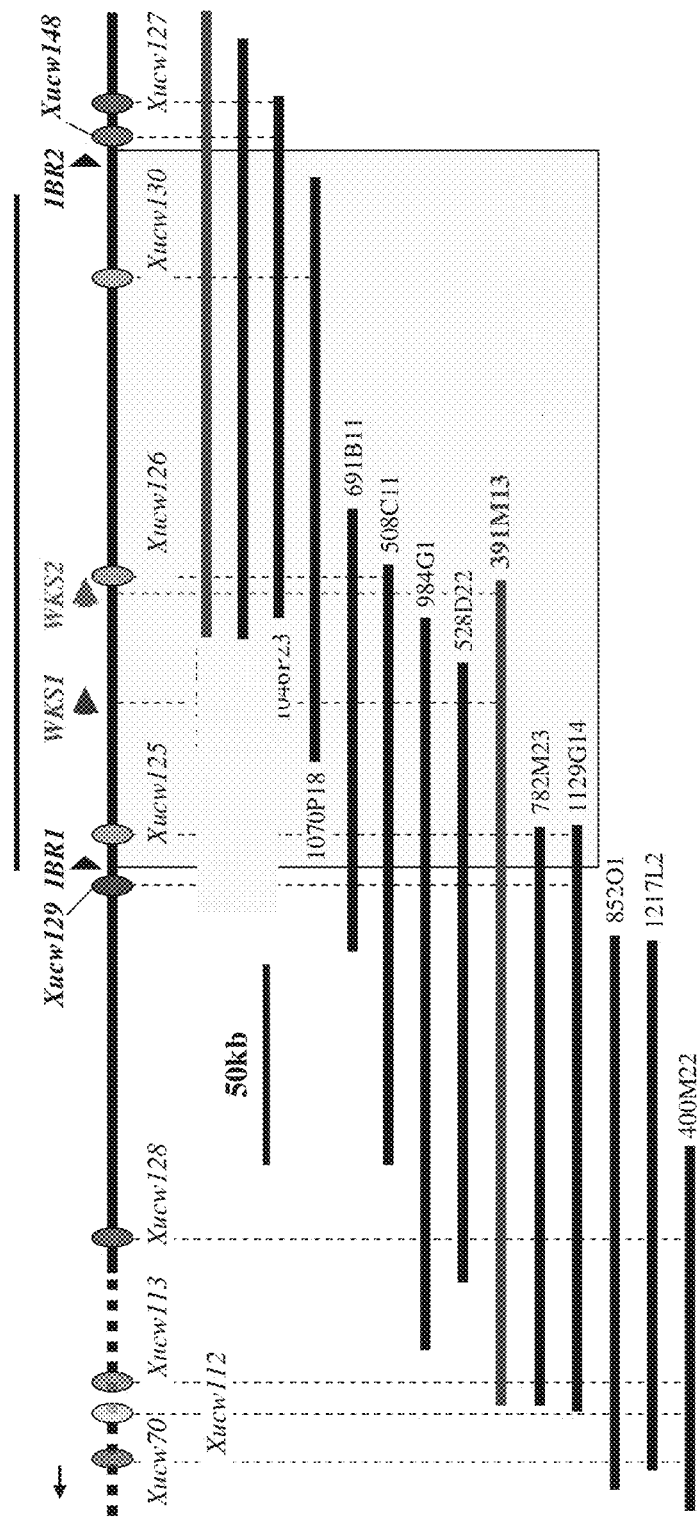

FIG. 5 depicts the physical contig of the Yr36 region. The top line summarizes the information from the HindIII fingerprinting of the B genome BACs listed below and the sequencing of BACS 391M13 and 1144M20 (in blue). Colored ovals represent markers used for the fine mapping of Yr36, whereas colored arrows represent genes WKS1, WKS2, IBR1, and IBR2 linked to Yr36. Markers Xucw129 and Xucw148 flank the Yr36 region (186-kb, yellow shaded square). Markers Xucw125, Xucw126, and Xucw130 and genes WKS1, WKS2, and IBR1 were not amplified in Langdon, suggesting the presence of a large deletion (between 149 and 183-kb long based on current markers). The left-pointing black arrow at the top line points in the direction of the telomere. The bar above the top line delineates the LDN deleted region.

Figure 6:
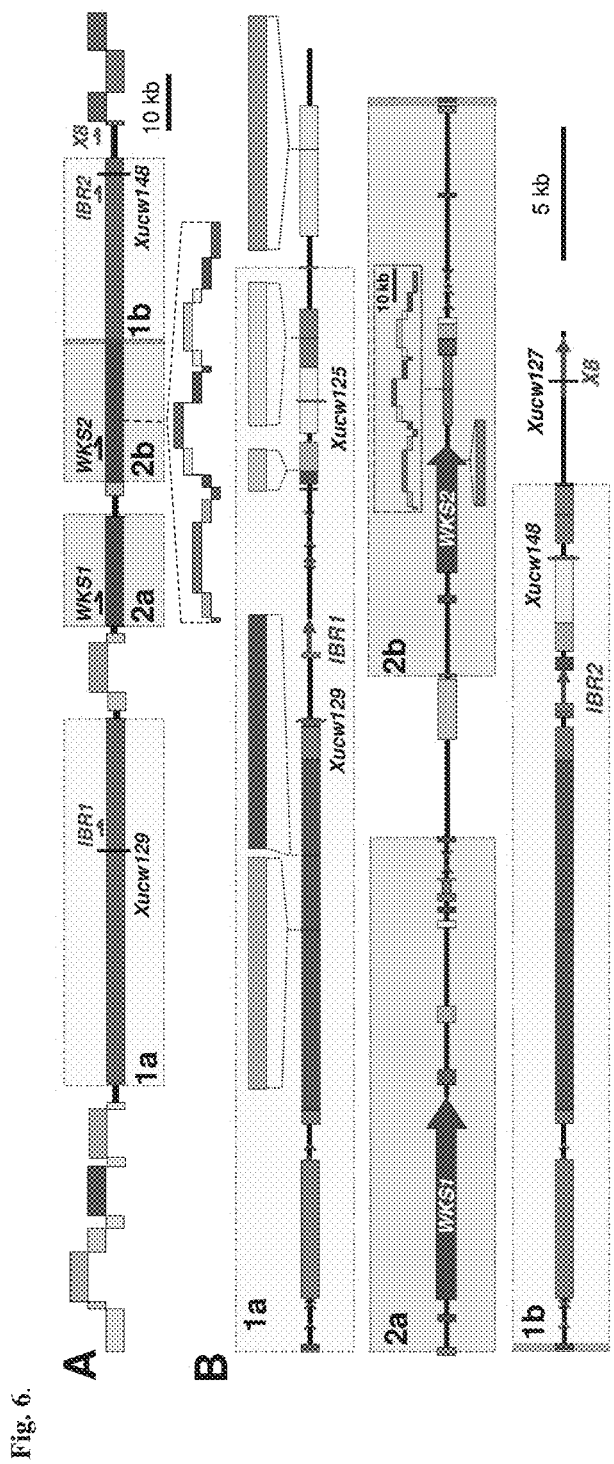

FIG. 6 depicts the sequence annotation of the Yr36 region. (Panel A) Graphic representation of the annotation of the 314-kb sequenced contig. Two large direct duplications were identified: 1a/1b and 2a/2b. The 1a and 1b duplicated regions each include a putative gene which encodes for a protein with an 'in between RING finger' domain (IBR), designated as IBR1 and IBR2. The 2a and 2b regions include genes WKS1 and WKS2, respectively. The X8 putative gene (=Xucw127) is outside the Yr36 critical region defined by markers Xucw129 and Xucw148. Boxes outside the duplicated regions represent transposable elements. Half-arrows indicate putative genes. The 262-bp overlap between the 2b and 1b duplication is indicated by a bright blue box. (Panel B) Detail of the duplicated regions. The 1a (64.5-kb) and 1b (32.3-kb) regions are 96% identical across 31.3-kb. The 1a region has four unique retrotransposon insertions and a series of repeats absent in the 1b segment. The 2a (19.0-kb) and 2b (94.9-kb) regions are 81% identical across 7.9-kb of shared sequence, suggesting that this duplication is older than the 1a/1b duplication. The 2b region is larger than the 2a region because of a 70.2-kb insertion of multiple nested retrotransposons (shown in different scale). Conserved sequences between the corresponding duplicated regions are represented by similar colors. GenBank accession EU835198 includes a detailed annotation of the region.

Figure 7:
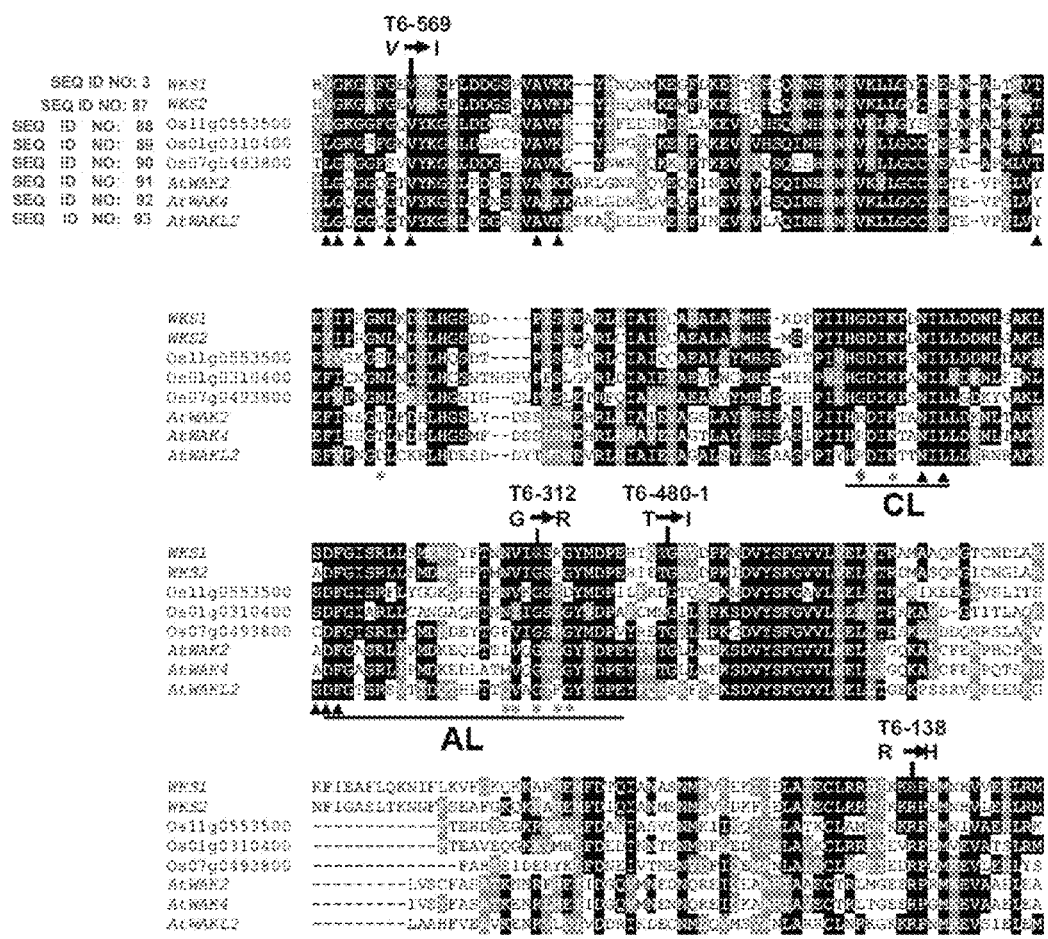

FIG. 7 shows selected mutations in the WKS1 kinase domain. CLUSTALW alignment of the kinase domains (smart00219) from the three closest rice and *Arabidopsis* homologues to WKS1 and WKS2. Amino acid residues that form the ATP (▲) and substrate (*)-binding pocket are labeled. Residues that form part of the catalytic (CL) or activation (AL) loop are underlined. The red diamond indicates the site of the conserved arginine (R) residue within the catalytic loop that is used to classify kinases as either RD on non-RD. WKS1 has a glycine (G) residue at this position, and is therefore a non-RD kinase. Amino acids affected by the mutations resulting in WKS1 loss of function are indicated by bold orange letters. The Targeting Induced Local Lesions in Genomes (TILLING) mutant line designation and the amino acid change in that line is indicated above the WKS1 sequence.

Figure 8A:
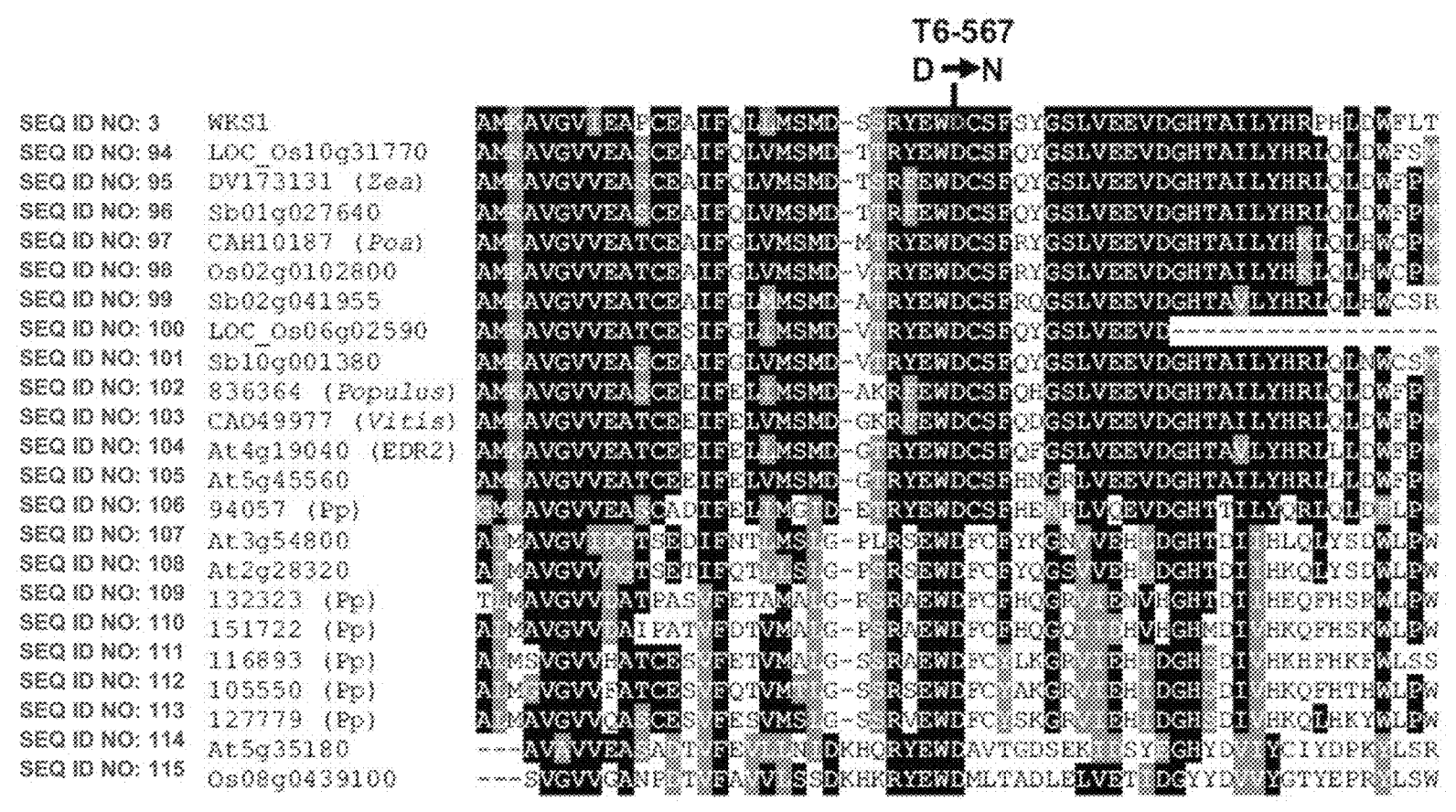
Figure 8B:
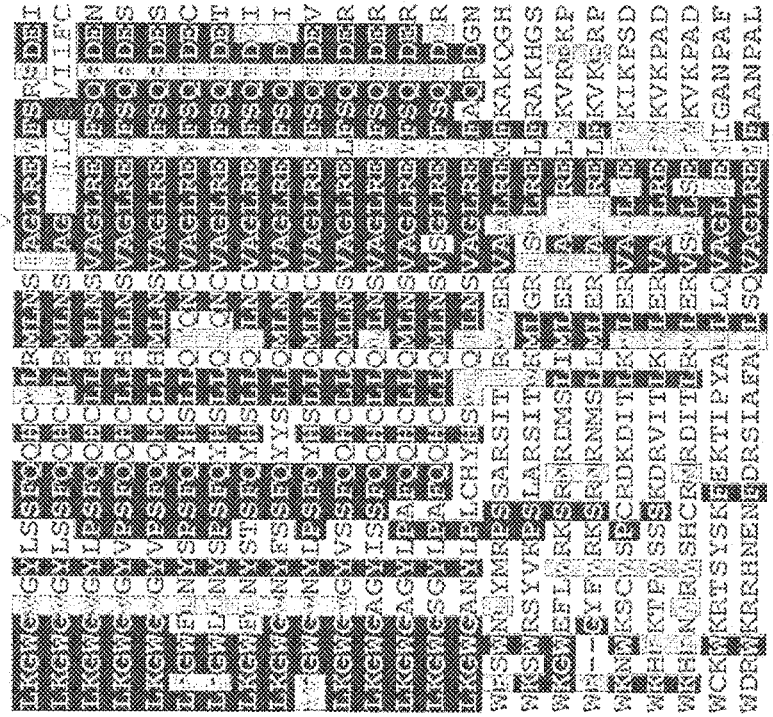

FIGS. 8A-B depict the aligned WKS1 START domain in several plant species. (A) CLUSTALW alignment of the START-domain region surrounding the D477N mutation in T6-567 (bold orange letter). The aspartic acid residue (D) is conserved across all plant species examined as well as across the closest human START genes (StarD6, D14, D15; not shown). The alignment includes the closest plant homologues from *Arabidopsis* (At), rice (Os), *Poa*, *Populus*, *Vitis*, *Sorghum* (Sb), *Zea*, and moss *Physcomitrella patens* (Pp). Complete sequences are available in Genbank or Phytozome (phytozome (dot) net/). (B) Partial alignment of the START domain C-terminus region. The orange arrow indicates the last common amino acid residue between WKS1 transcript variants WKS1.1 and WKS1.2.

Figure 9:
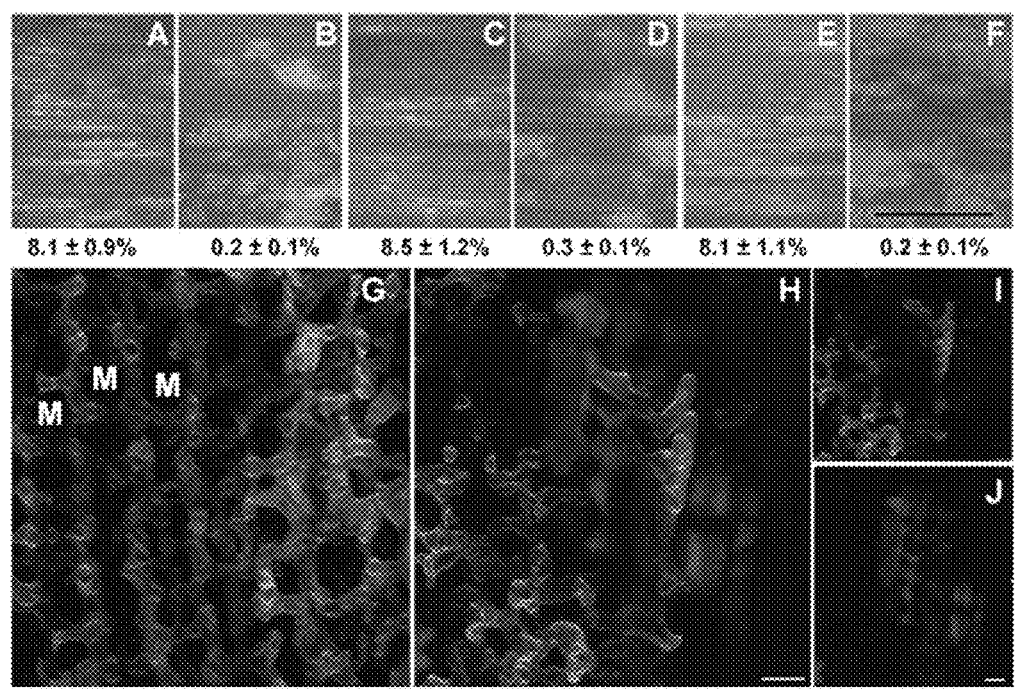
Figure 10A:
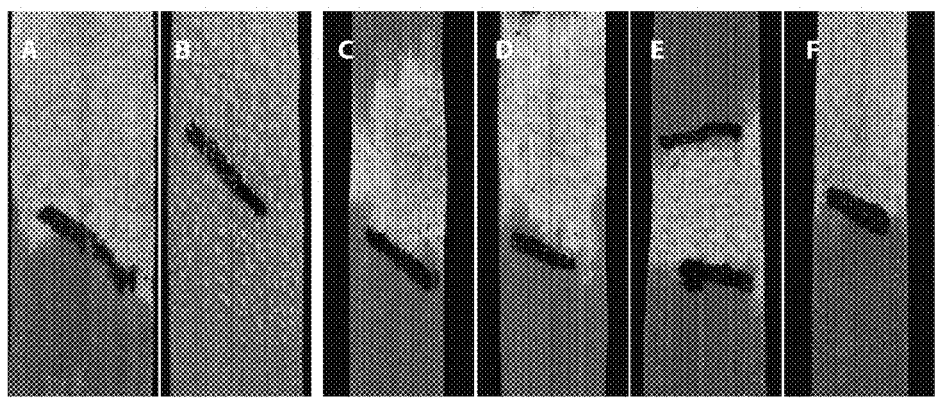
Figure 10B:
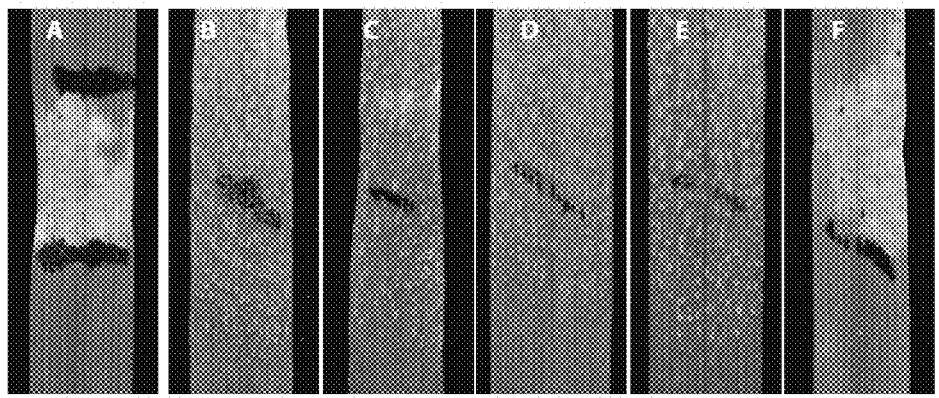
Figure 12:
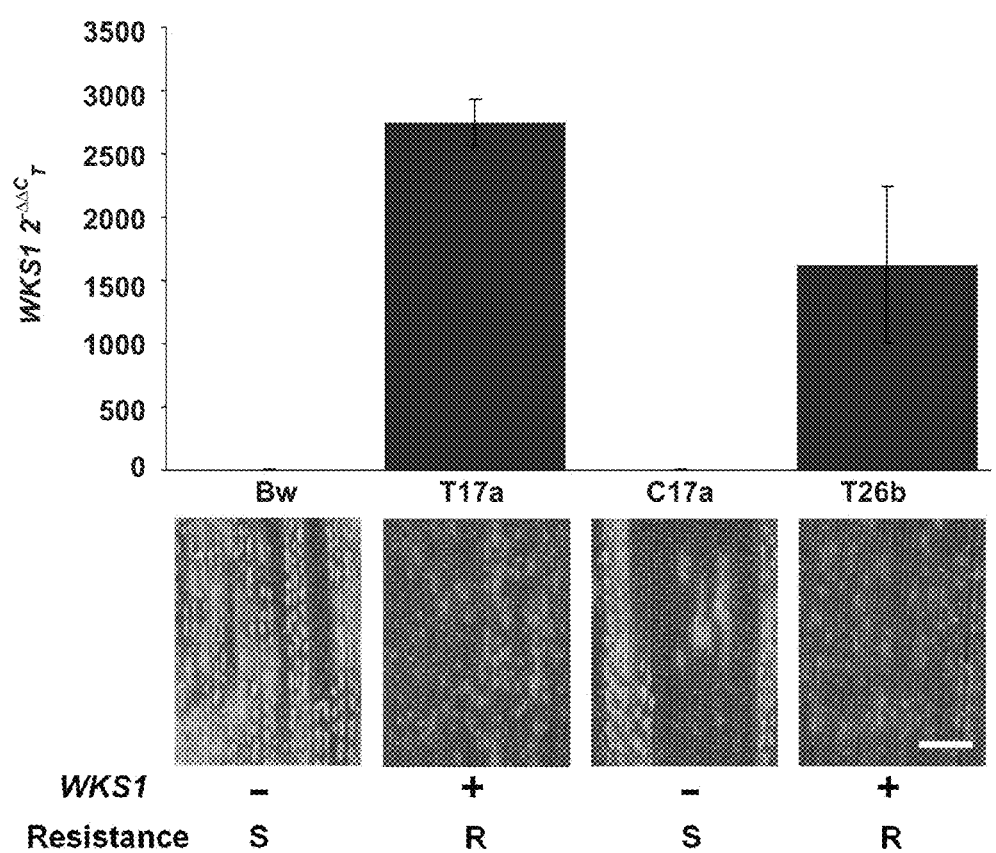

FIG. 9 shows micrographs of 6 mutants with changes in conserved amino acids in WKS1 for the functional validation of Yr36 by mutational analysis. (panels A to F) Leaf surfaces 11 days after PST inoculation. Bar=5 mm. Numbers below leaves are average percent leaf area with pustules±SEM (N=8, FIG. 12). An ANOVA of the log-transformed data showed significant differences (P<0.01) between mutant and control lines. (A) The common wheat breeding line UC1041 without Yr36. (B) UC1041+Yr36 isogenic line used for mutagenesis. (C and E) Lines T6138 and T6-312 with homozygous mutations in the WKS1 kinase domain. (D and F) Sister lines without the mutations (see Example 2). (G and H) A dual-channel, confocal microscopic z-series inside a wheat leaf 13 days after PST inoculation. Bar=20 μm. The uvitex-stained fungus (false-color blue) and autofluorescing wheat leaf cells (false color red) are visible. (G) The susceptible T6-312 mutant has an extensive mycelial network in which each (invisible) plant mesophyll cell (selected cells shown as M) is encircled by a hypha. (H) The T6-312 control line has a poorly developed fungal network surrounded by autofluorescent mesophyll cells that presumably were involved in the resistance response. (I and J) Separate channels of panel (H).

FIGS. 10A-B show the effect of WKS1 and WKS2 mutations on PST resistance (Mutant experiment 1). Three WKS2 (A) and 5 WKS1 mutants (B) (see Example 2) were inoculated at the 4th-leaf (juvenile) stage with race PST-113. The susceptible wheat line UC1041 (without Yr36) and the isogenic line UC1041+Yr36 were used as controls (FIG. 10A, panels B and A, respectively). Further in FIG. 10A:

WKS2 mutants T6-826 (panel D); T6-480-2 (panel E); T6-960 (panel F). In FIG. 10B: WKS1 mutants T6-312 (panel B); T6-138 (panel C) T6-569 (panel D); T6-480-1 (panel E); and T6-86 (panel F). Sister lines of mutants T6-826 FIG. 10A, panel C) and T6-312 (FIG. 10B, panel A) homozygous for the absence of the mutation also were included as controls. The margins of the leaf regions with pustules were marked with a black marker 15 days after inoculation and pictures were recorded five days later.

Figure 11:
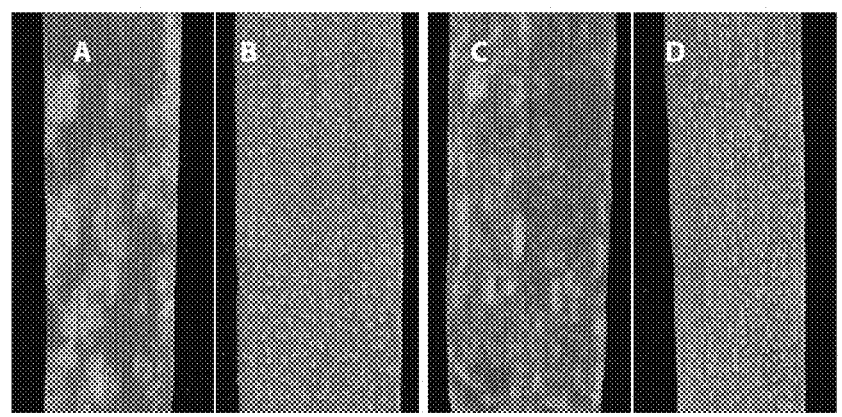

FIG. 11 shows loss of PST resistance in WKS1 START mutant T6-567 (Mutant experiment 3). The T6-567 line (discovered after Mutant experiments 1 and 2) has a mutation in a conserved codon in the START domain (FIG. 8A). PST infection in this mutant line (panel D) was compared with a sister line homozygous for the absence of this mutation (panel C). Susceptible UC1041 (panel B) and resistant UC1041+Yr36 (panel A) also were tested as controls. Plants were inoculated with race PST-113 at the stem elongation (adult plant) stage.

FIG. 12 depicts WKS1 transcript levels (upper panel) and resistance phenotype in transgenic wheat plants (lower panel). The transcript levels were analyzed using the $2^{-\Delta\Delta CT}$ method (see Example 2 and Materials & Methods). Average WKS1 transcript levels (±SEM) in independent transgenic events 17a (T17a; 5 plants) and 26b (T26b; 7 plants) were determined by quantitative RT-PCR. Negative controls are the un-transformed variety Bobwhite (Bw) and the average of three T1 sister lines of 17a without the transgene (C17a). Leaf phenotypes: S=susceptible, R=resistant. Bar=2 mm. Southern blots and transcription profiles of individual T1 plants are shown in FIG. 13.

FIG. 13 depicts the characterization of T1 plants from independent transgenic events 17a (T17a) and 26b (T26b) in hexaploid wheat variety Bobwhite (Bw). (panel A) Resistance (R) or susceptible (S) response on leaves after inoculation with race PST-113. (panel B) WKS1 transcript levels, analyzed using the $2^{-\Delta\Delta CT}$ method, before infection as determined by Q-PCR. Values are averages of 6 leaves±SE of the means. The red dotted line indicates WKS1 transcript level in a non-transgenic UC1041+Yr36 positive control. (panel C) Southern blots hybridized with WKS1 showed absence of the transgene in 17a-1, 17a-3 and 17a-18 (in red) and presence in the other five 17a lines. The blue arrow indicates the expected size of the restriction fragment that hybridizes with the WKS1 probe.

The 17a lines without the transgene were as susceptible as the negative Bobwhite control. Transgenic lines with WKS1 transcript levels similar or higher than the positive control UC1041+Yr36 (dotted red line) were resistant to PST-113 and showed little or no sporulation. Line 26-8, which had an intermediate resistance reaction (R/S), had the lowest WKS1 transcript levels of the transgenic lines. Since the endogenous WKS1 in UC1041+Yr36 is in a different genetic background, its transcript levels should be considered just as an approximate positive control.

FIG. 14 is a graphical representation of WKS1 alternative transcript variants. Cloning and sequencing of 56 WKS1 cDNA clones revealed six transcript variants designated WKS1.1 to WKS1.6. Primers WKS1_F5/R5 and WKS1_F4/R4 were used to amplify transcript variant WKS1.1 and WKS1.2-6, respectively. Primer WKS1_R5 anneals to the WKS1.1 exon 10-11 splice junction whereas primer WKS1_R4 anneals to the WKS1.2-6 sequence of exon 10 that is missing from WKS1.1. The kinase and START domains are shown in blue and red, respectively. Stop codon is marked by *. Bar=500 bp.

FIG. 15 shows the effect of temperature (T) and PST inoculation (I) on transcript levels of WKS1 transcript variants WKS1.1 and WKS1.2-6 in RSL65. Quantitative RT-PCR transcripts of WKS1.1 are indicated in black and those of WKS1.2-6 in gray. PST-inoculated plants (I+) are indicated by stripes and non-inoculated controls (I−) by solid colors. Leaf-samples from RSL65 plants were collected 3, 9 and 16 days post inoculation (DPI) with race PST-100. Half of the plants were not inoculated. Each datapoint is the average of 6 samples±SE of the mean. The transcript levels were analyzed using the $2^{-\Delta\Delta CT}$ method (see Example 2 and Materials & Methods). No significant interactions between temperature and inoculation were detected in the individual 2-way ANOVAs except for panel A (significant differences between inoculation classes only at low temperature). *: $P<0.05$, : $P<0.01$, *: $P<0.001$, and NS: not significant. Each data point is an average based on six replicates (±SEM).

FIG. 16 shows the effect of temperature and infection with PST on WKS1 transcript variants. The effect of high (10/35° C.) and low (10/15° C.) temperatures on transcript levels of WKS1.1 (black bars) and WKS1.2-6 (gray bars) was determined by Q-PCR. The transcript levels were analyzed using the $2^{-\Delta\Delta CT}$ method (see Example 2 and Materials & Methods). Leaf-samples from RSL65 plants were collected 3, 9 and 16 days post inoculation (DPI) with race PST-100. Half of the plants were not inoculated. Each datapoint is the average of 6 samples±SE of the mean. Since the ANOVAs showed significant interactions between transcript variants and temperatures, simple effects for transcript variants within each temperature are presented above each pair of bars. (panels A to C) Inoculated. (panels D to F) Non-inoculated. : $P<0.01$, *: $P<0.001$, and NS: not significant.

FIG. 17 shows in-gel kinase activity of GST-WKS1_Kinase. (panel A) Coomassie Blue stained gel of purified proteins from GST-WKS1_Kinase fusion protein (KIN, red arrow) and the GST control vector (GST). (panel B) In-gel kinase activity assay using casein (1 mg/mL) as a phosphorylation substrate. Radioactive bands were visualized using a Storm 860 PhosphorImager. The in-gel kinase assay was repeated twice with independently expressed fusion proteins with identical result. (panel C) Western blot using a GST-antibody.

FIG. 18 shows PCR markers used to determine WKS1 and WKS2 distribution among different *Triticeae* species. "+" indicates presence, and "−" indicates absence, of WKS1 or WKS2 in the *Triticeae* species indiciated at the top of each lane: A, UC1041+Yr36; B, Kronos (durum); C, *Ae. comosa*; D, *L. elongatum*. ID, Inter domain; rpt, repetitive.

DETAILED DESCRIPTION OF THE INVENTION

The novel nucleic acid sequence of WKS1 of the invention encodes for a polypeptide comprising both a steroidogenic acute regulatory protein related lipid transfer (START) domain and a kinase domain. The START domain is a protein domain spanning ~210 residues, which is conserved in plants and animals, serves as a binding interface for lipids and has been implicated in many distinct processes. The crystal structures of three human proteins comprising START domains have been solved, revealing a conserved 'helixgrip' fold that forms an inner tunnel wide enough to accommodate the hydrophobic lipid. As is shown in the Examples hereinafter, the amino acid sequence of the START region of WKS1 is of SEQ ID NO: 1.

It has further been found in accordance with the present invention that the WKS1 kinase has high similarity to several *Arabidopsis* WAK-like kinases, but WKS1 lacks the additional domains characteristic of WAK-like kinases. The WKS1 kinase, which has a Ser/Thr kinase domain, belongs to the non-RD kinases, which are frequently involved in the early steps of the innate immune response. The kinase domain of WKS1 has the amino acid sequence as set forth in SEQ ID NO: 2.

The term "Ser/Thr kinase" is used herein to indicate a kinase that is capable of phosphorylating the OH group of serine or threonine. The term "non-RD kinase domain" is used herein to indicate that the protein lacks the conserved arginine (R) residue within the catalytic loop that is used to classify kinases as either RD or non-RD kinases.

The combination of the kinase and START domains in WKS1 apparently is the result of a novel domain shuffling because, before the present invention, these two domains have not been found together in any other organism. For example, we searched the rice and Arabidopsis genomes for genes encoding for both kinase and START domains to look for a possible orthologue of WKS1. We did not find this combination in rice but in Arabidopsis we found putative gene MGH6.22 (AB026645) that encodes for a 1,088 amino acid protein (BAB01397). BAB01397 has a START domain in the N-terminal region followed by multiple leucine-rich repeats (LRRs), and a protein kinase catalytic domain in the C-terminal region. There is no full-length cDNA to support this annotation, and the protein record Q9LK66 has been discontinued and replaced by two adjacent but separate genes: At3g13062 (NP_850573, an unknown protein with similarity to a START domain) and SRF4 (STRUBBELIG-RECEPTOR FAMILY 4, serine/threonine kinase) supported by multiple ESTs.

Using primers from At3g13062 and SRF4, we cloned two full-length cDNAs from Arabidopsis (Columbia ecotype) that include both At3g13062 and SRF4 coding sequences. However, both cDNAs have premature stop codons between the START and the LRR repeats, one of which is similar to the stop codon in At3g13062 (GenBank FJ154117 and FJ154118).

The kinase and START domains of WKS1 are in a different order than in the At3g13062-SRF4 cDNA. In addition, the two WKS1 domains are more similar to other Arabidopsis proteins than to At3g13062-SRF4 (BLASTP searches of Arabidopsis RefSeq protein database). The START domain and the adjacent 5' inter-domain region of WKS1 are more similar to Arabidopsis EDR2 (NP_193639, 56% identity over 337 amino acids, $E=3e^{-103}$) than to At3g13062 (NP_850573, no BLASTP significant similarity). Similarly, the WKS1 kinase domain is more similar to the WALL ASSOCIATED KINASE 4 (NP_173544, 40% identity over 314 amino acids, $E=1e^{-51}$) than to SRF4 (30% identity over 280 amino acids, $E=1e^{-28}$). These results indicate that the domains encoded by At3g13062 and SRF4 are not likely orthologous to the kinase and START domains in WKS1.

A BLASTP search in rice showed that the closest protein to the WKS1 kinase domain is EAY97604 (60% identical over 323 amino acids $E=9e^{-105}$) and that the closest one to the START domain is ABB47745 (66% identical over 335 amino acids, $E=2e^{-123}$) which is 72% identical to Arabidopsis EDR2 over its entire length (E=0). These two genes (or closely related ones) are the most likely source of the shuffled domains that originated WKS1. The WKS1 kinase is classified as a non —RD kinase because it lacks the arginine (R) residue preceding the invariant aspartate (D) in the activation domain.

START domains are lipid/sterol binding modules that are conserved from animals to plants (Schrick et al., 2004). Although the specific ligands for some human START domain proteins are known (e.g. StAR protein binds cholesterol and CERT protein binds ceramides), a function in ligand binding has not been verified for any START plant protein so far. However, Arabidopsis plants with mutations in sterol biosynthesis genes share common phenotypes with mutants for homeodomain-START genes, which suggests that these proteins may be controlled by binding sterols. In addition, protein modeling of plant START domains based on the crystal structure of human START proteins implicates similar molecular ligands, and suggests that these proteins have retained common functions in evolution (Schrick et al., 2004). EDR2, a START domain protein involved in the Arabidopsis response to powdery mildew, localizes to the endoplasmatic reticulum, plasma membrane and endosomes, which is also consistent with a role of the START domain in lipid sensing and trafficking.

Amongst the 35 Arabidopsis proteins with START domains, the EDR2START domain is the closest to the WKS1 START domain. However, EDR2 and WKS1 differ in other conserved domains present in these proteins. WKS1 has an additional kinase domain, whereas EDR2 has additional PH (plekstrin homology) and DUF1336 (unknown function) domains. This may explain why WKS1 confers resistance, whereas EDR2 is a negative regulator of pathogen-induced disease resistance. In spite of these differences, the two genes share a late-acting resistance phenotype associated with necrotic lesions and programmed cell death. As shown in Example 2, wheat plants with a mutation in the WKS1 START domain are susceptible to PST and lack the necrotic lesions characteristic of plants with wild WKS1 alleles, which indicates that this domain is necessary to trigger the hypersensitive response.

The edr2 phenotype is very similar to the phenotype of both edr1 and edr1-edr2 double mutants suggesting that these two genes are part of the same signal transduction pathway. EDR1 encodes a CTR-1 Ser/Thr kinase suggesting that EDR2 might be a phosphorylation target of EDR1. Phosphorylation has been also shown to be important for START domain function for at least one animal protein and to modulate the role of ceramides in programmed cell death in *Arabidopsis*. The presence of an active kinase and a putative START domain within a single protein (WKS1) provides a new tool to study interactions between kinases and START domains, but more importantly, as is shown herein below in Example 2, both the kinase and START domains are necessary for the resistance response.

In view of the above, in one aspect, the present invention relates to an isolated nucleic acid molecule comprising a nucleotide sequence which encodes a polypeptide comprising both a START domain and a kinase domain. In certain embodiments, the START domain consists of SEQ ID NO: 1, or a variant or a fragment thereof, and the kinase domain is a non-RD kinase domain, such as a Ser/Thr kinase domain, for example of SEQ ID NO: 2, or a variant or a fragment thereof.

As is shown herein in the examples, the cloning and sequencing of 56 full-length WKS1 cDNAs revealed six alternative transcript variants (WKS1.1-6, Example 4). WKS1.1 encodes a complete WKS1 protein (SEQ ID NO: 3), whereas the other five (WKS1.2-6) lack exon 11 and encode proteins with truncated START domains (SEQ ID NOs: 4-7, respectively). Some of the missing amino acids are well conserved across the plant kingdom. Of course, any nucleotide sequence encoding the polypeptides of SEQ ID NOs: 3-7 could be used according to the present invention, preferably the nucleic acid sequence of the transcripts variants as set forth in SEQ ID NOs: 9-14 encoding for the proteins of SEQ ID NOs: 3-7, respectively, and most preferably the nucleic acid sequence of the transcript variant WKS1.1 of SEQ ID NO: 9.

Thus, in certain embodiments, the isolated nucleic acid molecule of the invention comprises a nucleotide sequence that encodes a polypeptide selected from the polypeptides herein designated WKS1.1 (SEQ ID NO: 3), WKS1.2 (SEQ ID NO: 4), WKS1.3 (SEQ ID NO: 5), WKS1.4 (SEQ ID NO: 6), WKS1.5 (SEQ ID NO: 7) and WKS1.6 (SEQ ID NO: 8), or a variant or a fragment of said polypeptide. In certain embodiments, the isolated nucleic acid molecule comprises any one of the nucleotide sequences of SEQ ID NOs: 9-14. In one embodiment, the isolated nucleic acid molecule comprises the nucleotide sequences of SEQ ID NOs: 9.

The variants of the present invention are nucleic acid molecules of a sequence having at least about 60% identity, for example, at least 85% sequence identity, at least 90% sequence identity, at least 95% sequence identity, or at least 99% sequence identity with a nucleic acid sequence identified above as well as nucleic acid molecules encoding the polypeptides of the invention but comprising degenerate codons. The sequence identity is based on known alignment methods, for example, the ClustalW alignment method. On the protein level, the polypeptide variants encoded by the nucleic acid molecules of the present invention have at least 60% identity, for example at least 70% sequence identity, at least 80% sequence identity, at least 85% sequence identity, at least 86% sequence identity, at least 90% sequence identity, at least 95% sequence identity, or at least 99% sequence identity with an amino acid sequence identified above. The variant may also be a splice variant of the polypeptide. Both the variants and fragments of the nucleic acid molecules and of the polypeptides encoded thereby are encompassed by the present invention as long as they exhibit the same biological activity as said polypeptides, i.e. that they have kinase activity and START domain activity such as the binding of sterols, and/or confer resistance to stripe rust in a cereal crop plant.

An accepted method of controlling plant diseases is the development of disease resistant plants expressing resistance genes. These genes may afford resistance to specific pathogen races or they may confer non-race specific resistance, or broad-spectrum resistance. Often, broad-spectrum resistance genes confer resistance to a variety of plant diseases caused by pathogens as different as viruses, fungi and bacteria.

A resistant plant is characterized by the appearance of necrotic patches in the leaves in response to the pathogen, whereas such patches do not appear in susceptible plants following infection. Furthermore, the terms "resistant and resistance" are used herein to describe the ability of the plant to withstand damage to plant tissue caused by a pathogen. For example, a variety or line resistant to a certain pathogen produce significantly higher yield than a susceptible variety in the presence of the pathogen. Plants can also be classified according their response to fungi into three infection types (IT) (R. F. Line, A. Qayoum, Technical Bulletin 1788, United State Department of Agriculture, 1992): 0-3 (resistant, none to trace level sporulation), 4-6 (intermediate, light to moderate sporulation), 7-9 (susceptible, abundant sporulation). In accordance with the findings of the present invention, susceptible lines exhibit IT values ranging between about 6 to about 7 and resistant lines exhibit IT values ranging between about 2 to about 3. Lines can also be classified according to relative leaf area covered with fungi pustules. Accordingly, lines that are not significantly different from the susceptible line LDN and significantly more susceptible than the resistant line RSL65 are classified as susceptible ("S"), whereas lines that are not significantly different from RSL65 but significantly more resistant than LDN are classified as resistant ("R"). Naturally, the reference susceptible and resistant lines may be chosen from any relevant susceptible or resistant lines, depending on the plant species, variety or line studied. As shown herein below, susceptible lines exhibit a percentage area covered with pustules ranging between about 6 and about 13, while resistant lines exhibit a percentage area covered with pustules ranging between about zero and about 3.

Thus, a plant to which broad-spectrum resistance to a certain pathogen has been conferred is a plant in which necrotic patches appear in the leaves in response to the pathogen. Furthermore, a plant which has acquired broad-spectrum resistance produces significantly higher yield than a susceptible variety in the presence of the pathogen; it can be characterized as a plant of infection type 4-6, preferably 2-4, and most preferably 0-3, or as a plant that has a relative leaf area covered with fungi pustules that is significantly lower than that of the susceptible line LDN (or a different susceptible line) and not significantly different from that of the resistant line RSL65 (or a different resistant line), preferably having a relative leaf area covered with fungi pustules ranging between about zero and about 3.

The term "significant" as used herein refers to its statistical meaning; i.e. when using a commonly known statistical test to analyze differences among two or more independent groups, such as a Student's t-test or ANOVA, and the calculated p-value is lower than $\alpha=0.05$, then the groups are significantly different.

The term "about" as used herein refers to the adjacent stated value plus or minus 10% or lower, such as 8%, 5% or 2%.

Thus, in one embodiment, the polypeptide encoded by the nucleic acid of the present invention, or a variant or a fragment thereof, confers to a plant broad-spectrum resistance to a plant disease, in particular a fungal plant disease. The plant protected by this polypeptide may be a cereal crop plant, such as, but not limited to wheat or barley. The wheat species contemplated by the present invention are, for example, but not limited to, common wheat or bread wheat (*T. aestivum*), durum (*T. durum*), einkorn (*T. monococcum*), and spelt (*T. spelta*). The barley cultivars contemplated by the present invention are for example, but not limited to, two-row barley (*Hordeum distichum, Hordeum vulgare*), and six-row barley (*Hordeum vulgare*).

The fungal plant disease may be caused by a *Erysiphales* or a *Puccinia* fungus. For example, the disease may be powdery mildew caused by a *Erysiphales* fungi, stem rust, also known as black rust or cereal rust caused by *Puccinia* graminis, brown rust of wheat caused by *Puccinia* recondite or wheat rust caused by *Puccinia* triticina.

In certain embodiments, the plant is cereal crop plant, such as wheat or barley and the fungal plant disease is a rust disease caused by a *Puccinia* fungus, such as *Puccinia striiformis*, in particular wheat stripe rust caused by *Puccinia striiformis* f. sp. *tritici*.

In another aspect, the present invention relates to at least one isolated nucleic acid molecule that is a complement of, i.e. is complementary to, a nucleic acid molecule comprising a nucleotide sequence which encodes a polypeptide comprising SEQ ID NO: 1 and/or SEQ ID NO: 2. This at least one nucleic acid molecule may be used to identify cells comprising nucleic acid sequences encoding for WKS1 polypeptides, variants or fragments thereof. The complement nucleic acid molecule may have a sequence of at least about 60% identity, for example, at least 85% sequence identity, at least 90% sequence identity, at least 95% sequence identity, or at least 99% sequence identity with the exact complement of SEQ ID NO: 1 and/or SEQ ID NO: 2.

It has further been found in accordance with the present invention that the nucleic acid sequence present upstream of the ATG start codon of the nucleic acid encoding the WKS1 protein of the present invention, comprises a temperature sensitive promoter which is up to about 3000 basepairs, or between about 1000 and about 2566 basepairs in length. This promoter may be utilized for driving the expression of genes conferring important traits to a plant in a temperature dependent manner, thus inducing the expression of such genes only at certain temperature, for example, above about 15° C.

Thus, in a further aspect, the present invention relates to an isolated nucleic acid molecule comprising a nucleotide sequence present upstream of the ATG having a size selected from about 3000 basepairs and between about 1000 and about 2566 basepairs, for example of SEQ ID NO: 15, having promoter function, or a variant or a fragment thereof, wherein the variant and the fragment maintain the promoter function of the intact promoter. In one embodiment, the nucleic acid molecule is operably linked to a heterologous transcribable polynucleotide molecule, such as, but not limited to a nucleic acid molecule of the present invention that is encoding a WKS1 polypeptide, variant or fragment thereof.

In another embodiment, the nucleic acid molecule having promoter function is induced at a temperature selected from at or above about 15° C., between about 15° C. and about 35° C., between about 20° C. and about 35° C., and between about 20° C. and about 25° C. or between about 25° C. and about 35° C.

The present invention further provides a vector comprising a nucleic acid molecule according to the present invention, and optionally a nucleotide sequence encoding a heterologous protein, wherein said nucleic acid molecule is operably linked to a promoter that drives expression of the coding sequence of said nucleic acid molecule in a plant cell. The heterologous protein maybe a marker for following protein expression or for facilitating purification, such as Green Fluorescent Protein, a His-tag (e.g. $His_6$), a $(His-Asn)_6$ tag, a Flag tag, or preferably glutathione S-transferase (GST).

The promoter driving the expression of the nucleic acid molecule may be a constitutive promoter such as a ubiquitin promoter, a pathogen-induced promoter such as a *Puccinia*-induced promoter or a temperature-sensitive promoter, such as the temperature sensitive promoter comprised by the nucleic acid sequence present upstream of the ATG start codon of the nucleic acid encoding the WKS1 protein of the present invention, as defined herein above.

The present invention further relates to a host cell that contains the vector or a nucleic acid molecule of the present invention, to a transgenic plant comprising a plant host cell that contains the vector or nucleic acid molecule of the present invention, and to a transformed seed comprising the vector or nucleic acid molecule according to the present invention. The host cell may be a bacterial, yeast or insect cell. In one embodiment, the cell is a plant cell.

The present invention further contemplates methods of transforming/transfecting plants with the nucleic acid molecule of the present invention, in order to confer to said plants resistance to a plant disease In certain embodiments, the nucleic acid molecule is inserted into a vector, e.g. a plasmid, comprising nucleotide sequences providing for the correct incorporation of the nucleic acid molecule into the genomic DNA of a host cell and/or for expression of the polypeptide encoded by the nucleic acid molecule. The vector may be circular or it may be a linear nucleic acid molecule.

Non-limiting examples of techniques for transformation of plant cells with foreign nucleic acids are: (i) *Agrobacterium*-mediated transformation, in which the foreign nucleic acid is introduced into the plant cell by first transfecting the *Agrobacterium* with a vector comprising the foreign nucleic acid and then bringing the *Agrobacterium* into contact with the plant or plant tissue to be transformed. The *Agrobacterium* then inserts the vector into the cell. Unfortunately, many plants are not transformable by this method; (ii) the nucleic acid molecules are inserted directly into the plant cells by known techniques, for example: (a) Bombardment, in which small gold or tungsten particles are coated with plasmids or nucleic acid fragments and propelled through the cell walls of young plant cells or plant embryos. Some genetic material will stay in the cells and transform them. The transformation efficiency can be lower than in *Agrobacterium*-mediated transformation, but most plants can be transformed with this method; (b) Electroporation, which makes transient holes in cell membranes using electric shock allowing the nucleic acid molecules to enter the cell; or (iii) viral transformation in which the desired genetic material is packaged into a suitable plant virus and the modified virus is allowed to infect the plant. If the genetic material is DNA, it can recombine with the chromosomes to produce transformant cells.

The present invention also provides a method for conferring resistance to stripe rust in a cereal crop plant, said method comprising transforming said plant with a vector or nucleic acid molecule according to the present invention. In one embodiment, the cereal crop plant is wheat.

In addition, the present invention provides a cereal crop plant, having stably incorporated into its genome a vector or nucleic acid molecule according to the present invention. In one embodiment, the cereal crop plant is wheat.

As described herein above, and in accordance with the present invention, the gene encoding for the WKS1 protein may give rise to six variant polypeptides due to alternative splicing. Thus, the present invention particularly relates to a transgenic wheat plant having stably incorporated into its genome a nucleic acid molecule comprising a nucleotide sequence selected from SEQ ID NO: 9 to 14. In one embodiment, the nucleic acid is of SEQ ID NO: 9.

The invention will now be illustrated by the following non-limiting examples:

EXAMPLES

Example 1

Cloning of the High-Temperature Stripe Rust Resistance Gene Yr36

We report here the positional cloning of the high-temperature stripe rust resistance gene Yr36. This gene was first discovered in wild emmer wheat (*T. turgidum* ssp. *dicoccoides* accession FA15-3) (DIC) (Uauy et al., 2005). Analysis of Yr36 isogenic lines in different genetic backgrounds confirmed that this gene confers partial resistance to PST under field conditions, and is associated with significant yield increases when the pathogen is present. In controlled environments, plants with Yr36 are resistant at relatively high temperatures (25-35° C.) but susceptible at lower temperatures (e.g. 15° C.) (Uauy et al., 2005). Yr36 resistance, originally discovered in adult plants, has some effectiveness in seedlings at high-temperatures (FIG. 1). The wheat—*P. striiformis* interaction differs in juvenile and adult plants. Part of the difference is due to changes in leaf anatomy. In younger leaves, a single infection event leads to fungus growth both between and across the veins giving rise to a wide lesion (FIGS. 1, A, B, E, and F). In contrast, in adult leaves a single infection event is primarily limited in growing between veins, which results in a "stripe" pattern of sporulation (FIGS. 1, C, D, G, and H).

In addition to this Yr36-independent developmental difference, there is also a Yr36-dependent difference between adult and juvenile plants. In juvenile resistant plants inoculated at the 1$^{st}$ leaf stage, necrotic patches appeared a few days later than the necrotic stripes observed in adult plants inoculated at later stages. Consequently, in some juvenile leaves, profuse sporulation was observed before any necrosis was detected (FIG. 1E). Later, necrotic patches encompassed the region with pustules and limited the growth of the pathogen, i.e., there was no further expansion of the region of sporulation (FIG. 1, E and F, see also FIG. 10). These necrotic regions were not observed in susceptible UC1041 plants at comparable developmental stages (FIG. 1, A and B). The Yr36 resistance response at juvenile stages differs from a hypersensitive response in the delayed appearance of the necrotic regions and the incomplete control of sporulation within these necrotic patches.

Other high-temperature non race-specific resistance genes have provided durable resistance to stripe rust and are used frequently in wheat breeding programs.

Figure 2:
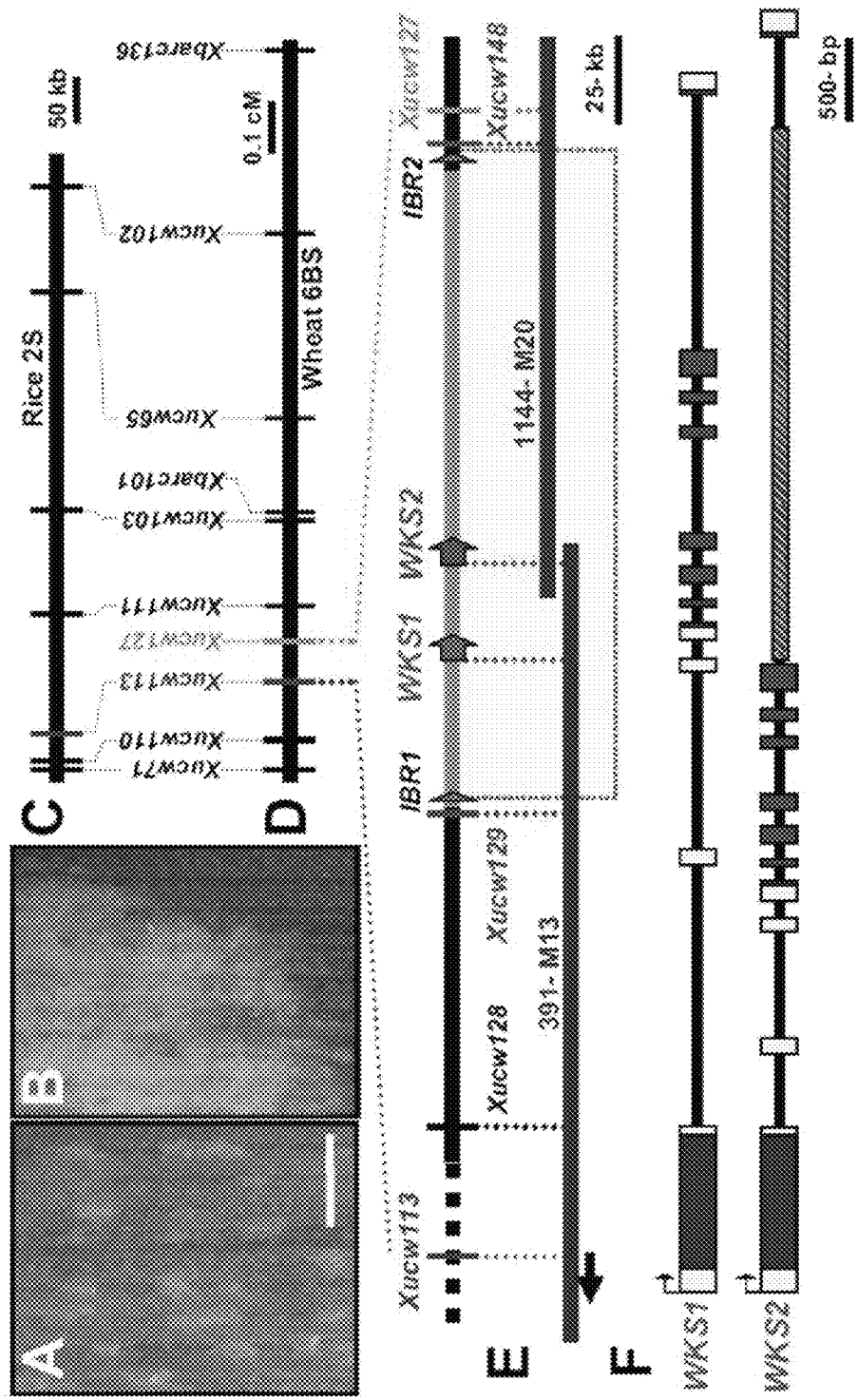

To clone Yr36, we crossed the susceptible durum wheat variety Langdon (LDN, FIG. 2A) with the resistant isogenic recombinant substitution line RSL65 (FIG. 2B), which carries Yr36 in a LDN genetic background. We screened a population of 4500 F2 plants using Yr36 flanking markers Xucw71 and Xbarc136 (Uauy et al., 2005) and identified 121 lines with recombination events between these two markers. Based on genes from the rice colinear region, nine PCR markers were developed to construct a high-density map of Yr36 (FIG. 2, C and D, Table 2). Using replicated field trials and controlled environment inoculations (Tables 3 and 4, FIGS. 3 and 4), Yr36 was mapped to a 0.14 cM interval delimited by markers Xucw113 and Xucw111 (FIG. 2D).

Screening the RSL65 BAC library (Cenci et al., *Theor. Appl. Genet.* 107, 931, 2003) with the distal marker Xucw113 yielded six BACs (FIG. 5). BAC ends were used to re-screen the library and extend the contig by chromosome walking. BAC-end marker Xucw127 (Table 2, FIG. 5) was mapped proximal to Yr36, thereby completing the physical map (FIG. 2E). BAC clones 391M13 and 1144M20 were sequenced and a contiguous 314-kb sequence including the flanking markers was annotated and deposited in GenBank (EU835198, FIG. 6). New markers were developed from the sequence (Table 2) and Yr36 resistance (eight PST races, Table 5) was mapped between Xucw129 and Xucw148 (0.02 cM).

This region has two pairs of duplicated genes (FIG. 6). The first pair includes two short putative genes (IBR1 and IBR2) with an 'in between RING finger' domain (IBR, pfam01485). The two other duplicated genes, which we designated WHEAT KINASE-START 1 and 2 (WKS1 and WKS2, FIG. 2F), encode 86% identical proteins that have a predicted kinase domain followed by a predicted steroidogenic acute regulatory protein-related lipid transfer domain (START, pfam01852). WKS1, WKS2 and IBR1 are deleted in the susceptible parent (FIG. 2E). The WKS genes were prioritized for functional characterization because their domains have been associated with plant responses to pathogens in other species (Dardick and Roland, 2006; Tang et al., 2005; Vorwerk et al., 2007).

Example 2

Functional Characterization of WKS1 and WKS2

Primers specific for WKS1 and WKS2 putative kinase and START domains (Table 6) were used to screen a population of 1,536 ethyl methanesulphonate (EMS) mutagenized M2 lines from the common wheat breeding line UC1041+Yr36 (see Materials and Methods). Of the 117 mutants found in the TILLING screen (McCallum, L. Comai, E. A. Greene, S. Henikoff, *Nat. Biotechnol.* 18, 455, 2000), we selected for functional characterization 6 mutants with changes in conserved amino acids in WKS1 (FIGS. 7 and 8) and 3 with premature stop codons in WKS2 (Table 7).

Of the 6 WKS1 mutants, 5 showed susceptible reactions similar to the susceptible UC1041 control line (FIG. 9, panels A to F, and FIGS. 10 and 11). In contrast, none of the WKS2 truncation mutants was susceptible (FIG. 10), suggesting that WKS1 is Yr36. Both the kinase (FIG. 10) and START domains (FIG. 11) were necessary for the resistance response. For example, the T6-567 mutant had a susceptible response similar to UC1041 (null Yr36) and was more susceptible than its sister control line. This result indicates that a functional START domain in WKS1 is necessary for stripe rust resistance. Similarly, the T6-569 mutant and three other mutants having mutations in the kinase region had a susceptible response (Table 7). Laser point scanning confocal microscopy showed that the T6-312 mutant had an unrestricted network of fungal growth, whereas the control line with a functional WKS1 gene had a resistance response inside the leaf with reduced fungal growth delimited by autofluorescing plant cells (FIG. 9, panels G to J).

Example 3

Transformation of a Susceptible Wheat Variety with WKS1 Confer Resistance to Stripe Rust To confirm the identity between WKS1 and Yr36, we transformed the susceptible wheat variety 'Bobwhite' with a 12.2-kb genomic fragment that includes the complete WKS1 coding and flanking regions (see Materials and Methods). Only two of the nine independent T1 transgenic lines had complete WKS1 transcripts and they were both resistant to stripe rust (FIG. 12 and FIG. 13) demonstrating that WKS1 is Yr36. Transgenic 26b lines showed a stronger hybridization signal than transgenic 17a lines, suggesting higher copy number of the transgene. Lines 26b-6 and 26b-15 showed high transcript levels (13B) and strong resistance (13A).

Example 4

Characterization of Temperature and Time Dependency of WKS1 Expression

Figure 14:
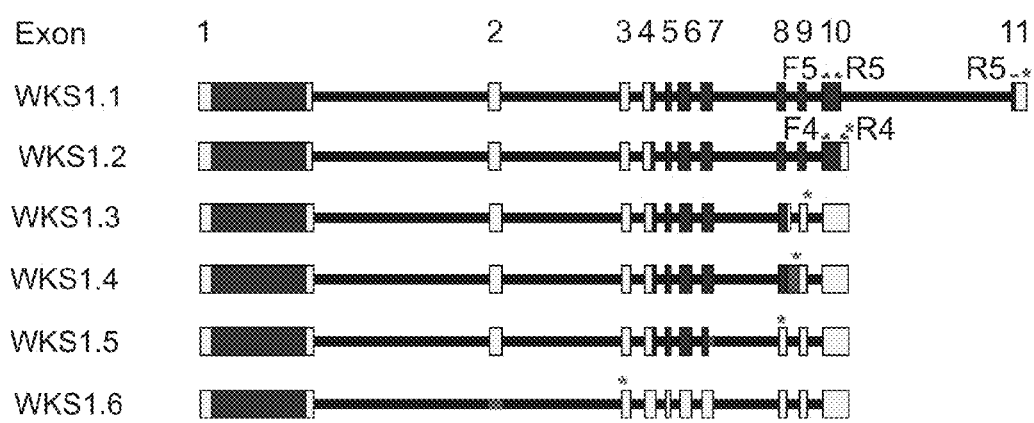

The cloning and sequencing of 56 full-length WKS1 cDNAs revealed six alternative transcript variants (WKS1.1-6, FIG. 14). WKS1.1 is the only variant with 11 exons coding for a complete START domain. WKS1.2-6 transcript variants do not include exon 11 and have an alternative polyadenylation signal located upstream from this exon. WKS1.2 transcripts continue beyond the GT splicing site after exon 10 until a stop codon 57-bp after this splicing site. WKS1.3 transcripts have an alternative GT splicing site located 4-bp after exon 8. This change in reading frame generates a premature stop codon in exon 9. WKS1.4 transcripts continue through the GT splicing site at the end of exon 8 until a stop codon in intron 8 (marked in red). WKS1.5 transcripts have a premature splicing site in exon 7 (56-bp before the conserved GT splice site, marked in red), which changes the reading frame and generates a stop codon within exon 8. WKS1.6 transcripts do not include the second exon (marked in red). This difference generates a change in reading frame and a premature stop codon in exon 3.

Several amino acids from the C terminal end of the START domain are well conserved from vascular plants to mosses. Deletions of the last 10 amino acids of the human StARD protein result in non functional proteins, indicating that this region is critical for its normal function. In the human START proteins, the C terminal α4 helix opens and closes the steroid binding pocket in the hydrophobic tunnel and is able to interact with lipid membranes. Therefore, it is possible that the elimination of the conserved C terminal region in WKS1.2-6 might alter or eliminate function (FIG. 8B).

Quantitative PCR showed that even the lowest transcript levels of WKS1.1 and WKS1.2-6 are only 3-fold lower than those of ACTIN, indicating relatively high transcript levels. Overall, high temperature up-regulates WKS1.1 (FIG. 15, panels A to C and FIG. 16) and down-regulates WKS1.2-6 (FIG. 15, panels D to F and FIG. 16) ($P<0.0001$, Table 8).

Figure 15:
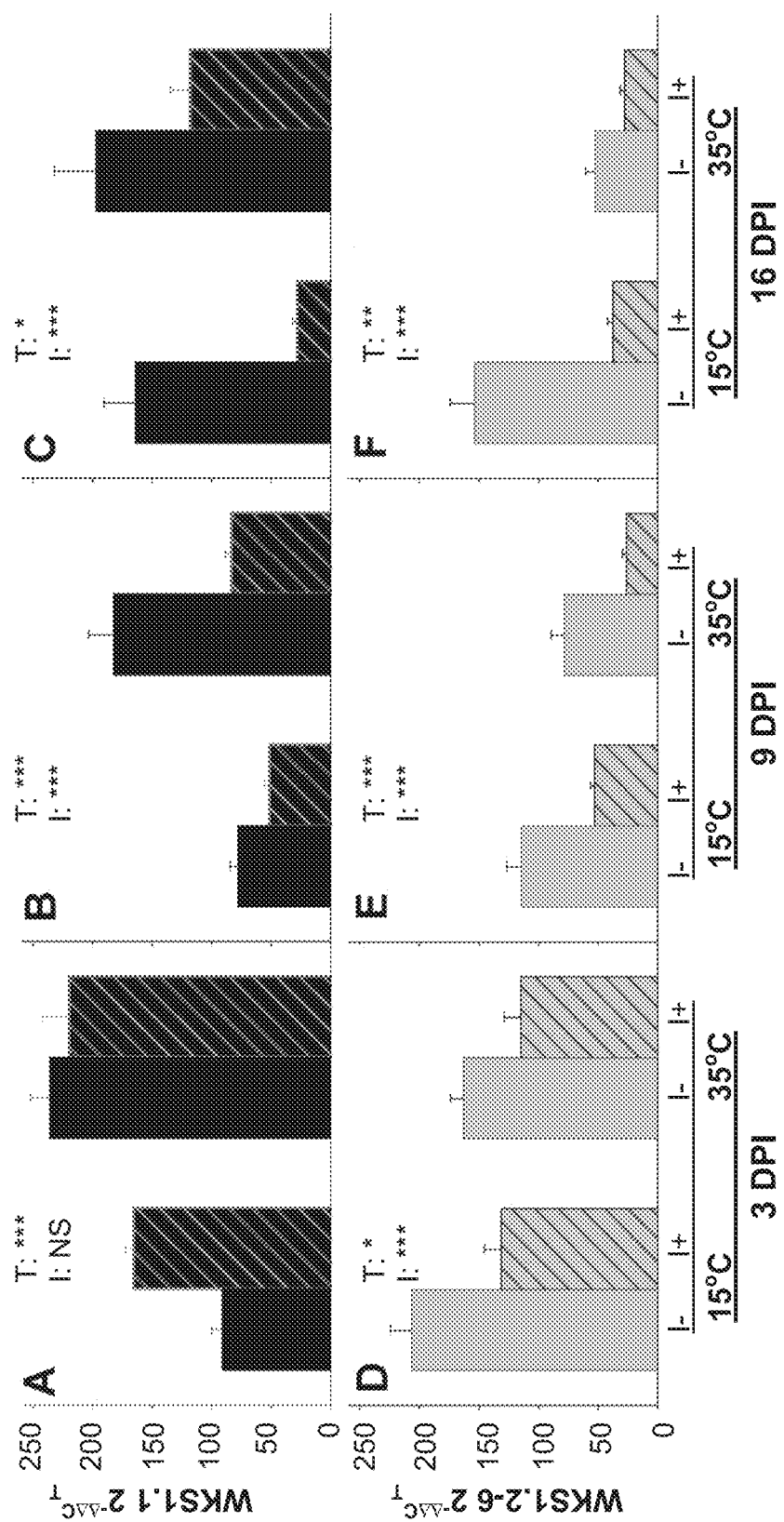
Figure 16:
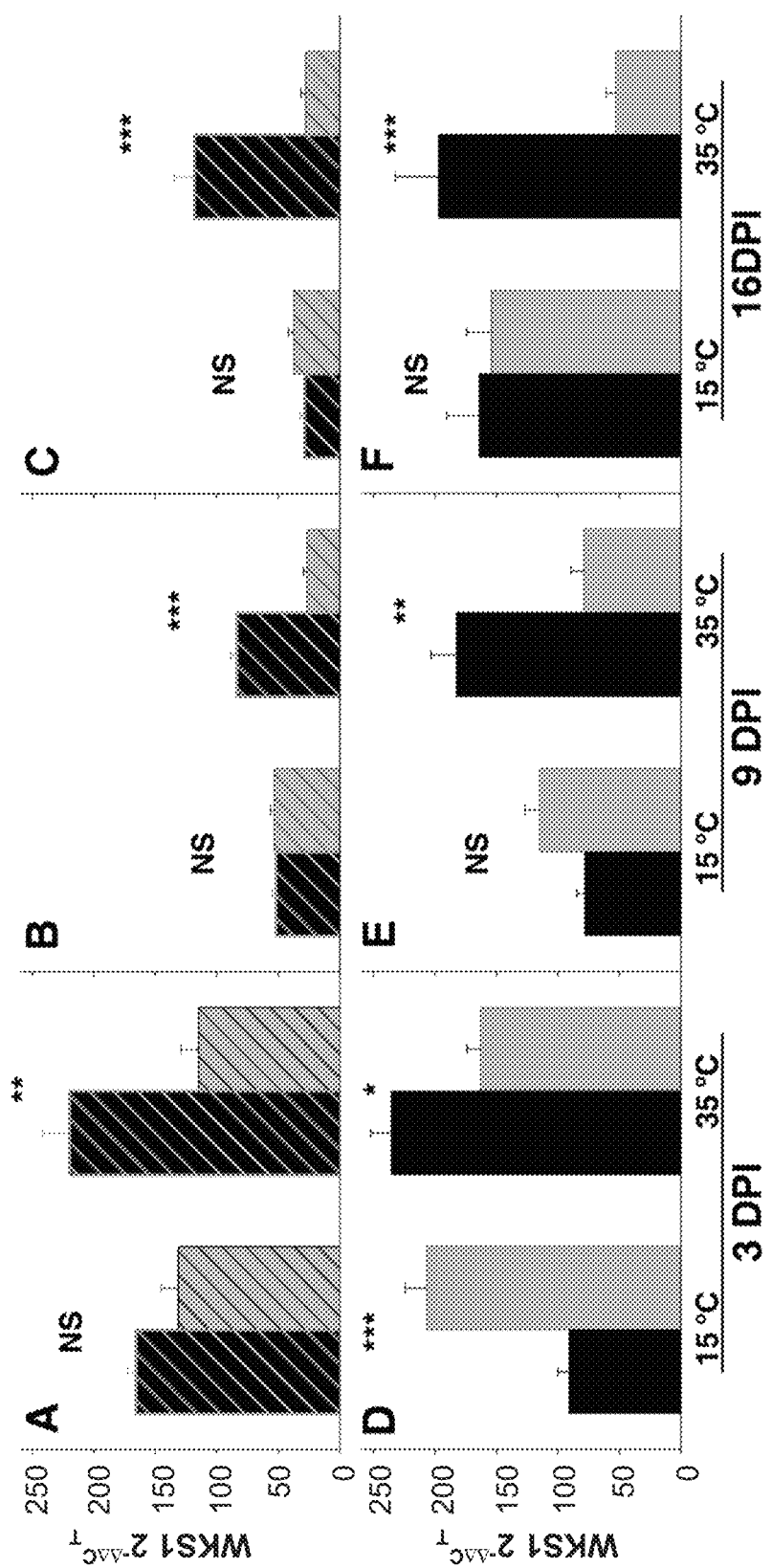
Figure 17:
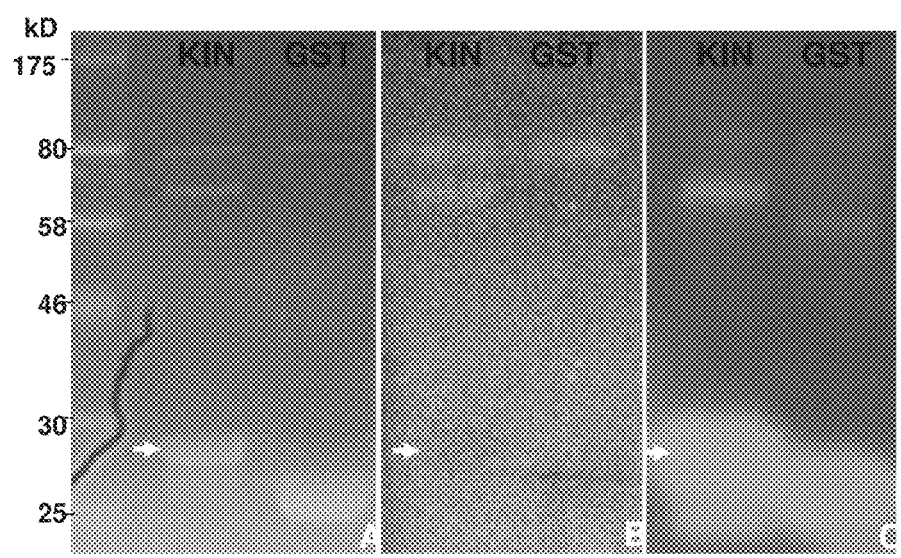

PST inoculation consistently down-regulated WKS1.2-6 across temperature and time, but the effect on WKS1.1 transcript levels varied with sampling times (FIG. 15, panels A to C). Comparisons between WKS1.1 and WKS1.2-6 transcript levels in PST-inoculated plants (FIG. 16, panels A to C) showed no significant differences at low temperature (susceptible response, $P>0.55$), and significantly higher values of WKS1.1 relative to WKS1.2-6 at high temperature (resistant response, $P<0.01$) for all three days.

The relative increase in transcript levels of the variant with the complete START domain (WKS1.1) at high temperature parallels the observed high-temperature resistance conferred by Yr36. START domain proteins in humans are known to play important roles in lipid trafficking, metabolism and sensing, and their binding with sterols and ceramides result in protein conformational changes. If the putative WKS1 START domain has the ability to bind lipids from, or redirected by PST at high-temperature and change its conformation, this may cause the kinase domain to initiate a signaling cascade leading to the observed programmed cell death (FIG. 9 and FIG. 10). The WKS1 Ser/Thr kinase domain (pfam00069) was confirmed to have kinase activity (FIG. 17).

Kinase fusion protein was confirmed by Western blot using a GST-antibody and by peptide sequencing of the ~66-kD protein band (WKS1-Kinase protein sequence coverage was >91%). The Western blot also shows that the strong band of ~28 kD in the GST-WKS1_Kinase construct (white arrow) has the GST protein and is likely the result of partial cleavage of the GST-WKS1_Kinase fusion protein in *E. coli*. As expected, this cleaved protein did not show kinase activity (FIG. 17, panel B). The ~80-kD protein band present in both KIN and GST is the *E. coli* chaperone protein HSP70 that is known to have kinase activity (FIG. 17, panel B) but lacks GST (FIG. 17, panel C). This experiment was repeated with identical results.

Discussion.

The combination of the kinase and START domains in WKS1 apparently is the result of a novel domain shuffling because these two domains are not found together in other organisms. The most similar protein in *Arabidopsis* to the putative WKS1 START domain is EDR2, a protein that negatively regulates plant defense to the powdery mildew pathogen Golovinomyces cichoracearum (12, 13). EDR2 has a PH (pfam00169) and a DUF1336 (pfam07059) domain, which are absent in WKS1. The WKS1 kinase has high similarity to several *Arabidopsis* WAK-like kinases (FIG. 7), but WKS1 lacks the additional domains characteristic of WAK-like kinases. The WKS1 kinase belongs to the non-RD kinases, which are frequently involved in the early steps of the innate immune response.

The appearance of this novel gene architecture preceded the origin of the *Triticeae* since WKS1 and WKS2 were detected in several species from this tribe (Table 9, FIG. 18). However, the presence of these two genes was rare among Triticeae species and varied across accessions within those species where they were detected. This suggests that WKS1 and WKS2 were lost repeatedly in several grass lineages, including the diploid donors of the A and D genomes of polyploid wheat (Table 9). Amongst 131 wild and cultivated tetraploid wheat accessions, WKS1 was detected only in wild wheat (24% of accessions) suggesting that WKS1 was not incorporated into the initial domesticated forms. In hexaploid wheat WKS1 was present only in five accessions where the DIC segment (see item 1 of Materials and Methods) was incorporated recently (Table 10).

Introgression of WKS1 in transgenic Bobwhite wheat and in susceptible varieties by backcrossing (Uauy et al., 2005) improved their resistance to stripe rust. This indicates that either WKS1 is sufficient to improve resistance, or that WKS1 can trigger intermediate genes that initiate the hypersensitive response, and that these genes are still present in the tested varieties. This, together with the absence of WKS1 in almost all modern commercial varieties of pasta and bread wheat (Table 10), suggests that the introgression of Yr36 could have a broad impact in improving resistance to this pathogen. Yr36 resistance has remained effective against the numerous stripe rust races present in California (2004 2008 field tests) and to all races tested so far in controlled environments (Table 5). Moreover, Yr36 has improved resistance in a variety carrying the non race-specific Yr18 resistance gene (Uauy et al., 2005), which suggests that pyramiding appropriate combinations of non race-specific resistance genes may provide adequate resistance against this pathogen. The discovery of different proteins and resistance mechanisms for non-race specific resistance genes Yr36 and Yr18/Lr34 (Schrick et al., 2004) suggests that this type of resistance may involve a heterogeneous group of genes and mechanisms.

Materials and Methods.

Gene sequences have been deposited in GenBank with accession numbers: EU835198-EU835200, FJ154103-FJ154118 and FJ155069-FJ155070.

1.—Plant Materials and Growing Conditions for Rust Bioassays

Mapping: The mapping population was developed from a cross between the tetraploid wheat (*Triticum turgidum* L ssp. *durum*) cv. Langdon (LDN) and RSL65, a near isogenic line of LDN with a 30-cM segment of chromosome arm 6BS from *T. turgidum* L. ssp. *dicoccoides* (accession FA15-3, designated as DIC hereafter) (1).

Targeted Induced Local Lesions IN Genome (TILLING): The TILLING population was developed using the hexaploid wheat (*T. aestivum* L.) breeding line UC1041+Yr36. UC1041 is a hexaploid spring breeding line derived from the cross Tadinia/Yecora Rojo. The DIC 6BS segment including Yr36 was introgressed from the wheat variety Glupro (I. A. Khan et al., Crop Sci. 40, 518 (2000) followed by six backcrosses into UC1041. UC1041 is susceptible to *Puccinia striiformis* f. sp. *tritici* (PST) race PST-113, which is virulent on the Yr1 resistance gene present in UC1041. Seeds from UC1041+Yr36 were mutagenized with 1% ethyl methane sulphonate (EMS) and M2 plants were produced from independent M1 mutants.

DNAs were extracted from 1,536 M2 lines and organized in 384 4-fold DNA pools that were screened using TILLING (C. M. McCallum, et al., Nat. Biotechnol. 18, 455, 2000).

Transgenics: The hexaploid spring wheat variety 'Bobwhite' was used for the transgenic complementation experiment. This variety is susceptible to PST-113.

Growing conditions and inoculation stages: All the chamber experiments used long day photoperiod (8 h dark, 16 h light). For the stripe rust inoculations in the controlled environment experiments, plants were placed in a dew chamber without light at 10° C. for 24 h. Plants were inoculated either at the 1-4 leaf stage ("seedling inoculation") or after flag leaves were fully emerged ("adult-plant inoculation") (FIG. 1). Plants were then moved to one of two different temperature regimes, both of which induce the expression of Yr36 resistance. The first one had a gradual change between a minimum of 10° C. at the middle of the dark period to a maximum of 35° C. at the middle of the light period (referred hereafter as 10/35° C.). This treatment was effective for the expression of Yr36 resistance in different genetic backgrounds. In the second temperature regime, plants were kept at constant 10° C. during the dark period and at constant 25° C. during the light period (referred hereafter as 10/25° C.). This treatment was also effective for the expression of Yr36 resistance (FIG. 1). When indicated, other conditions were used as described in the Materials and Methods.

In all experiments pots were randomized during infection and disease development. Plants were scored blind by two independent evaluators and either photographs or scans were taken to document the results.

Field tests were conducted in Davis (2006, 2007, and 2008) and organized in a complete randomized design (CRD, 2006 and 2007) or a randomized complete block design (RCBD, 2008). All field experiments included a border of "spreader rows" of the highly-susceptible wheat variety D6301 which was used to spread inoculum. One meter rows were used as experimental units. Seeds were sown in November and plants inoculated with PST-100, a race predominant throughout the US, were planted in the spreader rows in March. Additional races were likely present since severe natural infections were observed across the field in all three years. Infection severity was recorded twice from May to early June.

2.—Stripe Rust Races, Inoculation Procedures, and Confocal Images

Table S1 describes the PST races, their virulence profiles and the year they were first described. The PST races used in this study included some of the most virulent and predominant races from 2000 to 2007 in the U.S. For inoculation, urediniospores were mixed with laboratory-grade talcum powder (Fisher Scientific, Fairlawn, N.J., USA) and dusted on the leaf tissue. Rust severity was evaluated two to three weeks after inoculation using a 0-9 scale of infection type (IT) (R. F. Line, Technical Bulletin 1788 (United State Department of Agriculture, 1992): 0-3 (resistant, none to trace level sporulation), 4-6 (intermediate, light to moderate sporulation), 7-9 (susceptible, abundant sporulation). Alternatively, for the mapping and TILLING experiments, the percentage of leaf surface covered with PST pustules was quantified using the digital image analysis program "pd" (FIG. 3).

Confocal methods: Wheat leaves were processed for fluorescence microscopy as published before (J. Moldenhauer et al., Plant Pathol. 55, 469, 2006). The uvitex-stained leaves were examined first with a Nikon Microphot SA fluorescence microscope with a UV-2A DM 400 filter (Nikon, Melville, N.Y., USA). Images shown in FIG. 9, panels G to J, were taken on a laser point scanning confocal microscope (Olympus FV1000 spectral scanner with an UPLAPO 40' oil objective N.A. 1.0). Tissue was sequentially scanned with lasers at 405 and 543 nm to detect uvitex and autofluorescence, respectively. The laser power at 405 nm was reduced five-fold in the compatible interaction because of the greater concentration of uvitex-stained fungus. Each image is comprised of a z-series of 98 sections at 1.2 μm steps with a 0.124 μm per pixel resolution.

3.—High-Density Genetic Map

A total of 4,500 F2 plants from the cross LDN'RSL65 were screened for recombination between PCR markers Xucw71 and Xbarc136 (1) (FIG. 2) and 121 lines were selected (Table 3). Selected plants were self-pollinated and recombinant substitution lines (RSLs) homozygous for the recombinant chromosomes were obtained.

Wheat ESTs with homology to single or low copy number genes in the colinear region in rice (FIG. 2, Table 2) were used to develop additional PCR markers and to further characterize the 121 critical RSLs (Table 3). Briefly, primer pairs were designed for conserved regions between rice and wheat ESTs and were used to amplify predicted introns in LDN and RSL65. PCR products were cloned into the pGEM-T vector (Promega, Madison, Wis., USA). Clones from the A and B genomes were differentiated by restriction enzyme fingerprinting. Products from each genome were sequenced and polymorphisms between LDN and RSL65 were used to develop markers (Table 2). Additional markers were developed from Bacterial Artificial Chromosome (BAC) ends and BAC sequences generated during the construction of the physical map.

Seventy RSLs representing all the different recombination events present in the 121 critical lines (Table 3) were evaluated for adult plant resistance to PST-100 at 10/35° C. Thirty six RSLs were also evaluated for adult plant resistance in the field during 2006 at UC Davis. A summary of the host-pathogen interaction phenotype is presented in Table 3. To validate the mapping of Yr36, the 13 RSLs with the closest recombination events (0.14-cM interval between Xucw111 and Xucw113) were retested for resistance to PST-100 in different environmental conditions and growth stages (Table 4, FIG. 4).

An additional experiment using the same temperature conditions (10/35° C.) was performed using eight different PST races that are virulent on LDN (Table 1). The experiment included control lines LDN and RSL65 and five recombinant lines with the closest recombination events flanking Yr36 (RSL241, RSL402, RSL504, RSL1747, RSL39-14; Table 5).

4.—Physical Map

The physical map of the Yr36 region was constructed using the BAC library from the resistant parent RSL65 (A. Cenci et al., Theor. Appl. Genet. 107, 931, 2003) and a pooling PCR screening strategy that was described before (A. Cenci et al., Genome 47, 911, 2004). The initial screening was performed using B-genome specific primers for the distal marker Xucw113 (Table 2). Six positive BAC clones (391M13, 400M22, 782M23, 852O1, 1129G14, and 1217L2) were identified (FIG. 5).

The BAC end sequence of clone 1129G14 was used to generate the single copy marker Xucw125 (Table 2), which is absent in LDN and present in RSL65. This marker was mapped proximal to Xucw113 and completely linked to Yr36, which oriented the contig formed by these 6 BAC clones relative to the genetic map. Screening of the BAC library with the Xucw125 primers generated four new positive clones (508C11, 528D22, 691B11, and 984G1; FIG. 5). The BAC-end sequence of BAC clone 508C11 was used to generate marker Xucw126 (Table 2), which also was absent in LDN and present in RSL65, and was completely linked to Yr36. Xucw126 was used to screen the BAC library and four new positive BAC clones were identified (651E2, 1046P23, 1070P18, and 1144M20, FIG. 5).

BAC-end sequencing of clone 1046P23 was used to generate marker Xucw127 (LDN: 110-bp and RSL65:105-bp, Table 2). The 5-bp polymorphism was mapped proximal to Yr36 (Table 3), which completed the physical map (FIG. 5). Xucw127 is part of a predicted pectin lyase-like gene with an X8 domain (pfam07983).

5.—Contig Sequencing and Delimitation of the Yr36 Candidate Region

Overlapping BAC clones 391M13 and 11441M120 were sequenced and a 314,057-bp contig was generated, annotated, and deposited in GenBank (EU835198, 7.5-fold coverage at Phred: 20). This sequence includes the proximal region of BAC 391M13 and the complete sequence of BAC 1144M20. The annotated contig includes the complete 186-kb Yr36 region flanked by markers Xucw129 and Xucw148.

The proximal recombination event in RSL504 occurred between the DIC IN BETWEEN RING finger1 (pfam01485) IBR1 and LDN IBR2 genes as confirmed by sequencing (FJ155069 and FJ155070). Based on the location of this recombination event the promoter and proximal 250-bp of the IBR1 gene were excluded from the Yr36 candidate gene region.

Over 80% of the sequence was identified as repetitive using the Triticeae Repeat Sequence Database (TREP wheat (dot) pw (dot) usda (dot) gov/ITMI/Repeats/index (dot) shtml) and the TIGR Cereal Repeat Database (tigrblast (dot) tigr (dot) org/eukblast/index (dot) cgi?project=tae1). The non-repetitive sequence was annotated using BLAST searches in GenBank, the wheat EST collection at GrainGenes (graingenes (dot) org/) and the TIGR Wheat Genome Database (tigrblast (dot) tigr (dot) org/euk-blast/index (dot) cgi?project=tae1), and the gene prediction programs Genscan(genes (dot) mit (dot) edu/GENSCAN.html) and FGENESH (softberry (dot) com/berry (dot) phtml) (FIG. 6).

6.—TILLING Mutants

The UC1041+Yr36 mutant population was screened for mutations in two regions of WKS1 and WKS2. The first one included the complete kinase domain and was 1,371 bp and 1,460-bp in WKS1 and WKS2, respectively. The second region included part of the START domain (pfam01852) and was 1,270-bp and 1,532-bp in WKS1 and WKS2, respectively. The targeted WKS regions were selected using the CODDLE program (proweb (dot) org/coddle/), which helps Choose codons to Optimize the Detection of Deleterious Lesions. Primers specific for each of these region (Table 6) were used to screen 1,536 DNAs for WKS1 and 768 for WKS2. Using the PARSESNP and Blockmaker programs (http://www.proweb.org/Tools), we selected mutations that were predicted to have the strongest effect based on Position-Specific Scoring Matrix (PSSM) differences and Sorting Intolerant From Tolerant (SIFT) scores (P. C. Ng, S. Henikoff, Genome Res. 11, 863, 2001), or that led to premature truncations (Table 7).

For each mutation, M3 plants homozygous for the mutant alleles were selected. For WKS1 lines T6-312, T6-138, and T6-567, and for WKS2 line T6-826, M3 plants homozygous for the non-mutant alleles were also selected as additional controls (FIGS. 9 to 11). Resistance to race PST-113 was evaluated at 10/25° C. in three separate experiments that included different mutants and controls as they became available.

Mutant experiment 1: In this experiment plants were inoculated at the 4th-leaf (juvenile) stage. Fifteen days after inoculation the edge of the areas covered with pustules was marked with a black line. Five days later the same leaves were scanned to evaluate the progression of the disease beyond the mark (FIG. 10). When pustules were restricted to the marked area, plants were considered resistant and when they spread beyond the marked border they were considered susceptible (FIG. 10).

Mutant experiment 2: In this experiment we retested WKS1 mutant lines T6-138 and T6-312, their corresponding non-mutant sister lines, and the susceptible and resistant control lines for PST resistance at the flag leaf (adult) stage. The percent of leaf area covered by pustules was quantified in eight leaves per line using the pd program (FIG. 3). Percentage area was log-transformed to achieve homogeneity of variance and differences were tested using ANOVA (FIG. 9). Images in FIG. 9 were obtained from plants used in this experiment.

Mutant experiment 3: The third experiment was performed to test mutant line T6-567 (discovered later), which has a mutation in the START domain affecting a conserved amino acid (FIG. 8A). Sister lines homozygous for the presence and absence of this mutation were compared for resistance to race PST-113 at the elongation (adult) stage (FIG. 11). Lines UC1041 and UC1041+Yr36 were included as additional controls.

7.—Complementation Using Transgenic WKS1 Plants

To confirm that WKS1 confers partial resistance to stripe rust, we transformed the susceptible common wheat variety Bobwhite with the pWKS1 plasmid, which includes the complete WKS1 gene. We used the High-Fidelity DNA Polymerase Phusion™ enzyme (Finnzymes, Espoo, Finland) to amplify a 12,205-bp genomic DNA fragment from RSL65 by PCR. SbfI and NotI restriction sites were added to the primers for cloning (YR36_S1F1/S1R4, Table 6). This fragment included 3,503-bp upstream from the WKS1 start codon, the complete WKS1 coding region, and 1,415 bp downstream from the stop codon.

The PCR product was cut by restriction enzymes SbfI and NotI, recovered from a 1% agarose gel, and cloned into a SbfI-NotI linearized pGEM®-T vector (Promega, Madison, Wis., USA). To reduce the frequency of breaks within the coding sequence during transformation, the previous construct was digested with SbfI and further cloned into a SbfI linearized pPZP201 vector to increase the size of the non-genic region (the pWKS1 final construct is ~22.3-kb). The nucleotide sequence of pPZP201 vector is disclosed in P. Haidukiewicz, Z. Svab, P. Maliga, *Plant Mol. Biol.* 25, 989 0994). The WKS1 region (12,205-bp) was sequenced and showed no differences with the wild type allele. Embryonic calluses of hexaploid spring variety Bobwhite were bombarded using a 1:1 molar ratio of pWKS1 and UBI::BAR selectable marker plasmids (15.5 μg total) coated onto Seashell 1000 nm gold particles (La Jolla, Calif., USA), according to the manufacturer's instructions. Transformants were selected as previously described (C. Uauy, A. Distelfeld, T. Fahima, A. Blechl, J. Dubcovsky, Science 314, 1298, 2006).

In total, nine independent transgenic T1 lines were obtained and positive plants were confirmed by PCR using primer pair YR36_13104F/13692R (Table 6). Transcription of the full length WKS1 gene in the transgenic T1 plants was confirmed by reverse transcriptase PCR(RT-PCR) using WKS1 transcript specific primers WKS1_150F, 151R, and 174R (Table 6). Of the nine transgene-positive lines, only 17a and 26b yielded full-length WKS1 cDNAs and were used for functional studies. Transcript levels of the WKS1 transgene (all transcript variants) were determined by real-time quantitative PCR (Q-PCR) with primers WKS1_F1/R1 (Table 6)

before PST inoculation. Transgenic and control lines were tested for PST resistance with race PST-113, which is virulent on Bobwhite (FIG. 3 and FIG. 13A).

Figure 13:
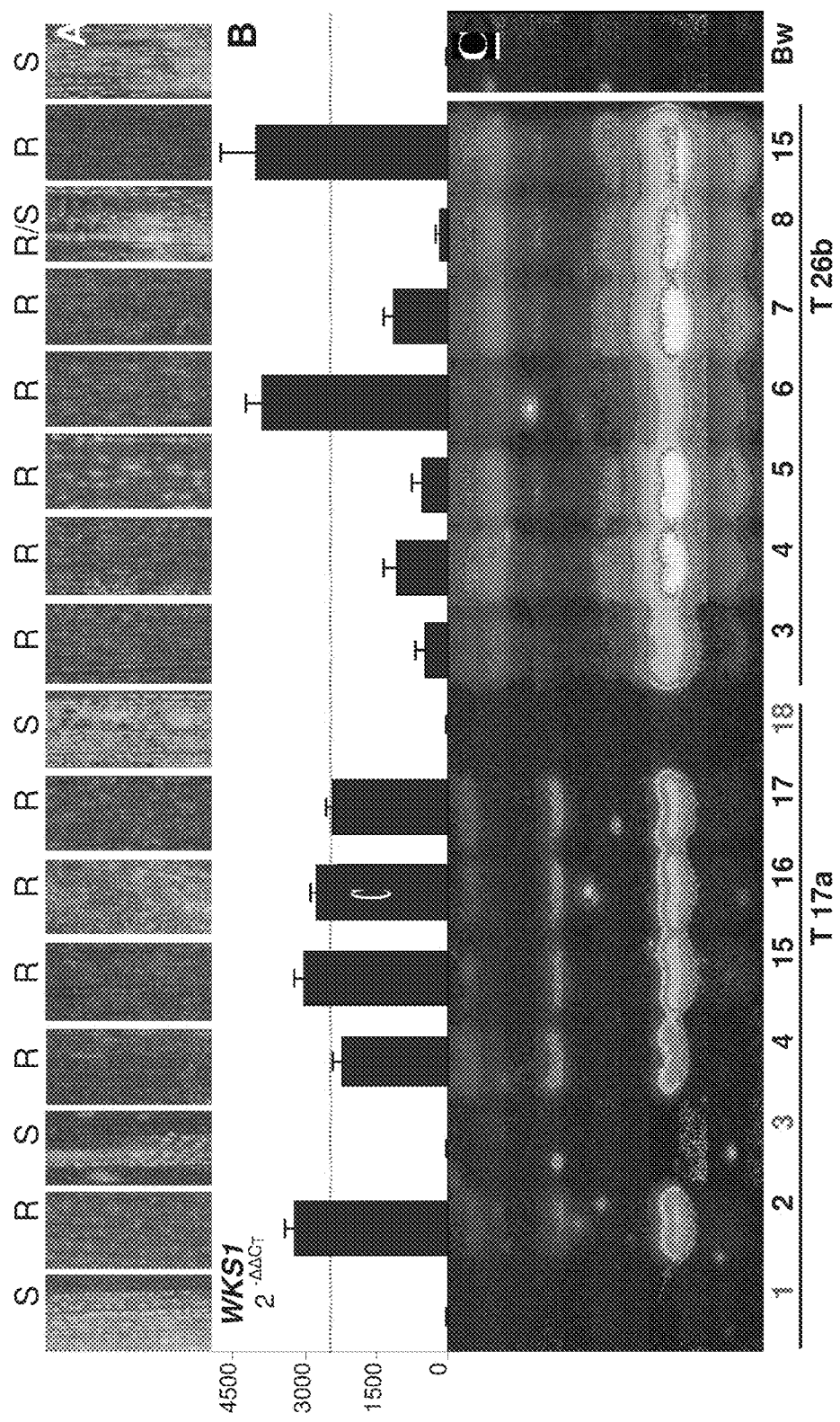

Southern blots including DNAs digested with HindIII from eight 17a T1 plants and seven 26b T1 plants were hybridized with a 942-bp WKS1 fragment derived from PCR primers YR36_PF/PR (Table 6). Radioactive probes were prepared with Prime-a-Gene® Labeling System (Promega, Madison, Wis., USA) and purified by MicroSpin™ G-50 columns (Amersham, Piscataway, N.J., USA). Three 17a T1 plants showed no transgene insertion and were retained as additional negative controls (FIG. 13). The construct has two HindIII sites flanking the probe region so a fragment of similar size is expected in different transgenic events (blue arrow, FIG. 13). Pre-hybridization, hybridization, and washing were performed as described before (Dubcovsky et al., Theor. Appl. Genet. 87, 957, 1994).

8. —WKS1 transcription

WKS1 alternative transcript variants (WKS1.#). Sequencing of 56 cDNA clones amplified with poly T primer and/or WKS1 specific primers showed six alternative transcript variants (WKS1.1-6, FIG. 14). These six variants were classified into two groups based on the presence or absence of exon 11, the last exon. Transcript variant WKS1.1 included the complete gene with the poly A sequence starting 80-bp after the stop codon in exon 11. For transcript variants WKS1.2-6 the poly A tail started 80-95 bp downstream of the splicing site of exon 10, approximately 1,450-bp upstream from the start of exon 11. As a result of the exclusion of exon 11, WKS1.2-6 variants encode for shorter proteins with a truncated START domain (FIG. 14).

For the Q-PCR experiments, primers WKS1_F5/R5 were used to amplify transcript variant WKS1.1 and primers WKS1_F4/R4 to amplify transcript variants WKS1.2-6 (Table 6). The reverse primer was unique to each group with WKS1_R5 annealing to the splice junction of exons 10 and 11 (unique for WKS1.1) and WKS1_R4 annealing to the unique WKS1.2-6 sequence of exon 10 that is missing from WKS1.1 (FIG. 14). Conserved primers WKS1_F1/R1 were used to amplify simultaneously all six transcript variants (Table 6).

Real-time quantitative PCR(Q-PCR). Total RNA was extracted using TRIZOL (Invitrogen, Carlsbad, Calif., USA) and first strand cDNA was synthesized using the SuperScript™ First-Strand Synthesis System (Invitrogen, Carlsbad, Calif., USA). Q-PCR was performed on an ABI PRISM 7000 SDS (Applied Biosystems, Foster City, Calif., USA) using SYBR® GREEN. PCR setup and reaction conditions were as reported before (Fu et al., Mol. Gen. Genomics 277, 301, 2007). The $2^{-\Delta\Delta C_T}$ method (Livak and Schmittgen, Methods 25, 402, 2001) was used to normalize and calibrate transcript values relative to the endogenous ACTIN control (Table 6).

Efficiencies of each pair of primers were calculated using six 2-fold dilutions (1:1, 1:2, 1:4, 1:8, 1:16 and 1:32) in triplicates. Amplification efficiencies were higher than 95% for all three systems. The same calibrator was used for all transcript variants within each experiment so their values are comparable ($2^{-\Delta\Delta C_T}$ values represent number of RNA copies per copy in the calibrator sample).

Effect of temperature, PST inoculation, and days post inoculation (DPI) on WKS1 transcript levels. Tetraploid RSL65 (resistant parental line in the mapping population) was used for this experiment. Seedlings were initially grown at a low temperature regime, which was constant 10° C. during the 8 h dark period and constant 15° C. during the 16 h light period. Half of the plants were kept at low temperature and the other half were moved to the 10/35° C. temperature cycle. Chambers for all treatments were maintained at the same photoperiod (16 h of light and 8 h dark) and light intensity (145 μmol m$^{-2}$ s$^{-1}$). In all cases, samples were collected between noon and 1:00 pm.

Plants at the three-leaf stage within each temperature treatment were divided in two groups. The first group was inoculated with PST-100 and the other group was used as non-inoculated control. Six samples were collected 3, 9, and 16 days after inoculation for each of the four treatment combinations (total 72 samples). The effects of temperature, PST inoculation, days after inoculation, and their respective interactions on WKS1.1 and WKS1.2-6 transcript levels were analyzed using three-way factorial ANOVAs. Since there was a significant three-way interaction between temperature, inoculation and DPI, we analyzed separately the effect of temperature and inoculation at 3, 9 and 16 DPI. Results are summarized in FIG. 15 and FIG. 16 and in Table 8.

9.—Distribution of the WKS1 and WKS2 Genes Among Different Triticeae Species.

Samples for the Triticeae species were generously provided by Dr. J. Dvorak (University of California Davis, USA, DV numbers Table 9), the University of Haifa (Israel) germplasm collection and the USDA National Small Grain Collection (NSGC Aberdeen, Id.) (Table 9). The accessions of wild emmer (Table 10) were from the University of Haifa collection and from the USDA-NSGC. *T. turgidum* ssp. *diccocum* accessions were from the USDA-NSGC. Durum and bread wheat accessions were kindly provided by M. C. Sanguineti (Bologna University, Italy) or were from the UC Davis collection.

Figure 18:
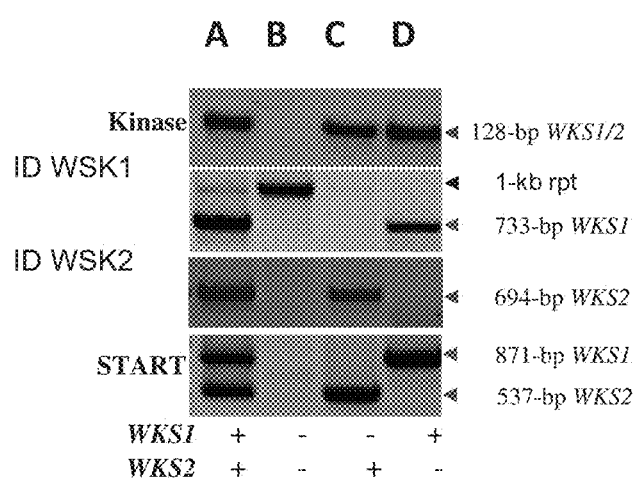

PCR conditions and sizes of the amplified products are described in the legend of FIG. 18 and primer sequences are shown in Table 6.

Primers for the kinase domain amplify fragments of 128-bp for both WKS1 and WKS2 (see Example 2). These primers require an initial touchdown with a decrease of 0.5° C. per cycle from 70 to 66° C. (30 s per cycle). Two pairs of primers, each specific for one of the WKS genes, were used to determine the presence of the inter-domain region. The first one amplifies a product of 733-bp when WKS1 is present and no product in its absence. The second inter-domain primer pair amplifies a product of 694-bp when WKS2 is present and no product when it is absent. These primers require an initial touchdown with a decrease of 0.5° C. (60 s) per cycle from 65 to 60° C. for the first pair and from 64 to 59° C. for the second pair (60 s per cycle). The primer pair specific for the START domain amplifies products of 871-bp from WKS1 and 537-bp from WKS2. Size differences are partially due to the insertion of a miniature inverted repeat transposable elements (MITE) in the WKS1 intron amplified by these primers. These primers require an initial touchdown with a decrease of 0.5° C. per cycle from 70 to 65° C. (60 s per cycle).

10.—In-Gel Kinase Assay

Plasmid construction: A GST fusion construct including the complete kinase domain (WKS1 amino acids 1-332, GenBank accession EU835199) was developed for the kinase activity assay. This sequence was PCR amplified from cDNA using primers GST_EcoRI_F1 and GST XhoI_R1 (Table 6) and initially cloned into pGEM-T Easy vector (Promega, Madison, Wis., USA). Restriction enzymes EcoRI and XhoI were used to clone this fragment into expression vector pGEX-6P-1 (GE Healthcare, Piscataway, N.J., USA), resulting in construct GST-WKS1_Kinase. Sequencing confirmed that no PCR errors were introduced.

Expression and purification of fusion proteins: GST-WKS1_Kinase was transformed into *E. coli* strains pLysS (Gene Choice, Frederick, Md., USA) and BL21(DE3). Bacteria were grown in 50 mL of LB media containing ampicillin (100 μg/ml) to O.D.$_{600}$ of 0.6-0.8. Before induction of the fusion protein, cells were collected by centrifugation at 5000 rpm for 5 minutes. Cells were resuspended in 50 mL of fresh LB media containing ampicillin (100 μg/ml) and 1 mM of isopropyl-1thio-p-D-galactopyranoside (IPTG) and incubated at 37° C. for 6-8 hours. Cells were harvested by centrifugation and resuspended in 1×PBS buffer (137 mM NaCl, 2.7 mM KCl, 4.3 mM Na$_2$HPO$_4$, 1.47 mM KH$_2$PO$_4$, pH 7.4) supplemented with Complete Protease Inhibitor Cocktail Tablets (Roche, USA) and lysozyme (Sigma-Aldrich, St. Louis, Mo., USA). The resuspended cells were lysed by sonication and the lysate was centrifuged at 5000 g for 5 m. The GST-fusion protein was purified using glutathione-Sepharose 4B (GE Healthcare, Piscataway, N.J., USA) according to manufacturer's instructions and dialyzed overnight against 50 mM HEPES-NaOH, pH 7.4, using the Mini Dialysis Kit (GE Healthcare, Piscataway, N.J., USA).

In-gel kinase assays: In-gel kinase assays were performed as described by Romeis et al. (Romeis et al., *Plant Cell* 11, 273, 1999) except that the SDS-PAGE gel was co-polymerized with casein (1 mg/ml, C4032, Sigma-Aldrich, St. Louis, Mo., USA) as the phosphorylation substrate and a different kinase buffer was used. The kinase buffer included 50 mM HEPES-NaOH, pH 7.4, 10 mM MgCl2, 10 mM MnCl2, 1 mM DTT, phosphatase inhibitors (pglycerophosphate, NaF, Na3VO4; Cayman Chemical, Ann Arbor, Mich., USA) and 75 μCi of [γ-$^{32}$P]ATP (6000 Ci/mmol, Perkin Elmer Life Sciences, Boston, Mass., USA. Gels were analyzed using a Storm 860 PhosphorImager (GE Healthcare, Piscataway, N.J., USA). The size of the phosphorylated proteins was estimated by using a prestained molecular mass marker.

Peptide Sequencing: To confirm the identity of the induced GST-WKS1_kinase fusion protein, we prepared the protein corresponding to the ~66-kD band for MS analysis using standard reduction, alkylation, and tryptic digest procedures (Rosenfeld et al., *Anal. Biochem.* 203, 173, 1992). Digested peptides were analyzed by LC-MS/MS on an LTQ with Michrom Paradigm LC and CTC Pal autosampler at the UC Davis Genome Center Proteomics Core Facility (proteomics (dot) ucdavis (dot) edu/). All MS/MS samples were analyzed using Sequest (ThermoFinnigan, San Jose, Calif.; version SRF v. 3) to search a custom database assuming the digestion enzyme trypsin. Scaffold (version Scaffold_2_01_01, Proteome Software Inc., Portland, Oreg.) was used to validate MS/MS based peptide and protein identifications.

Western blots. GST-WKS1_kinase and GST proteins were transferred to Amersham Hybond™ ECL™ membranes by a vertical blotting unit using protein transfer buffer (1L: 3.03 g Trizma base, 14.4 g Glycine, 200 ml Methanol, pH 8.3). The presence of GST was tested using a rabbit GST antibody and detected using the ECL plus Western Blotting Detection System (Amersham Bioscience, Buckinghamshire, UK).

REFERENCES

Dardick, P. Ronald, *PLOS Pathog.* 2, 14 (2006).
Schrick, Nguyen, W. M. Karlowski, K. F. X. Mayer, Genome Biol. 5, (2004)
Singh, H. M. William, J. Huerta-Espino, G. Rosewarne, Proc. 4 Int. Crop Science Congress, Brisbane, Australia, 26 Sep.-1 Oct. (2004).
Tang, J. Ade, C. A. Frye, R. W. Innes, *Plant J.* 44, 245 (2005).
Uauy et al., *Theor. Appl. Genet.* 112, 97 (2005).
Vorwerk et al., *BMC Plant Biology* 7, 1 (2007).

Tables

TABLE 1

Races of PST used in seedling and adult plant resistance tests.

| Races | Susceptible wheat differential genotypes[1] | Year isolated |
|---|---|---|
| PST-17 | 1, 2, 3, 9, 11. | 1977 |
| PST-37 | 1, 3, 6, 8, 9, 10, 11, 12. | 1987 |
| PST-45 | 1, 3, 12, 13, 15. | 1990 |
| PST-100 | 1, 3, 8, 9, 10, 11, 12, 16, 17, 18, 19, 20. | 2004 |
| PST-113 | 1, 2, 3, 8, 9, 10, 11, 12, 14, 16, 17, 18, 19, 20. | 2004 |
| PST-116 | 1, 3, 4, 5, 8, 9, 10, 11, 12, 14, 16, 17, 18, 19, 20. | 2005 |
| PST-127 | 1, 2, 3, 5, 6, 8, 9, 10, 11, 12, 13, 15, 16, 17, 18, 19, 20. | 2007 |
| PST-130 | 1, 3, 4, 8, 10, 11, 12, 16, 17, 18, 19, 20. | 2007 |

[1]Numbers indicate the wheat differential genotypes used to identify the race: 1 = Lemhi, 2 = Chinese 166, 3 = Heines VII, 4 = Moro, 5 = Paha, 6 = Druchamp, 8 = Produra, 9 = Yamhill, 10 = Stephens, 11 = Lee, 12 = Fielder, 13 = Tyee, 14 = Tres, 15 = Hyak, 16 = Express, 17 = Avocet S + Yr8, 18 = Avocet S + Yr9, 19 = Clement, and 20 = Compair.

TABLE 2

PCR markers used to produce the genetic map. Markers are listed from the telomeric to the centromeric location.

| Locus | Marker | Primers | SEQ ID NO: | Ann. (° C.)[1] | Ext. (s)[1] | Rest. Enz.1 | Polym. (bp)[1] | Rice homolog |
|---|---|---|---|---|---|---|---|---|
| Xucw110[2] | CAPS[3] | GGAGCAGCCACATCGTCG | 16 | 57[5] | 210 | MspI | L[4] ≅ 2000 | Os02g0139200 |
| | | GCCTGCTCCAACAACCATC | 17 | | | | | |

TABLE 2-continued

PCR markers used to produce the genetic map. Markers are listed from the telomeric to the centromeric location.

| Locus | Marker | Primers | SEQ ID NO: | Ann. (° C.)[1] | Ext. (s)[1] | Rest. Enz.[1] | Polym. (bp)[1] | Rice homolog |
|---|---|---|---|---|---|---|---|---|
| Xucw70 | CAPS | GTCTGTCCATGGGTTCTC | 18 | 57[5] | 180 | DpnII | L ≅ 1850 | Os02g0139300 |
|  |  | GTCATGAAGCCTTGGTTGAAG | 19 |  |  |  | D ≅ 850 |  |
| Xucw112 | CAPS | GGAGTGGAACCAGAGGAGC | 20 | 57[5] | 120 | HaeIII | L ≅ 390 | Os06g0703500 |
|  |  | ATGATGTGCACCATGCGG | 21 |  |  |  | D ≅ 300 |  |
| Xucw113 | CAPS | GCTGGAGGTGAGTGGTGAAT | 22 | 57 | 30 | TaqI | L = 252 | Os02g0139500 |
|  |  | AATCTCCTCCCTTCGATGCT | 23 |  |  |  | D = 175 |  |
| Xucw128 | BACs[3] | TTAGATGGAGTCCCGTGGAG | 24 | 58 | 40 | none | L ≅ 195 | (wheat genomic) |
|  |  | TGAAGCCAGCAATGAAGTTG | 25 |  |  |  | D ≅ 189 |  |
| Xucw129a[2] | BACs | AAGGACTCTGCTCCTGACGA | 26 | 58 | 130 | none | D = 1452 | (wheat genomic) |
|  |  | GAAGATGCTCTGAACGCACA | 27 |  |  |  |  |  |
| Xucw129b[2] | BACs | AAGGACTCTGCTCCTGACGA | 28 | 55 | 60 | Tsp509I | L ≅ 760 | (wheat genomic) |
|  |  | TGTCGAGGGACACAATACCA | 29 |  |  |  |  |  |
| Xucw125[2] | BACe[3] | CAAGCGATGTCAACATGTCC | 30 | 57 | 30 | none | D = 143 | (wheat genomic) |
|  |  | TCAAATGACAGCTCCACTCG | 31 |  |  |  |  |  |
| Xucw126[2] | BACe | GATGGTGCCTGCGATAATTT | 32 | 57[5] | 180 | none | D = 2725 | (wheat genomic) |
|  |  | GCTGTCGACATTCCCCTAGA | 33 |  |  |  |  |  |
| Xucw130[2] | BACs | CACGCAAATAAATGCTGGTG | 34 | 64 | 40 | none | D = 161 | (wheat genomic) |
|  |  | TGCATAGTTTCAGCCAGGTG | 35 |  |  |  |  |  |
| Xucw148[2] | BACs | CCCTTTGTGCCACATTTCTT | 36 | 57[5] | 240 | RsaI | D = 462[6] | (wheat genomic) |
|  |  | GGCAGGTGGAAGTCAACATT | 37 |  |  |  |  |  |
| Xucw127[7] | BACe | GTACGTCCTGCTCACCATCA | 38 | 65 | 30 | none | L = 110 | (wheat genomic) |
|  |  | AGAAGAACAACGGAGGACGA | 39 |  |  |  | D = 105 |  |
| Xucw111 | CAPS | ACCCGTAAGATGCAATAACTTG | 40 | 59 | 30 | RsaI | L ≅ 306 | Os02g0139700 |
|  |  | GCAGGACTGCTCTTGAAG | 41 |  |  |  | D = 215 |  |
| Xucw69 | dCAPS[3] | AGTTGTCATGTAATAGGTTGTACC | 42 | 45 | 30 | SphI | L = 140 | Os02g0141300 |
|  |  | ATACATCAGTATKTATGTGGCATG[8,9] | 43 |  |  |  | D = 120 |  |
| Xucw103 | dCAPS | CTTTGTTTCCTGTATACGAATGCTTT[8] | 44 | 45 | 30 | PstI & XmnI[10] | L = 217 | Os02g0142500 |
|  |  | AGAAGAATTTACAAATACACAGC | 45 |  |  |  | D = 239 |  |
| Xucw65 | CAPS | GCATGTTTCAGTTTGGTTATCA | 46 | 53 | 40 | NcoI | L = 418 | Os02g0146600 |
|  |  | CTCATCATCACATCACAAAGGAA | 47 |  |  |  | D = 684 |  |
| Xucw102 | dCAPS | AACATAAGAGGGAGGTCGAG | 48 | 59 | 30 | DraIII | L = 205 | Os02g0148600 |
|  |  | GAACAAGAGCACAGCACGTTGT[8] | 49 |  |  |  | D = 188 |  |

[1]Ann.: annealing temperatures, Ext.: extension time, Rest. Enz.: restriction enzyme, and Polym.: polymorphic band size.
[2]Dominant marker.
[3]CAPS: Cleavage Amplified Polymorphic Sequences, dCAPS: degenerate CAPS (Michaels and Amasino, Plant J. 14, 381 (1998).), BACe: BAC end sequence, BACs: BAC sequence.
[4]L: Langdon; D: T. turgidum ssp. dicoccoides accession FA15-3.
[5]Initial touch-down: 8 cycles of decreasing 1° C. steps from 65° C. to 57° C.
[6]The amplification product is 2.68-kb and the polymorphic digested band is 462-bp.
[7]Xucw127 is part of a predicted pectin lyase-like gene with an X8 domain (outside Yr36 region).
[8]Underlined letters indicate degenerate nucleotides that were introduced to generate polymorphic restriction sites.
[9]The reverse Xucw69 primer includes a degenerate K nucleotide (G or T).
[10]Polymorphism is detected by XmnI, and PstI is used to reduce fragment size for convenient visualization in polyacrylamide gel

TABLE 3

Genotypes of the 121 recombinant substitution lines (RSLs) used for genetic mapping of Yr36. The 13 critical RSLs with the closest recombination events flanking Yr36 are indicated in bold, and their detailed phenotypic evaluation is presented in Table 4. Primers are listed in Table 2 except for Xucw71, XbarcI01, and Xbarc136, which were described before (Uauy et al., Theor. Appl. Genet. 112, 97, 2005).

| No. of RSLs | Xucw71 | Xucw110 | Xucw70 | Xucw112 | Xucw113 | Xucw128 | Xucw129 | Xucw125 | Yr36 | Xucw126 | Xucw130 | Xucw148 | Xucw127 | Xucw111 | Xucw69 | Xucw103 | Xbarc101 | Xucw65 | Xucw102 | Xbarc136 |
|---|---|---|---|---|---|---|---|---|---|---|---|---|---|---|---|---|---|---|---|---|
| LDN | L¹ | L | L | L | L | L | L | L | S | L | L | L | L | L | L | L | L | L | L | L |
| 2 | D | D | D | D | D | D | D | D | R | D | D | D | D | D | D | D | D | D | D | D |
| 3 | D | L | L | L | L | L | L | L | S | L | L | L | L | L | L | L | L | L | L | L |
| 6 | L | L | L | D | D | D | D | D | R | D | D | D | D | D | D | D | D | D | D | D |
| 4 | D | D | L | L | L | L | L | L | S | L | L | L | L | L | L | L | L | L | L | L |
| 1 | D | D | D | D | D | L | L | L | S | L | L | L | L | L | L | L | L | L | L | L |
| 1 | D | D | D | D | D | D | D | L | S | L | L | L | L | L | L | L | L | L | L | L |
| 1 | D | D | D | D | D | D | D | D | R | D | L | L | L | L | L | L | L | L | L | L |
| 1 | L | L | L | L | L | L | L | L | S | L | L | D | D | D | D | D | D | D | D | D |
| 3 | D | D | D | D | D | D | D | D | R | D | D | L | L | L | L | L | L | L | L | L |
| 3 | L | L | L | L | L | L | L | L | S | L | L | L | D | D | D | D | D | D | D | D |
| 3 | D | D | D | D | D | D | D | D | R | D | D | D | L | L | L | L | L | L | L | L |
| 7 | L | L | L | L | L | L | L | L | S | L | L | L | L | D | D | D | D | D | D | D |
| 8 | D | D | D | D | D | D | D | D | R | D | D | D | D | L | L | L | L | L | L | L |
| 1 | L | L | L | L | L | L | L | L | S | L | L | L | L | L | L | D | D | D | D | D |
| 4 | L | L | L | L | L | L | L | L | S | L | L | L | L | L | L | L | D | D | D | D |
| 12 | D | D | D | D | D | D | D | D | R | D | D | D | D | D | D | D | D | L | L | L |
| 15 | L | L | L | L | L | L | L | L | S | L | L | L | L | L | L | L | L | D | D | D |
| 16 | D | D | D | D | D | D | D | D | R | D | D | D | D | D | D | D | D | D | L | L |
| 15 | L | L | L | L | L | L | L | L | S | L | L | L | L | L | L | L | L | L | L | D |
| 15 | D | D | D | D | D | D | D | D | R | D | D | D | D | D | D | D | D | D | D | L |
| RSL 65 | D | D | D | D | D | D | D | D | R | D | D | D | D | D | D | D | D | D | D | D |

¹L = Langdon, D (shaded) = RSL65, S = susceptible, R = resistant.

TABLE 4

Genotypes and phenotypes of 13 RSLs with the closest recombination events flanking Yr36. Race PST-100 was used for inoculations in all experiments, but additional races may have been present in the field experiments. Daily temperature cycles in the greenhouse were 10/35° C. and in the chambers were 10/25° C.

| | RSL genotypes[1] | | | | | | | | | Wheat reaction to PST[2] | | | |
|---|---|---|---|---|---|---|---|---|---|---|---|---|---|
| | | | | Yr36 | | | | | | Adult plant | | Seedling | |
| Parents & RSL | Xucw 113 | Xucw 128 | Xucw 129 | Xucw 125 | Xucw 126 | Xucw 130 | Xucw 148 | Xucw 127 | Xucw 111 | Field (R/S) | GH (IT ± SE)[3] | Chamber (R/S) | Chamber (% pustules)[3] |
| LDN | L | L | L | L | L | L | L | L | L | S | 6.8 ± 0.2 | S | 7.51 ± 0.9 |
| 39-14 | L | L | L | L | L | L | L | D | D | S | 7.0 ± 0.0[S] | S | 7.5 ± 0.8[S] |
| 11-19 | L | L | L | L | L | L | L | L | D | S | 6.3 ± 0.5[S] | S | 8.0 ± 1.1[S] |
| 291 | L | L | L | L | L | L | L | L | D | S | 6.3 ± 0.7[S] | S | 5.9 ± 0.7[S] |
| 324 | L | L | L | L | L | L | L | L | D | S | — | S | 9.1 ± 1.1[S] |
| 17-47 | D | L | L | L | L | L | L | L | L | S | 6.8 ± 0.2[S] | S | 8.8 ± 0.7[S] |
| 504 | D | D | D | L | L | L | L | L | L | S | 6.7 ± 0.3[S] | S | 7.0 ± 1.4[S] |
| 241 | D | D | D | D | D | D | L | L | L | R | 4.3 ± 0.8[R] | R | 2.8 ± 0.8[R] |
| 3-28 | D | D | D | D | D | D | D | L | L | R | 2.5 ± 0.3[R] | R | 3.1 ± 0.8[R] |
| 4-36 | D | D | D | D | D | D | D | L | L | R | 2.3 ± 0.3[R] | R | 1.2 ± 0.4[R] |
| 402 | D | D | D | D | D | D | D | L | L | R | 2.0 ± 0.0[R] | R | 0.2 ± 0.1[R] |
| 22-4 | D | D | D | D | D | D | D | D | L | R | 2.0 ± 0.0[R] | R | 1.4 ± 0.4[R] |
| 27-15 | D | D | D | D | D | D | D | D | L | R | 2.1 ± 0.1[R] | R | 2.7 ± 0.7[R] |
| 28-1 | D | D | D | D | D | D | D | D | L | R | 2.0 ± 0.0[R] | R | 1.5 ± 0.3[R] |
| RSL65 | D | D | D | D | D | D | D | D | D | R | 2.8 ± 0.7 | R | 0.2 ± 0.1 |

[1]'L' (white cells): alleles of the susceptible parent LDN, 'D' (shaded cells): alleles of the resistant parent RSL65. Because markers are listed in the same order as they are found on the chromosomes, changes in shading represent recombinant chromosome segments in each RSL.

[2]The 2007 and 2008 field experiments at UCD are summarized by an overall resistant (R) or susceptible (S) score. The greenhouse experiment was performed at Pullman, WA in 2006. Numbers are averages of infection scores of 6-10 plants ± SEM. R and S superscripts indicate resistant or susceptible classification based on the statistical analyses described below.
In the 1$^{st}$ chamber experiment lines were simply classified as resistant or susceptible, whereas in the 2$^{nd}$ experiment leaves were scanned and the percentage of leaf area covered with PST pustules was digitally analyzed using the pd program (FIG. S2). These studies confirmed that Yr36 is located between Xucw 129 and Xucw 148, and linked to Xucw125, Xucw126, and Xucw130.

[3]After the ANOVA, each RSL was compared with LDN and RSL65 controls using Dunnett tests. Lines that were not significantly different from LDN and significantly more susceptible than RSL65 (P < 0.01) were classified as susceptible ("S"), whereas lines that were not significantly different from RSL65 but significantly more resistant than LDN (P < 0.01) were classified as resistant ("R"). IT = Infection type. 0-3 (resistant), 4-6 (intermediate), and 7-9 (susceptible).

TABLE 5

Effect of different PST races on infection scores in RSLs with and without Yr36.

| | Infection score[1] | | |
|---|---|---|---|
| Race | RSLs with WKS1 | RSLs without WKS1 | P value |
| PST-17 | 2.3 ± 0.3 | 7.0 ± 0.0[2] | <0.0001 |
| PST-37 | 3.0 ± 0.0 | 7.0 ± 0.0 | <0.0001 |
| PST-45 | 1.0 ± 0.0 | 6.5 ± 0.6 | <0.0001 |
| PST-100 | 1.0 ± 0.0 | 7.8 ± 0.3 | <0.0001 |
| PST-113 | 1.0 ± 0.0 | 7.0 ± 0.0 | <0.0001 |
| PST-116 | 1.0 ± 0.0 | 7.0 ± 0.0 | <0.0001 |
| PST-127 | 4.3 ± 0.6 | 7.0 ± 0.0 | <0.0001 |
| PST-130 | 3.7 ± 0.6 | 7.0 ± 0.0 | <0.0001 |

[1]Scale of infection type (IT) (5): 0-3 (resistant, none to trace level sporulation), 4-6 (intermediate, light to moderate sporulation), 7-9 (susceptible, abundant sporulation)
[2]Some race genotype combinations showed no variation among genotypes (SE = 0), resulting in 0 variance and lack of normality.

Infection scores were obtained from three RSLs with the functional WKS1 allele (65, 241, and 402) and three RSLs with the null allele (504, 17-47, and 39-14) plus the susceptible parental line LDN. These RSLs were the critical ones used to map Yr36 within the Xucw129 and Xucw148 interval (Table 3). A total of 3 to 6 plants per race-genotype combination were evaluated. Genotype averages were used as replications and individual plants were used as subsamples for the statistical analysis. Amongst races virulent on LDN, races representing a wide range of virulences (Table 1) were selected. Yr36 resistance to PST races 100, 101 and 111 was shown before (1).

For all races, RSLs with the WKS1 allele showed lower infection scores (P<0.0001) than RSLs without WKS1, indicating that the gene (s) conferring resistance to these eight PST races is located between markers Xucw129 and Xucw148. This conclusion was further supported by ANOVA using different markers for genotype classification (the model included race, genotype, and race*genotype interaction). When WKS1 was used as the classification variable, the F value (F=1,331) was more than 30-fold higher than when flanking markers Xucw129 (F=42) or Xucw148 (F=39) were used as classification variables. These results confirmed that the gene (s) that determines the resistance to these races is located between Xucw129 and Xucw148.

TABLE 6

PCR primers used for the functional characterization of WKS genes and for germplasm screening.

| Gene | Function | Primer name | Primer Sequence | SEQ ID NO: |
|---|---|---|---|---|
| TILLING | | | | |
| WKS1 | Kinase domain | Till_1_F1 | AAGAATAAAATTGGTTTTTAATTTCGGAAAAGGTC | 50 |
| | | Till_1_R1 | ATGGAGGTGTTGGCTTTTGTGAGATGTTT | 51 |
| WKS1 | START domain | Till_1_F2 | TGCTGGAACTTGGAGCCATATAAAAATGC | 52 |
| | | Till_1_R2 | TGAACGGAGGGAGTGTTAACTAGCATAGG | 53 |
| WKS2 | Kinase domain | Till_2_F3 | GCCATGAACAACGAACAATCACACGATA | 54 |
| | | Till_2_R3 | TAAGTTGTTACTCAGCCCCAGCGCAATAC | 55 |
| WKS2 | START domain | Till_2_F4 | TCTGCTCCCAGACCCACCTCATACTTAAA | 56 |
| | | Till_2_R4 | GCAAAAGAGAAAAATGTTAAGCAGCGGAAA | 57 |
| Transgenics | | | | |
| WKS1 | Cloning pWKS1 plasmid | YR36_S1F1 | AATTACCTGCAGGTGAATGTTTCGACGCG[1] | 58 |
| | | YR36_S1R4 | AATTAGCGGCCGCTCCTGGACTACCTCC | 59 |
| WKS1 | Transgenic screening | YR36_13104F | GTGGCCAAAGGGTAGATTAG | 60 |
| | | YR36_13692R | CATCATTGTGCACGAGCTAG | 61 |
| WKS1 | Confirm WKS1.1-6 | WKS1_150F | ATGGAGCTCCCACGAAACAAAC | 62 |
| | transcript WKS1.2-6 | WKS1_151R | GAGACTAGGACACATAACATTAATTG | 63 |
| | length WKS1.1 | WKS1_174R | ACTTTCACCACTTCCTGAAGAC | 64 |
| WKS1 | Probe for Southern blot | YR36_PF | ATCGTCTCAGGCCGTGGTA | 65 |
| | hybridization | YR36_PR | CCACTTTGCCTTTGCCTTTA | 66 |
| Transcription | | | | |
| WKS1 | Q-PCR all WKS1.1-6 | WKS1_F1 | AATCAACATCCATTATTGCGAAGA | 67 |
| | variants in transgenics | WKS1_R1 | ATACTTCGTCAGGGCCTCCTATG | 68 |
| WKS1 | Q-PCR WKS1.1 | WKS1_F5 | CACAAGTACAATACCTTATGAAGATGG | 69 |
| | | WKS1_R5 | CCTGAGCCCAGCAATACTGT | 70 |
| WKS1 | Q-PCR WKS1.2-6 | WKS1_F4 | CTCCACTGAAAACCCGTAATG | 71 |
| | | WKS1_R4 | AACCAAGAGTTTTACCAGCAATACTG | 72 |
| WKS2 | Q-PCR | WKS2_F1 | ATCACGAACGTTTGTTTAGTCAAGAA | 73 |
| | | WKS2_R1 | GAGGACCATTTGCAATTGATGTT | 74 |
| ACTIN | Q-PCR | Actin_F | ACCTTCAGTTGCCCAGCAAT | 75 |
| | | Actin_R | CAGAGTCGAGCACAATACCAGTTG | 76 |
| Germplasm screen | | | | |
| WKS1 | Kinase domain | WKS_K_F | ATCCATTGCCAAGTCAACCAC | 77 |
| WKS2 | | WKS_K_R | TCACTTCCATGAAGGAGGTC | 78 |

TABLE 6-continued

PCR primers used for the functional characterization of WKS genes and for germplasm screening.

| Gene | Function | Primer name | Primer Sequence | SEQ ID NO: |
|---|---|---|---|---|
| WKS1 | Inter domain | WKS1_I_F | CGAAGAAAATCAACATCCATTATT | 79 |
|  |  | WKS1_I_R | GTGTGGCCATCTACCTCCTC | 80 |
| WKS2 | Inter domain | WKS2_I_F | GAAAAATCAGAAATATTTTACGTGGA | 81 |
|  |  | WKS2_I_R | AGCTGCAGTCCCACCTAAAA | 82 |
| WKS1 | START domain | WKS_S_F | GGCCACACTGCAATACTATACC | 83 |
| WKS2 |  | WKS_S_R | CACAAATCCTGGCTGTGGAC | 84 |
| Kinase |  |  |  |  |
| WKS1 | Construct for GST- kinase fusion protein | GST_EcoRI_F1 | TTGAATTCATGGAGCTCCCACGAAACA[2] | 85 |
|  |  | GST_XhoI_R1 | TCACTCGAGATGAAGGAGGTC | 86 |

[1]Sequences highlighted in gray are SbfI and NotI restriction sites for cloning. The underlined bases correspond to the target sequence.
[2]Sequences highlighted in grey areEcoRI and XhoI restriction sites for cloning

TABLE 7

WKS1 and WKS2 mutants evaluated for PST resistance.

| Gene | Screened region | Allele | Line ID | Nucleotide change[1] | Effect on amino acid[2] | PSSM | SIFT | Reaction to PST |
|---|---|---|---|---|---|---|---|---|
| WKS1 | Kinase | wks1a | T6-569[3] | G 163 A | V 55 I | 11.5 | 0.00 | Susceptible |
|  |  | — | T6-89 | G 508 A | D 170 N | 10.4 | 0.46 | Resistant |
|  |  | wks1b | T6-312[3] | G 595 A | G 199 R | 19.7 | 0.00 | Susceptible |
|  |  | wks1c | T6-480-1[3] | C 632 T | T 211 I | 12.6 | 0.01 | Susceptible |
|  |  | wks1d | T6-138[3] | G 914 A | R 305 H | 13.6 | 0.01 | Susceptible |
|  | START | wks1e | T6-567[3] | G 4437 A | D 477 N | 12.3 | 0.00 | Susceptible |
| WKS2 | Kinase | — | T6-960 | C 13 T | R 5 * | —[4] | — | Resistant |
|  |  | — | T6-480-2[3] | G 72 A | W 24 * | — | — | Resistant |
|  | START | — | T6-826 | G 2221 A | W 379 * | — | — | Resistant |

[1]The first letter indicates the wild-type nucleotide, the number its position from the ATG start codon, and the last letter the mutant nucleotide.
[2]The first letter indicates the wild-type amino acid, the number its position from the start methionine, and the last letter the mutant amino acid.
[3]Complete WKS1 or WKS2 coding regions were sequenced. No additional mutations were found.
[4]PSSM and SIFT scores are not reported for mutations that cause premature stop codons.

From the 117 mutations affecting the kinase and START domains, we selected six in WKS1 and three in WKS2. The three mutations in WKS2 resulted in premature stop codons, but no such mutations were available for WKS1. The WKS1 mutations were ranked using the bioinformatics programs SIFT (Sorting Intolerant From Tolerant) (Ng and Henikoff, Nucleic Acids Res. 31, 3812, 2003) and ParseSNP (Project Aligned Related Sequences and Evaluate SNPs) (Taylor and Greene, Nucleic Acids Res. 31, 3808, 2003) which estimate the severity of each missense change. High PSSM (>10) and low SIFT scores (<0.05) predict mutations with severe effects on protein function.

The $M_2$ line T6-480 was heterozygous for mutations in both WKS1 (C632T) and WKS2 (G72A) in repulsion. Homozygous $M_3$ progenies containing mutants for one or the other gene were selected and designated T6-480-1 (WKS1) and T6-480-2 (WKS2).

Five of the 6 selected WKS1 mutants were susceptible and were assigned allele names wks1a through wks1e. T6-89 was the only WKS1 mutation tested with a resistant phenotype. This mutation has the lowest PSSM value and a non-significant SIFT score, suggesting that the mutated amino acid may not be essential for resistance.

None of the WKS2 mutations affected PST resistance suggesting that the gene responsible for resistance is WKS1. The C13T and G72A mutations are upstream of the kinase domain and the G2221A mutation is in the inter-domain region.

TABLE 8

Effect of temperature and PST inoculation on WKS1.1 and WKS1.2-6 transcript levels at 3, 9 and 16 days post inoculation (DPI). Numbers in the body of the Table are P values of the two-way ANOVAs.

| Source | WKS1.1 | | | WKS1.2-6 | | |
|---|---|---|---|---|---|---|
| | 3* | 9* | 16 | 3 | 9* | 16* |
| Temperature (Temp.) | <.0001 | <.0001 | 0.016 | 0.05 | <.0001 | 0.004 |
| Inoculation (Inoc.) | 0.15 | <.0001 | 0.0002 | 0.0003 | <.0001 | <.0001 |
| Temp.* Inoc. | 0.02 | 0.92 | 0.24 | 0.36 | 0.13 | 0.79 |

*Data was transformed to meet assumptions of normally distributed errors and homogeneity of variance.

A 3-way factorial ANOVA showed significant effects of temperature, inoculation and DPI on WKS1.1 (P<0.0001) and WKS1.2-6 (P<0.0001) transcript levels. The three way interaction of these main effects was also significant in both WKS1.1 (P<0.01) and WKS1.2-6 (P<0.05) analyses. Therefore the analysis for each transcript variant was conducted separately for each DPI.

The interactions between temperature and PST inoculation were not-significant for all 2-way ANOVAs except for WKS1.1 at 3 DPI. At this early stage WKS1.1 was significantly up-regulated (P<0.05) in the inoculated samples at low temperature, whereas no significant differences were detected between control and inoculated samples at high temperature (FIG. 4A). At all other time points PST inoculation consistently down-regulated both transcript variants. The effect of temperature was also consistent across DPI. Higher temperatures significantly increased transcript levels of WKS1.1, whereas those from WKS1.2-6 significantly decreased with higher temperature.

An independent experiment including 12 inoculated and 12 control plants at low temperature 3DPI confirmed the increase of WKS1.1 after inoculation (38%) but the values were more variable and therefore the difference was not significant (P=0.10).

TABLE 9

Distribution of WKS1 and WKS2 among different Triticeae species. Presence or absence of WKS1 and WKS2 was assessed by PCR for three different regions of the gene (Table 6) and by sequencing the PCR products (GenBank accessions FJ154103 to FJ154116).

| WKS1 | WKS2 | Species |
|---|---|---|
| Detected | Detected | Aegilops longissima[1], T. turgidum ssp. dicoccoides[2]. |
| Detected | Not detected | Dasypyrum villosum[3], Lophopyrum elongatum[4], Pseudoroegneria gracillima[5], Thinopyrum bessarabicum[6]. |
| Not detected | Detected | Ae. comosa[7]. |
| Not detected | Not detected | Ae. bicornis, Ae. crassa, Ae. markgrafii, Ae. juvenalis, Ae. mutica, Ae. searsii, Ae. sharonensis, Ae. speltoides, Ae. tauschii, Ae. umbellulata, Ae. vavilovii, Agropyron cristatum, Eremopyrum orientale, Heteranthelium piliferum, Psathyrostachys juncea, Pseudoroegneria libanotica, P. spicata, P. strigosa, Secale cereale, Taeniatherum caput-medusae, Triticum aestivum, T. monococcum, T. turgidum ssp. dicoccum, T. turgidum ssp. durum, T. urartu. |

[1]Present in G509 (J. G. Waines, FJ154103 and FJ154104) and absent in DV1252 (J. Dvorak).
[2]See Table 10 for intraspecific variation in WKS1 and WKS2 distribution.
[3]Present in DV1062 (J. Dvorak, FJ154105 and FJ154106) and absent in D-2990 (D. Dewey).
[4]Present in e3 (J. Dvorak, FJ154107 to FJ154109) and absent in e2 (J. Dvorak).
[5]Present in PI 440000 (FJ154110 and FJ154111).
[6]Present in D-3483 (D. Dewey, FJ154112 and FJ154113). Only kinase and inter-domain PCR products were observed in DV013 and DV727 (J. Dvorak).
[7]Present in G1288, G1289, and G5029 (J. G. Waines, FJ154114 to FJ154116) and absent in G659, G601, G5036, and G5307 (J. G. Waines). The LINE retrotransposon insertion detected in RSL65 in WKS2 intron 10 was not detected in WKS2 from Ae. comosa.

Amongst accessions tested in this study; most species with WKS1, WKS2, or both genes showed intraspecific variability for the presence and absence of these genes. Therefore, other accessions of the species listed in the group with no detected WKS gene may still carry one or both WKS genes. Despite this uncertainty, the results above are sufficient to conclude that the duplication that originated WKS1 and WKS2 predated the divergence of the Triticeae species listed above, and that these two genes have been deleted repeatedly in several Triticeae lineages.

TABLE 10

T. turgidum and T. aestivum germplasm used in the allelic diversity study.

| Wheat | No. | WKS1/2 | Germplasm Number[1]/Variety Name |
|---|---|---|---|
| T. turgidum ssp. dicoccoides Southern population[2] | 16 | Present | PI428015, PI428113, PI487252, PI503315, PI538672, PI538673, PI538678, PI538688, PI538697, PI538699, 5-61, 7-4, 8-12, 9-36, 19-14, 30-22 |
| | 24 | Deleted | PI352324, PI428107, PI428111, PI428117, PI428119, PI428123, PI428126, PI428130, PI428135, PI428139, PI428141, PI428143, PI470981, PI470984, PI487264, PI503313, PI503314, PI538681, PI538719, PI560697, PI560872, 1-22, 27-37, 28-50 |

TABLE 10-continued

*T. turgidum* and *T. aestivum* germplasm used in the allelic diversity study.

| Wheat | No. | WKS1/2 | Germplasm Number[1]/Variety Name |
|---|---|---|---|
| *T. turgidum* ssp. *dicoccoides* Northern population[3] | 28 | Deleted | PI428016, PI428028, PI428036, PI428041, PI428047, PI428055, PI428058, PI428061, PI428065, PI428070, PI428072, PI428079, PI428082, PI428087, PI428089, PI428098, PI428145, PI503310, PI538626, PI554580, PI554581, PI554582, PI554583, PI554584, PI560874, 42-8736, 43-8811, 44-8821 |
| *T. turgidum* ssp. *dicoccum* Domesticated emmer | 23 | Deleted | PI182743, PI254158, PI254180, PI319868, PI319869, PI347230, PI352329, PI352347, PI352352, PI352357, PI352367, PI355454, PI355496, PI355498, PI470737, PI470738, PI470739, PI606325, PI94626, PI94627, PI94640, CItr17675, CItr17676 |
| *T. turgidum* ssp. *durum* Cultivated durum[4] | 40 | Deleted | Aconchi 89, Adamello, Altar 84, Appio, Appulo, Capelli, Ciccio, Cirillo, Colorado, Colosseo, Duilio, Durfort, Exeldur, Inrat 69, Karel, Karim, Khiar, Kronos, L35, Langdon, Latino, Maier, Messapia, Mexicali 75, Nefer, Neodur, Ofanto, Produra, Rugby, Russello Sg7, San Carlo, Saragolla, Trinakria, Valbelice, Valforte, Valnova, Varano, Vitron, Wb 881, Zenit |
| *Triticum aestivum* Bread wheat | 45 | Deleted | Bobwhite[5], Caledonia, Cayuga, RSI5, Express, Pio 26R61, Kanqueen, CO940610, Eltan, Finch, Foster, Grandin*5/ND614, Harry, Heyne, IDO444, IDO556, Jagger, Jaypee, Jupeteco, KS01HW163-4, Louise, McCormick, McNeal, NY18/Clark's Cream 40-1, OR9900553, Penawawa, Pio 25R26, Pioneer 26R46, PI 610750, PI610752, P91193, P92201, Platte, Reeder/Bw-277, Rio Blanco, Stephens, SS550, TAM 105, Thatcher, UC1110, USG3209, Weebill, Wesley, Zak, 2174. |
|  | 5 | Present[6] | Glupro, Lassik, Farnum, ND683, PI 638740. |

[1]PI and CItr germplasm correspond to Germplasm Resources Information Network (GRIN) numbers. Other numbers correspond to 'Location-Genotype' identification numbers from the University of Haifa wheat germplasm collection (Nevo et al., *Evolution of wild emmer and wheat improvement: population genetics, genetic resources, and genome organization of wheat's progenitor, Triticum dicoccoides.*, (Springer-Verlag, Berlin, 2002), pp. 364).
[2]Wild emmer from Israel, Lebanon, and Syria (Luo et al., *Theor. Appl. Genet.* 114, 947, 2007).
[3]Wild emmer from Iran, Iraq and Turkey. WKS1 was not found in this sub-population. Tetraploid wheat was domesticated from the Northern populations explaining the absence of Yr36 from the domesticated forms.
[4]The country of origin of the cultivated durum varieties is described in (Uauy et al., *Science* 314, 1298, 2006).
[5]Deletion of WKS1 and WKS2 in hexaploid Bobwhite was confirmed by Southern blot (FIG. S10).
[6]Yr36 has been found only in varieties selected for the closely linked GPC-B1 gene. Lassik and Farnum are new Yr36 stripe rust resistant varieties from California and Washington (USA), respectively.

The invention claimed is:

1. A vector comprising an isolated nucleic acid molecule comprising a nucleotide sequence which encodes a polypeptide comprising both a steroidogenic acute regulatory protein-related lipid transfer (START) domain set forth in SEQ ID NO:1 and a kinase domain set forth in SEQ ID NO:2, and a heterologous promoter operably linked to said isolated nucleic acid molecule.

2. The vector of claim 1, wherein said nucleotide sequence comprising the nucleotide sequence of SEQ ID NO: 9.

3. The vector of claim 1, wherein said polypeptide confers stripe rust resistance of a wheat plant.

4. A vector comprising an isolated nucleic acid molecule comprising a nucleotide sequence of SEQ ID NO: 15 having promoter function, or a variant or a fragment thereof, wherein said promoter is temperature sensitive operably linked to a heterologous transcribable nucleic acid molecule.

5. The vector of claim 4, wherein said heterologous transcribable nucleic acid molecule is a molecule comprising a nucleotide sequence which encodes a polypeptide comprising both a steriodogenic acute regulatory protein-related lipid transfer (START) domain and a kinase domain.

6. The vector of claim 4, wherein said nucleic acid molecule having promoter function is induced at or above a temperature of about 15° C., said temperature being selected from the group of ranges consisting of 15° C.-35° C., 20° C.-35° C., 20° C.-25° C. and 25° C.-35° C.

7. The vector of claim 1, wherein said promoter drives expression of said nucleotide sequence in a plant cell.

8. The vector of claim 7, wherein said promoter is a constitutive promoter, a pathogen-induced promoter, or a temperature-sensitive promoter.

9. The vector of claim 8, wherein said constitutive promoter is a ubiquitin promoter.

10. The vector of claim 8, wherein said temperature-sensitive promoter is comprised of an isolated nucleic acid molecule comprising a nucleotide sequence of SEQ ID NO: 15 having promoter function, or a variant or a fragment thereof, wherein said promoter is temperature sensitive.

11. A host cell comprising the vector of claim 1, wherein said operably linked heterologous promoter drives expression of the coding sequence of said nucleic acid molecule in a plant cell.

12. The host cell of claim 11 that is a plant, bacterial, yeast or insect host cell.

13. The host cell of claim 12 that is a plant cell.

14. A transgenic plant comprising the host cell of claim 13.

15. The transgenic plant of claim 14, which is a wheat plant.

16. A transformed seed comprising the vector of claim 1, wherein said operably linked heterologous promoter drives expression of the coding sequence of said nucleic acid molecule in a plant cell.

17. A method for conferring resistance to stripe rust in a cereal crop plant, said method comprising transforming said plant with the vector of claim 1, wherein said operably linked heterologous promoter drives expression of the coding sequence of said nucleic acid molecule in a plant cell.

18. The method of claim 17, wherein said cereal crop plant is a wheat plant.

19. A transgenic cereal crop plant having stably incorporated into its genome the vector of claim 1, wherein said operably linked heterologous promoter drives expression of the coding sequence of said nucleic acid molecule in a plant cell.

20. The transgenic cereal crop plant of claim 19, which is a wheat plant.

21. The transgenic wheat plant according to claim 20, wherein said nucleotide sequence is of SEQ ID NO: 9.

22. The vector of claim 5, wherein said nucleic acid molecule having promoter function is induced at or above a temperature of about 15° C., said temperature being selected from the group of ranges consisting of 15° C.-35° C., 20° C.-35° C., 20° C.-25° C. and 25° C.-35° C.

* * * * *

SEQUENCE LISTING

<160> NUMBER OF SEQ ID NOS: 115

<210> SEQ ID NO 1
<211> LENGTH: 212
<212> TYPE: PRT
<213> ORGANISM: Artificial Sequence
<220> FEATURE:
<223> OTHER INFORMATION: Synthetic peptide

<400> SEQUENCE: 1

Asp Trp Thr Cys Gly Asn Asp Ile Gly Gly Pro Asp Glu Val Phe Ser
1               5                   10                  15

Gly Gly His Trp Arg Leu Leu Gly Cys Gln Asn Gly Leu His Ile Phe
            20                  25                  30

Glu Ala Leu Glu Asp Val Asp Tyr Leu Val Arg Ala Val Gly Lys Ala
        35                  40                  45

Met Lys Ala Val Gly Val Ile Glu Ala Pro Cys Glu Ala Ile Phe Gln
    50                  55                  60

Leu Leu Met Ser Met Asp Ser Ser Arg Tyr Glu Trp Asp Cys Ser Phe
65                  70                  75                  80

Ser Tyr Gly Ser Leu Val Glu Glu Val Asp Gly His Thr Ala Ile Leu
                85                  90                  95

Tyr His Arg Pro His Leu Asp Trp Phe Leu Thr Phe Val Trp Pro Arg
            100                 105                 110

Asp Leu Cys Tyr Val Arg Tyr Trp Gln Arg Asn Asp Asp Gly Gly Tyr
            115                 120                 125

Val Val Leu Phe Gln Ser Arg Glu His Pro Lys Cys Gly Pro Gln Pro
        130                 135                 140

Gly Phe Val Arg Ala Tyr Ile Glu Ile Gly Phe Lys Ile Ser Pro
145                 150                 155                 160

Leu Lys Thr Arg Asn Gly Arg Thr Arg Thr Gln Val Gln Tyr Leu Met
                165                 170                 175

Lys Met Asp Leu Lys Gly Trp Gly Val Gly Tyr Leu Ser Ser Phe Gln
            180                 185                 190

Gln His Cys Val Leu Arg Met Leu Asn Ser Ile Ala Gly Leu Arg Glu
        195                 200                 205

Trp Phe Ser Arg
    210

<210> SEQ ID NO 2
<211> LENGTH: 255
<212> TYPE: PRT
<213> ORGANISM: Artificial Sequence
<220> FEATURE:
<223> OTHER INFORMATION: Synthetic peptide

<400> SEQUENCE: 2

Val Gly Lys Gly Ala Phe Gly Glu Val Phe Arg Gly Phe Leu Asp Asp
1               5                   10                  15

Gly Ser Pro Val Ala Val Lys Lys Tyr Met Asn Gln Asn Met Lys Glu
            20                  25                  30

Gly Phe Asp Lys Glu Ile Thr Ile His Cys Gln Val Asn His Lys Asn
        35                  40                  45

Ile Val Lys Leu Leu Gly Tyr Cys Ser Glu Glu Asn Ala Leu Thr Met
    50                  55                  60

Val Thr Glu Tyr Ile Pro Arg Gly Asn Leu Lys Asp Leu Leu His Gly
65                  70                  75                  80

Ser Asp Asp Pro Ile Ser Phe Glu Ala Arg Leu Arg Ile Ala Ile Asp
                85                  90                  95

Cys Ala Asp Ala Leu Ala Phe Met His Ser Lys Asp Pro Pro Ile Ile
            100                 105                 110

His Gly Asp Ile Lys Pro Asp Asn Ile Leu Leu Asp Asp Asn Leu Gly
        115                 120                 125

Ala Lys Leu Ser Asp Phe Gly Ile Ser Arg Leu Leu Ser Met Glu Asn
    130                 135                 140

Ser Tyr Phe Thr Asn Asn Val Ile Gly Ser Arg Gly Tyr Met Asp Pro
145                 150                 155                 160

Glu His Ile Gln Thr Gly Arg Val Asp Pro Lys Asn Asp Val Tyr Ser
                165                 170                 175

Phe Gly Val Val Leu Val Glu Leu Val Thr Arg Ala Met Ala Ala Gln
            180                 185                 190

Asn Gly Thr Cys Asn Asp Leu Ala Lys Lys Phe Ile Glu Ala Phe Leu
        195                 200                 205

Gln Lys Asn Ile Phe Leu Lys Val Phe Gly Lys Gln Lys Lys Ala Arg
    210                 215                 220

Arg Glu Met Phe Asp Thr Gln Ile Ala Asn Ala Ser Asn Met Glu Val
225                 230                 235                 240

Leu Glu Lys Ile Gly Glu Leu Ala Ile Glu Cys Leu Arg Arg Asp
                245                 250                 255

<210> SEQ ID NO 3
<211> LENGTH: 645
<212> TYPE: PRT
<213> ORGANISM: Triticum turgidum
<220> FEATURE:
<221> NAME/KEY: VARSPLIC
<222> LOCATION: (1)..(645)
<223> OTHER INFORMATION: transcript variant WKS1.1

<400> SEQUENCE: 3

Met Glu Leu Pro Arg Asn Lys Leu Ala Asp Leu Asn Gln Gly Asn Glu
1               5                   10                  15

Asn Leu Lys Ala Lys Ala Lys Trp Thr Pro Asn Ala Arg Arg Phe Thr
            20                  25                  30

Glu His Gln Ile Lys Arg Ile Thr Lys Asn Tyr Arg Thr His Val Gly
        35                  40                  45

Lys Gly Ala Phe Gly Glu Val Phe Arg Gly Phe Leu Asp Asp Gly Ser
    50                  55                  60

Pro Val Ala Val Lys Lys Tyr Met Asn Gln Asn Met Lys Glu Gly Phe
65                  70                  75                  80

Asp Lys Glu Ile Thr Ile His Cys Gln Val Asn His Lys Asn Ile Val
                85                  90                  95

Lys Leu Leu Gly Tyr Cys Ser Glu Glu Asn Ala Leu Thr Met Val Thr
            100                 105                 110

Glu Tyr Ile Pro Arg Gly Asn Leu Lys Asp Leu Leu His Gly Ser Asp
        115                 120                 125

Asp Pro Ile Ser Phe Glu Ala Arg Leu Arg Ile Ala Ile Asp Cys Ala
    130                 135                 140

Asp Ala Leu Ala Phe Met His Ser Lys Asp Pro Pro Ile Ile His Gly
145                 150                 155                 160

Asp Ile Lys Pro Asp Asn Ile Leu Leu Asp Asp Asn Leu Gly Ala Lys
                165                 170                 175

Leu Ser Asp Phe Gly Ile Ser Arg Leu Leu Ser Met Glu Asn Ser Tyr
            180                 185                 190

Phe Thr Asn Asn Val Ile Gly Ser Arg Gly Tyr Met Asp Pro Glu His
        195                 200                 205

Ile Gln Thr Gly Arg Val Asp Pro Lys Asn Asp Val Tyr Ser Phe Gly
    210                 215                 220

Val Val Leu Val Glu Leu Val Thr Arg Ala Met Ala Ala Gln Asn Gly
225                 230                 235                 240

Thr Cys Asn Asp Leu Ala Lys Lys Phe Ile Glu Ala Phe Leu Gln Lys
                245                 250                 255

Asn Ile Phe Leu Lys Val Phe Gly Lys Gln Lys Lys Ala Arg Arg Glu
            260                 265                 270

Met Phe Asp Thr Gln Ile Ala Asn Ala Ser Asn Met Glu Val Leu Glu
        275                 280                 285

Lys Ile Gly Glu Leu Ala Ile Glu Cys Leu Arg Arg Asp Ile Lys Lys
    290                 295                 300

Arg Pro Glu Met Asn His Val Val Glu Arg Leu Arg Met Leu Gly Lys
305                 310                 315                 320

Asp His Glu Lys Arg Gln Asp Arg Lys Pro Glu Lys Gln His Gly Val
                325                 330                 335

Val Pro Pro Asp Gly Asn Thr Thr Phe Ser Ser Trp Pro Lys Gly
            340                 345                 350

Arg Leu Glu Asn Gly Arg Lys Ser Ser Ser Asp Ala Lys Ser Leu
            355                 360                 365

Phe Ser His Arg Gly Val Glu Ala Val Asp Glu Asn Gln His Pro
    370                 375                 380

Leu Leu Arg Arg Thr Ser Ile Gly Asn Gly Pro Pro Gly Ser Phe His
385                 390                 395                 400

Asp Trp Thr Cys Gly Asn Asp Ile Gly Gly Pro Asp Glu Val Phe Ser
                405                 410                 415

Gly Gly His Trp Arg Leu Leu Gly Cys Gln Asn Gly Leu His Ile Phe
                420                 425                 430

Glu Ala Leu Glu Asp Val Asp Tyr Leu Val Arg Ala Val Gly Lys Ala
            435                 440                 445

Met Lys Ala Val Gly Val Ile Glu Ala Pro Cys Glu Ala Ile Phe Gln
450                 455                 460

Leu Leu Met Ser Met Asp Ser Ser Arg Tyr Glu Trp Asp Cys Ser Phe
465                 470                 475                 480

Ser Tyr Gly Ser Leu Val Glu Glu Val Asp Gly His Thr Ala Ile Leu
                485                 490                 495

Tyr His Arg Pro His Leu Asp Trp Phe Leu Thr Phe Val Trp Pro Arg
                500                 505                 510

Asp Leu Cys Tyr Val Arg Tyr Trp Gln Arg Asn Asp Asp Gly Gly Tyr
            515                 520                 525

Val Val Leu Phe Gln Ser Arg Glu His Pro Lys Cys Gly Pro Gln Pro
            530                 535                 540

Gly Phe Val Arg Ala Tyr Ile Glu Ile Gly Gly Phe Lys Ile Ser Pro
545                 550                 555                 560

Leu Lys Thr Arg Asn Gly Arg Thr Arg Thr Gln Val Gln Tyr Leu Met
                565                 570                 575

Lys Met Asp Leu Lys Gly Trp Gly Val Gly Tyr Leu Ser Ser Phe Gln
            580                 585                 590

Gln His Cys Val Leu Arg Met Leu Asn Ser Ile Ala Gly Leu Arg Glu
        595                 600                 605

Trp Phe Ser Arg Ser Asp Glu Ile Pro Thr Ser Met Asp Gln Ser Arg
    610                 615                 620

Tyr Ser Thr Met Leu Glu Glu Glu Ser Asp Glu Asp Glu Leu Ser Ser
625                 630                 635                 640

Gly Ser Gly Glu Ser
            645

<210> SEQ ID NO 4
<211> LENGTH: 623
<212> TYPE: PRT
<213> ORGANISM: Triticum turgidum
<220> FEATURE:
<221> NAME/KEY: VARSPLIC
<222> LOCATION: (1)..(623)
<223> OTHER INFORMATION: transcript variant WKS1.2

<400> SEQUENCE: 4

Met Glu Leu Pro Arg Asn Lys Leu Ala Asp Leu Asn Gln Gly Asn Glu
1                   5                   10                  15

Asn Leu Lys Ala Lys Ala Lys Trp Thr Pro Asn Ala Arg Arg Phe Thr
                20                  25                  30

Glu His Gln Ile Lys Arg Ile Thr Lys Asn Tyr Arg Thr His Val Gly
            35                  40                  45

Lys Gly Ala Phe Gly Glu Val Phe Arg Gly Phe Leu Asp Asp Gly Ser

```
              50                  55                  60
Pro Val Ala Val Lys Lys Tyr Met Asn Gln Asn Met Lys Glu Gly Phe
 65                  70                  75                  80

Asp Lys Glu Ile Thr Ile His Cys Gln Val Asn His Lys Asn Ile Val
                 85                  90                  95

Lys Leu Leu Gly Tyr Cys Ser Glu Glu Asn Ala Leu Thr Met Val Thr
                100                 105                 110

Glu Tyr Ile Pro Arg Gly Asn Leu Lys Asp Leu Leu His Gly Ser Asp
                115                 120                 125

Asp Pro Ile Ser Phe Glu Ala Arg Leu Arg Ile Ala Ile Asp Cys Ala
                130                 135                 140

Asp Ala Leu Ala Phe Met His Ser Lys Asp Pro Pro Ile Ile His Gly
145                 150                 155                 160

Asp Ile Lys Pro Asp Asn Ile Leu Leu Asp Asp Asn Leu Gly Ala Lys
                165                 170                 175

Leu Ser Asp Phe Gly Ile Ser Arg Leu Leu Ser Met Glu Asn Ser Tyr
                180                 185                 190

Phe Thr Asn Asn Val Ile Gly Ser Arg Gly Tyr Met Asp Pro Glu His
                195                 200                 205

Ile Gln Thr Gly Arg Val Asp Pro Lys Asn Asp Val Tyr Ser Phe Gly
210                 215                 220

Val Val Leu Val Glu Leu Val Thr Arg Ala Met Ala Ala Gln Asn Gly
225                 230                 235                 240

Thr Cys Asn Asp Leu Ala Lys Lys Phe Ile Glu Ala Phe Leu Gln Lys
                245                 250                 255

Asn Ile Phe Leu Lys Val Phe Gly Lys Gln Lys Lys Ala Arg Arg Glu
                260                 265                 270

Met Phe Asp Thr Gln Ile Ala Asn Ala Ser Asn Met Glu Val Leu Glu
                275                 280                 285

Lys Ile Gly Glu Leu Ala Ile Glu Cys Leu Arg Arg Asp Ile Lys Lys
                290                 295                 300

Arg Pro Glu Met Asn His Val Val Glu Arg Leu Arg Met Leu Gly Lys
305                 310                 315                 320

Asp His Glu Lys Arg Gln Asp Arg Lys Pro Glu Lys Gln His Gly Val
                325                 330                 335

Val Pro Pro Asp Gly Asn Thr Thr Phe Ser Ser Ser Trp Pro Lys Gly
                340                 345                 350

Arg Leu Glu Asn Gly Arg Lys Ser Ser Ser Asp Ala Lys Ser Leu
                355                 360                 365

Phe Ser His Arg Gly Val Glu Ala Val Asp Glu Glu Asn Gln His Pro
                370                 375                 380

Leu Leu Arg Arg Thr Ser Ile Gly Asn Gly Pro Gly Ser Phe His
385                 390                 395                 400

Asp Trp Thr Cys Gly Asn Asp Ile Gly Gly Pro Asp Glu Val Phe Ser
                405                 410                 415

Gly Gly His Trp Arg Leu Leu Gly Cys Gln Asn Gly Leu His Ile Phe
                420                 425                 430

Glu Ala Leu Glu Asp Val Asp Tyr Leu Val Arg Ala Val Gly Lys Ala
                435                 440                 445

Met Lys Ala Val Gly Val Ile Glu Ala Pro Cys Glu Ala Ile Phe Gln
                450                 455                 460

Leu Leu Met Ser Met Asp Ser Ser Arg Tyr Glu Trp Asp Cys Ser Phe
465                 470                 475                 480
```

```
Ser Tyr Gly Ser Leu Val Glu Val Asp Gly His Thr Ala Ile Leu
            485             490                 495

Tyr His Arg Pro His Leu Asp Trp Phe Leu Thr Phe Val Trp Pro Arg
                500                 505                 510

Asp Leu Cys Tyr Val Arg Tyr Trp Gln Arg Asn Asp Asp Gly Gly Tyr
        515                 520                 525

Val Val Leu Phe Gln Ser Arg Glu His Pro Lys Cys Gly Pro Gln Pro
    530                 535                 540

Gly Phe Val Arg Ala Tyr Ile Glu Ile Gly Gly Phe Lys Ile Ser Pro
545                 550                 555                 560

Leu Lys Thr Arg Asn Gly Arg Thr Arg Thr Gln Val Gln Tyr Leu Met
                565                 570                 575

Lys Met Asp Leu Lys Gly Trp Gly Val Gly Tyr Leu Ser Ser Phe Gln
                580                 585                 590

Gln His Cys Val Leu Arg Met Leu Asn Ser Ile Ala Gly Lys Thr Leu
            595                 600                 605

Gly Ser Val Ile Ile Phe Cys Thr Thr Phe Ala Arg Tyr His Asn
    610                 615                 620

<210> SEQ ID NO 5
<211> LENGTH: 552
<212> TYPE: PRT
<213> ORGANISM: Triticum turgidum
<220> FEATURE:
<221> NAME/KEY: VARSPLIC
<222> LOCATION: (1)..(552)
<223> OTHER INFORMATION: transcript variant WKS1.3

<400> SEQUENCE: 5

Met Glu Leu Pro Arg Asn Lys Leu Ala Asp Leu Asn Gln Gly Asn Glu
1               5                   10                  15

Asn Leu Lys Ala Lys Ala Lys Trp Thr Pro Asn Ala Arg Arg Phe Thr
                20                  25                  30

Glu His Gln Ile Lys Arg Ile Thr Lys Asn Tyr Arg Thr His Val Gly
            35                  40                  45

Lys Gly Ala Phe Gly Glu Val Phe Arg Gly Phe Leu Asp Asp Gly Ser
    50                  55                  60

Pro Val Ala Val Lys Lys Tyr Met Asn Gln Asn Met Lys Glu Gly Phe
65                  70                  75                  80

Asp Lys Glu Ile Thr Ile His Cys Gln Val Asn His Lys Asn Ile Val
                85                  90                  95

Lys Leu Leu Gly Tyr Cys Ser Glu Glu Asn Ala Leu Thr Met Val Thr
            100                 105                 110

Glu Tyr Ile Pro Arg Gly Asn Leu Lys Asp Leu Leu His Gly Ser Asp
        115                 120                 125

Asp Pro Ile Ser Phe Glu Ala Arg Leu Arg Ile Ala Ile Asp Cys Ala
    130                 135                 140

Asp Ala Leu Ala Phe Met His Ser Lys Asp Pro Ile Ile His Gly
145                 150                 155                 160

Asp Ile Lys Pro Asp Asn Ile Leu Leu Asp Asp Asn Leu Gly Ala Lys
                165                 170                 175

Leu Ser Asp Phe Gly Ile Ser Arg Leu Leu Ser Met Glu Asn Ser Tyr
            180                 185                 190

Phe Thr Asn Asn Val Ile Gly Ser Arg Gly Tyr Met Asp Pro Glu His
        195                 200                 205
```

```
Ile Gln Thr Gly Arg Val Asp Pro Lys Asn Asp Val Tyr Ser Phe Gly
    210                 215                 220
Val Val Leu Val Glu Leu Val Thr Arg Ala Met Ala Ala Gln Asn Gly
225                 230                 235                 240
Thr Cys Asn Asp Leu Ala Lys Lys Phe Ile Glu Ala Phe Leu Gln Lys
                245                 250                 255
Asn Ile Phe Leu Lys Val Phe Gly Lys Gln Lys Lys Ala Arg Arg Glu
            260                 265                 270
Met Phe Asp Thr Gln Ile Ala Asn Ala Ser Asn Met Glu Val Leu Glu
        275                 280                 285
Lys Ile Gly Glu Leu Ala Ile Glu Cys Leu Arg Arg Asp Ile Lys Lys
    290                 295                 300
Arg Pro Glu Met Asn His Val Val Glu Arg Leu Arg Met Leu Gly Lys
305                 310                 315                 320
Asp His Glu Lys Arg Gln Asp Arg Lys Pro Glu Lys Gln His Gly Val
                325                 330                 335
Val Pro Pro Asp Gly Asn Thr Thr Phe Ser Ser Trp Pro Lys Gly
            340                 345                 350
Arg Leu Glu Asn Gly Arg Lys Ser Ser Ser Asp Ala Lys Ser Leu
        355                 360                 365
Phe Ser His Arg Gly Val Glu Ala Val Asp Glu Glu Asn Gln His Pro
    370                 375                 380
Leu Leu Arg Arg Thr Ser Ile Gly Asn Gly Pro Pro Gly Ser Phe His
385                 390                 395                 400
Asp Trp Thr Cys Gly Asn Asp Ile Gly Gly Pro Asp Glu Val Phe Ser
                405                 410                 415
Gly Gly His Trp Arg Leu Leu Gly Cys Gln Asn Gly Leu His Ile Phe
            420                 425                 430
Glu Ala Leu Glu Asp Val Asp Tyr Leu Val Arg Ala Val Gly Lys Ala
        435                 440                 445
Met Lys Ala Val Gly Val Ile Glu Ala Pro Cys Glu Ala Ile Phe Gln
    450                 455                 460
Leu Leu Met Ser Met Asp Ser Ser Arg Tyr Glu Trp Asp Cys Ser Phe
465                 470                 475                 480
Ser Tyr Gly Ser Leu Val Glu Glu Val Asp Gly His Thr Ala Ile Leu
                485                 490                 495
Tyr His Arg Pro His Leu Asp Trp Phe Leu Thr Phe Val Trp Pro Arg
            500                 505                 510
Asp Leu Cys Tyr Val Arg Tyr Trp Gln Arg Asn Asp Asp Gly Gly Tyr
        515                 520                 525
Gly Cys Gly Val Val Pro Ile Gln Arg Ala Pro Glu Met Trp Ser Thr
    530                 535                 540
Ala Arg Ile Cys Glu Gly Ile His
545                 550

<210> SEQ ID NO 6
<211> LENGTH: 556
<212> TYPE: PRT
<213> ORGANISM: Triticum turgidum
<220> FEATURE:
<221> NAME/KEY: VARSPLIC
<222> LOCATION: (1)..(556)
<223> OTHER INFORMATION: transcript variant WKS1.4

<400> SEQUENCE: 6

Met Glu Leu Pro Arg Asn Lys Leu Ala Asp Leu Asn Gln Gly Asn Glu
```

```
1               5                    10                        15
Asn Leu Lys Ala Lys Ala Lys Trp Thr Pro Asn Ala Arg Arg Phe Thr
                20                  25                  30
Glu His Gln Ile Lys Arg Ile Thr Lys Asn Tyr Arg Thr His Val Gly
                35                  40                  45
Lys Gly Ala Phe Gly Glu Val Phe Arg Gly Phe Leu Asp Asp Gly Ser
                50                  55                  60
Pro Val Ala Val Lys Lys Tyr Met Asn Gln Asn Met Lys Glu Gly Phe
65                  70                  75                  80
Asp Lys Glu Ile Thr Ile His Cys Gln Val Asn His Lys Asn Ile Val
                85                  90                  95
Lys Leu Leu Gly Tyr Cys Ser Glu Glu Asn Ala Leu Thr Met Val Thr
                100                 105                 110
Glu Tyr Ile Pro Arg Gly Asn Leu Lys Asp Leu Leu His Gly Ser Asp
                115                 120                 125
Asp Pro Ile Ser Phe Glu Ala Arg Leu Arg Ile Ala Ile Asp Cys Ala
                130                 135                 140
Asp Ala Leu Ala Phe Met His Ser Lys Asp Pro Ile Ile His Gly
145                 150                 155                 160
Asp Ile Lys Pro Asp Asn Ile Leu Leu Asp Asn Leu Gly Ala Lys
                165                 170                 175
Leu Ser Asp Phe Gly Ile Ser Arg Leu Leu Ser Met Glu Asn Ser Tyr
                180                 185                 190
Phe Thr Asn Asn Val Ile Gly Ser Arg Gly Tyr Met Asp Pro Glu His
                195                 200                 205
Ile Gln Thr Gly Arg Val Asp Pro Lys Asn Asp Val Tyr Ser Phe Gly
                210                 215                 220
Val Val Leu Val Glu Leu Val Thr Arg Ala Met Ala Ala Gln Asn Gly
225                 230                 235                 240
Thr Cys Asn Asp Leu Ala Lys Lys Phe Ile Glu Ala Phe Leu Gln Lys
                245                 250                 255
Asn Ile Phe Leu Lys Val Phe Gly Lys Gln Lys Ala Arg Arg Glu
                260                 265                 270
Met Phe Asp Thr Gln Ile Ala Asn Ala Ser Asn Met Glu Val Leu Glu
                275                 280                 285
Lys Ile Gly Glu Leu Ala Ile Glu Cys Leu Arg Arg Asp Ile Lys Lys
                290                 295                 300
Arg Pro Glu Met Asn His Val Val Glu Arg Leu Arg Met Leu Gly Lys
305                 310                 315                 320
Asp His Glu Lys Arg Gln Asp Arg Lys Pro Glu Lys Gln His Gly Val
                325                 330                 335
Val Pro Pro Asp Gly Asn Thr Thr Phe Ser Ser Trp Pro Lys Gly
                340                 345                 350
Arg Leu Glu Asn Gly Arg Lys Ser Ser Ser Asp Ala Lys Ser Leu
                355                 360                 365
Phe Ser His Arg Gly Val Glu Ala Val Asp Glu Glu Asn Gln His Pro
                370                 375                 380
Leu Leu Arg Arg Thr Ser Ile Gly Asn Gly Pro Pro Gly Ser Phe His
385                 390                 395                 400
Asp Trp Thr Cys Gly Asn Asp Ile Gly Gly Pro Asp Glu Val Phe Ser
                405                 410                 415
Gly Gly His Trp Arg Leu Leu Gly Cys Gln Asn Gly Leu His Ile Phe
                420                 425                 430
```

```
Glu Ala Leu Glu Asp Val Asp Tyr Leu Val Arg Ala Val Gly Lys Ala
            435                 440                 445

Met Lys Ala Val Gly Val Ile Glu Ala Pro Cys Glu Ala Ile Phe Gln
450                 455                 460

Leu Leu Met Ser Met Asp Ser Ser Arg Tyr Glu Trp Asp Cys Ser Phe
465                 470                 475                 480

Ser Tyr Gly Ser Leu Val Glu Glu Val Asp Gly His Thr Ala Ile Leu
            485                 490                 495

Tyr His Arg Pro His Leu Asp Trp Phe Leu Thr Phe Val Trp Pro Arg
            500                 505                 510

Asp Leu Cys Tyr Val Arg Tyr Trp Gln Arg Asn Asp Asp Gly Gly Tyr
            515                 520                 525

Gly Trp Tyr Phe Gln Ser Ser Thr Leu Ile Leu Met Cys Thr Ser Thr
            530                 535                 540

Lys His Arg Tyr Leu Glu Cys Ser His Leu Phe Ser
545                 550                 555

<210> SEQ ID NO 7
<211> LENGTH: 493
<212> TYPE: PRT
<213> ORGANISM: Triticum turgidum
<220> FEATURE:
<221> NAME/KEY: VARSPLIC
<222> LOCATION: (1)..(493)
<223> OTHER INFORMATION: transcript variant WKS1.5

<400> SEQUENCE: 7

Met Glu Leu Pro Arg Asn Lys Leu Ala Asp Leu Asn Gln Gly Asn Glu
1               5                   10                  15

Asn Leu Lys Ala Lys Ala Lys Trp Thr Pro Asn Ala Arg Arg Phe Thr
            20                  25                  30

Glu His Gln Ile Lys Arg Ile Thr Lys Asn Tyr Arg Thr His Val Gly
            35                  40                  45

Lys Gly Ala Phe Gly Glu Val Phe Arg Gly Phe Leu Asp Asp Gly Ser
    50                  55                  60

Pro Val Ala Val Lys Lys Tyr Met Asn Gln Asn Met Lys Glu Gly Phe
65                  70                  75                  80

Asp Lys Glu Ile Thr Ile His Cys Gln Val Asn His Lys Asn Ile Val
                85                  90                  95

Lys Leu Leu Gly Tyr Cys Ser Glu Glu Asn Ala Leu Thr Met Val Thr
            100                 105                 110

Glu Tyr Ile Pro Arg Gly Asn Leu Lys Asp Leu Leu His Gly Ser Asp
            115                 120                 125

Asp Pro Ile Ser Phe Glu Ala Arg Leu Arg Ile Ala Ile Asp Cys Ala
    130                 135                 140

Asp Ala Leu Ala Phe Met His Ser Lys Asp Pro Ile Ile His Gly
145                 150                 155                 160

Asp Ile Lys Pro Asp Asn Ile Leu Leu Asp Asn Leu Gly Ala Lys
                165                 170                 175

Leu Ser Asp Phe Gly Ile Ser Arg Leu Leu Ser Met Glu Asn Ser Tyr
            180                 185                 190

Phe Thr Asn Asn Val Ile Gly Ser Arg Gly Tyr Met Asp Pro Glu His
            195                 200                 205

Ile Gln Thr Gly Arg Val Asp Pro Lys Asn Asp Val Tyr Ser Phe Gly
    210                 215                 220
```

Val Val Leu Val Glu Leu Val Thr Arg Ala Met Ala Ala Gln Asn Gly
225                 230                 235                 240

Thr Cys Asn Asp Leu Ala Lys Lys Phe Ile Glu Ala Phe Leu Gln Lys
            245                 250                 255

Asn Ile Phe Leu Lys Val Phe Gly Lys Gln Lys Lys Ala Arg Arg Glu
        260                 265                 270

Met Phe Asp Thr Gln Ile Ala Asn Ala Ser Asn Met Glu Val Leu Glu
    275                 280                 285

Lys Ile Gly Glu Leu Ala Ile Glu Cys Leu Arg Arg Asp Ile Lys Lys
290                 295                 300

Arg Pro Glu Met Asn His Val Val Glu Arg Leu Arg Met Leu Gly Lys
305                 310                 315                 320

Asp His Glu Lys Arg Gln Asp Arg Lys Pro Glu Lys Gln His Gly Val
            325                 330                 335

Val Pro Pro Asp Gly Asn Thr Thr Phe Ser Ser Trp Pro Lys Gly
        340                 345                 350

Arg Leu Glu Asn Gly Arg Lys Ser Ser Ser Asp Ala Lys Ser Leu
    355                 360                 365

Phe Ser His Arg Gly Val Glu Ala Val Asp Glu Glu Asn Gln His Pro
370                 375                 380

Leu Leu Arg Arg Thr Ser Ile Gly Asn Gly Pro Pro Gly Ser Phe His
385                 390                 395                 400

Asp Trp Thr Cys Gly Asn Asp Ile Gly Gly Pro Asp Glu Val Phe Ser
            405                 410                 415

Gly Gly His Trp Arg Leu Leu Gly Cys Gln Asn Gly Leu His Ile Phe
        420                 425                 430

Glu Ala Leu Glu Asp Val Asp Tyr Leu Val Arg Ala Val Gly Lys Ala
    435                 440                 445

Met Lys Ala Val Gly Val Ile Glu Ala Pro Cys Glu Ala Ile Phe Gln
450                 455                 460

Leu Leu Met Ser Met Asp Ser Ser Arg Tyr Glu Trp Asp Cys Ser Phe
465                 470                 475                 480

Ser Tyr Gly Ser Leu Val Glu Glu Val Cys Leu Ala Ser
            485                 490

<210> SEQ ID NO 8
<211> LENGTH: 335
<212> TYPE: PRT
<213> ORGANISM: Triticum turgidum
<220> FEATURE:
<221> NAME/KEY: VARSPLIC
<222> LOCATION: (1)..(335)
<223> OTHER INFORMATION: transcript variant WKS1.6

<400> SEQUENCE: 8

Met Glu Leu Pro Arg Asn Lys Leu Ala Asp Leu Asn Gln Gly Asn Glu
1               5                   10                  15

Asn Leu Lys Ala Lys Ala Lys Trp Thr Pro Asn Ala Arg Arg Phe Thr
            20                  25                  30

Glu His Gln Ile Lys Arg Ile Thr Lys Asn Tyr Arg Thr His Val Gly
        35                  40                  45

Lys Gly Ala Phe Gly Glu Val Phe Arg Gly Phe Leu Asp Asp Gly Ser
    50                  55                  60

Pro Val Ala Val Lys Lys Tyr Met Asn Gln Asn Met Lys Glu Gly Phe
65                  70                  75                  80

Asp Lys Glu Ile Thr Ile His Cys Gln Val Asn His Lys Asn Ile Val

```
                     85                  90                  95
Lys Leu Leu Gly Tyr Cys Ser Glu Glu Asn Ala Leu Thr Met Val Thr
            100                 105                 110

Glu Tyr Ile Pro Arg Gly Asn Leu Lys Asp Leu Leu His Gly Ser Asp
            115                 120                 125

Asp Pro Ile Ser Phe Glu Ala Arg Leu Arg Ile Ala Ile Asp Cys Ala
        130                 135                 140

Asp Ala Leu Ala Phe Met His Ser Lys Asp Pro Ile Ile His Gly
145                 150                 155                 160

Asp Ile Lys Pro Asp Asn Ile Leu Leu Asp Asn Leu Gly Ala Lys
                165                 170                 175

Leu Ser Asp Phe Gly Ile Ser Arg Leu Leu Ser Met Glu Asn Ser Tyr
            180                 185                 190

Phe Thr Asn Asn Val Ile Gly Ser Arg Gly Tyr Met Asp Pro Glu His
            195                 200                 205

Ile Gln Thr Gly Arg Val Asp Pro Lys Asn Asp Val Tyr Ser Phe Gly
210                 215                 220

Val Val Leu Val Glu Leu Val Thr Arg Ala Met Ala Ala Gln Asn Gly
225                 230                 235                 240

Thr Cys Asn Asp Leu Ala Lys Lys Phe Ile Glu Ala Phe Leu Gln Lys
                245                 250                 255

Asn Ile Phe Leu Lys Val Phe Gly Lys Gln Lys Lys Ala Arg Arg Glu
            260                 265                 270

Met Phe Asp Thr Gln Ile Ala Asn Ala Ser Asn Met Glu Val Leu Glu
        275                 280                 285

Lys Ile Gly Glu Leu Ala Ile Glu Cys Leu Arg Arg Asp Ile Lys Lys
290                 295                 300

Arg Pro Glu Met Asn His Val Val Glu Arg Leu Arg Met Leu Gly Lys
305                 310                 315                 320

Asp His Glu Lys Arg Gln Asp Arg Lys Pro Glu Lys Val Gln Ser
                325                 330                 335

<210> SEQ ID NO 9
<211> LENGTH: 9287
<212> TYPE: DNA
<213> ORGANISM: Triticum turgidum

<400> SEQUENCE: 9
gcgttgctgc tccctcagcc tctccttccg caccctctct atcaagtgtc ggccggagca      60
atcagaagca gctagctagg ctagctaaca cgtcgtcggc cttctcaaac caggccgtcg     120
tcggccggat atcgtctcag gccgtggtat gtatccgcag ctctcttccc ttttttgattt    180 gatcttactt tgctggttcg atattatttt ttctgcgacc acaatcctct ttttgatagg     240
ctagacccct ttcattagta aggaaatcaa agttgtacct cgtcggccac cccttgaata     300
gcagccagtc cagcaaacga acttaacaac cgagcgaact gaagctcaaa acaaggctgt     360
ctaaattcta agtaaaaaca acccagacag ggctgctagt ttctctttct tgggatccaa     420
gggctacagc tttctaccag cttgatagac ttcagccgtg acctgttcca gtacttttgc     480
gcacatgtct gcagttttag agatatttag cggatgagga ctaaagagca atgttcatga     540
cttcaagatc caagatcccc agccaccat gatcctttgg caaacagacc cgaggccggt      600
ttgtcaagtg acatttcctt ttggttttgt ccgcactctt tctctctctc tctctctata     660
tatatatata tagcaactat tacattagaa tgctttgaat ccaaaattca agaactacaa     720
```

```
agtagctcat acaactaaga attacgacga aacttgttga agatatctta cgacgaaact    780
tcttaatatt agttgtactc gaagaataaa attggttttt aatttcggaa aaggtcaaat    840
attttgtctt tctgcgattg ttccatcaat ttaatgtaga gttttgttat tctcaagcat    900
atttcaatac tgccaattta tgtttggtga ctgaccgaca ggtgtggtgt acaaagtttt    960
actcaaagat caactatata atcttttttg gtgccataag atggagctcc cacgaaacaa   1020
acttgcagat ttgaaccaag gaaatgaaaa tttaaaggca aaggcaaagt ggacacccaa   1080
tgccaggagg ttcacagaac atcagattaa aagaattact aagaactata gaactcatgt   1140
tggcaaaggt gcctttggtg aggttttccg aggttttctt gacgatggca gtccagttgc   1200
agtgaagaag tacatgaacc agaatatgaa agaagggttt gacaaagaga taactatcca   1260
ttgccaagtc aaccacaaga acatagtcaa gcttttgggt tattgttcag aggaaaatgc   1320
cttgacgatg gtcactgagt acattcccag aggaaacctc aaagacctcc ttcatggaag   1380
tgatgatccc atttcttttg aggcaagatt gcgtattgct atagattgtg cagatgcatt   1440
agccttcatg cattcaaagg atccgccaat cattcacggt gacatcaaac ctgacaatat   1500
actcttggat gataacttgg gtgcaaaatt atctgacttt ggaatatcaa ggttgctttc   1560
tatggagaat agttatttta ctaataatgt aataggaagc agaggttaca tggatccaga   1620
acacattcag actggccggg ttgatcctaa gaatgatgtt tacagttttg gggttgtttt   1680
ggtagaacta gttaccagag ctatggcagc tcagaatggg acatgtaacg accttgcaaa   1740
gaaattcatt gaagctttcc tccaaaaaaa tatttttttg aaagttttg gaaagcaaaa   1800
aaaggcaaga agagagatgt tgatacccca gatagcaaat gcgagcaaca tggaggttct   1860
agaaaaaatt ggagagctgg caattgagtg tctcagaagg gatatcaaga aacgtcctga   1920
aatgaatcat gttgtagaac gtcttcgaat gcttggtaaa gatcacgaaa aaagacaaga   1980
tagaaagcca gaaaaggtaa gcctatgacg tctaaggttt tcaagctat agctcgagca   2040
cttctacccct tggttggggt gtgaccatgt gatgctgctt tagagaaagt tgcgcatatt   2100
ttcatttaaa aaaaatacat gggtcctccg tcttcatcta aataaacatc tcacaaaagc   2160
caacaccctcc atctaaaaaa agtaaaaaaa aaagtaaata atttaccacc gcagcctatc   2220
agcgggctcc actatgcata gccctccatt taaaaaaata catagggtcc tcaccttgat   2280
ctaaaaaaac atttataaaa atctcacctt catttaaaaa attttatttca aaagcttttt   2340
caccgcggcc aaccagcttg cgccacatgg catagctggt tggccgtcac cttcatttaa   2400
aaatcttatt ccaaaagtgt tttcaccgcg gccaaccagc ttgcgctacg tggcatagct   2460
ggttgaccgc caccttcatt taaaaagttt atttcaaaag cttttaatc acggccaacc   2520
agcttgcggc acgtggcata gctggttgac catcaccttg atttaaaaaa tatttcaaaa   2580
gcttttcac cgcggccaac cagcttgcgc acatggcat agctgattga ccatccttca   2640
cgctacgctt aatgggttta attaatgcaa accatatagt ccactaccgc atgacttggc   2700
ctgagttttt cagttcaaac catccaacag ctgttcttca tgtttagtta aatgttcaat   2760
ggccagtctg caaattgcac cagatggtgg cattcaatat gcatcaagtt ttgacgtgca   2820
acctcttgat ctcacgtgta ttgtaccggg gctgattaac aacttagctc ttcttttgctc   2880
cgtaaggtat tacttcctcc atgccaaaat agtctcaact ttgtactaaa gttgtactag   2940
gcttgagaca catattttga gacggaggga gtattaaata agcacataca aaaataaaaa   3000
gatattgaga gtggttttc tacacccag ttcagtgcac ccgcagtgca cccacacaag   3060
aaaacatagc aaaacatttt gaaaaatcag aaacattgtg agaatgatta tgaacaaatg   3120
```

```
ctatggatgc ttgcaaagtt tggtggtcaa ataacatccg aggagtttgt acaaaaaaac   3180
aaaattactc aaaatgtacg tgcactgttt gagcagaatt tgtaattttg tttttttgcag  3240 aactccttgc atgttatttg accaccaaac tttgcaagca tccataatac ttgctcataa   3300
ttattcccac aaagtttcat ttttttttca aaatacttcg ctatgttttc tcacgtgggt   3360
gcaccgagct agggttcagc acccatgttg cagactggag tagtcactag tatataaaat   3420
taattataaa ttttatgaat ctatggcaaa tgacaagttt ttcgggggtt ttcatgacct   3480
aaaaagaata tatttaatag catgcatgat gccctaatat acttaaagtt attcttctca   3540
atcaatcagc aacatggagt ggtgcctcct gatggtaata caacctttag ctcttcgtgg   3600
ccaaagggta gattagaaaa tggaaggaaa tcttcttcct ctgatgccaa gagtctgtaa   3660
gtggaagatt gccgtatttc tcttgcaagt acacatttcc tttttactct ttgttttgta   3720
cactttatcc ttttgatcc tttatcttag tttttacagt cttacgaccg tgttctctaa    3780
gtttctttag ttataatatc atctagatct cctaggaaca tacgtgtcag taattttgt    3840 attgttttat caattttat gagtactgtg agtgcatctc tcatcgtttt tcgtcagaac    3900
gctacagtag tactctagaa catcatgctc ccctttaatt gcattttca ttctaatcat    3960 tattttagcc tgttgagaaa tttaatcata gtctttgttg gttcctttat atggagccta   4020
ctctgtgtat cccattcaga taaacaatta ttttaatcta aaactaaaaa aagcaaggac   4080
cgcattatgt tttttttcgc gaatacgcaa aagctttgcg tatctttgca ttgatagata   4140
gagtagcaat atatgggagt cttacaagat gaaggaaagg ctaactagct cgtgcacaat   4200
gatggccagc atcggtagcc ttgacgcaca gacggcgggg tgtgcagccc gatcggacct   4260
agcctacgtc tccggcagga tgagggccat gcccttggcg ccggcgcgcg cccatagccg   4320
cgcctcctcc tggatcatgt gcactgcgcg tcccacggca ggctggtcgc cgtcgaatag   4380
acacccgttc cgccgcatta tgtctctccc tcttccgtca tttggttata gtatggacat   4440
tatgagcata tgatttggtc aatgttaaag aaagaaggcg cacactgtgc tggaacttgg   4500
agccatataa aaatgccttt ctaatttatt ttattatgga gaattgtttc tcaaacccctt   4560 tgtagctcca atgtaaaaaa taatttgaac tcttgaatta tgtctgctca tagatgcacc   4620
tcatacttat atctactgat gttttgtgt aaatttgttt acgttttgt tcagtgtcaa    4680 cctggtagaa tcaatatgac atctagtctt tatttttccgg caggttcagt catagggggg   4740
tggaagcagt agacgaagaa atcaacatc cattattgcg aagaacgtca attggaaatg    4800
gtctgtgaat acgacactgg agatggctgg tctattctct gattccttcc ataaatgttt   4860
tttgttccaa tacttaacaa agaactgctt aatttctgcc atttgcaggt cctccaggat   4920
catttcatga ttggacctgt gggaacgaca taggaggccc tgacgaagta ttctctggag   4980
gacactggcg tcttctcgga tgccagaatg gcaagaactt tgttttgtcc cttgctctgt   5040
ttcaattgtt gcaactgagc tgcttatttg acgtgttaat ttggattttt catcaggcct   5100
ccacattttt gaggcgctcg aggatgttga ttaccttgta agttgttgat gaatgtcagt   5160
atgaataggt agtttgaatc ttttggccg cataccttg ttgcttgatc catgtgcact    5220
tcccataggt aagagccgtt ggcaaagcaa tgaaggccgt tggtgtgatt gaggcaccct   5280
gcgaggctat atttcagctt ctcatgagca tggacagtag ccgttatgag taattcttct   5340
tttgtttcaa taaatcaacc ccacaattgt gtattagtac ctctttttc aaagaattct    5400 cattttttcac tgttttttctt tcgttatttt aggtgggact gcagcttctc gtatggtagt   5460
```

```
ctagtggagg aggtagatgg ccacactgca atactatacc ataggccaca cctagattgg    5520
ttcttgacgt atgttttgct tctttctgga attattcctt tttttcatg ctgtgttcta     5580 caagaagcat cgaactcact gcaaaattaa aagccacgag acatcttctt tctttcattg    5640
gcaaacaaac atgccattat cttatattca tgagtcatga caaatgttca cttattttac   5700
ttgtacattt ggtaggttta atgactacc tatgctagtt aacactccct ccgttcacta    5760
ttactagatg ttttggatat ttcagtatgg actacataca gctgaaatga gtgaataatt   5820
aaacacacta aaatgtgtct atgtacattc gattcggaaa aaaaattagc acatctcata   5880
atagtgaacg gaggaagtgt tgatttttg gtgtatatac atagaaatgt tgttccggct    5940
ggtgaacaca agctcataaa acctgatatt atctgatatt gtgcctttaa gctttagaat   6000
tatagagcat ctttcatcat ccaaccatac cacattttgg cgaatttcag tctttataaa   6060
attgttgtga tctagcatgg ttatgatgaa tactttaaca ggtttgtttg gcctcgtgat   6120
ctttgttatg tacgatattg gcagcgtaac gacgacggag gttacggttg gtattttcag   6180
agttctacac taatattgat gtgcacaagc accaaacata ggtacctcga atgtagtcat   6240
ttgttttcat gacttatgtt tgatggttgc attctgtaat tggtggtttg cagtggtgtt   6300
gttccaatcc agagagcacc cgaaatgtgg tccacagcca ggatttgtga gggcatacat   6360
tgagagtaag agaattgatc agatgaattc acttatgttg atgtattgtg gctaccagat   6420
ttccgttgct taacattttt ctcttttaca tttattttag ttggcgggtt caaaatttct    6480
ccactgaaaa cccgtaatgg aagaactcga acacaagtac aataccttat gaagatggat   6540
ttgaagggtt ggggcgttgg ttacttatcc tcgtttcagc agcattgcgt cctccgcatg   6600
ctgaacagta ttgctggtaa aactcttggt tctgtaataa tcttctgtac aacttttgca   6660
agataccaca attaatgtta tgtgtcctag tctctaaata ctattgagga tcatgtttgt   6720
tttgtttggg gcagagttta gggatttaga gtaacttatc ggaatgacta attttgtct    6780 tagtctatta gttggcagt gtccagacat tatcttacat tagatcattg taactggttc    6840
agagttattt gagctatttt actttgctca ctactccctc cgttctgaaa taattgtctt   6900
tctagatatt tcaacaagtg actacatacg gagcaaaatg agtgaatcta cactctaaaa  6960
catgtctata tacatccgta tgttgtagtc catttgagat ggctagagag acaattattt   7020
cggaacggag ggagtagtaa agagtcgttg tggtttgttg acgtcaattt tttttccatc  7080
ccaatgagcc caatgcaagt tcccttctct ccgggatgat gtgatggatc aatggttctt   7140
gcggtgattt tatgttacct tactaacaat attaatagtg tgtggttctt tttgaggttt   7200 ttttttgcg gtgaaaaagg aagctttatt taattactga tgatggtaag attacatcag   7260
tagccagcag gctaaccaga gcatcaggca catcgtgcaa ccacaactca gttcagtgct   7320
ctgctatcga ccaataggct agtcgatctg cagccctatt ctgcgaacga tcaaaacata   7380
aaaggacaag ctccctctct cctaacatct ccttagtttc ctcaataaca tggcccaagt    7440
atgacttatt catctccttc tcttttagta ccttcacagc cgcagcacaa tctgtctgaa   7500
cctgaagtgg tgccgtagag tgcatcattg ctgcccgtac tccctctctg attgccaaaa   7560
gttcagcttc aaaagcatcg ttgcaatgag gcacaaacca acaggccgaa agaacatgcc   7620
ttccgctgct gtctctagtt atcattgccg tgcccgcacc attatcttta tttggagggg   7680
aggttttctc cttttgccgt gttcaatccc tcattcagct tgaaacccg agttcttcaa     7740 aactaagcct atttccacct tgggtctcat cagatcatca ctatagattc tcaagccttc    7800
tcatcctgca tcttgttgta aactgccatt cacggcacac atctgaaatg tatgctccaa   7860
```

```
attttttatg tgactcaagt ttatctttat gcttgctaaa catctgcaaa aagaaaaaaa      7920
aatcttgtgt atcacatctt gtatattttc tacaatatga tcaacttgga ttgttagttc      7980
tgcaaatatt tagcagacca taacaaactt ttattgttgg tatatctctt cgtctctaga      8040
cactgtttaa ctactcgtta ttacacgcat atggatgccc aacatgagat atgatgttaa      8100
gttgatctgt gtgcagtacc acttacgctc tgcggcctca ccttcttttt ttctactgat      8160
agggctcagg gaatggtttt cacgaagtga tgaaattcca acttcgatgg atcaaagtag      8220
atattctaca atgcttgaag aggagtcaga tgaagacgag ttgtcttcag gaagtggtga      8280
aagttgatag gatttctgct aaggccagta tgattccatc tgtttcatcg aagtactgat      8340
cacaaagtat atattctaaa atgcttgaag aggaatcttt ttttcttcgc atacttgatg      8400
aggagtctgg ttgacaagaa taactcaaaa tgaaaccgtc atctaatggc cggcttcaaa      8460
tcagcgatag aattcctgga gctaaaaaga gctaaatctc ctgggcagga gatttacttg      8520
gtctagtgaa caacaaaatc caaccgtttg tttggttcac tgctcctatt tcccaccttg      8580
ggtctcatca gatcatcgct gtagattttc acgccttctc attcctcatc ttgttgtaaa      8640
ctgccattca cgtcacacat ctgcaattta tgctggaaat tttatatttg ggaatcaaga      8700
tttatcaata tccttgctaa gcttttgcaa ataactcttt tgtatcacac accttgcatc      8760
ttttctacag tatatgatca acttggattt acggtcctgc aaatatttag cagaccgtaa      8820
cgaactttta ttcttggtat atatactccc ttatcgtccc tagacactgc ttaaccactc      8880
gtttaagtct tattacacac gcatagggat gtccaacacg aatgatattc tgggaagttg      8940
atccgtgcaa tagcacttac acactgcagt ccggcgtccg cgccttcttt taccactgac      9000
agggttcagg gaatggtttt catgaatcta taggtcaa atcctgttgt aaactgacag      9060
gcctgtacca caaccaacta ctgaatctga atttcaagca ctaggccaga tctgaaattg      9120
aagctcttgt gtgtgtgtgt gtgtgttagc aaaaactaag acaaattaaa ggggaagtcc      9180
gatcagatta gcagtactac gtttatacag tgtaccttgg ctaatccggt ggtgagtcga      9240
cgcggttgcg gacgtacgca agggtagcaa cgaaggtcac ggcggca                   9287
```

<210> SEQ ID NO 10
<211> LENGTH: 1872
<212> TYPE: DNA
<213> ORGANISM: Triticum turgidum

<400> SEQUENCE: 10

```
atggagctcc cacgaaacaa acttgcagat ttgaaccaag gaaatgaaaa tttaaaggca       60
aaggcaaagt ggacacccaa tgccaggagg ttcacagaac atcagattaa aagaattact      120
aagaactata gaactcatgt tggcaaaggt gcctttggtg aggttttccg aggttttctt      180
gacgatggca gtccagttgc agtgaagaag tacatgaacc agaatatgaa agaagggttt      240
gacaaagaga taactatcca ttgccaagtc aaccacaaga acatagtcaa gcttttgggt      300
tattgttcag aggaaaatgc cttgacgatg gtcactgagt acattcccag aggaaacctc      360
aaagacctcc ttcatggaag tgatgatccc atttcttttg aggcaagatt gcgtattgct      420
atagattgtg cagatgcatt agccttcatg cattcaaagg atccgccaat cattcacggt      480
gacatcaaac ctgacaatat actcttggat gataacttgg gtgcaaaatt atctgacttt      540
ggaatatcaa ggttgctttc tatggagaat agttatttta ctaataatgt aataggaagc      600
agaggttaca tggatccaga acacattcag actggccggg ttgatcctaa gaatgatgtt      660
```

-continued

```
tacagttttg gggttgtttt ggtagaacta gttaccagag ctatggcagc tcagaatggg      720
acatgtaacg accttgcaaa gaaattcatt gaagctttcc tccaaaaaaa tattttttg       780 aaagttttg gaaagcaaaa aaggcaaga agagagatgt tgatacccca gatagcaaat        840
gcgagcaaca tggaggttct agaaaaaatt ggagagctgg caattgagtg tctcagaagg      900
gatatcaaga aacgtcctga aatgaatcat gttgtagaac gtcttcgaat gcttggtaaa      960
gatcacgaaa aaagacaaga tagaaagcca gaaaagcaac atggagtggt gcctcctgat      1020
ggtaatacaa cctttagctc ttcgtggcca aagggtagat tagaaaatgg aaggaaatct     1080
tcttcctctg atgccaagag tctgttcagt catagggggg tggaagcagt agacgaagaa    1140
aatcaacatc cattattgcg aagaacgtca attggaaatg gtcctccagg atcatttcat   1200
gattggacct gtgggaacga cataggaggc cctgacgaag tattctctgg aggacactgg    1260
cgtcttctcg gatgccagaa tggcctccac attttttgagg cgctcgagga tgttgattac  1320
cttgtaagag ccgttggcaa agcaatgaag gccgttggtg tgattgaggc accctgcgag    1380
gctatatttc agcttctcat gagcatggac agtagccgtt atgagtggga ctgcagcttc   1440
tcgtatggta gtctagtgga ggaggtagat ggccacactg caatactata ccataggcca   1500
cacctagatt ggttcttgac gttttgtttgg cctcgtgatc tttgttatgt acgatattgg  1560
cagcgtaacg acgacggagg ttacgtggtg ttgttccaat ccagagagca cccgaaatgt   1620
ggtccacagc caggatttgt gagggcatac attgagattg cgggttcaa aatttctcca    1680 ctgaaaaccc gtaatggaag aactcgaaca caagtacaat accttatgaa gatggatttg    1740
aagggttggg gcgttggtta cttatcctcg tttcagcagc attgcgtcct ccgcatgctg    1800
aacagtattg ctggtaaaac tcttggttct gtaataatct tctgtacaac ttttgcaaga    1860
taccacaatt aa                                                         1872
```

<210> SEQ ID NO 11
<211> LENGTH: 1659
<212> TYPE: DNA
<213> ORGANISM: Triticum turgidum

<400> SEQUENCE: 11

```
atggagctcc cacgaaacaa acttgcagat ttgaaccaag gaaatgaaaa tttaaaggca      60
aaggcaaagt ggacacccaa tgccaggagg ttcacagaac atcagattaa agaattact     120 aagaactata gaactcatgt tggcaaaggt gcctttggtg aggttttccg aggttttctt    180
gacgatggca gtccagttgc agtgaagaag tacatgaacc agaatatgaa agaagggttt    240
gacaaagaga taactatcca ttgccaagtc aaccacaaga acatagtcaa gcttttgggt    300
tattgttcag aggaaaatgc cttgacgatg gtcactgagt acattcccag aggaaacctc    360
aaagacctcc ttcatggaag tgatgatccc atttctttg aggcaagatt gcgtattgct     420
atagattgtg cagatgcatt agccttcatg cattcaaagg atccgccaat cattcacggt    480
gacatcaaac ctgacaatat actcttggat gataacttgg gtgcaaaatt atctgacttt    540
ggaatatcaa ggttgctttc tatggagaat agttatttta ctaataatgt aataggaagc    600
agaggttaca tggatccaga acacattcag actggccggg ttgatcctaa gaatgatgtt    660
tacagttttg gggttgtttt ggtagaacta gttaccagag ctatggcagc tcagaatggg    720
acatgtaacg accttgcaaa gaaattcatt gaagctttcc tccaaaaaaa tattttttg    780 aaagttttg gaaagcaaaa aaggcaaga agagagatgt tgatacccca gatagcaaat     840
gcgagcaaca tggaggttct agaaaaaatt ggagagctgg caattgagtg tctcagaagg    900
```

```
gatatcaaga aacgtcctga aatgaatcat gttgtagaac gtcttcgaat gcttggtaaa    960
gatcacgaaa aaagacaaga tagaaagcca gaaaagcaac atggagtggt gcctcctgat   1020
ggtaatacaa cctttagctc ttcgtggcca aagggtagat tagaaaatgg aaggaaatct   1080
tcttcctctg atgccaagag tctgttcagt catagggggg tggaagcagt agacgaagaa   1140
aatcaacatc cattattgcg aagaacgtca attggaaatg gtcctccagg atcatttcat   1200
gattggacct gtgggaacga cataggaggc cctgacgaag tattctctgg aggacactgg   1260
cgtcttctcg gatgccagaa tggcctccac atttttgagg cgctcgagga tgttgattac   1320
cttgtaagag ccgttggcaa agcaatgaag gccgttggtg tgattgaggc accctgcgag   1380
gctatatttc agcttctcat gagcatggac agtagccgtt atgagtggga ctgcagcttc   1440
tcgtatggta gtctagtgga ggaggtagat ggccacactg caatactata ccataggcca   1500
cacctagatt ggttcttgac gtttgtttgg cctcgtgatc tttgttatgt acgatattgg   1560
cagcgtaacg acgacggagg ttacggttgt ggtgttgttc caatccagag agcacccgaa   1620
atgtggtcca cagccaggat ttgtgagggc atacattga                           1659
```

```
<210> SEQ ID NO 12
<211> LENGTH: 1671
<212> TYPE: DNA
<213> ORGANISM: Triticum turgidum

<400> SEQUENCE: 12
atggagctcc cacgaaacaa acttgcagat ttgaaccaag gaaatgaaaa tttaaaggca     60
aaggcaaagt ggacacccaa tgccaggagg ttcacagaac atcagattaa agaattact    120 aagaactata gaactcatgt tggcaaaggt gcctttggtg aggttttccg aggttttctt    180
gacgatggca gtccagttgc agtgaagaag tacatgaacc agaatatgaa agaagggttt    240
gacaaagaga taactatcca ttgccaagtc aaccacaaga acatagtcaa gcttttgggt    300
tattgttcag aggaaaatgc cttgacgatg gtcactgagt acattccag aggaaacctc    360 aaagacctcc ttcatggaag tgatgatccc atttctttg aggcaagatt gcgtattgct    420
atagattgtg cagatgcatt agccttcatg cattcaaagg atccgccaat cattcacggt    480
gacatcaaac ctgacaatat actcttggat gataacttgg gtgcaaaatt atctgacttt    540
ggaatatcaa ggttgctttc tatggagaat agttatttta ctaataatgt aataggaagc    600
agaggttaca tggatccaga acacattcag actggccggg ttgatcctaa gaatgatgtt    660
tacagttttg gggttgtttt ggtagaacta gttaccagag ctatggcagc tcagaatggg    720
acatgtaacg accttgcaaa gaaattcatt gaagctttcc tccaaaaaa tatttttttg    780 aaagttttg gaaagcaaaa aaaggcaaga agagagatgt tgatacccca gatagcaaat    840
gcgagcaaca tggaggttct agaaaaaatt ggagagctgg caattgagtg tctcagaagg    900
gatatcaaga aacgtcctga aatgaatcat gttgtagaac gtcttcgaat gcttggtaaa    960
gatcacgaaa aaagacaaga tagaaagcca gaaaagcaac atggagtggt gcctcctgat   1020
ggtaatacaa cctttagctc ttcgtggcca aagggtagat tagaaaatgg aaggaaatct   1080
tcttcctctg atgccaagag tctgttcagt catagggggg tggaagcagt agacgaagaa   1140
aatcaacatc cattattgcg aagaacgtca attggaaatg gtcctccagg atcatttcat   1200
gattggacct gtgggaacga cataggaggc cctgacgaag tattctctgg aggacactgg   1260
cgtcttctcg gatgccagaa tggcctccac atttttgagg cgctcgagga tgttgattac   1320
```

```
cttgtaagag ccgttggcaa agcaatgaag gccgttggtg tgattgaggc accctgcgag    1380
gctatatttc agcttctcat gagcatggac agtagccgtt atgagtggga ctgcagcttc    1440
tcgtatggta gtctagtgga ggaggtagat ggccacactg caatactata ccataggcca    1500
cacctagatt ggttcttgac gtttgtttgg cctcgtgatc tttgttatgt acgatattgg    1560
cagcgtaacg acgacggagg ttacggttgg tattttcaga gttctacact aatattgatg    1620
tgcacaagca ccaaacatag gtacctcgaa tgtagtcatt tgttttcatg a             1671

<210> SEQ ID NO 13
<211> LENGTH: 1482
<212> TYPE: DNA
<213> ORGANISM: Triticum turgidum

<400> SEQUENCE: 13
atggagctcc cacgaaacaa acttgcagat ttgaaccaag gaaatgaaaa tttaaaggca      60
aaggcaaagt ggacacccaa tgccaggagg ttcacagaac atcagattaa agaattact     120 aagaactata gaactcatgt tggcaaaggt gcctttggtg aggttttccg aggttttctt    180
gacgatggca gtccagttgc agtgaagaag tacatgaacc agaatatgaa agaagggttt    240
gacaaagaga taactatcca ttgccaagtc aaccacaaga acatagtcaa gcttttgggt    300
tattgttcag aggaaaatgc cttgacgatg gtcactgagt acattcccag aggaaacctc    360
aaagacctcc ttcatggaag tgatgatccc atttcttttg aggcaagatt gcgtattgct    420
atagattgtg cagatgcatt agccttcatg cattcaaagg atccgccaat cattcacggt    480
gacatcaaac ctgacaatat actcttggat gataacttgg gtgcaaaatt atctgacttt    540
ggaatatcaa ggttgctttc tatggagaat agttatttta ctaataatgt aataggaagc    600
agaggttaca tggatccaga acacattcag actggccggg ttgatcctaa gaatgatgtt    660 tacagtttg gggttgtttt ggtagaacta gttaccagag ctatggcagc tcagaatggg    720
acatgtaacg accttgcaaa gaaattcatt gaagctttcc tccaaaaaaa tatttttttg    780 aaagttttg gaaagcaaaa aaaggcaaga agagagatgt tgataccca gatagcaaat    840 gcgagcaaca tggaggttct agaaaaaatt ggagagctgg caattgagtg tctcagaagg    900
gatatcaaga aacgtcctga aatgaatcat gttgtagaac gtcttcgaat gcttggtaaa    960
gatcacgaaa aaagacaaga tagaaagcca gaaaagcaac atggagtggt gcctcctgat   1020
ggtaatacaa cctttagctc ttcgtggcca aagggtagat tagaaaatgg aaggaaatct   1080
tcttcctctg atgccaagag tctgttcagt cataggggg tggaagcagt agacgaagaa   1140
aatcaacatc cattattgcg aagaacgtca attggaaatg gtcctccagg atcatttcat   1200
gattggacct gtgggaacga cataggaggc cctgacgaag tattctctgg aggacactgg   1260
cgtcttctcg gatgccagaa tggcctccac attttttgagg cgctcgagga tgttgattac   1320
cttgtaagag ccgttggcaa agcaatgaag gccgttggtg tgattgaggc accctgcgag   1380
gctatatttc agcttctcat gagcatggac agtagccgtt atgagtggga ctgcagcttc   1440
tcgtatggta gtctagtgga ggaggtttgt ttggcctcgt ga                        1482

<210> SEQ ID NO 14
<211> LENGTH: 1008
<212> TYPE: DNA
<213> ORGANISM: Triticum turgidum

<400> SEQUENCE: 14
atggagctcc cacgaaacaa acttgcagat ttgaaccaag gaaatgaaaa tttaaaggca      60
```

```
aaggcaaagt ggacacccaa tgccaggagg ttcacagaac atcagattaa aagaattact    120
aagaactata gaactcatgt tggcaaaggt gcctttggtg aggttttccg aggttttctt    180
gacgatggca gtccagttgc agtgaagaag tacatgaacc agaatatgaa agaagggttt    240
gacaaagaga taactatcca ttgccaagtc aaccacaaga acatagtcaa gcttttgggt    300
tattgttcag aggaaaatgc cttgacgatg gtcactgagt acattcccag aggaaacctc    360
aaagacctcc ttcatggaag tgatgatccc atttcttttg aggcaagatt gcgtattgct    420
atagattgtg cagatgcatt agccttcatg cattcaaagg atccgccaat cattcacggt    480
gacatcaaac ctgacaatat actcttggat gataacttgg gtgcaaaatt atctgacttt    540
ggaatatcaa ggttgctttc tatggagaat agttatttta ctaataatgt aataggaagc    600
agaggttaca tggatccaga acacattcag actggccggg ttgatcctaa gaatgatgtt    660
tacagttttg ggttgttttt ggtagaacta gttaccagag ctatggcagc tcagaatggg    720
acatgtaacg accttgcaaa gaaattcatt gaagctttcc tccaaaaaaa tattttttg    780 aaagttttg gaaagcaaaa aaaggcaaga agagagatgt tgataccca gatagcaaat    840 gcgagcaaca tggaggttct agaaaaaatt ggagagctgg caattgagtg tctcagaagg    900
gatatcaaga aacgtcctga aatgaatcat gttgtagaac gtcttcgaat gcttggtaaa    960
gatcacgaaa aaagacaaga tagaaagcca gaaaaggttc agtcatag                1008
```

<210> SEQ ID NO 15
<211> LENGTH: 2566
<212> TYPE: DNA
<213> ORGANISM: Triticum turgidum
<220> FEATURE:
<221> NAME/KEY: promoter
<222> LOCATION: (1)..(2566)

<400> SEQUENCE: 15

```
tgttggttgt tgaaataca aggaaaaac ccttttcgg caaatctgtg caaaagttac       60
cgatttcaat tgttgctgaa attttcctga aactgaaagc ggaaatccca catgccaaac   120
aattcgttgt gctgccatgt aggatgtaaa attgtgaata caaccccaac ttgcttcttc   180
gctgtcttga tctttggttg ttaaataaca ttgtcgaaaa gtacaacttg cttccttatc   240
tccttcgcta caactgtaag tctacgcgtg aaccaacctg tggttggatg gttaggagga   300
cagtggtatc cgcaaccctg atgggtttaa atcctggtgt ttgcatttat cctatgttta   360
ttttagaatt tccggcgatg tgtattcagt gggatgagac atttccgtct actacgaggc   420
gactacggtg acttcataaa ttatcaggat gatatgccgg ctcagtctct cgaatatgct   480
cataaagata gggtgagcgt ctgtgcgttc atagggtaag tgtatgcatg tatatatggg   540
cgtttgtgtc tgtattgtgt taaagaaaac tgtaggtcac gttttggacc gttccctct    600 ctcccgtctg caatagagag aggagaatct ttgggcgatc ccgtcttccc cacctcgccg   660
gcgccgattt cgacggatcc ctcggcctcc gccggccgct tcggcggcgg gaggctgggg   720
ggtccccgta tcacgtctgt atatagcgta ggggtaggta gggcttcagc cggcggcgct   780
agggaggtgg aggtgccggc gatggtgtgt ttgcggtcga tttgctcttc ctccggcgtt   840
agcgctctct ggagctcgag cgtgcgcgga ttgacttcct cgagctcttc gttcttcggt   900
gcatcgagct cgtcgttccc catccggtgc cggcgtgacg gcggccgttt tgaagatcct   960
gaaggagagg ttgcgattca ccaagatggc ctcgccgccc gtggtgcagg gtggaggtgt  1020
catgccgagg agcgtcgact tccttgtcgc cgaggggagc ctccgagtcc aagagtgcgg  1080
```

```
agggatggcg gcgggattcg ccggcgcagc gttctgctct gcggaagagg aagtcagagt    1140
tcagcaaggg cctacttgta atttctttgt tttcctggac ttttctgtaa gaatcttggt    1200
gtaatgcaat tcagtccttc tgcggaaaaa aaaagaaaaa ctgtaagtct acgccgagat    1260
cgagagagtt tcttctagat gagatcgaga gttgctcaca ttatcaacct tttcctttca    1320
aaaaaaggaa aaaaaaaaaa agaagactcc ggcgaatgac ttggacgcct tccgggtgcg    1380
acttggcggt ggtacaatta ttcagcgtac aaacaaaatg gaagaagat aggaagcgga     1440 cttgtgtaca gcgtaccacc agagaaacca cgagacgggg tctacccacc agctgtcaga    1500
aaaattggcg acgaaatggc caaacatgat taaagccagc cccttccgtt ggcgagcgca    1560
cacacagcgt tgctgctccc tcagcctctc cttccgcacc cctcttatca agtgtcggcc    1620
ggagcaatca gaagcagcta gctaggctag ctaacacgtc gtcggccttc tcaaaccagg    1680
ccgtcgtcgg ccggatatcg tctcaggccg tggtatgtat ccgcagctct cttccctttt    1740
tgatttgatc ttactttgct ggttcgatat tattttttct gcgaccacaa tcctcttttt    1800
gataggctag acccctttca ttagtaagga aatcaaagtt gtacctcgtc ggccacccct    1860
tgaatagcag ccagtccagc aaacgaactt aacaaccgag cgaactgaag ctcaaaacaa    1920
ggctgtctaa attctaaagt aaaacaaccc agacagggct gctagtttct cttctttggg    1980
atccaagggc tacagctttc taccagcttg atagacttca gccgtgacct gttccagtac    2040
ttttgcgcac atgtctgcag ttttagagat atttagcgga tgaggactaa agagcaatgt    2100
tcatgacttc aagatccaag atccccagcc caccatgatc ctttggcaaa cagacccgag    2160
gccggtttgt caagtgacat ttccttttgg ttttgtccgc actctttctc tctctctctc    2220
tctatatata tatatatagc aactattaca ttagaatgct ttgaatccaa aattcaagaa    2280
ctacaaagta gctcatacaa ctaagaatta cgacgaaact tgttgaagat atcttacgac    2340
gaaacttctt aatattagtt gtactcgaag aataaaattg gttttttaatt tcggaaaagg    2400 tcaaatattt tgtctttctg cgattgttcc atcaatttaa tgtagagttt tgttattctc    2460
aagcatattt caatactgcc aatttatgtt tggtgactga ccgacaggtg tggtgtacaa    2520
agttttactc aaagatcaac tatataatct tttttggtgc cataag                   2566
```

<210> SEQ ID NO 16
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 16
ggagcagcca catcgtcg                                                   18

<210> SEQ ID NO 17
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 17
gcctgctcca acaaccatc                                                  19

<210> SEQ ID NO 18
<211> LENGTH: 18
<212> TYPE: DNA

```
<213> ORGANISM: Artificial Sequence
<220> FEATURE:
<223> OTHER INFORMATION: synthetic oligonucleotide

<400> SEQUENCE: 18
gtctgtccat gggttctc                                              18

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 19
gtcatgaagc cttggttgaa g                                          21

<210> SEQ ID NO 20
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 20
ggagtggaac cagaggagc                                             19

<210> SEQ ID NO 21
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 21
atgatgtgca ccatgcgg                                              18

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22
gctggaggtg agtggtgaat                                            20

<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 23
aatctcctcc cttcgatgct                                            20

<210> SEQ ID NO 24
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 24
ttagatggag tcccgtggag                                            20
```

<210> SEQ ID NO 25
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 25
tgaagccagc aatgaagttg                                               20

<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
aaggactctg ctcctgacga                                               20

<210> SEQ ID NO 27
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 27
gaagatgctc tgaacgcaca                                               20

<210> SEQ ID NO 28
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 28
aaggactctg ctcctgacga                                               20

<210> SEQ ID NO 29
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 29
tgtcgaggga cacaatacca                                               20

<210> SEQ ID NO 30
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 30
caagcgatgt caacatgtcc                                               20

<210> SEQ ID NO 31
<211> LENGTH: 20
<212> TYPE: DNA
<213> ORGANISM: Artificial Sequence
<220> FEATURE:

<223> OTHER INFORMATION: synthetic oligonucleotide

<400> SEQUENCE: 31
tcaaatgaca gctccactcg                                                      20

<210> SEQ ID NO 32
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 32
gatggtgcct gcgataattt                                                      20

<210> SEQ ID NO 33
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 33
gctgtcgaca ttcccctaga                                                      20

<210> SEQ ID NO 34
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 34
cacgcaaata aatgctggtg                                                      20

<210> SEQ ID NO 35
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 35
tgcatagttt cagccaggtg                                                      20

<210> SEQ ID NO 36
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 36
ccctttgtgc cacatttctt                                                      20

<210> SEQ ID NO 37
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 37
ggcaggtgga agtcaacatt                                                      20

```
<210> SEQ ID NO 38
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 38
gtacgtcctg ctcaccatca                                               20

<210> SEQ ID NO 39
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 39
agaagaacaa cggaggacga                                               20

<210> SEQ ID NO 40
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 40
acccgtaaga tgcaataact tg                                            22

<210> SEQ ID NO 41
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 41
gcaggactgc tcttgaag                                                 18

<210> SEQ ID NO 42
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 42
agttgtcatg taataggttg tacc                                          24

<210> SEQ ID NO 43
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 43
atacatcagt atktatgtgg catg                                          24

<210> SEQ ID NO 44
<211> LENGTH: 26
<212> TYPE: DNA
<213> ORGANISM: Artificial Sequence
<220> FEATURE:
<223> OTHER INFORMATION: synthetic oligonucleotide
```

```
<400> SEQUENCE: 44
ctttgtttcc tgtatacgaa tgcttt                                          26

<210> SEQ ID NO 45
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 45
agaagaattt acaaatacac agc                                             23

<210> SEQ ID NO 46
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 46
gcatgtttca gtttggttat ca                                              22

<210> SEQ ID NO 47
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 47
ctcatcatca catcacaaag gaa                                             23

<210> SEQ ID NO 48
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 48
aacataagag ggaggtcgag                                                 20

<210> SEQ ID NO 49
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 49
gaacaagagc acagcacgtt gt                                              22

<210> SEQ ID NO 50
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 50
aagaataaaa ttggttttta atttcggaaa aggtc                                35

<210> SEQ ID NO 51
<211> LENGTH: 29
```

```
<212> TYPE: DNA
<213> ORGANISM: Artificial Sequence
<220> FEATURE:
<223> OTHER INFORMATION: synthetic oligonucleotide

<400> SEQUENCE: 51
atggaggtgt tggcttttgt gagatgttt                                    29

<210> SEQ ID NO 52
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 52
tgctggaact tggagccata taaaaatgc                                    29

<210> SEQ ID NO 53
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 53
tgaacggagg gagtgttaac tagcatagg                                    29

<210> SEQ ID NO 54
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 54
gccatgaaca acgaacaatc acacgata                                     28

<210> SEQ ID NO 55
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 55
taagttgtta ctcagcccca gcgcaatac                                    29

<210> SEQ ID NO 56
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 56
tctgctccca gacccacctc atacttaaa                                    29

<210> SEQ ID NO 57
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 57
```
gcaaaagaga aaaatgttaa gcagcggaaa                              30

<210> SEQ ID NO 58
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 58
aattacctgc aggtgaatgt ttcgacgcg                               29

<210> SEQ ID NO 59
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 59
aattagcggc cgctcctgga ctacctcc                                28

<210> SEQ ID NO 60
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 60
gtggccaaag ggtagattag                                         20

<210> SEQ ID NO 61
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 61
catcattgtg cacgagctag                                         20

<210> SEQ ID NO 62
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 62
atggagctcc cacgaaacaa ac                                      22

<210> SEQ ID NO 63
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 63
gagactagga cacataacat taattg                                  26

<210> SEQ ID NO 64
<211> LENGTH: 22
<212> TYPE: DNA
<213> ORGANISM: Artificial Sequence

```
<220> FEATURE:
<223> OTHER INFORMATION: synthetic oligonucleotide

<400> SEQUENCE: 64
actttcacca cttcctgaag ac                                          22

<210> SEQ ID NO 65
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 65
atcgtctcag gccgtggta                                              19

<210> SEQ ID NO 66
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 66
ccactttgcc tttgccttta                                             20

<210> SEQ ID NO 67
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 67
aatcaacatc cattattgcg aaga                                        24

<210> SEQ ID NO 68
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 68
atacttcgtc agggcctcct atg                                         23

<210> SEQ ID NO 69
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 69
cacaagtaca ataccttatg aagatgg                                     27

<210> SEQ ID NO 70
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 70
cctgagccca gcaatactgt                                             20
```

<210> SEQ ID NO 71
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 71
ctccactgaa aacccgtaat g                                      21

<210> SEQ ID NO 72
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 72
aaccaagagt tttaccagca atactg                                 26

<210> SEQ ID NO 73
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 73
atcacgaacg tttgtttagt caagaa                                 26

<210> SEQ ID NO 74
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 74
gaggaccatt tgcaattgat gtt                                    23

<210> SEQ ID NO 75
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 75
accttcagtt gcccagcaat                                        20

<210> SEQ ID NO 76
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 76
cagagtcgag cacaatacca gttg                                   24

<210> SEQ ID NO 77
<211> LENGTH: 21
<212> TYPE: DNA
<213> ORGANISM: Artificial Sequence
<220> FEATURE:
<223> OTHER INFORMATION: synthetic oligonucleotide

```
<400> SEQUENCE: 77
atccattgcc aagtcaacca c                                          21

<210> SEQ ID NO 78
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 78
tcacttccat gaaggaggtc                                            20

<210> SEQ ID NO 79
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 79
cgaagaaaat caacatccat tatt                                       24

<210> SEQ ID NO 80
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 80
gtgtggccat ctacctcctc                                            20

<210> SEQ ID NO 81
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 81
gaaaaatcag aaatatttta cgtgga                                     26

<210> SEQ ID NO 82
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 82
agctgcagtc ccacctaaaa                                            20

<210> SEQ ID NO 83
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 83
ggccacactg caatactata cc                                         22

<210> SEQ ID NO 84
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 84
cacaaatcct ggctgtggac                                               20

<210> SEQ ID NO 85
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 85
ttgaattcat ggagctccca cgaaaca                                       27

<210> SEQ ID NO 86
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 86
tcacttccat gaaggaggtc                                               20

<210> SEQ ID NO 87
<211> LENGTH: 649
<212> TYPE: PRT
<213> ORGANISM: Triticum turgidum

<400> SEQUENCE: 87
```

Met Glu Leu Pro Arg Asn Lys Val Ala Gly Ser Asn Gln Gly Asn Glu
1               5                   10                  15

Asn Leu Lys Ala Lys Ala Lys Trp Gly Ser Asp Ile Lys Lys Phe Ser
            20                  25                  30

Glu His Gln Ile Lys Arg Ile Thr Lys Asn Tyr Ser Thr His Val Gly
        35                  40                  45

Lys Gly Ala Phe Gly Glu Val Phe Arg Gly Phe Leu Asp Asp Gly Ser
    50                  55                  60

Pro Val Ala Val Lys Lys Tyr Ile His Gln Asn Met Lys Glu Trp Phe
65                  70                  75                  80

Asp Lys Glu Ile Thr Ile His Cys Gln Val Asn His Lys Asn Ile Val
                85                  90                  95

Lys Leu Leu Gly Tyr Cys Ser Glu Glu Asn Ala Leu Met Met Leu Thr
            100                 105                 110

Glu Tyr Ile Pro Arg Gly Asn Leu Lys Asp Leu Leu His Gly Ser Asp
        115                 120                 125

Asp Pro Ile Ser Phe Glu Ala Arg Leu Cys Ile Ala Ile Asp Cys Ala
    130                 135                 140

Glu Ala Leu Ala Phe Met His Ser Met Ser Pro Pro Ile Ile His Gly
145                 150                 155                 160

Asp Ile Lys Pro Asp Asn Ile Leu Leu Asp Asp Asn Leu Gly Ala Lys
                165                 170                 175

Leu Ala Asp Phe Gly Ile Ser Arg Leu Leu Ser Met Asp Asn Thr His
            180                 185                 190

Phe Thr Met Asn Val Ile Gly Ser Arg Gly Tyr Met Asp Pro Glu His

-continued

```
            195                 200                 205
Ile Glu Thr Gly Arg Val Asp Pro Lys Ile Asp Val Tyr Ser Phe Gly
210                 215                 220

Val Val Leu Val Glu Leu Val Thr Arg Asp Met Ala Ser Gln Asn Gly
225                 230                 235                 240

Ile Cys Asn Gly Leu Ala Arg Asn Phe Ile Gly Ala Ser Leu Thr Lys
                245                 250                 255

Asn Asn Phe Phe Ser Glu Ala Phe Gly Lys Gln Lys Lys Ala Arg Glu
                260                 265                 270

Met Phe Asp Ile Gln Ile Ala Asn Met Ser Asn Met Glu Val Leu Asp
            275                 280                 285

Lys Phe Gly Glu Leu Ala Val Glu Cys Leu Arg Arg Asp Ile Lys Lys
290                 295                 300

Arg Pro Glu Met Asn His Val Leu Glu Arg Leu Met Leu Gly Lys
305                 310                 315                 320

Asp His Glu Lys Gly Gln Asp Arg Val Lys Glu His Gly Val Leu Pro
                325                 330                 335

Pro Phe Ser Ser Gln Pro Lys Gly Arg Leu Glu Thr Gly Arg Lys
                340                 345                 350

Ser Ser Ser Ser Asp His Glu Arg Leu Phe Ser Gln Glu Val Val Glu
                355                 360                 365

Gln Glu Glu Lys Asn Gln Lys Tyr Phe Thr Trp Arg Thr Ser Ile Ala
370                 375                 380

Asn Gly Pro Pro Glu Ser Phe Tyr Asp Trp Ile Arg Gly Asn Asp Leu
385                 390                 395                 400

Glu Ile Pro Asn Gln Arg Ser Pro Asp Glu Val Phe Ser Arg Gly Arg
                405                 410                 415

Trp Arg Leu Leu Thr Cys Gln Asn Gly Leu Arg Ile Phe Glu Val Leu
                420                 425                 430

Glu Pro Ala Val Tyr Leu Ala Arg Ala Ile Gly Lys Ala Met Lys Ala
                435                 440                 445

Val Gly Val Ile Asp Ala Ser Ser Glu Ala Ile Phe Gln Leu Val Met
            450                 455                 460

Ser Met Asp Asp Thr Arg His Lys Trp Asp Cys Ser Tyr Lys Tyr Gly
465                 470                 475                 480

Ser Leu Val Glu Glu Val Asp Gly His Thr Ala Ile Leu Tyr His Arg
                485                 490                 495

Leu Arg Leu Asp Trp Phe Leu Thr Phe Val Trp Pro Arg Asp Leu Cys
                500                 505                 510

Tyr Val Arg His Trp Arg Arg Tyr Tyr Asp Gly Ser Tyr Val Val Leu
                515                 520                 525

Phe Gln Ser Arg Glu His Pro Asn Cys Gly Pro Gln Pro Gly Phe Val
            530                 535                 540

Arg Ala His Val Glu Ile Gly Gly Phe Arg Ile Ser Pro Leu Lys Ser
545                 550                 555                 560

His Glu Gly Arg Pro Arg Thr Gln Val Gln Tyr Leu Met Gln Ile Asp
                565                 570                 575

Leu Lys Gly Trp Gly Val Gly Tyr Leu Ser Ser Phe Gln Gln His Cys
                580                 585                 590

Val Leu Arg Met Leu Asn Thr Ile Ala Glu Leu Arg Glu Trp Phe Ser
            595                 600                 605

Arg Ser Asp Asp Arg Pro Ile Ser Ala Lys Ala Ser Leu Thr Met Asp
610                 615                 620
```

```
Gln Ser Lys Cys Thr Thr Ile Leu Glu Glu Glu Phe Asp Glu Asp Glu
625                 630                 635                 640

Trp Leu Ser Gln Ser Asp Glu Ser Gln
                645

<210> SEQ ID NO 88
<211> LENGTH: 679
<212> TYPE: PRT
<213> ORGANISM: Oryza sativa

<400> SEQUENCE: 88

Met Glu Val Pro Glu Ser Lys Leu Gly Asp Phe Ile Gln Gly Asp Asp
1               5                   10                  15

Arg Ala Lys Trp Ile Ala Asp Ser Asn His Asn Ile Thr Lys Phe Thr
            20                  25                  30

Glu Asp Glu Ile Lys Arg Ile Thr Asp Asn Tyr Ser Thr Val Ile Gly
        35                  40                  45

Lys Gly Gly Phe Gly Gln Val Tyr Lys Gly Val Leu Asp Asp Asn Arg
    50                  55                  60

Val Val Ala Val Lys Arg Tyr Ile Phe Glu Asp Ser Met Glu Asp Leu
65                  70                  75                  80

Ala Lys Glu Val Ile Ala His Ser Gln Val Asn His Lys Asn Val Val
                85                  90                  95

Arg Leu Val Gly Tyr Ser Ile Glu Gln Asn Asn Ala Leu Met Val Val
            100                 105                 110

Thr Glu Tyr Val Ser Lys Gly Ser Leu His Asp Ile Leu His Gln Ser
        115                 120                 125

Asp Thr Pro Ile Ser Leu Asp Thr Arg Leu Cys Ile Ala Ile Gln Cys
    130                 135                 140

Ala Glu Ala Leu Gly Tyr Met His Ser Ser Met Tyr Thr Pro Ile Val
145                 150                 155                 160

His Gly Asp Ile Lys Pro Ser Asn Ile Leu Leu Asp Asp Asn Leu Asp
                165                 170                 175

Ala Lys Ile Ser Asp Phe Gly Ile Ser Arg Phe Leu Tyr Gly Gly Lys
            180                 185                 190

Thr Arg His Thr Lys Asn Val Lys Gly Ser Ile Asp Tyr Met Asp Pro
        195                 200                 205

Ile Leu Phe Arg Asp Gly Thr Gln Ser Ser Lys Asn Asp Val Tyr Ser
    210                 215                 220

Phe Gly Ala Val Leu Leu Glu Leu Ile Thr Arg Lys Arg Ile Lys Glu
225                 230                 235                 240

Glu Gly Lys Val Ser Leu Ile Thr Ser Phe Thr Glu His Asp Ser Glu
                245                 250                 255

Gly Lys Arg Met Lys Asp Leu Phe Asp Ala Asn Ile Ala Ser Val Ser
            260                 265                 270

Asn Met Lys Ile Ile Asn Gln Ile Gly Lys Leu Ala Thr Lys Cys Leu
        275                 280                 285

Ala Met Asp Met Lys Lys Arg Pro Lys Met Asn Ile Val Ala Glu His
290                 295                 300

Leu Arg Lys Leu Arg Glu Tyr Arg Asn Gly His Asp Asn Thr
305                 310                 315                 320

Leu Trp Arg Ser Phe Ser Val Thr Gln Asp Leu Phe Glu Lys Tyr Lys
                325                 330                 335

Gln Ser Thr Arg Asn Ala Ser Tyr Gly Ser Thr Lys His Pro Lys Lys
```

```
                340                 345                 350
Lys Lys Lys Lys Ser Phe Ala Ile Phe Lys His Asn Ser Gly Asn Ser
            355                 360                 365

Lys Leu Leu Glu Lys Leu Gly Ala Val Arg Ile Phe Thr Lys Lys Glu
        370                 375                 380

Leu Lys Lys Phe Thr Met Asp Tyr Ser Cys Leu Leu Lys Asp Gly
385                 390                 395                 400

Leu Ala Glu Tyr His Arg Gly Ile Leu Glu Asp Asn Thr Leu Val Thr
                405                 410                 415

Val Lys Thr Pro Tyr Asp Gly Asp Glu Ser Leu Lys Asn Cys Phe Leu
            420                 425                 430

Met Glu Met Met Ile Leu Ser His Ile Ser His Lys Asn Met Val Lys
            435                 440                 445

Leu Leu Gly Cys Cys Leu Glu Ala Asn Ile Pro Ile Leu Val His Glu
        450                 455                 460

Tyr Thr Ala Lys Gly Ser Leu Ser Asp Ile Val His His Gln Pro Gly
465                 470                 475                 480

Tyr Phe Ser Leu Pro Leu Arg Leu Lys Ile Ala Ser Glu Thr Ser Glu
                485                 490                 495

Ala Leu Ala His Ile His Ser Ser Thr Val Gly Gly Ile Val His Gly
            500                 505                 510

Pro Leu Thr Pro Tyr Asp Val Leu Leu Asp Glu Asn Phe Met Pro Met
            515                 520                 525

Val Ser Cys Phe Leu Ser Ser Arg Ser Ile Thr Lys Asp Lys Asp His
        530                 535                 540

Ile Val Pro Val Leu Arg Met Thr Arg Cys Asn Asp Pro Val Tyr Met
545                 550                 555                 560

Gln Thr Gly Ile Ala Lys Asn Glu Ser Phe Val Tyr Ser Phe Gly Val
                565                 570                 575

Ile Leu Met Val Leu Ile Arg Gly Arg Met Pro Lys Asp His Asn Phe
            580                 585                 590

Val Ser Glu Phe Ile Gln Ala Tyr Glu Ala Glu Asp Ser Gly Glu Arg
            595                 600                 605

Met Phe His Leu Ser Ile Thr Gly Asp Gln Glu Asp Arg Met Ala Ile
        610                 615                 620

Leu Glu Glu Met Gly Arg Met Ala Val Arg Cys Val Ser Pro Glu Glu
625                 630                 635                 640

Asp Gly Arg Pro Thr Met Ala Glu Val Ala Glu Arg Leu Glu Leu Leu
                645                 650                 655

Arg Ser Gln Asn Phe Asp Ser Ala Val Glu Asp His Asp Ala His Thr
            660                 665                 670

Tyr Ala Trp Arg Lys Ser Leu
            675

<210> SEQ ID NO 89
<211> LENGTH: 873
<212> TYPE: PRT
<213> ORGANISM: Oryza sativa

<400> SEQUENCE: 89

Met Glu Ser Cys Val Cys Ala Cys Ala Trp Pro Thr Ala Pro Thr Val
1               5                   10                  15

Val Ala Leu Phe Ala Thr Gly Tyr Glu Glu Gly Val Ala Glu Ala Pro
            20                  25                  30
```

-continued

His Asp Val Asp Pro Met Thr Asn Gly His Val Val Phe Gln Arg Val
        35                  40                  45

Glu Asn Asn Cys Ser Leu Arg Tyr Phe Thr Glu Asn Glu Ile Arg Gln
 50                  55                  60

Ile Thr Arg Gly Tyr Ser Ile Leu Leu Gly Lys Gly Ser Phe Gly Lys
65                   70                  75                  80

Val Tyr Lys Gly Met Leu Asp Gly Arg Cys Pro Val Ala Val Lys Arg
                85                  90                  95

Tyr Ile His Gly Thr Arg Lys Glu Glu Phe Ala Lys Glu Val Ile Val
            100                 105                 110

His Ser Gln Ile Asn His Lys Asn Val Val Arg Leu Leu Gly Cys Cys
        115                 120                 125

Thr Glu Glu Asn Ala Leu Met Ile Val Met Glu Phe Ile Cys Asn Gly
130                 135                 140

Asn Leu Asn Asp Ile Leu His Cys Ser Asn Thr Asn Gly Arg Val Pro
145                 150                 155                 160

Phe Ser Leu Gly Lys Arg Leu Asp Ile Ala Ile Glu Val Ala Glu Val
                165                 170                 175

Leu Trp Cys Met His Ser Met Tyr Asn Pro Val Leu His Gly Asp Ile
            180                 185                 190

Lys Pro Ala Asn Ile Leu Val Asp Glu Asn Leu Ser Pro Lys Leu Ser
        195                 200                 205

Asp Phe Gly Ile Ala Arg Leu Leu Cys Ala Asn Gly Ala Gln His Thr
    210                 215                 220

Asn Asn Ile Ile Gly Ser Ile Gly Tyr Val Asp Pro Ala Phe Cys Met
225                 230                 235                 240

Asn Gly Ile Leu Thr Pro Lys Ser Asp Val Tyr Ser Phe Gly Val Val
                245                 250                 255

Leu Leu Glu Ile Ile Thr Arg Lys Lys Ala Val Asp Gly Thr Ile Thr
            260                 265                 270

Leu Ala Gln Arg Phe Thr Glu Ala Val Glu Gln Gly Lys Lys Val Met
        275                 280                 285

His Leu Phe Asp Glu Asp Ile Asn Asn Thr Lys Asn Met Asn Phe Leu
    290                 295                 300

Glu Asp Ile Gly Lys Leu Ala Val Lys Cys Leu Arg Arg Glu Val Glu
305                 310                 315                 320

Val Arg Pro Glu Met Val Glu Val Ala Thr Ser Leu Arg Met Ile Arg
                325                 330                 335

Lys Ala Leu Glu Glu Glu Gly Asn Leu Ile Gln Gln Asn Ile Ser
        340                 345                 350

Ala Pro Ser Asn Ser Ile Pro Ser Lys Asn Val Lys Ser Ser Ala Gln
    355                 360                 365

Gln Phe Gly Asn Leu Lys Ile Phe Lys Gln Glu Ile Lys Leu Met
        370                 375                 380

Thr Lys Asn Tyr Ser Met Lys Phe Arg Glu Glu Phe Cys Glu Arg Leu
385                 390                 395                 400

Tyr Asn Gly Val Ile Gly Thr Thr His Ala Val Ile Val Lys Gln Val
                405                 410                 415

Arg Thr Ser Ser Glu Ser Asp Arg Met Met Phe Leu Lys Thr Met Ser
            420                 425                 430

Ile Leu Ser Gln Lys Tyr His Lys Asn Ile Ala Asn Val Ala Gly Phe
        435                 440                 445

His Leu Gly Asp Ser Ile Ser Glu Cys Val Tyr Glu Ser Cys Cys Asp

```
            450                 455                 460
Leu Ser Gln Gly Asn Asp Gly His Val Cys Phe Cys Asn Arg Asn Leu
465                 470                 475                 480

Tyr Asp Ile Ile Cys Thr Arg Glu Lys Leu Pro Leu His Leu Arg Leu
                    485                 490                 495

Ser Ile Ala Val Gln Cys Ala Glu Gly Leu Val His Ile His Ser Leu
                500                 505                 510

Leu Ala Glu Asn Pro Asp Ser His Ser Thr Gly Leu Leu Gly Asn Phe
            515                 520                 525

Arg Ser Ile Asn Ile Phe Leu Asp Lys Asn Phe Val Pro Lys Val Phe
        530                 535                 540

Asn Ser Asn Leu Ser Thr Phe Leu Gly Leu Ser Val Met Gln Lys His
545                 550                 555                 560

Thr Ala Ser Val Asp Arg Pro Asn Asp Gln Arg Ser Gln Ile Tyr Tyr
                    565                 570                 575

Leu Asp Gly Arg Asp Ile Ser Gly Gln Leu Phe Asn Pro Lys Ser Asp
                580                 585                 590

Val Tyr Ser Phe Gly Ala Val Leu Leu Glu Leu Ile Thr Trp Lys Thr
            595                 600                 605

Val Arg Tyr Met Ser Ser Gly Arg Val His Met Leu Thr Lys Asp Phe
        610                 615                 620

Leu Asp Thr Tyr Arg Ile Asp His Ser Ala Ala Ile Ser Phe Gly Lys
625                 630                 635                 640

Lys Val Tyr Asp Glu Gln Ala Ser Gly Asp Asn Lys Pro Asn Gln His
                    645                 650                 655

Val Ala Pro Pro Leu Thr Lys Lys Phe Val Lys Thr Pro Pro Thr Ile
                660                 665                 670

Val Ser Ile Ile Pro Leu Asn Ile Leu Glu Lys Ile Thr Ser Asn Phe
            675                 680                 685

Ser Asn Asp Ala Leu Ile Gly Glu Gly Pro Asp Ala Arg Val Phe Phe
        690                 695                 700

Gly Glu Leu Ser Asp Gly Gln Lys Ser Ala Ile Lys Lys Leu Asp Pro
705                 710                 715                 720

Asn Glu Lys Ile Val Val Gln Val Leu Thr Ile Ser Arg Met Leu Lys
                    725                 730                 735

His Asp Asn Ile Val Gln Ile Leu Gly Tyr Phe Ile Glu Gly Glu Asn
                740                 745                 750

Arg Val Leu Ala Tyr Glu Tyr Ala Pro Lys Gly Ser Leu His Asp Ile
            755                 760                 765

Leu His Glu Gly Val Arg Gly Ala Gln Pro Gly Thr Pro Leu Ser Trp
        770                 775                 780

Glu Gln Arg Val Lys Ile Ala Leu Ser Ala Ala Lys Gly Leu Glu Phe
785                 790                 795                 800

Leu His Glu Lys Ala Val Pro Pro Val Ile His Thr Asn Ile Arg Ser
                    805                 810                 815

Asn Asn Ile Phe Ile Phe Gly Asn Asp Val Ala Lys Ile Gly Asp Leu
                820                 825                 830

Gly Val Ser Lys Gln Leu Tyr Pro Glu Ser Asp Asn Asp Tyr Tyr Asn
            835                 840                 845

Thr Arg Leu Tyr Pro Leu Arg Ser Phe Gly Tyr Asp Ala Ile Ala Pro
        850                 855                 860

Glu Tyr Ala Met Lys Asp Phe His Ala
865                 870
```

<210> SEQ ID NO 90
<211> LENGTH: 677
<212> TYPE: PRT
<213> ORGANISM: Oryza sativa

<400> SEQUENCE: 90

Met Gly Asp Trp Tyr Asp Lys Leu Ser Gln Ser Phe Arg Asp Thr Ala
1               5                   10                  15

Lys Glu Val Leu Ala Lys Ala Asp Ile Asp Pro Asn Val Arg Cys Phe
            20                  25                  30

Thr Arg Arg Gln Met Lys Arg Ile Thr Asn Asn Tyr Ser Thr Thr Leu
        35                  40                  45

Gly Arg Gly Gly Phe Ser Val Val Tyr Lys Gly Met Leu Asp Asp Gly
    50                  55                  60

His Ser Val Ala Val Lys Gln Tyr Asn Trp Arg Thr Gln Lys Lys Glu
65                  70                  75                  80

Phe Thr Lys Glu Val Ile Ile Gln Ser Gln Cys Ser His Arg Asn Ile
                85                  90                  95

Val Arg Leu Leu Gly Cys Cys Val Glu Ala Asp Ala Pro Met Leu Val
            100                 105                 110

Thr Glu Phe Val Pro Asn Gly Asn Leu Ser Glu Leu Leu His Gly Asn
        115                 120                 125

Ile Gly Gln Leu Pro Val Ser Leu Glu Thr Arg Phe Gln Ile Ala Leu
    130                 135                 140

Asp Val Ala Glu Ala Val Val Tyr Met His Tyr Ser Gln Asn His Pro
145                 150                 155                 160

Ile Leu His Gly Asp Ile Lys Pro Ser Asn Ile Leu Leu Gly Asp Lys
                165                 170                 175

Tyr Val Ala Lys Leu Cys Asp Phe Gly Ile Ser Arg Leu Leu Cys Met
            180                 185                 190

Asp Asn Asp Glu Tyr Thr Gly Phe Val Ile Gly Ser Met Gly Tyr Met
        195                 200                 205

Asp Pro Val Tyr Arg Glu Thr Gly Arg Leu Ser Pro Lys Cys Asp Val
    210                 215                 220

Tyr Ser Phe Gly Val Val Leu Leu Glu Leu Ile Thr Arg Ser Lys Gly
225                 230                 235                 240

Ile Asp Asp Gln Asn Arg Ser Leu Ala Arg Val Phe Ala His Ser Ser
                245                 250                 255

Ile Asp Glu Arg Tyr Lys Leu Phe Asp Asn Glu Ile Val Thr Asn Glu
            260                 265                 270

Asn Val Asp Phe Ile Gln Glu Met Ala Asn Leu Ala Leu Asp Cys Leu
        275                 280                 285

Lys Ser Glu Ile Glu Asp Arg Pro Gln Met Lys Glu Val Leu Glu His
    290                 295                 300

Leu Tyr Ser Leu Lys Arg Lys Met Leu Glu Glu Arg Lys Ile Ala
305                 310                 315                 320

Glu Leu Met Glu Glu Arg Arg Ile Ala Glu Leu Thr Glu Arg Arg Thr
                325                 330                 335

Val Ala Phe Arg Glu Ile Lys Ala Ile Leu Gln Asp Ile Gly Phe Glu
            340                 345                 350

Arg Leu Val Thr Lys Glu Lys Ile Asp Ser Ile Val Gly Asn Pro Lys
        355                 360                 365

Gln Val Ser Thr Ser Glu Ala Phe Ser Gly Lys Ser Ser Val Leu Ile

```
                370                 375                 380
Gln Arg Ala Ile Gly Lys Ile Cys Met Gly His Leu Lys Asn Ile Arg
385                 390                 395                 400

Phe Ile Val Ile Lys Met Ser Val Glu Ala Asp Glu Ile Trp Lys Glu
                405                 410                 415

Met Phe Leu Tyr Glu Met Ile Lys Gln Ser Arg Ile Glu His Cys Asn
                420                 425                 430

Val Ala Lys Leu Phe Gly Cys Cys Leu Asp His Val Asp Ala Pro Val
                435                 440                 445

Leu Val Tyr Lys Tyr Gly Asp Ile Gly Leu His Asp Ala Leu Phe Gly
            450                 455                 460

Asn Ala Trp Gln Gln Phe Asp Cys Pro Phe Ala Cys Glu Ile Arg Leu
465                 470                 475                 480

Glu Ile Ala Val Gly Ala Glu Gly Leu Ala His Leu His Ser Leu
                485                 490                 495

Asn Val Val His Gly Asp Val Arg Thr Ala Asn Val Val Leu Asp Val
                500                 505                 510

Tyr Ser Lys Ser Lys Leu Glu Met Pro Gly Ile Thr Ala Phe Met Ala
            515                 520                 525

Lys Ile Ala Gly Tyr Gly Thr Gln Arg Leu Leu Ser Leu Asp Lys Ala
            530                 535                 540

Lys His Glu Ile Phe Leu Thr Glu Asn Ile His Tyr Lys Asp Pro His
545                 550                 555                 560

Phe Leu Lys Thr Gly Leu Met Ala Lys Glu Tyr Asp Val Tyr Gly Phe
                565                 570                 575

Gly Val Val Leu Val Glu Leu Phe Ala Gln Asn Met Val Gln Met His
                580                 585                 590

Asp Val Asn Met Val Leu Lys Glu Leu Asp Gly Ile Pro Ala Arg Cys
                595                 600                 605

His His Leu Lys Glu Ile Lys Lys Leu Ala Ser Trp Cys Leu Ala Ser
            610                 615                 620

Lys Val Thr Glu Arg Pro Ala Met Asp Lys Val Val Arg Cys Leu Arg
625                 630                 635                 640

Ala Val Leu Thr Asn Leu Gln Asn Leu His Asp Pro Cys Asn Cys Lys
                645                 650                 655

Ser Met Tyr Asn Lys Ser Ala Met Gln Ser Glu Gln Ile Thr Ser Ala
                660                 665                 670

Lys Ser Ala Ser Ser
            675

<210> SEQ ID NO 91
<211> LENGTH: 732
<212> TYPE: PRT
<213> ORGANISM: Arabidopsis thaliana

<400> SEQUENCE: 91

Met Lys Val Gln Glu Gly Leu Phe Val Val Ala Val Phe Tyr Leu Ala
1               5                   10                  15

Tyr Thr Gln Leu Val Lys Gly Gln Pro Arg Lys Glu Cys Gln Thr Arg
                20                  25                  30

Cys Gly Asn Val Ala Val Glu Tyr Pro Phe Gly Thr Ser Pro Gly Cys
            35                  40                  45

Tyr Tyr Pro Gly Asp Glu Ser Phe Asn Leu Thr Cys Asn Glu Gln Glu
        50                  55                  60
```

-continued

```
Lys Leu Phe Phe Gly Asn Met Pro Val Ile Asn Met Ser Leu Ser Gly
 65                  70                  75                  80

Gln Leu Arg Val Arg Leu Val Arg Ser Arg Val Cys Tyr Asp Ser Gln
                 85                  90                  95

Gly Lys Gln Thr Asp Tyr Ile Ala Gln Arg Thr Thr Leu Gly Asn Phe
            100                 105                 110

Thr Leu Ser Glu Leu Asn Arg Phe Thr Val Val Gly Cys Asn Ser Tyr
        115                 120                 125

Ala Phe Leu Arg Thr Ser Gly Val Glu Lys Tyr Ser Thr Gly Cys Ile
130                 135                 140

Ser Ile Cys Asp Ser Ala Thr Thr Lys Asn Gly Ser Cys Ser Gly Glu
145                 150                 155                 160

Gly Cys Cys Gln Ile Pro Val Pro Arg Gly Tyr Ser Phe Val Arg Val
                165                 170                 175

Lys Pro His Ser Phe His Asn His Pro Thr Val His Leu Phe Asn Pro
            180                 185                 190

Cys Thr Tyr Ala Phe Leu Val Glu Asp Gly Met Phe Asp Phe His Ala
        195                 200                 205

Leu Glu Asp Leu Asn Asn Leu Arg Asn Val Thr Thr Phe Pro Val Val
210                 215                 220

Leu Asp Trp Ser Ile Gly Asp Lys Thr Cys Lys Gln Val Glu Tyr Arg
225                 230                 235                 240

Gly Val Cys Gly Gly Asn Ser Thr Cys Phe Asp Ser Thr Gly Gly Thr
                245                 250                 255

Gly Tyr Asn Cys Lys Cys Leu Glu Gly Phe Glu Gly Asn Pro Tyr Leu
            260                 265                 270

Pro Asn Gly Cys Gln Asp Ile Asn Glu Cys Ile Ser Ser Arg His Asn
        275                 280                 285

Cys Ser Glu His Ser Thr Cys Glu Asn Thr Lys Gly Ser Phe Asn Cys
290                 295                 300

Asn Cys Pro Ser Gly Tyr Arg Lys Asp Ser Leu Asn Ser Cys Thr Arg
305                 310                 315                 320

Lys Val Arg Pro Glu Tyr Phe Arg Trp Thr Gln Ile Phe Leu Gly Thr
                325                 330                 335

Thr Ile Gly Phe Ser Val Ile Met Leu Gly Ile Ser Cys Leu Gln Gln
            340                 345                 350

Lys Ile Lys His Arg Lys Asn Thr Glu Leu Arg Gln Lys Phe Phe Glu
        355                 360                 365

Gln Asn Gly Gly Gly Met Leu Ile Gln Arg Val Ser Gly Ala Gly Pro
370                 375                 380

Ser Asn Val Asp Val Lys Ile Phe Thr Glu Lys Gly Met Lys Glu Ala
385                 390                 395                 400

Thr Asn Gly Tyr His Glu Ser Arg Ile Leu Gly Gln Gly Gly Gln Gly
                405                 410                 415

Thr Val Tyr Lys Gly Ile Leu Pro Asp Asn Ser Ile Val Ala Ile Lys
            420                 425                 430

Lys Ala Arg Leu Gly Asn Arg Ser Gln Val Glu Gln Phe Ile Asn Glu
        435                 440                 445

Val Leu Val Leu Ser Gln Ile Asn His Arg Asn Val Val Lys Val Leu
450                 455                 460

Gly Cys Cys Leu Glu Thr Glu Val Pro Leu Leu Val Tyr Glu Phe Ile
465                 470                 475                 480

Asn Ser Gly Thr Leu Phe Asp His Leu His Gly Ser Leu Tyr Asp Ser
```

```
                    485                 490                 495

Ser Leu Thr Trp Glu His Arg Leu Arg Ile Ala Thr Glu Val Ala Gly
            500                 505                 510

Ser Leu Ala Tyr Leu His Ser Ser Ala Ser Ile Pro Ile Ile His Arg
        515                 520                 525

Asp Ile Lys Thr Ala Asn Ile Leu Leu Asp Lys Asn Leu Thr Ala Lys
    530                 535                 540

Val Ala Asp Phe Gly Ala Ser Arg Leu Ile Pro Met Asp Lys Glu Gln
545                 550                 555                 560

Leu Thr Thr Ile Val Gln Gly Thr Leu Gly Tyr Leu Asp Pro Glu Tyr
                565                 570                 575

Tyr Asn Thr Gly Leu Leu Asn Glu Lys Ser Asp Val Tyr Ser Phe Gly
            580                 585                 590

Val Val Leu Met Glu Leu Leu Ser Gly Gln Lys Ala Leu Cys Phe Glu
        595                 600                 605

Arg Pro His Cys Pro Lys Asn Leu Val Ser Cys Phe Ala Ser Ala Thr
    610                 615                 620

Lys Asn Asn Arg Phe His Glu Ile Ile Asp Gly Gln Val Met Asn Glu
625                 630                 635                 640

Asp Asn Gln Arg Glu Ile Gln Glu Ala Ala Arg Ile Ala Ala Glu Cys
                645                 650                 655

Thr Arg Leu Met Gly Glu Glu Arg Pro Arg Met Lys Glu Val Ala Ala
            660                 665                 670

Glu Leu Glu Ala Leu Arg Val Lys Thr Thr Lys Tyr Lys Trp Ser Asp
        675                 680                 685

Gln Tyr Arg Glu Thr Gly Glu Ile Glu His Leu Leu Gly Val Gln Ile
    690                 695                 700

Leu Ser Ala Gln Gly Glu Thr Ser Ser Ile Gly Tyr Asp Ser Ile
705                 710                 715                 720

Arg Asn Val Thr Thr Leu Asp Ile Glu Ala Gly Arg
                725                 730

<210> SEQ ID NO 92
<211> LENGTH: 738
<212> TYPE: PRT
<213> ORGANISM: Arabidopsis thaliana

<400> SEQUENCE: 92

Met Lys Val Gln Arg Leu Phe Leu Val Ala Ile Phe Cys Leu Ser Tyr
1               5                   10                  15

Met Gln Leu Val Lys Gly Gln Thr Leu Pro Arg Cys Pro Glu Lys Cys
            20                  25                  30

Gly Asn Val Thr Leu Glu Tyr Pro Phe Gly Phe Ser Pro Gly Cys Trp
        35                  40                  45

Arg Ala Glu Asp Pro Ser Phe Asn Leu Ser Cys Val Asn Glu Asn Leu
    50                  55                  60

Phe Tyr Lys Gly Leu Glu Val Val Glu Ile Ser His Ser Ser Gln Leu
65                  70                  75                  80

Arg Val Leu Tyr Pro Ala Ser Tyr Ile Cys Tyr Asn Ser Lys Gly Lys
                85                  90                  95

Phe Ala Lys Gly Thr Tyr Tyr Trp Ser Asn Leu Gly Asn Leu Thr Leu
            100                 105                 110

Ser Gly Asn Asn Thr Ile Thr Ala Leu Gly Cys Asn Ser Tyr Ala Phe
        115                 120                 125
```

```
Val Ser Ser Asn Gly Thr Arg Arg Asn Ser Val Gly Cys Ile Ser Ala
    130                 135                 140

Cys Asp Ala Leu Ser His Glu Ala Asn Gly Glu Cys Asn Gly Glu Gly
145                 150                 155                 160

Cys Cys Gln Asn Pro Val Pro Ala Gly Asn Asn Trp Leu Ile Val Arg
                165                 170                 175

Ser Tyr Arg Phe Asp Asn Asp Thr Ser Val Gln Pro Ile Ser Glu Gly
            180                 185                 190

Gln Cys Ile Tyr Ala Phe Leu Val Glu Asn Gly Lys Phe Lys Tyr Asn
        195                 200                 205

Ala Ser Asp Lys Tyr Ser Tyr Leu Gln Asn Arg Asn Val Gly Phe Pro
210                 215                 220

Val Val Leu Asp Trp Ser Ile Arg Gly Glu Thr Cys Gly Gln Val Gly
225                 230                 235                 240

Glu Lys Lys Cys Gly Val Asn Gly Ile Cys Ser Asn Ser Ala Ser Gly
                245                 250                 255

Ile Gly Tyr Thr Cys Lys Cys Lys Gly Phe Gln Gly Asn Pro Tyr
            260                 265                 270

Leu Gln Asn Gly Cys Gln Asp Ile Asn Glu Cys Thr Thr Ala Asn Pro
    275                 280                 285

Ile His Lys His Asn Cys Ser Gly Asp Ser Thr Cys Glu Asn Lys Leu
290                 295                 300

Gly His Phe Arg Cys Asn Cys Arg Ser Arg Tyr Glu Leu Asn Thr Thr
305                 310                 315                 320

Thr Asn Thr Cys Lys Pro Lys Gly Asn Pro Glu Tyr Val Glu Trp Thr
                325                 330                 335

Thr Ile Val Leu Gly Thr Thr Ile Gly Phe Leu Val Ile Leu Leu Ala
            340                 345                 350

Ile Ser Cys Ile Glu His Lys Met Lys Asn Thr Lys Asp Thr Glu Leu
        355                 360                 365

Arg Gln Gln Phe Phe Glu Gln Asn Gly Gly Met Leu Met Gln Arg
    370                 375                 380

Leu Ser Gly Ala Gly Pro Ser Asn Val Asp Val Lys Ile Phe Thr Glu
385                 390                 395                 400

Glu Gly Met Lys Glu Ala Thr Asp Gly Tyr Asp Glu Asn Arg Ile Leu
                405                 410                 415

Gly Gln Gly Gly Gln Gly Thr Val Tyr Lys Gly Ile Leu Pro Asp Asn
                420                 425                 430

Ser Ile Val Ala Ile Lys Lys Ala Arg Leu Gly Asp Asn Ser Gln Val
        435                 440                 445

Glu Gln Phe Ile Asn Glu Val Leu Val Leu Ser Gln Ile Asn His Arg
450                 455                 460

Asn Val Val Lys Leu Leu Gly Cys Cys Leu Glu Thr Glu Val Pro Leu
465                 470                 475                 480

Leu Val Tyr Glu Phe Ile Ser Ser Gly Thr Leu Phe Asp His Leu His
                485                 490                 495

Gly Ser Met Phe Asp Ser Ser Leu Thr Trp Glu His Arg Leu Arg Met
            500                 505                 510

Ala Val Glu Ile Ala Gly Thr Leu Ala Tyr Leu His Ser Ser Ala Ser
        515                 520                 525

Ile Pro Ile Ile His Arg Asp Ile Lys Thr Ala Asn Ile Leu Leu Asp
530                 535                 540

Glu Asn Leu Thr Ala Lys Val Ala Asp Phe Gly Ala Ser Arg Leu Ile
```

```
545                 550                 555                 560
Pro Met Asp Lys Glu Asp Leu Ala Thr Met Val Gln Gly Thr Leu Gly
                565                 570                 575
Tyr Leu Asp Pro Glu Tyr Tyr Asn Thr Gly Leu Leu Asn Glu Lys Ser
            580                 585                 590
Asp Val Tyr Ser Phe Gly Val Val Met Glu Leu Leu Ser Gly Gln
        595                 600                 605
Lys Ala Leu Cys Phe Glu Arg Pro Gln Thr Ser Lys His Ile Val Ser
610                 615                 620
Tyr Phe Ala Ser Ala Thr Lys Glu Asn Arg Leu His Glu Ile Ile Asp
625                 630                 635                 640
Gly Gln Val Met Asn Glu Asn Gln Arg Glu Ile Gln Lys Ala Ala
                645                 650                 655
Arg Ile Ala Val Glu Cys Thr Arg Leu Thr Gly Glu Glu Arg Pro Gly
                660                 665                 670
Met Lys Glu Val Ala Ala Glu Leu Gly Ala Leu Arg Val Thr Lys Thr
                675                 680                 685
Lys His Lys Trp Ser Asp Glu Tyr Pro Glu Gln Glu Asp Thr Glu His
                690                 695                 700
Leu Val Gly Val Gln Lys Leu Ser Ala Gln Gly Glu Thr Ser Ser Ser
705                 710                 715                 720
Ile Gly Tyr Asp Ser Ile Arg Asn Val Ala Ile Leu Asp Ile Glu Ala
                725                 730                 735
Gly Arg

<210> SEQ ID NO 93
<211> LENGTH: 748
<212> TYPE: PRT
<213> ORGANISM: Arabidopsis thaliana

<400> SEQUENCE: 93

Met Lys Thr Glu Thr His Asn Arg Gln Cys Ile Pro Leu Ala Ile Ser
1               5                   10                  15

Val Leu Ser Leu Phe Ile Asn Gly Val Ser Ser Ala Arg Gln Pro Pro
            20                  25                  30

Asp Arg Cys Asn Arg Val Cys Gly Glu Ile Ser Ile Pro Phe Pro Phe
        35                  40                  45

Gly Ile Gly Gly Lys Asp Cys Tyr Leu Asn Pro Trp Tyr Glu Val Val
    50                  55                  60

Cys Asn Ser Thr Asn Ser Val Pro Phe Leu Ser Arg Ile Asn Arg Glu
65                  70                  75                  80

Leu Val Asn Ile Ser Leu Asn Gly Val Val His Ile Lys Ala Pro Val
                85                  90                  95

Thr Ser Ser Gly Cys Ser Thr Gly Thr Ser Gln Pro Leu Thr Pro Pro
            100                 105                 110

Pro Leu Asn Val Ala Gly Gln Gly Ser Pro Tyr Phe Leu Thr Asp Lys
        115                 120                 125

Asn Leu Leu Val Ala Val Gly Cys Lys Phe Lys Ala Val Met Ala Gly
    130                 135                 140

Ile Thr Ser Gln Ile Thr Ser Cys Glu Ser Ser Cys Asn Glu Arg Asn
145                 150                 155                 160

Ser Ser Ser Gln Glu Gly Arg Asn Lys Ile Cys Asn Gly Tyr Lys Cys
                165                 170                 175

Cys Gln Thr Arg Ile Pro Glu Gly Gln Pro Gln Val Ile Ser Val Asp
```

-continued

```
            180             185             190
Ile Glu Ile Pro Gln Gly Asn Asn Thr Thr Gly Glu Gly Gly Cys Arg
            195             200             205
Val Ala Phe Leu Thr Ser Asp Lys Tyr Ser Ser Leu Asn Val Thr Glu
            210             215             220
Pro Glu Lys Phe His Gly His Gly Tyr Ala Ala Val Glu Leu Gly Trp
225             230             235             240
Phe Phe Asp Thr Ser Asp Ser Arg Asp Thr Gln Pro Ile Ser Cys Lys
            245             250             255
Asn Ala Ser Asp Thr Thr Pro Tyr Thr Ser Asp Thr Arg Cys Ser Cys
            260             265             270
Ser Tyr Gly Tyr Phe Ser Gly Phe Ser Tyr Arg Asp Cys Tyr Cys Asn
            275             280             285
Ser Pro Gly Tyr Lys Gly Asn Pro Phe Leu Pro Gly Gly Cys Val Asp
            290             295             300
Val Asp Glu Cys Lys Leu Asp Ile Gly Arg Asn Gln Cys Lys Asp Gln
305             310             315             320
Ser Cys Val Asn Leu Pro Gly Trp Phe Asp Cys Gln Pro Lys Lys Pro
            325             330             335
Glu Gln Leu Lys Arg Val Ile Gln Gly Val Leu Ile Gly Ser Ala Leu
            340             345             350
Leu Leu Phe Ala Phe Gly Ile Phe Gly Leu Tyr Lys Phe Val Gln Lys
            355             360             365
Arg Arg Lys Leu Ile Arg Met Arg Lys Phe Phe Arg Arg Asn Gly Gly
            370             375             380
Met Leu Leu Lys Gln Gln Leu Ala Arg Lys Glu Gly Asn Val Glu Met
385             390             395             400
Ser Arg Ile Phe Ser Ser His Glu Leu Glu Lys Ala Thr Asp Asn Phe
            405             410             415
Asn Lys Asn Arg Val Leu Gly Gln Gly Gly Gln Gly Thr Val Tyr Lys
            420             425             430
Gly Met Leu Val Asp Gly Arg Ile Val Ala Val Lys Arg Ser Lys Ala
            435             440             445
Val Asp Glu Asp Arg Val Glu Glu Phe Ile Asn Glu Val Val Val Leu
            450             455             460
Ala Gln Ile Asn His Arg Asn Ile Val Lys Leu Leu Gly Cys Cys Leu
465             470             475             480
Glu Thr Glu Val Pro Val Leu Val Tyr Glu Phe Val Pro Asn Gly Asp
            485             490             495
Leu Cys Lys Arg Leu His Asp Glu Ser Asp Asp Tyr Thr Met Thr Trp
            500             505             510
Glu Val Arg Leu His Ile Ala Ile Glu Ile Ala Gly Ala Leu Ser Tyr
            515             520             525
Leu His Ser Ala Ala Ser Phe Pro Ile Tyr His Arg Asp Ile Lys Thr
            530             535             540
Thr Asn Ile Leu Leu Asp Glu Arg Asn Arg Ala Lys Val Ser Asp Phe
545             550             555             560
Gly Thr Ser Arg Ser Val Thr Ile Asp Gln Thr His Leu Thr Thr Gln
            565             570             575
Val Ala Gly Thr Phe Gly Tyr Val Asp Pro Glu Tyr Phe Gln Ser Ser
            580             585             590
Lys Phe Thr Glu Lys Ser Asp Val Tyr Ser Phe Gly Val Val Leu Val
            595             600             605
```

```
Glu Leu Leu Thr Gly Glu Lys Pro Ser Ser Arg Val Arg Ser Glu Glu
    610                 615                 620

Asn Arg Gly Leu Ala Ala His Phe Val Glu Ala Val Lys Glu Asn Arg
625                 630                 635                 640

Val Leu Asp Ile Val Asp Asp Arg Ile Lys Asp Glu Cys Asn Met Asp
                645                 650                 655

Gln Val Met Ser Val Ala Asn Leu Ala Arg Arg Cys Leu Asn Arg Lys
            660                 665                 670

Gly Lys Lys Arg Pro Asn Met Arg Glu Val Ser Ile Glu Leu Glu Met
        675                 680                 685

Ile Arg Ser Ser His Tyr Asp Ser Gly Ile His Ile Glu Asp Asp
    690                 695                 700

Glu Glu Asp Asp Gln Ala Met Glu Leu Asn Phe Asn Asp Thr Trp Glu
705                 710                 715                 720

Val Gly Ala Thr Ala Pro Ala Ser Met Phe Asn Asn Ala Ser Pro Thr
                725                 730                 735

Ser Asp Ala Glu Pro Leu Val Pro Leu Arg Thr Trp
            740                 745

<210> SEQ ID NO 94
<211> LENGTH: 725
<212> TYPE: PRT
<213> ORGANISM: Oryza sativa

<400> SEQUENCE: 94

Met Ser Ser Ser Ser Ser Val Val Tyr Glu Gly Trp Met Val Arg
1               5                   10                  15

Tyr Gly Arg Arg Lys Ile Gly Arg Ser Phe Ile His Met Arg Tyr Phe
                20                  25                  30

Val Leu Glu Thr Arg Leu Leu Ser Tyr Tyr Lys Arg Lys Pro Gln His
            35                  40                  45

Lys Met Pro Lys Leu Pro Ile Lys Ser Leu His Ile Asp Gly Asn Cys
50                  55                  60

Arg Val Glu Asp Arg Gly Leu Lys Met His His Gly His Met Leu Tyr
65                  70                  75                  80

Val Leu Cys Val Tyr Asn Lys Arg Glu Lys His Gln Arg Ile Thr Met
                85                  90                  95

Ala Ala Phe Asn Ile Gln Glu Ala Leu Ile Trp Lys Glu Lys Ile Glu
            100                 105                 110

Met Val Ile Asp Gln Gln Gly Val Val Ala Ser Asp Gly Asn Leu
        115                 120                 125

Ala His Ser Ser Ser Gln Gln Lys Val Ser Leu Glu Asn Gly Arg Lys
130                 135                 140

Ser Ser Phe Ser Asp His Glu Ser Leu Tyr Ser His Glu Glu Glu Glu
145                 150                 155                 160

Glu Glu Glu Asp Asn Gln Arg Ser Leu Met Arg Arg Thr Thr Ile Gly
                165                 170                 175

Asn Gly Pro Pro Glu Ser Leu Tyr Asp Trp Thr Arg Glu Asn Asp Leu
            180                 185                 190

Gly Ile Ser Asn Gln Gly Ser Pro Asp His Val Phe Ser Arg Arg His
        195                 200                 205

Trp Arg Leu Val Arg Cys Gln Asn Gly Leu Arg Ile Phe Glu Glu Leu
    210                 215                 220

Gln Asp Val Asp Tyr Leu Ala Arg Ser Cys Ser Arg Ala Met Lys Ala
```

```
            225                 230                 235                 240

Val Gly Val Val Glu Ala Ser Cys Glu Ala Ile Phe Gln Leu Val Met
                        245                 250                 255

Ser Met Asp Thr Thr Arg Tyr Glu Trp Asp Cys Ser Phe Gln Tyr Gly
                        260                 265                 270

Ser Leu Val Glu Glu Val Asp Gly His Thr Ala Ile Leu Tyr His Arg
                        275                 280                 285

Leu Gln Leu Asp Trp Phe Ser Met Phe Val Trp Pro Arg Asp Leu Cys
                        290                 295                 300

Tyr Val Arg Tyr Trp Arg Arg Asn Asp Asp Gly Ser Tyr Val Val Leu
        305                 310                 315                 320

Phe Gln Ser Arg Glu His Pro Asn Cys Gly Pro Gln Pro Gly Phe Val
                        325                 330                 335

Arg Ala Gln Ile Glu Ser Gly Gly Phe Asn Ile Ser Pro Leu Lys Ser
                        340                 345                 350

Arg Asn Gly Arg Ile Arg Thr Gln Val Gln His Leu Met Gln Ile Asp
                        355                 360                 365

Leu Lys Gly Trp Gly Val Gly Tyr Leu Pro Ser Phe Gln Gln His Cys
                        370                 375                 380

Leu Leu His Met Leu Asn Ser Val Ala Gly Leu Arg Glu Trp Phe Ser
        385                 390                 395                 400

Gln Ser Asp Glu Asn Leu Ile Leu Pro Arg Ile Pro Val Met Ala Asn
                        405                 410                 415

Met Ala Pro Pro Val Ser Ser Lys Lys Gly Arg Thr Thr Gln Asp Asn
                        420                 425                 430

Thr Met Gln Thr Gly Leu Gln Met Asp Gln Ser Arg Gln Ser Thr Met
                        435                 440                 445

Leu Asp Glu Glu Ser Asp Glu Asp Glu Asp Gln Ile Pro Glu Ser Glu
                        450                 455                 460

Gln Glu Thr Ser Thr His Gly His Asp Ala Pro Val Lys Leu Pro Val
        465                 470                 475                 480

Leu Asp Glu Glu Asp Ser Asp Gln Ile Asp Val Ser Gly Phe Ser Gly
                        485                 490                 495

Asn Leu Arg Arg Asp Asp Arg Asp Asn Thr Arg Asp Cys Trp Arg Met
                        500                 505                 510

Ser Asp Gly Asn Asn Phe Arg Val Arg Ser Lys Thr Phe Ile Tyr Asp
                        515                 520                 525

Lys Ser Lys Ile Pro Ala Gly Lys Pro Leu Met Lys Leu Val Ala Val
        530                 535                 540

Asp Trp Phe Lys Asp Val Lys Arg Met Asp His Val Ala Arg Arg Lys
        545                 550                 555                 560

Gly Cys Ala Val Gln Val Ala Ala Glu Lys Gly Leu Phe Ala Leu Ala
                        565                 570                 575

Val Asn Leu Gln Val Pro Gly Thr Thr Asn Tyr Ser Met Val Phe Tyr
                        580                 585                 590

Phe Val Thr Lys Lys Leu Ile Pro Asn Ser Leu Leu Gln Arg Phe Val
                        595                 600                 605

Asp Gly Asp Asp Glu Phe Arg Asn Ser Arg Phe Lys Leu Ile Pro Ser
                        610                 615                 620

Val Pro Lys Gly Ser Trp Ile Val Arg Gln Ser Val Gly Ser Thr Pro
        625                 630                 635                 640

Cys Leu Leu Gly Lys Ala Val Asp Ile Thr Tyr Ile Arg Gly Pro Asn
                        645                 650                 655
```

```
Tyr Leu Glu Ile Asp Val Asp Ile Gly Ser Ser Thr Val Ala Asn Gly
            660                 665                 670

Val Leu Gly Leu Val Cys Gly Val Ile Thr Thr Leu Val Val Asp Met
            675                 680                 685

Ala Phe Leu Val Gln Gly Asn Thr Tyr Glu Glu Leu Pro Glu Arg Leu
            690                 695                 700

Ile Gly Ala Val Arg Val Ser His Ile Glu Leu Lys Ser Ala Ile Val
705                 710                 715                 720

Pro Val Leu Gly Asp
            725

<210> SEQ ID NO 95
<211> LENGTH: 264
<212> TYPE: PRT
<213> ORGANISM: Zea mays

<400> SEQUENCE: 95

Met Ala Pro Pro Glu Ser Leu Tyr Asp Trp Thr Arg Glu Asn Asp Leu
1               5                   10                  15

Gly Ile Ser Asn Gln Gly Ser Pro Asp Gln Val Phe Ser Arg Gly His
            20                  25                  30

Trp Arg Leu Val Arg Cys Gln Asn Gly Leu Arg Ile Phe Glu Glu Leu
            35                  40                  45

Gln Asp Val Asp Tyr Leu Ala Arg Ser Cys Ser Arg Ala Met Lys Ala
        50                  55                  60

Val Gly Val Val Glu Ala Ser Cys Glu Ala Ile Phe Gln Leu Val Met
65                  70                  75                  80

Ser Met Asp Thr Ser Arg Phe Glu Trp Asp Cys Ser Phe Gln Tyr Gly
                85                  90                  95

Ser Leu Val Glu Glu Val Asp Gly His Thr Ala Ile Leu Tyr His Arg
            100                 105                 110

Leu Gln Leu Asp Trp Phe Pro Met Phe Val Trp Pro Arg Asp Leu Cys
            115                 120                 125

Tyr Val Arg Tyr Trp Arg Arg Asn Asp Asp Gly Ser Tyr Val Val Leu
        130                 135                 140

Phe Gln Ser Arg Glu His Gln Asn Cys Gly Pro Gln Pro Gly Phe Val
145                 150                 155                 160

Arg Ala His Ile Glu Ser Gly Gly Phe Asn Ile Ser Pro Leu Lys Ser
                165                 170                 175

Arg Asn Gly Arg Ile Arg Thr Gln Val Gln His Leu Met Gln Ile Asp
            180                 185                 190

Leu Lys Gly Trp Gly Val Gly Tyr Val Pro Ser Phe Gln Gln His Cys
            195                 200                 205

Leu Leu His Met Leu Asn Ser Val Ala Gly Thr Asn Lys Leu Leu Asn
        210                 215                 220

Lys Ile Tyr Met Val Ser Leu Leu Ile Phe Cys Val His Ser Thr
225                 230                 235                 240

Gln Lys Thr Phe Val Tyr Leu Ile Arg Leu Gly Phe Gly Val Thr Ser
                245                 250                 255

Gln Leu Arg Arg His Leu Phe Val
            260

<210> SEQ ID NO 96
<211> LENGTH: 731
<212> TYPE: PRT
```

<213> ORGANISM: Sorghum bicolor

<400> SEQUENCE: 96

```
Met Met Ser Ser Ser Ser Ser Val Val Tyr Glu Gly Trp Met
1               5                   10                  15

Val Arg Tyr Gly Arg Arg Lys Ile Gly Arg Ser Phe Val His Thr Arg
            20                  25                  30

Tyr Phe Val Leu Glu Pro Arg Met Leu Ser Tyr Lys Arg Lys Pro
        35                  40                  45

Gln His Lys Ala Asp Lys Val Gly Gly Lys Leu Pro Ile Lys Ser Leu
    50                  55                  60

Pro Ile Asp Gly Asn Cys Arg Val Glu Asp Arg Gly Leu Lys Met His
65                  70                  75                  80

His Gly His Met Leu Tyr Val Leu Cys Val Tyr Asn Lys Arg Glu Lys
                85                  90                  95

His Asn Arg Ile Thr Met Ala Ala Phe Asn Ile Gln Glu Ala Leu Ile
            100                 105                 110

Trp Lys Glu Lys Ile Glu Met Val Ile Asp Gln Arg Gln Gly Val Ala
        115                 120                 125

Pro Ser Asp Gly Asn Lys Ala Phe Ser Thr Ser Gln Gln Lys Ala Ser
    130                 135                 140

Leu Glu Asn Gly Arg Lys Ser Ser Ser Asp His Glu Ser Gln Tyr
145                 150                 155                 160

Ser His Glu Glu Glu Glu Glu Asn Gln Arg Ser Leu Leu Arg
            165                 170                 175

Arg Thr Thr Ile Gly Asn Gly Pro Pro Glu Ser Leu Tyr Asp Trp Thr
            180                 185                 190

Arg Glu Asn Asp Leu Gly Ile Ser Asn Gln Gly Ser Pro Asp Gln Val
        195                 200                 205

Phe Ser Arg Gly His Trp Arg Leu Val Arg Cys Gln Asn Gly Leu Arg
    210                 215                 220

Ile Phe Glu Glu Leu Gln Asp Val Asp Tyr Leu Ala Arg Ser Cys Ser
225                 230                 235                 240

Arg Ala Met Lys Ala Val Gly Val Glu Ala Ser Cys Glu Ala Ile
            245                 250                 255

Phe Gln Leu Val Met Ser Met Asp Thr Thr Arg Phe Glu Trp Asp Cys
        260                 265                 270

Ser Phe Gln Tyr Gly Ser Leu Val Glu Glu Val Asp Gly His Thr Ala
    275                 280                 285

Ile Leu Tyr His Arg Leu Gln Leu Asp Trp Phe Pro Met Phe Val Trp
290                 295                 300

Pro Arg Asp Leu Cys Tyr Val Arg Tyr Trp Arg Arg Asn Asp Asp Gly
305                 310                 315                 320

Ser Tyr Val Val Leu Phe Arg Ser Arg Glu His Gln Asn Cys Gly Pro
            325                 330                 335

Gln Pro Gly Phe Val Arg Ala His Ile Glu Ser Gly Gly Phe Asn Ile
        340                 345                 350

Ser Pro Leu Lys Ser Arg Asn Gly Arg Ile Arg Thr Gln Val Gln His
    355                 360                 365

Leu Met Gln Ile Asp Leu Lys Gly Trp Gly Val Gly Tyr Val Pro Ser
370                 375                 380

Phe Gln Gln His Cys Leu Leu His Met Leu Asn Ser Val Ala Gly Leu
385                 390                 395                 400
```

```
Arg Glu Trp Phe Ser Gln Ser Asp Glu Ser Gln Val Leu Pro Arg Ile
                405                 410                 415

Pro Val Met Val Asn Met Thr Gln Ser Val Ser Ser Lys Lys Gly Arg
            420                 425                 430

Lys Ala Gln Glu Ser Thr Thr Gln Thr Ser Ile Gln Met Asp Pro Ser
        435                 440                 445

Arg His Ser Thr Ala Leu Glu Glu Glu Ser Asp Glu Asp Asp Glu Phe
    450                 455                 460

Leu Ile Pro Glu Ser Glu Pro Glu Pro Ser Thr Arg Glu Asp Ala Ala
465                 470                 475                 480

Asp Ile Arg Gln Ser Gly Arg Asn Glu Asp Asp Ser Asp Gln Ile Asp
                485                 490                 495

Leu Ser Gly Phe Ser Gly Asn Leu Arg Arg Asp Asp Arg Asp Asn Ser
            500                 505                 510

Arg Asp Cys Trp Arg Ile Ser Asp Gly Asn Asn Phe Arg Val Arg Ser
        515                 520                 525

Lys Asn Phe Val Tyr Asp Lys Ser Lys Val Pro Ala Gly Lys Pro Leu
    530                 535                 540

Met Glu Leu Val Ala Val Asp Trp Phe Lys Asp Ala Lys Arg Met Asp
545                 550                 555                 560

His Val Ala Arg Arg Lys Gly Cys Ala Val Gln Val Ala Ala Glu Lys
                565                 570                 575

Gly Leu Phe Ala Leu Ala Ile Asn Leu Gln Val Pro Gly Thr Thr Asn
            580                 585                 590

Tyr Ser Met Val Phe Tyr Phe Val Thr Lys Lys Leu Ile Pro Asn Ser
        595                 600                 605

Leu Leu Gln Arg Phe Val Asp Gly Asp Asp Glu Tyr Arg Asn Ser Arg
    610                 615                 620

Phe Lys Leu Ile Pro Ser Val Pro Lys Gly Ser Trp Ile Val Arg Gln
625                 630                 635                 640

Ser Val Gly Ser Thr Pro Cys Leu Leu Gly Lys Ala Val Asp Ile Thr
                645                 650                 655

Tyr Ile Arg Gly Ser Asn Tyr Leu Glu Ile Asp Val Asp Ile Gly Ser
            660                 665                 670

Ser Thr Val Ala Asn Gly Val Leu Gly Leu Val Cys Gly Val Ile Thr
        675                 680                 685

Thr Leu Val Val Asp Met Ala Phe Leu Val Gln Ala Asn Thr Tyr Glu
    690                 695                 700

Glu Leu Pro Glu Arg Leu Ile Gly Ala Val Arg Met Ser His Ile Glu
705                 710                 715                 720

Leu Ser Ser Ala Ile Val Pro Val Leu Glu Asp
                725                 730

<210> SEQ ID NO 97
<211> LENGTH: 728
<212> TYPE: PRT
<213> ORGANISM: Poa pratensis

<400> SEQUENCE: 97

Met Val Arg Tyr Gly Arg Arg Lys Ile Gly Arg Ser Ile Phe Gln Thr
1               5                   10                  15

Arg Tyr Phe Val Leu Glu Ser Lys Leu Leu Ala Tyr Tyr Lys Lys Lys
            20                  25                  30

Pro Lys Asp Ser Met Val Pro Leu Lys Ser Leu Leu Ile Asp Gly Asn
        35                  40                  45
```

```
Cys Arg Val Glu Asp Arg Gly Leu Lys Thr His His Gly Gln Met Ile
 50                  55                  60

Tyr Val Leu Cys Val Tyr Asn Lys Lys Glu Lys Glu His Gln Ile Thr
 65                  70                  75                  80

Met Gly Ala Tyr Asp Ile Glu Asp Ala Leu Ala Trp Lys Lys Lys Ile
                 85                  90                  95

Glu Gln Ile Ile Asp Gln Gln Asp Thr Met Thr Ala Glu Asn Arg Lys
            100                 105                 110

Ala Phe Ala Ser Met Asp Phe Asp Ala Glu Leu Gly Gly Gln Phe Ser
            115                 120                 125

Phe Ser Asp His Asp Ser Ala Ala Glu Asp Glu Glu Arg Pro Thr
            130                 135                 140

Leu Thr Arg Arg Thr Thr Ile Gly Asn Gly Pro Pro Glu Ser Ile His
145                 150                 155                 160

Asp Trp Thr Asn Glu Pro Asp Ile Gly Leu Ser Asn Gln Ser Asp Pro
                165                 170                 175

Ala Gln Ser Phe Ser Lys Lys Asn Trp Arg Leu Leu Arg Cys Gln Asn
            180                 185                 190

Gly Leu Arg Ile Phe Glu Glu Leu Leu Glu Val Asp Tyr Leu Ala Arg
            195                 200                 205

Ser Cys Ser Arg Ala Met Arg Ala Val Gly Val Glu Ala Thr Cys
210                 215                 220

Glu Ala Ile Phe Gly Leu Val Met Ser Met Asp Met Thr Arg Tyr Glu
225                 230                 235                 240

Trp Asp Cys Ser Phe Arg Tyr Gly Ser Leu Val Glu Glu Val Asp Gly
                245                 250                 255

His Thr Ala Ile Leu Tyr His Lys Leu Gln Leu His Trp Cys Pro Met
            260                 265                 270

Leu Val Trp Pro Lys Asp Leu Cys Tyr Val Arg Tyr Trp Arg Arg Asn
            275                 280                 285

Asp Asp Gly Ser Tyr Val Val Leu Phe Arg Ser Ile Glu His Pro Asn
            290                 295                 300

Cys Gly Arg Gln Arg Gly Tyr Val Arg Ala Phe Ile Glu Ser Gly Gly
305                 310                 315                 320

Phe Lys Ile Ser Pro Leu Lys Cys Arg Asn Gly Arg Pro Arg Thr Gln
                325                 330                 335

Val Gln His Leu Met Gln Ile Asp Leu Arg Gly Trp Phe Leu Asn Tyr
            340                 345                 350

Ser Pro Ser Phe Gln Tyr His Ser Leu Leu Gln Ile Gln Asn Cys Val
            355                 360                 365

Ala Gly Leu Arg Glu Tyr Phe Ser Gln Thr Asp Glu Cys His Ile Thr
            370                 375                 380

Pro Arg Ile Pro Val Met Glu Asn Met Val Asp Pro Ser Met Pro Lys
385                 390                 395                 400

Ser Gln Lys Leu His Glu Met Glu Ser Lys Thr Lys Pro Ala His Gly
                405                 410                 415

Gly Gln Ala Asp Asn Lys Ser Met Ser Ile Ile Asp Glu Glu Ser Asp
            420                 425                 430

Glu Asp Asp Asp Tyr Gln Val Pro Glu Ala Asn Ile Glu Glu Asp Ser
            435                 440                 445

Asn Lys Ser Asp Asn Asp Ala Lys Arg Thr Glu Glu Pro Pro Glu Lys
450                 455                 460
```

```
Ile Asp Leu Ser Cys Phe Ser Gly Ile Leu His Arg Asp Thr Asp Glu
465                 470                 475                 480

Lys Ser Arg Asn Tyr Trp Thr Val Pro Asp Ser Thr Leu Phe Lys Val
            485                 490                 495

Arg Ser Lys Asn Phe Pro Thr Asp Lys Ser Lys Ile Pro Ala Pro Ser
            500                 505                 510

Tyr Leu Met Glu Leu Ala Ala Ile Asp Trp Phe Lys Asp Thr Lys Arg
            515                 520                 525

Met Asp Asn Val Gly Arg Gln Lys Gly Cys Val Ala Gln Val Ala Ala
            530                 535                 540

Glu Lys Gly Met His Thr Phe Val Ala Asn Ile Gln Ile Pro Gly Ser
545                 550                 555                 560

Thr His Tyr Ser Leu Val Met Tyr Phe Val Thr Ser Cys Met Lys Lys
                565                 570                 575

Gly Ser Leu Leu Gln Arg Phe Phe Asp Gly Asp Glu Phe Arg Asn
                580                 585                 590

Ser Arg Leu Lys Leu Ile Pro Ala Val Pro Lys Gly Ser Trp Ile Val
            595                 600                 605

Arg Gln Ser Val Gly Ser Thr Pro Cys Leu Leu Gly Lys Ala Val Asp
            610                 615                 620

Cys Ser Tyr Val Arg Gly Pro Gly Tyr Leu Glu Val Asp Val Asp Ile
625                 630                 635                 640

Gly Ser Ser Ala Val Ala Asn Gly Val Leu Gly Leu Val Phe Gly Val
                645                 650                 655

Val Thr Thr Leu Val Val Asp Met Ala Phe Leu Ile Gln Ala Asn Thr
            660                 665                 670

Tyr Asp Glu Leu Pro Glu Gln Val Ile Gly Ala Ala Arg Leu Ala His
            675                 680                 685

Val Glu Pro Ala Ala Ala Val Val Pro Asp Leu Asp Asn Asn Ser Asp
            690                 695                 700

Ser Lys Asp Ser Ser Asn Asp Asn Asn Asn Thr Ser Ser Asp
705                 710                 715                 720

Asp Asp Ser Ser Lys Lys Thr Asn
                725

<210> SEQ ID NO 98
<211> LENGTH: 804
<212> TYPE: PRT
<213> ORGANISM: Oryza sativa

<400> SEQUENCE: 98

Met Met Leu Ser Ser Ala Ser Arg Arg Glu Val Gly Gly Gly
1               5                   10                  15

Ala Ala Ser Ser Thr Lys Ser Gly Glu Leu Ser Leu Ser Lys Val Ala
                20                  25                  30

Ser Val Ala Ile Arg Glu Ser Ser Gly Ser Gly Gly Ile Ser
            35                  40                  45

Lys Ser Ser Glu Leu Leu Ser Arg Ala Gly Thr Met Ala Ala Ala Arg
    50                  55                  60

Glu Ala Ala Ala Ala Val His His Glu Gly Trp Met Val Arg Tyr
65                  70                  75                  80

Gly Arg Arg Lys Ile Gly Arg Ser Phe Phe His Thr Arg Tyr Phe Val
                85                  90                  95

Leu Asp Ser Arg Leu Leu Ala Tyr Tyr Lys Lys Pro Lys Asp Asn
            100                 105                 110
```

```
Met Val Pro Leu Lys Ser Leu Leu Ile Asp Gly Asn Cys Arg Val Glu
            115                 120                 125

Asp Arg Gly Leu Lys Thr His His Gly Gln Met Val Tyr Val Leu Cys
    130                 135                 140

Val Tyr Asn Lys Lys Glu Lys Glu His Gln Ile Thr Met Gly Ala Tyr
145                 150                 155                 160

Asp Ile Glu Asp Ala Leu Ala Trp Lys Lys Asn Ile Glu Leu Ile Ile
                165                 170                 175

Asp Gln Gln Glu Asn Met Thr Ser Lys Asn Arg Lys Ala Phe Ala Ser
            180                 185                 190

Met Asp Phe Asp Thr Glu Leu Gly Gly Gln Phe Ile Phe Ser Asp His
            195                 200                 205

Asp Ser Ala Ala Glu Asp Glu Glu Arg Pro Met Leu Ile Arg Arg
210                 215                 220

Thr Thr Ile Gly Asn Gly Pro Pro Glu Ser Ile His Asp Trp Thr Lys
225                 230                 235                 240

Glu His Asp Ile Gly Pro Pro Asn Gln Ile Asp Pro Ile Gln Val Ser
                245                 250                 255

Ser Lys Lys Asn Trp Arg Leu Leu Arg Cys Gln Asn Gly Leu Arg Ile
            260                 265                 270

Phe Glu Glu Leu Leu Glu Phe Asp Tyr Leu Ala Arg Ser Cys Ser Arg
    275                 280                 285

Ala Met Arg Ala Val Gly Val Val Glu Ala Thr Cys Glu Ala Ile Phe
    290                 295                 300

Gly Leu Val Met Ser Met Asp Val Thr Arg Tyr Glu Trp Asp Cys Ser
305                 310                 315                 320

Phe Arg Tyr Gly Ser Leu Val Glu Glu Val Asp Gly His Thr Ala Ile
                325                 330                 335

Leu Tyr His Lys Leu Gln Leu His Trp Cys Pro Met Leu Val Trp Pro
            340                 345                 350

Arg Asp Leu Cys Tyr Val Arg Tyr Trp Arg Arg Asn Asp Asp Gly Ser
    355                 360                 365

Tyr Val Val Leu Phe Arg Ser Thr Glu His Pro Asn Cys Gly Arg Gln
    370                 375                 380

Lys Gly Tyr Val Arg Ala Phe Ile Glu Ser Gly Gly Phe Lys Ile Ser
385                 390                 395                 400

Pro Leu Lys Cys Arg Asn Gly Arg Pro Arg Thr Gln Val Gln His Leu
                405                 410                 415

Met Gln Ile Asp Leu Arg Gly Trp Leu Leu Asn Tyr Ser Pro Ser Phe
            420                 425                 430

Gln Tyr His Ser Leu Leu Gln Ile Gln Asn Cys Val Ala Gly Leu Arg
    435                 440                 445

Glu Tyr Phe Ser Gln Thr Asp Glu Thr His Ile Thr Pro Arg Ile Pro
    450                 455                 460

Val Met Glu Asn Met Val Asp Thr Ser Ala Val Gln Lys Asp Asp Lys
465                 470                 475                 480

Lys Ser Thr Glu Glu Val Asp Ser Lys Thr Lys Thr Pro Asp Arg Gly
                485                 490                 495

Gln Ala Asp Ser Lys Asn Met Gly Ile Ile Asp Glu Glu Thr Asp Glu
            500                 505                 510

Asp Glu Asp Tyr Gln Val Pro Glu Ala Asn Ile Glu Glu Asp Pro Asn
    515                 520                 525
```

Lys Asp Ala Lys Arg Ala Asp Glu Pro Pro Glu Lys Ile Asp Leu Ser
            530                 535                 540

Cys Phe Ser Gly Ile Leu Arg Cys Asp Ala Asp Glu Lys Ser Arg Asn
545                 550                 555                 560

Cys Trp Thr Val Pro Asp Ser Lys Leu Phe Lys Val Arg Ser Lys Asn
                565                 570                 575

Phe Pro His Asp Lys Ser Lys Ile Pro Ala Ala Ser Tyr Leu Met Glu
            580                 585                 590

Leu Ala Ala Ile Asp Trp Phe Lys Asp Ser Lys Arg Met Asp Asn Val
            595                 600                 605

Gly Arg Gln Lys Gly Cys Val Ala Gln Val Ala Ala Glu Lys Gly Met
610                 615                 620

His Thr Phe Val Ala Asn Ile Gln Ile Pro Gly Ser Thr His Tyr Ser
625                 630                 635                 640

Leu Val Met Tyr Phe Val Thr Lys Ser Leu Lys Lys Gly Ser Leu Leu
                645                 650                 655

Gln Arg Phe Phe Asp Gly Asp Asp Glu Phe Arg Asn Ser Arg Leu Lys
            660                 665                 670

Leu Ile Pro Ser Val Pro Lys Gly Ser Trp Ile Val Arg Gln Ser Val
            675                 680                 685

Gly Ser Thr Pro Cys Leu Leu Gly Lys Ala Val Asp Cys Ser Tyr Val
690                 695                 700

Arg Gly Ala Gly Tyr Leu Glu Val Asp Val Asp Ile Gly Ser Ser Ala
705                 710                 715                 720

Val Ala Asn Gly Val Leu Gly Leu Val Phe Gly Val Val Thr Thr Leu
                725                 730                 735

Val Val Asp Met Ala Phe Leu Ile Gln Ala Asn Thr Tyr Glu Glu Leu
            740                 745                 750

Pro Glu Gln Val Ile Gly Ala Ala Arg Leu Ala His Val Glu Pro Ala
            755                 760                 765

Ala Ala Ile Val Pro Gln Asp Leu Thr Pro Pro Pro Ala Leu Ala
770                 775                 780

Asp Asp Asp Asn Ala Ala Ala Ser Ser Ser Glu Asp Asp His Leu Ser
785                 790                 795                 800

Lys Lys Thr Asn

<210> SEQ ID NO 99
<211> LENGTH: 805
<212> TYPE: PRT
<213> ORGANISM: Sorghum bicolor

<400> SEQUENCE: 99

Met Leu Ser Ser Leu Ser Ser Ser Ala Ser Arg Arg Glu Ala Thr Ala
1               5                   10                  15

Ala Arg Ala Thr Arg Ser Gly Glu Leu Pro Lys Ser Ala Ala Ile Ser
            20                  25                  30

Trp Lys Asp Val Ala Ala Thr Ala Lys Asn Gly Glu Leu Ser Lys Ala
        35                  40                  45

Val Gly Gly Ala Glu Leu Ser Lys Ala Val Gly Ala Glu Leu Ser
    50                  55                  60

Lys Ala Val Ala Ala Val Arg Glu Ala Ala Ala Val His His Glu Gly
65                  70                  75                  80

Trp Met Val Arg Tyr Gly Arg Arg Lys Ile Gly Arg Ser Phe Phe His
                85                  90                  95

-continued

```
Thr Arg Tyr Phe Val Leu Glu Ser Arg Leu Leu Ala Tyr Lys Lys
            100                 105                 110

Lys Pro Lys Asp Asn Met Val Pro Leu Lys Ser Leu Leu Ile Asp Gly
            115                 120                 125

Asn Cys Arg Val Glu Asp Arg Gly Leu Lys Asn His His Gly Gln Met
130                 135                 140

Ile Tyr Val Leu Cys Val Tyr Asn Gln Lys Glu Lys Asp His Gln Ile
145                 150                 155                 160

Thr Met Gly Ala His Asp Ile Glu Asp Ala Leu Ala Trp Lys Lys Lys
                165                 170                 175

Ile Glu Leu Leu Ile Asp Gln Gln Pro Asp Ser Ala Ala Lys Thr His
            180                 185                 190

Lys Ala Phe Ala Thr Met Asp Phe Asp Met Glu Leu Gly Gly Gln Phe
            195                 200                 205

Ser Leu Ser Asp His Asp Ser Ala Ala Glu Asp Glu Glu Arg Pro
            210                 215                 220

Thr Leu Val Arg Arg Thr Thr Ile Gly Asn Gly Pro Pro Ala Ser Ile
225                 230                 235                 240

His Asp Trp Thr Lys Asp Ala Asp Phe Gly Met Ser Ser Gln Asn Asp
                245                 250                 255

Pro Thr Gln Leu Tyr Ser Lys Lys Asn Trp Arg Leu Leu Arg Cys Gln
            260                 265                 270

Asn Gly Leu Arg Ile Tyr Glu Glu Leu Leu Glu Val Glu Tyr Leu Ala
            275                 280                 285

Arg Ser Cys Ser Arg Ala Met Arg Ala Val Gly Val Glu Ala Thr
290                 295                 300

Cys Glu Ala Ile Phe Gly Leu Met Met Ser Met Asp Ala Thr Arg Tyr
305                 310                 315                 320

Glu Trp Asp Cys Ser Phe Arg Gln Gly Ser Leu Val Glu Glu Val Asp
                325                 330                 335

Gly His Thr Ala Val Leu Tyr His Arg Leu Gln Leu His Trp Cys Ser
            340                 345                 350

Arg Leu Ile Trp Pro Arg Asp Leu Cys Tyr Val Arg Tyr Trp Arg Arg
            355                 360                 365

Asn Asp Asp Gly Ser Tyr Val Val Leu Phe Arg Ser Thr Glu His Pro
370                 375                 380

Asn Cys Asn Arg Gln Arg Gly Phe Val Arg Ala Phe Ile Glu Ser Gly
385                 390                 395                 400

Gly Phe Lys Ile Cys Pro Leu Lys Ser Arg Asn Gly Arg Pro Arg Thr
                405                 410                 415

Gln Val Gln His Leu Met Gln Ile Asp Leu Lys Gly Trp Phe Leu Asn
            420                 425                 430

Tyr Ser Thr Ser Phe Gln Tyr His Ser Leu Leu Gln Ile Leu Asn Cys
            435                 440                 445

Val Ala Gly Leu Arg Glu Tyr Phe Ser Gln Thr Asp Asp Ile His Ile
450                 455                 460

Thr Pro Arg Ile Pro Ala Met Glu Ser Met Ala Asp Val Asn Thr Ala
465                 470                 475                 480

Gln Lys Asp Glu Lys Leu Thr Glu Ile Asp Ser Asn Thr Lys Pro Thr
                485                 490                 495

Asp Gln Glu His Leu Glu Asn Lys Asn Met Gly Thr Ile Asp Glu Glu
            500                 505                 510

Ser Asp Asp Asp Glu Glu Tyr Gln Val Pro Glu Ala Asp Ile Glu Val
```

```
            515                 520                 525
Gln Gln Arg Tyr Phe Asn Met Thr Asp Glu Pro Pro Glu Lys Ile
    530                 535                 540

Asp Leu Ser Cys Phe Ser Gly Ile Leu His His Asp Pro Asp Glu Lys
545                 550                 555                 560

Ser Arg Asn Cys Trp Thr Val Pro Asp Ser Lys Leu Phe Lys Val Arg
                565                 570                 575

Ser Lys Asn Phe Pro Asn Asp Lys Ser Glu Ile Pro Ala Ala Ser Tyr
            580                 585                 590

Leu Met Glu Leu Ala Ala Ile Asp Trp Tyr Lys Asp Thr Lys Arg Met
        595                 600                 605

Asp Asn Val Gly Arg Gln Lys Asn Cys Val Ala Gln Ile Ala Ala Glu
    610                 615                 620

Lys Gly Met His Thr Phe Ile Val Asn Leu Gln Ile Pro Gly Ser Thr
625                 630                 635                 640

His Tyr Ser Met Val Met Tyr Phe Val Thr Ser Ser Leu Lys Lys Gly
                645                 650                 655

Ser Leu Leu Gln Arg Phe Phe Asp Gly Asp Asp Phe Arg Asn Ser
            660                 665                 670

Arg Leu Lys Leu Ile Pro Ser Val Pro Lys Gly Ser Trp Ile Val Arg
        675                 680                 685

Gln Ser Val Gly Ser Ser Pro Cys Leu Leu Gly Lys Ala Leu Asp Cys
    690                 695                 700

Ser Tyr Val Arg Thr Pro Ser Val Leu Gln Val Asp Val Asp Ile Gly
705                 710                 715                 720

Ser Ser Ala Val Ala Asn Gly Val Leu Gly Leu Val Phe Gly Val Val
                725                 730                 735

Thr Thr Leu Val Val Asp Met Ala Phe Leu Ile Gln Ala Asn Thr Tyr
            740                 745                 750

Glu Glu Leu Pro Glu Gln Val Ile Gly Ala Ala Arg Leu Ser Asn Val
        755                 760                 765

Glu Pro Ala Thr Ala Val Val Pro Asp Leu Glu Asn Asn Ser Asp Ser
    770                 775                 780

Asn Lys Asn Asn Asn Ser Asn Asp Ala Thr Ser Ser Glu Asp Asp Ser
785                 790                 795                 800

Ser Lys Lys Thr Asn
                805

<210> SEQ ID NO 100
<211> LENGTH: 653
<212> TYPE: PRT
<213> ORGANISM: Oryza sativa

<400> SEQUENCE: 100

Met Ala Arg Ser Gly Glu Leu Pro Lys Val Ser Ala Ala Ala Thr Ala
1               5                   10                  15

Ala Val Arg His Glu Gly Trp Met Leu Arg Tyr Gly Arg Arg Lys Ile
            20                  25                  30

Gly Arg Ser Phe Val Arg Thr Arg Tyr Phe Val Leu Asp Asn Lys Leu
        35                  40                  45

Leu Ala Tyr Tyr Lys Lys Gln Pro Lys Asp Asn Met Val Pro Val Lys
    50                  55                  60

Ala Leu Gln Ile Asp Gly Asn Cys Arg Val Glu Asp Arg Gly Leu Lys
65                  70                  75                  80
```

```
Thr His His Gly Gln Met Val Tyr Val Leu Cys Ile Tyr Asn Lys Lys
                85                  90                  95

Glu Lys Glu Asn His Ile Thr Met Gly Ala His Asp Ile Glu Asp Ala
            100                 105                 110

Leu Val Trp Lys Lys Lys Leu Glu Leu Leu Ile Asp Gln Gln Gln Asp
        115                 120                 125

Thr Met Thr Ala Lys Asn Arg Lys Ala Phe Ala Ser Leu Asp Phe Asp
130                 135                 140

Met Glu Phe Gly Gly Pro Leu Ser Phe Ser Asp Arg Asp Ser Gly Gln
145                 150                 155                 160

Ala Leu Leu Ile Arg Tyr Met Ile Gly Pro Arg Ser Leu Ile Leu Gly
                165                 170                 175

Cys Gln Ile Arg Met Thr Pro Thr Met Leu Thr Gln Glu Arg Thr Gly
            180                 185                 190

Gly Tyr Leu Asp Val Arg Met Ala Arg Ser Cys Ser Arg Ala Met Arg
        195                 200                 205

Ala Val Gly Val Val Glu Ala Thr Cys Glu Ser Ile Phe Gly Leu Ile
210                 215                 220

Met Ser Met Asp Val Thr Arg Tyr Glu Trp Asp Cys Ser Phe Gln Tyr
225                 230                 235                 240

Gly Ser Leu Val Glu Glu Val Asp Val Val Leu Phe Arg Ser Thr Glu
                245                 250                 255

His Gln Asn Cys Gly Pro Gln Pro Gly Phe Val Arg Ala Phe Ile Glu
            260                 265                 270

Ser Gly Gly Phe Lys Ile Ser Pro Leu Lys Cys Val Asn Gly Arg Pro
        275                 280                 285

Arg Thr Gln Val Gln His Leu Met Gln Ile Asp Leu Lys Gly Trp Gly
290                 295                 300

Val Asn Tyr Phe Ser Ser Phe Gln Tyr Tyr Ser Leu Leu Gln Met Leu
305                 310                 315                 320

Asn Cys Val Ala Gly Leu Arg Glu Tyr Phe Ser Gln Thr Asp Asp Ile
                325                 330                 335

His Pro Val Pro Arg Ile Pro Val Met Ser Thr Met Ala Thr Val Ser
            340                 345                 350

Lys Leu Lys Lys Asp Lys Lys Leu Gln Glu Thr Asp Leu Lys Thr Lys
        355                 360                 365

Gln Ala Asp Phe Gly Gln Val Asp Asn Lys Asn Leu Asp Met Ile Asp
370                 375                 380

Glu Glu Ser Glu Glu Asp Asp Asp Tyr Gln Val Pro Glu Ala Asn Leu
385                 390                 395                 400

Glu Glu Ala Pro Thr Arg Ser Asp Ser Asp Ala Lys Tyr Thr Asp Pro
                405                 410                 415

Ile Asp Leu Ser Cys Phe Ser Gly Ile Ile Arg Arg Asp Ala Asn Glu
            420                 425                 430

Lys Ser Arg Asn Cys Trp Thr Val Pro Asp Ser Lys Leu Phe Lys Val
        435                 440                 445

Arg Ser Glu Ser Phe Pro His Asp Lys Ser Lys Val Pro Ala Thr Lys
450                 455                 460

Tyr Leu Met Glu Leu Val Ala Ile Asp Trp Leu Arg Asp Ile Lys Arg
465                 470                 475                 480

Met Asp His Val Ala Arg Arg Lys Gly Cys Ala Ala Gln Val Ala Ala
                485                 490                 495

Glu Lys Gly Met Phe Thr Phe Val Val Asn Ile Gln Ile Pro Gly Ser
```

```
                500                 505                 510
Ser His Tyr Ser Leu Val Leu Tyr Phe Val Thr Arg Thr Leu Glu Lys
        515                 520                 525

Gly Ser Leu Leu Gln Arg Phe Ala Asp Gly Asp Asp Phe Arg Asn
        530                 535                 540

Ser Arg Leu Lys Leu Ile Pro Ser Val Pro Lys Gly Ser Trp Ile Val
545                 550                 555                 560

Arg Gln Ser Val Gly Ser Thr Pro Cys Leu Leu Gly Lys Ala Val Asp
                565                 570                 575

Cys Ser Tyr Met Arg Gly Gln Glu Tyr Ile Glu Val Asp Val Asp Ile
                580                 585                 590

Gly Ser Ser Ala Val Ala Asn Gly Val Leu Gly Leu Val Phe Gly Val
            595                 600                 605

Val Thr Thr Leu Ile Val Asp Met Ala Phe Leu Ile Gln Ala Asn Thr
        610                 615                 620

Tyr Asp Glu Leu Pro Glu Gln Leu Leu Gly Ala Ala Arg Leu Ser Asn
625                 630                 635                 640

Ile Glu Pro Ser Ser Ala Ile Val Pro Val Leu Asp Lys
                645                 650

<210> SEQ ID NO 101
<211> LENGTH: 689
<212> TYPE: PRT
<213> ORGANISM: Sorghum bicolor

<400> SEQUENCE: 101

Met Ala Arg Ser Glu Glu Leu Pro Lys Gly Gly Cys Ala Gly Pro Thr
1               5                   10                  15

Pro Ala Ala Val Arg His Glu Gly Trp Met Val Arg His Gly Arg Arg
            20                  25                  30

Lys Ile Gly Arg Ser Phe Phe His Thr Arg Tyr Phe Val Leu Asp Asn
        35                  40                  45

Arg Val Leu Ala Tyr Tyr Lys Lys Gln Pro Arg Asp Ser Met Ile Pro
    50                  55                  60

Leu Lys Ser Ile Val Ile Asp Gly Asn Cys Arg Val Glu Asp Arg Gly
65                  70                  75                  80

Leu Lys Thr His His Gly Gln Met Ile Tyr Leu Leu Cys Ile Tyr Asn
                85                  90                  95

Lys Lys Glu Lys Glu Asn Gln Ile Thr Met Gly Gly Tyr Asn Ile Gln
            100                 105                 110

Asp Thr Leu Ala Trp Lys Arg Lys Ile Glu Leu Leu Ile Asp Gln Gln
        115                 120                 125

Gln Asp Thr Thr Thr Ala Lys His Arg Lys Ala Phe Ala Ser Leu Asp
    130                 135                 140

Phe Asp Ile Asp Leu Gly Gly Pro Phe Ser Phe Ser Asp His Asp Ser
145                 150                 155                 160

Gly Gln Val Lys Pro Glu Asp Glu Asp Glu Glu Glu Pro Arg
                165                 170                 175

Pro Thr Leu Leu Arg Arg Thr Thr Ile Gly Asn Gly Leu Arg Ile Phe
            180                 185                 190

Glu Glu Leu Val Glu Val Glu Tyr Leu Ala Arg Ser Cys Ser Arg Ala
        195                 200                 205

Met Arg Ala Val Gly Val Val Glu Ala Ser Cys Glu Ala Ile Phe Gly
    210                 215                 220
```

```
Leu Val Met Ser Met Asp Val Thr Arg Tyr Glu Trp Asp Cys Ser Phe
225                 230                 235                 240

Gln Tyr Gly Ser Leu Val Glu Glu Val Asp Gly His Thr Ala Ile Leu
            245                 250                 255

Tyr His Arg Leu Gln Leu Asn Trp Cys Ser Met Leu Val Trp Pro Arg
        260                 265                 270

Asp Leu Cys Tyr Leu Arg Tyr Trp Arg Arg Asn Asp Asp Gly Ser Tyr
    275                 280                 285

Val Val Leu Phe Arg Ser Thr Glu His Gln Asn Cys Gly Pro Gln Pro
290                 295                 300

Gly Phe Val Arg Ala Ser Ile Glu Ser Gly Gly Phe Lys Ile Ser Pro
305                 310                 315                 320

Leu Lys Ser Leu Asn Gly Arg Pro Arg Thr Gln Val Gln His Leu Met
            325                 330                 335

Gln Ile Asp Val Arg Gly Trp Gly Val Asn Tyr Leu Pro Ser Phe Gln
        340                 345                 350

Tyr His Ser Leu Leu Gln Met Leu Asn Cys Val Ala Gly Leu Arg Glu
    355                 360                 365

Tyr Phe Ser Gln Thr Asp Glu Val His Thr Val Pro Arg Ile Pro Val
370                 375                 380

Met His Thr Met Phe Asn Ala Val Ser Met Lys Lys Asp Gln Asn Leu
385                 390                 395                 400

Gln Glu Pro Asp Ser Lys Thr Lys Gln Thr Asp Ser Lys His Leu Asp
            405                 410                 415

Met Val Asp Glu Glu Ser Glu Asp Asp Asp Tyr Gln Ala Pro Glu
        420                 425                 430

Ala Asp Leu Glu Glu Glu Pro Thr Lys Ser Asp Ser Asp Ala Lys Ser
    435                 440                 445

Ser Asp Pro Ile Asp Leu Ser Trp Phe Ser Gly Thr Ile Arg Gln Asp
450                 455                 460

Thr Asn Glu Lys Ser Arg Asn Cys Trp Ala Val Pro Asp Ser Lys Ile
465                 470                 475                 480

Phe Lys Val Arg Ser Lys Thr Phe Pro His Asp Lys Ser Lys Val Pro
            485                 490                 495

Ala Gly Lys Tyr Leu Met Glu Leu Val Ala Ile Asp Trp Phe Lys Asp
        500                 505                 510

Thr Lys Arg Met Asp His Val Ala Arg Arg Lys Gly Ser Ala Ala Gln
    515                 520                 525

Val Ala Ala Asp Lys Gly Met Phe Thr Phe Leu Val Asn Ile Gln Ile
530                 535                 540

Pro Gly Pro Ser His Tyr Ser Leu Val Leu Tyr Phe Val Ser Asn Ser
545                 550                 555                 560

Leu Glu Lys Gly Ser Leu Leu Gln Arg Phe Ala Asp Gly Asp Asp Asp
            565                 570                 575

Phe Arg Asn Ser Arg Leu Lys Leu Ile Pro Ser Val Pro Lys Gly Ser
        580                 585                 590

Trp Ile Val Arg Gln Ser Val Gly Ser Thr Pro Cys Leu Leu Gly Lys
    595                 600                 605

Ala Val Asp Cys Ser Tyr Leu Arg Gly Pro Asp Tyr Leu Glu Val Asp
610                 615                 620

Val Asp Ile Gly Ser Ser Ala Val Ala Asn Gly Val Leu Gly Leu Val
625                 630                 635                 640

Phe Gly Val Val Thr Thr Leu Val Val Asp Met Ala Phe Leu Ile Gln
```

```
                        645                 650                 655
Ala Asn Thr Tyr Asp Glu Leu Pro Glu Gln Leu Leu Gly Ala Ala Arg
                    660                 665                 670

Leu Ser His Ile Glu Pro Ser Ala Ala Val Cys Pro Asp Leu Glu Asn
            675                 680                 685

Ile

<210> SEQ ID NO 102
<211> LENGTH: 725
<212> TYPE: PRT
<213> ORGANISM: Populus trichocarpa

<400> SEQUENCE: 102

Met Ser Lys Val Ile Phe Glu Gly Trp Met Val Arg Tyr Gly Arg Arg
1               5                   10                  15

Lys Ile Gly Arg Ser Phe Ile His Met Arg Tyr Phe Val Leu Glu Pro
            20                  25                  30

Thr Leu Ala Tyr Tyr Lys Lys Lys Pro Glu Asp Asn Gln Val Pro
        35                  40                  45

Ile Lys Thr Leu Leu Ile Asp Gly Asn Cys Arg Val Glu Asp Arg Gly
    50                  55                  60

Leu Lys Thr Gln His Gly His Met Val Tyr Val Leu Ser Val Tyr Asn
65                  70                  75                  80

Lys Lys Asp Lys Tyr Asn Arg Ile Thr Met Ala Ala Phe Asn Ile Gln
                85                  90                  95

Glu Gln Leu Met Trp Lys Gly Lys Ile Glu Phe Val Ile Asp Gln His
            100                 105                 110

Gln Glu Ser Gln Val Pro Asn Gly Asn Lys Tyr Ala Ser Phe Glu Tyr
        115                 120                 125

Lys Ser Gly Met Asp Asn Gly Arg Thr Ala Ser Ser Asp Cys Glu
    130                 135                 140

Ile Gln Phe Ile Ala Gln Glu Asp Glu Asp Ser His Thr Asn Leu
145                 150                 155                 160

Leu Arg Arg Thr Thr Ile Gly Asn Gly Pro Pro Ala Ser Val Phe Asp
                165                 170                 175

Trp Thr Gln Glu Phe Asp Ser Asp Leu Thr Asn Gln Asn Ala Asn Asn
            180                 185                 190

Gln Ala Phe Ser Arg Lys His Trp Arg Leu Leu Gln Cys Gln Asn Gly
        195                 200                 205

Leu Arg Ile Phe Glu Glu Leu Leu Glu Val Glu Tyr Leu Pro Arg Ser
    210                 215                 220

Cys Ser Arg Ala Met Lys Ala Val Gly Val Val Glu Ala Ser Cys Glu
225                 230                 235                 240

Glu Ile Phe Glu Leu Ile Met Ser Met Asp Ala Lys Arg Phe Glu Trp
                245                 250                 255

Asp Cys Ser Phe Gln His Gly Ser Leu Val Glu Val Asp Gly His
            260                 265                 270

Thr Ala Ile Leu Tyr His Arg Leu Gln Leu Asp Trp Phe Pro Ile Phe
        275                 280                 285

Val Trp Pro Arg Asp Leu Cys Tyr Val Arg Tyr Trp Arg Arg Asn Asp
    290                 295                 300

Asp Gly Ser Tyr Val Val Leu Phe Arg Ser Arg Val His Glu Lys Cys
305                 310                 315                 320

Asp Pro Gln Pro Gly Tyr Val Arg Ala Asn Ile Glu Ser Gly Gly Phe
```

```
            325                 330                 335
Ile Ile Ser Pro Leu Lys Pro Cys Asn Glu Lys Pro Arg Thr Gln Val
            340                 345                 350
Gln His Leu Met Gln Ile Asp Leu Lys Gly Trp Gly Val Gly Tyr Val
            355                 360                 365
Ser Ser Phe Gln Gln His Cys Leu Leu Gln Met Leu Asn Ser Val Ala
            370                 375                 380
Gly Leu Arg Glu Leu Phe Ser Gln Thr Asp Glu Arg Gly Ala Pro Pro
385                 390                 395                 400
Arg Ile Ala Val Met Ala Asn Met Ala Ser Ala Ser Ala Pro Ser Lys
                    405                 410                 415
Lys Asn Val Lys Val Pro Glu Ser Ser Val His Pro Thr Pro Pro Ser
            420                 425                 430
Leu Asp Gln Ile Asn Ala Ala Ser Arg His Ser Val Met Asp Glu Asp
            435                 440                 445
Thr Asp Asp Asp Glu Glu Phe Pro Ile Ala Glu Glu Gln Glu Ala
450                 455                 460
Phe Arg Ala Lys His Glu Asn Asp Ala Lys Arg Thr Ala Leu Glu Glu
465                 470                 475                 480
Glu Ser Val Asp Gln Ile Asp Leu Ser Cys Phe Ser Gly Asn Leu Arg
                    485                 490                 495
Arg Asp Asp Arg Asp Asn Ala Arg Asp Cys Trp Arg Ile Ser Asp Gly
                500                 505                 510
Asn Asn Phe Arg Val Arg Ser Lys Arg Phe Cys Phe Asp Lys Ser Lys
            515                 520                 525
Val Pro Ala Gly Lys His Leu Met Asp Leu Val Ala Val Asp Trp Phe
530                 535                 540
Lys Asp Thr Lys Arg Met Asp His Val Ala Arg Arg Gln Gly Cys Ala
545                 550                 555                 560
Ala Gln Val Ala Ser Glu Lys Gly His Phe Ser Val Val Phe Asn Leu
                565                 570                 575
Gln Val Pro Gly Ser Thr His Tyr Ser Met Val Phe Tyr Phe Val Thr
            580                 585                 590
Lys Glu Leu Val Pro Gly Ser Leu Leu Gln Arg Phe Val Asp Gly Asp
            595                 600                 605
Asp Glu Phe Arg Asn Ser Arg Phe Lys Leu Ile Pro Ser Val Pro Lys
            610                 615                 620
Gly Ser Trp Ile Val Arg Gln Ser Val Gly Ser Thr Pro Cys Leu Leu
625                 630                 635                 640
Gly Lys Ala Val Asp Cys Asn Tyr Ile Arg Gly Pro Lys Tyr Leu Glu
                    645                 650                 655
Val Asp Val Asp Ile Gly Ser Ser Thr Val Ala Asn Gly Val Leu Gly
                660                 665                 670
Leu Val Ile Gly Val Ile Thr Thr Leu Val Val Asp Met Ala Phe Leu
                675                 680                 685
Val Gln Ala Asn Thr Thr Glu Glu Leu Pro Glu Arg Leu Ile Gly Ala
            690                 695                 700
Val Arg Val Ser His Ile Glu Leu Ser Ser Ala Ile Val Pro Lys Leu
705                 710                 715                 720
Asp Pro Asp Pro Ser
                725
```

<210> SEQ ID NO 103

```
<211> LENGTH: 710
<212> TYPE: PRT
<213> ORGANISM: Vitis vinifera

<400> SEQUENCE: 103
```

| | | | | | | | | | | | | | | |
|---|---|---|---|---|---|---|---|---|---|---|---|---|---|---|
|Met|Val|Arg|Cys|Gly|Arg|Arg|Lys|Ile|Gly|Arg|Ser|Tyr|Ile|His|Met|
|1| | | |5| | | | |10| | | | |15| |

Arg Tyr Phe Val Leu Glu Ser Arg Leu Leu Ala Tyr Tyr Lys Arg Lys
            20                  25                  30

Pro Gln His Asn Val Val Pro Ile Lys Thr Leu Leu Ile Asp Gly Asn
        35                  40                  45

Cys Arg Val Glu Asp Arg Gly Leu Lys Thr His His Gly Tyr Met Val
 50                  55                  60

Tyr Val Leu Ser Ile Tyr Asn Lys Lys Glu Lys Tyr His Arg Ile Thr
 65                  70                  75                  80

Met Ala Ala Phe Asn Ile Gln Glu Ala Leu Leu Trp Lys Glu Lys Ile
                85                  90                  95

Glu Ser Val Ile Asp Gln His Gln Asp Leu Gln Val Ala Asn Gly Asn
            100                 105                 110

Lys Tyr Ile Ser Phe Glu Tyr Lys Ser Gly Met Asp Asn Gly Arg Ala
        115                 120                 125

Ala Ser Ser Ser Asp His Glu Ser Gln Phe Ser Ala Gln Asp Asp Glu
130                 135                 140

Glu Asp Thr His Arg Asp Leu Val Arg Arg Lys Thr Ile Gly Asn Gly
145                 150                 155                 160

Ile Pro Asp Ser Val Leu Asp Trp Thr Arg Glu Ile Asp Ser Glu Leu
                165                 170                 175

Ser Asn Gln Asn Ile Asn Asn Gln Ala Phe Ser Arg Lys His Trp Arg
            180                 185                 190

Leu Leu Gln Cys Gln Asn Gly Leu Arg Ile Phe Glu Glu Leu Leu Glu
        195                 200                 205

Val Asp Tyr Leu Pro Arg Ser Cys Ser Arg Ala Met Lys Ala Val Gly
210                 215                 220

Val Val Glu Ala Thr Cys Glu Glu Ile Phe Glu Leu Val Met Ser Met
225                 230                 235                 240

Asp Gly Lys Arg Phe Glu Trp Asp Cys Ser Phe Gln Asp Gly Ser Leu
                245                 250                 255

Val Glu Glu Val Asp Gly His Thr Ala Ile Leu Tyr His Arg Leu Gln
            260                 265                 270

Leu Asp Trp Phe Pro Met Phe Val Trp Pro Arg Asp Leu Cys Tyr Val
        275                 280                 285

Arg Tyr Trp Arg Arg Asn Asp Asp Gly Ser Tyr Val Val Leu Phe Arg
290                 295                 300

Ser Arg Glu His Glu Asn Cys Gly Pro Gln Pro Gly Phe Val Arg Ala
305                 310                 315                 320

His Leu Glu Ser Gly Gly Phe Asn Ile Ser Pro Leu Lys Pro Arg Asn
                325                 330                 335

Gly Arg Pro Arg Thr Gln Val Gln His Leu Leu Gln Ile Asp Leu Lys
            340                 345                 350

Gly Trp Gly Ala Gly Tyr Ile Ser Ser Phe Gln His Cys Leu Leu
        355                 360                 365

Gln Val Leu Asn Ser Val Ala Gly Leu Arg Glu Trp Phe Ser Gln Thr
370                 375                 380

Asp Glu Arg Asn Ala Gln Pro Arg Ile Pro Val Met Val Asn Met Ala

```
                385                 390                 395                 400
        Ser Ala Ser Val Thr Ser Lys Lys Asn Gln Lys Pro Gln Glu Tyr Ser
                            405                 410                 415

Asp Gln Ser Asn Ala Thr Gly Arg Asn Ser Met Met Met Asp Glu Asp
                            420                 425                 430

Ser Asp Glu Asp Glu Glu Phe Gln Val Pro Glu Arg Glu Gln Glu Ala
                            435                 440                 445

Tyr Ser Met Ser Leu Gln Asn Glu Val Lys Gly Thr Ala Met Glu Glu
                            450                 455                 460

Glu Pro Gln Asp Lys Ile Asp Val Ser Cys Phe Ser Gly Asn Leu Arg
        465                 470                 475                 480

Arg Asp Asp Arg Asp Lys Gly Arg Asp Cys Trp Thr Ile Ser Asp Gly
                            485                 490                 495

Asn Asn Phe Arg Val Arg Cys Lys His Phe Phe Tyr Asp Lys Thr Lys
                            500                 505                 510

Ile Pro Ala Gly Lys His Leu Met Asp Leu Val Ala Val Asp Trp Phe
                            515                 520                 525

Lys Asp Ser Lys Arg Ile Asp His Val Ala Arg Arg Gln Gly Cys Ala
                            530                 535                 540

Ala Gln Val Ala Ser Glu Lys Gly Leu Phe Ser Ile Ile Asn Leu
        545                 550                 555                 560

Gln Val Pro Gly Ser Thr His Tyr Ser Met Val Phe Tyr Phe Val Ser
                            565                 570                 575

Lys Glu Leu Val Thr Gly Ser Leu Leu Gln Arg Phe Val Asp Gly Asp
                            580                 585                 590

Asp Glu Phe Arg Asn Ser Arg Leu Lys Leu Ile Pro Ser Val Pro Lys
                            595                 600                 605

Gly Ser Trp Ile Val Arg Gln Ser Val Gly Ser Thr Pro Cys Leu Leu
                            610                 615                 620

Gly Lys Ala Val Asp Cys Asn Tyr Ile Arg Gly Pro Lys Tyr Leu Glu
        625                 630                 635                 640

Ile Asp Val Asp Ile Gly Ser Ser Thr Val Ala Asn Gly Val Leu Gly
                            645                 650                 655

Leu Val Cys Gly Val Ile Thr Thr Leu Val Asp Met Ala Phe Leu
                            660                 665                 670

Val Gln Ala Asn Thr Val Asp Glu Leu Pro Glu Arg Leu Ile Gly Ala
                            675                 680                 685

Val Arg Val Ser His Val Glu Leu Ser Ser Ala Ile Val Pro Lys Leu
                            690                 695                 700

Asp Pro Asp Thr Cys Ala
        705                 710

<210> SEQ ID NO 104
<211> LENGTH: 720
<212> TYPE: PRT
<213> ORGANISM: Arabidopsis thaliana

<400> SEQUENCE: 104

Met Ser Lys Val Val Tyr Glu Gly Trp Met Val Arg Tyr Gly Arg Arg
1               5                   10                  15

Lys Ile Gly Arg Ser Tyr Ile His Met Arg Tyr Phe Val Leu Glu Pro
                20                  25                  30

Arg Leu Leu Ala Tyr Tyr Lys Lys Lys Pro Gln Asp Tyr Gln Val Pro
            35                  40                  45
```

```
Ile Lys Thr Met Leu Ile Asp Gly Asn Cys Arg Val Glu Asp Arg Gly
         50                  55                  60
Leu Lys Thr His His Gly His Met Val Tyr Val Leu Ser Val Tyr Asn
 65                  70                  75                  80
Lys Lys Glu Lys Ser His Arg Ile Thr Met Ala Ala Phe Asn Ile Gln
                 85                  90                  95
Glu Ala Leu Met Trp Lys Glu Lys Ile Glu Ser Val Ile Asp Gln His
                100                 105                 110
Gln Glu Ser Gln Val Pro Asn Gly Gln Gln Tyr Val Ser Phe Glu Tyr
                115                 120                 125
Lys Ser Gly Met Asp Thr Gly Arg Thr Ala Ser Ser Ser Asp His Glu
        130                 135                 140
Ser Gln Phe Ser Ala Ala Glu Asp Glu Glu Asp Ser Arg Arg Ser Leu
145                 150                 155                 160
Met Arg Arg Thr Thr Ile Gly Asn Gly Pro Pro Glu Ser Val Leu Asp
                    165                 170                 175
Trp Thr Lys Glu Phe Asp Ala Glu Leu Ala Asn Gln Asn Ser Asp Asn
                180                 185                 190
Gln Ala Phe Ser Arg Lys His Trp Arg Leu Leu Gln Cys Gln Asn Gly
                195                 200                 205
Leu Arg Ile Phe Glu Glu Leu Leu Glu Val Asp Tyr Leu Pro Arg Ser
        210                 215                 220
Cys Ser Arg Ala Met Lys Ala Val Gly Val Val Glu Ala Thr Cys Glu
225                 230                 235                 240
Glu Ile Phe Glu Leu Leu Met Ser Met Asp Gly Thr Arg Tyr Glu Trp
                    245                 250                 255
Asp Cys Ser Phe Gln Phe Gly Ser Leu Val Glu Glu Val Asp Gly His
                260                 265                 270
Thr Ala Val Leu Tyr His Arg Leu Leu Leu Asp Trp Ile Val Trp Pro
        275                 280                 285
Arg Asp Leu Cys Tyr Val Arg Tyr Trp Arg Arg Asn Asp Asp Gly Ser
        290                 295                 300
Tyr Val Val Leu Phe Arg Ser Arg Glu His Glu Asn Cys Gly Pro Gln
305                 310                 315                 320
Pro Gly Cys Val Arg Ala His Leu Glu Ser Gly Gly Tyr Asn Ile Ser
                    325                 330                 335
Pro Leu Lys Pro Arg Asn Gly Arg Pro Arg Thr Gln Val Gln His Leu
                340                 345                 350
Ile Gln Ile Asp Leu Lys Gly Trp Gly Ala Gly Tyr Leu Pro Ala Phe
                355                 360                 365
Gln Gln His Cys Leu Leu Gln Met Leu Asn Ser Val Ala Gly Leu Arg
        370                 375                 380
Glu Trp Phe Ser Gln Thr Asp Glu Arg Gly Val His Thr Arg Ile Pro
385                 390                 395                 400
Val Met Val Asn Met Ala Ser Ser Leu Ser Leu Thr Lys Ser Gly
                    405                 410                 415
Lys Ser Leu His Lys Ser Ala Phe Ser Leu Asp Gln Thr Asn Ser Val
                420                 425                 430
Asn Arg Asn Ser Leu Leu Met Asp Glu Ser Asp Asp Asp Glu
                435                 440                 445
Phe Gln Ile Ala Glu Ser Glu Gln Glu Pro Glu Thr Ser Lys Pro Glu
        450                 455                 460
Thr Asp Val Lys Arg Pro Gly Val His Pro Ile Lys Glu Glu Pro Ala
```

```
                465                 470                 475                 480
His Asn Ile Asp Leu Ser Cys Phe Ser Gly Asn Leu Lys Arg Asn Glu
                    485                 490                 495

Asn Glu Asn Ala Arg Asn Cys Trp Arg Ile Ser Asp Gly Asn Asn Phe
                500                 505                 510

Lys Val Arg Gly Lys Asn Phe Gly Gln Glu Lys Arg Lys Ile Pro Ala
            515                 520                 525

Gly Lys His Leu Met Asp Leu Val Ala Val Asp Trp Phe Lys Asp Ser
        530                 535                 540

Lys Arg Ile Asp His Val Ala Arg Arg Lys Gly Cys Ala Ala Gln Val
545                 550                 555                 560

Ala Ala Glu Lys Gly Leu Phe Ser Met Val Val Asn Val Gln Val Pro
                565                 570                 575

Gly Ser Thr His Tyr Ser Met Val Phe Tyr Phe Val Met Lys Glu Leu
                580                 585                 590

Val Pro Gly Ser Leu Leu Gln Arg Phe Val Asp Gly Asp Asp Glu Phe
            595                 600                 605

Arg Asn Ser Arg Leu Lys Leu Ile Pro Leu Val Pro Lys Gly Ser Trp
        610                 615                 620

Ile Val Arg Gln Ser Val Gly Ser Thr Pro Cys Leu Leu Gly Lys Ala
625                 630                 635                 640

Val Asp Cys Asn Tyr Ile Arg Gly Pro Thr Tyr Leu Glu Ile Asp Val
                645                 650                 655

Asp Ile Gly Ser Ser Thr Val Ala Asn Gly Val Leu Gly Leu Val Ile
                660                 665                 670

Gly Val Ile Thr Ser Leu Val Val Glu Met Ala Phe Leu Val Gln Ala
            675                 680                 685

Asn Thr Ala Glu Glu Gln Pro Glu Arg Leu Ile Gly Ala Val Arg Val
        690                 695                 700

Ser His Ile Glu Leu Ser Ser Ala Ile Val Pro Asn Leu Glu Ser Glu
705                 710                 715                 720

<210> SEQ ID NO 105
<211> LENGTH: 719
<212> TYPE: PRT
<213> ORGANISM: Arabidopsis thaliana

<400> SEQUENCE: 105

Met Ser Lys Val Val Tyr Glu Gly Trp Met Val Arg Tyr Gly Arg Arg
1               5                   10                  15

Lys Ile Gly Arg Ser Tyr Ile His Met Arg Tyr Phe Val Leu Glu Pro
            20                  25                  30

Arg Leu Leu Ala Tyr Tyr Lys Lys Lys Pro Gln Asp Asn Gln Leu Pro
        35                  40                  45

Ile Lys Thr Met Val Ile Asp Gly Asn Cys Arg Val Glu Asp Arg Gly
    50                  55                  60

Leu Lys Thr His His Gly His Met Val Tyr Val Leu Ser Ile Tyr Asn
65                  70                  75                  80

Lys Lys Glu Lys His His Arg Ile Thr Met Ala Ala Phe Asn Ile Gln
                85                  90                  95

Glu Ala Leu Met Trp Lys Glu Lys Ile Glu Cys Val Ile Asp Gln His
            100                 105                 110

Gln Asp Ser Leu Val Pro Ser Gly Gln Gln Tyr Val Ser Phe Glu Tyr
        115                 120                 125
```

-continued

```
Lys Pro Gly Met Asp Ala Gly Arg Thr Ala Ser Ser Ser Asp His Glu
    130                 135                 140

Ser Pro Phe Ser Ala Leu Glu Asp Glu Asn Asp Ser Gln Arg Asp Leu
145                 150                 155                 160

Leu Arg Arg Thr Thr Ile Gly Asn Gly Pro Pro Glu Ser Ile Leu Asp
                165                 170                 175

Trp Thr Lys Glu Phe Asp Ala Glu Leu Ser Asn Gln Ser Ser Ser Asn
            180                 185                 190

Gln Ala Phe Ser Arg Lys His Trp Arg Leu Leu Gln Cys Gln Asn Gly
        195                 200                 205

Leu Arg Ile Phe Glu Glu Leu Leu Glu Val Asp Tyr Leu Pro Arg Ser
    210                 215                 220

Cys Ser Arg Ala Met Lys Ala Val Gly Val Val Glu Ala Thr Cys Glu
225                 230                 235                 240

Glu Ile Phe Glu Leu Val Met Ser Met Asp Gly Thr Arg Tyr Glu Trp
                245                 250                 255

Asp Cys Ser Phe His Asn Gly Arg Leu Val Glu Val Asp Gly His
            260                 265                 270

Thr Ala Ile Leu Tyr His Arg Leu Leu Leu Asp Trp Phe Pro Met Val
        275                 280                 285

Val Trp Pro Arg Asp Leu Cys Tyr Val Arg Tyr Trp Arg Arg Asn Asp
    290                 295                 300

Asp Gly Ser Tyr Val Val Leu Phe Arg Ser Arg Glu His Glu Asn Cys
305                 310                 315                 320

Gly Pro Gln Pro Gly Phe Val Arg Ala His Leu Glu Ser Gly Gly Phe
                325                 330                 335

Asn Ile Ala Pro Leu Lys Pro Arg Asn Gly Arg Pro Arg Thr Gln Val
            340                 345                 350

Gln His Leu Ile Gln Ile Asp Leu Lys Gly Trp Gly Ser Gly Tyr Leu
        355                 360                 365

Pro Ala Phe Gln Gln His Cys Leu Leu Gln Met Leu Asn Ser Val Ser
    370                 375                 380

Gly Leu Arg Glu Trp Phe Ser Gln Thr Asp Asp Arg Gly Gln Pro Ile
385                 390                 395                 400

Arg Ile Pro Val Met Val Asn Met Ala Ser Ser Ser Leu Ala Leu Gly
                405                 410                 415

Lys Gly Gly Lys His His His Lys Ser Ser Leu Ser Ile Asp Gln Thr
            420                 425                 430

Asn Gly Ala Ser Arg Asn Ser Val Leu Met Asp Glu Asp Ser Asp Asp
        435                 440                 445

Asp Asp Glu Phe Gln Ile Pro Asp Ser Glu Pro Glu Pro Glu Thr Ser
    450                 455                 460

Lys Gln Asp Gln Glu Thr Asp Ala Lys Lys Thr Glu Glu Pro Ala Leu
465                 470                 475                 480

Asn Ile Asp Leu Ser Cys Phe Ser Gly Asn Leu Arg His Asp Asp Asn
                485                 490                 495

Glu Asn Ala Arg Asn Cys Trp Arg Ile Ser Asp Gly Asn Asn Phe Lys
            500                 505                 510

Val Arg Gly Lys Ser Phe Cys Asp Asp Lys Arg Lys Ile Pro Ala Gly
        515                 520                 525

Lys His Leu Met Asp Leu Val Ala Val Asp Trp Phe Lys Asp Thr Lys
    530                 535                 540

Arg Met Asp His Val Val Arg Arg Lys Gly Cys Ala Ala Gln Val Ala
```

```
               545                 550                 555                 560
Ala Glu Lys Gly Leu Phe Ser Thr Val Val Asn Val Gln Val Pro Gly
                    565                 570                 575

Ser Thr His Tyr Ser Met Val Phe Tyr Phe Val Thr Lys Glu Leu Val
                580                 585                 590

Pro Gly Ser Leu Phe Gln Arg Phe Val Asp Gly Asp Asp Glu Phe Arg
            595                 600                 605

Asn Ser Arg Leu Lys Leu Ile Pro Leu Val Pro Lys Gly Ser Trp Ile
        610                 615                 620

Val Arg Gln Ser Val Gly Ser Thr Pro Cys Leu Leu Gly Lys Ala Val
625                 630                 635                 640

Asp Cys Asn Tyr Ile Arg Gly Pro Thr Tyr Leu Glu Ile Asp Val Asp
                645                 650                 655

Ile Gly Ser Ser Thr Val Ala Asn Gly Val Leu Gly Leu Val Ile Gly
            660                 665                 670

Val Ile Thr Ser Leu Val Val Glu Met Ala Phe Leu Val Gln Ala Asn
        675                 680                 685

Thr Pro Glu Glu Leu Pro Glu Arg Leu Ile Gly Ala Val Arg Val Ser
    690                 695                 700

His Val Glu Leu Ser Ser Ala Ile Val Pro Asn Leu Asp Ser Asp
705                 710                 715
```

<210> SEQ ID NO 106
<211> LENGTH: 623
<212> TYPE: PRT
<213> ORGANISM: Physcomitrella patens

<400> SEQUENCE: 106

```
Met Thr Gly Pro Thr Met Glu Gly Trp Met Val Arg Tyr Gly Arg Arg
1               5                   10                  15

Lys Ile Gly Arg Ser Tyr Phe His Lys Arg Tyr Phe Val Leu Glu Ser
            20                  25                  30

Leu Ile Leu Ala Tyr Tyr Lys Arg Gln Pro Ser Ala Asn Glu Val Pro
        35                  40                  45

Ile Lys Thr Leu Pro Ile Asp Gly Asn Cys Arg Val Glu Asp Arg Gly
    50                  55                  60

Leu Glu Thr His His Gly His Thr Val Tyr Val Leu Ser Val Ile Asn
65                  70                  75                  80

Lys Lys Glu Pro Ser His Arg Ile Thr Met Ala Ala Phe Asn Val Gln
                85                  90                  95

Asp Ala Ser Ala Trp Lys Glu Ala Leu Glu Gln Val Ile Asp Gln Ile
            100                 105                 110

Asp Pro Asp Arg Asp Ala Ser Ser Ser Asp His Asp Ser Gln Phe Leu
        115                 120                 125

Ser Arg Pro Ser Phe Ser Leu Gly Pro Pro Glu Ser Ile Glu Asp Trp
    130                 135                 140

Ser Arg Gly Ile Asp Pro Arg Trp Lys Asp Thr Gly Thr Leu Ser Val
145                 150                 155                 160

Val Arg Met Ala Ser Leu Arg Leu Val Thr Cys Asp Thr Phe Leu Cys
                165                 170                 175

Arg Ser Tyr Val Ser Ser Gly Thr Cys Gly Met Lys Ala Val Gly Val
            180                 185                 190

Val Glu Ala Ser Cys Ala Asp Ile Phe Glu Leu Ile Met Gly Ile Asp
        195                 200                 205
```

-continued

```
Glu Thr Arg Tyr Glu Trp Asp Cys Ser Phe His Glu Ala Arg Leu Val
    210                 215                 220

Gln Glu Val Asp Gly His Thr Thr Ile Leu Tyr Gln Arg Leu Gln Leu
225                 230                 235                 240

Asp Phe Leu Pro Met Phe Leu Trp Pro Arg Asp Leu Cys Tyr Leu Arg
                245                 250                 255

Tyr Trp Arg Arg Asn Asp Asp Gly Ser Tyr Val Ile Leu Phe Arg Ser
                260                 265                 270

Lys Glu His Pro Ser Cys Pro Pro Glu Pro Gly Cys Val Arg Ala His
                275                 280                 285

Ile Glu Ser Gly Gly Phe Thr Ile Ser Pro Leu Lys Ser His Pro Asn
290                 295                 300

Gly Asp Pro Arg Ala Arg Val Gln Gln Leu Val His Ile Asp Leu Lys
305                 310                 315                 320

Gly Trp Gly Ala Asn Tyr Leu Pro Leu Cys His Tyr His Ser Val Ile
                325                 330                 335

Gln Ile Leu Asn Ser Val Ala Gly Leu Arg Glu Trp Phe Ala Gln Arg
                340                 345                 350

Asp Gly Asn Cys Gln Ser Asn Tyr Asp Glu Ser Glu Tyr Asp Asp Asp
                355                 360                 365

Asp Met Gln Phe Tyr Ala Asp Ser Glu Val Lys Ser Val Ser Glu Pro
                370                 375                 380

Pro Pro Val Ser Leu Asp Leu Ser Met Leu Ser Gly Asn Leu Gly Lys
385                 390                 395                 400

Gly Asp Leu Asp Asn Gly Lys Asn Cys Trp Ser Ile Pro Asp Cys Asn
                405                 410                 415

Asn Phe Arg Val Arg Ser Lys His Phe Leu Ile Asp Arg Ser Lys Ala
                420                 425                 430

Ser Glu Pro Leu Met Gln Leu Val Ala Val Asp Trp Phe Lys Asp Ile
                435                 440                 445

Lys Arg Ile Asp His Val Ala Lys Arg Lys Gly Cys Val Ala Gln Val
                450                 455                 460

Ala Gly Glu Met Gly Leu Phe Thr Val Ala Phe Asn Val Gln Val Pro
465                 470                 475                 480

Ala Ala Ser His Tyr Ser Met Ile Phe Tyr Phe Val Ala Pro Lys Ala
                485                 490                 495

Pro Gln Gly Ser Leu Leu Gln Arg Phe Val Asp Gly Asp Asp Asn Phe
                500                 505                 510

Arg Asn Ser Arg Leu Lys Leu Ile Pro Ser Val Pro Gln Gly Ser Trp
                515                 520                 525

Ile Val Arg Gln Ser Val Gly Thr Thr Pro Cys Ile Leu Gly Lys Ala
530                 535                 540

Val Asp Cys Thr Tyr Tyr Arg Gly Ser Asn Tyr Leu Glu Val Asp Ile
545                 550                 555                 560

Asp Ile Gly Ser Ser Thr Val Ala Asn Gly Val Leu Gly Leu Val Phe
                565                 570                 575

Gly Val Val Ser Ala Leu Val Val Asp Met Ala Phe Leu Ile Gln Gly
                580                 585                 590

Asn Gly Met Glu Glu Leu Pro Glu Arg Leu Ile Gly Ala Val Arg Val
                595                 600                 605

Ser Arg Leu Ser Leu Ala Ser Ala Thr Thr Pro Pro Glu Ala Asp
610                 615                 620
```

<210> SEQ ID NO 107
<211> LENGTH: 733
<212> TYPE: PRT
<213> ORGANISM: Arabidopsis thaliana

<400> SEQUENCE: 107

| Met | Gly | Val | Ser | Gln | Thr | Asp | Gly | Arg | Met | Glu | Gly | Trp | Leu | Tyr | Thr |
|---|---|---|---|---|---|---|---|---|---|---|---|---|---|---|---|
| 1 | | | | 5 | | | | | 10 | | | | | 15 | |

| Ile | Arg | His | Asn | Arg | Phe | Gly | Leu | Gln | Phe | Ser | Arg | Lys | Arg | Tyr | Phe |
| | | | 20 | | | | | 25 | | | | | 30 | | |

| Val | Leu | His | Glu | Asn | Asn | Leu | Thr | Ser | Phe | Lys | Ser | Val | Pro | Ser | Asp |
| | | | 35 | | | | 40 | | | | | 45 | | | |

| His | Asn | Glu | Glu | Pro | Glu | Arg | Arg | Ala | Ser | Leu | Asp | Cys | Cys | Ile | Arg |
| | 50 | | | | | 55 | | | | | 60 | | | | |

| Val | Thr | Asp | Asn | Gly | Arg | Glu | Ser | Phe | His | Arg | Lys | Ile | Leu | Phe | Ile |
| 65 | | | | | 70 | | | | | 75 | | | | | 80 |

| Phe | Thr | Leu | Tyr | Asn | Thr | Ser | Asn | His | Leu | Asp | Gln | Leu | Lys | Leu | Gly |
| | | | | 85 | | | | | 90 | | | | | 95 | |

| Ala | Ser | Ser | Pro | Glu | Glu | Ala | Ala | Lys | Trp | Ile | Arg | Ser | Leu | Gln | Asp |
| | | | 100 | | | | | 105 | | | | | 110 | | |

| Ala | Ser | Gln | Lys | Gly | Phe | Pro | Ile | Pro | Asp | Cys | Glu | Phe | Phe | Val | Ser |
| | | | 115 | | | | | 120 | | | | | 125 | | |

| His | Ala | Glu | Lys | Gly | Leu | Val | Lys | Leu | Asp | Val | Ser | Lys | Arg | Asn | Arg |
| | 130 | | | | | 135 | | | | | 140 | | | | |

| Arg | Lys | Asn | Ser | Val | Asp | Trp | Thr | Asn | Tyr | Ser | Ser | Thr | Asn | Tyr | Ser |
| 145 | | | | | 150 | | | | | 155 | | | | | 160 |

| Ser | Thr | Ser | Leu | Asn | Val | Glu | Thr | Asn | Val | Ala | Pro | Asp | Val | Ile | Ala |
| | | | | 165 | | | | | 170 | | | | | 175 | |

| Pro | Ser | Pro | Trp | Lys | Ile | Phe | Gly | Cys | Gln | Asn | Gly | Leu | Arg | Leu | Phe |
| | | | 180 | | | | | 185 | | | | | 190 | | |

| Lys | Glu | Ala | Lys | Asp | Trp | Asp | Ser | Arg | Gly | Arg | His | Trp | Asp | Asp | His |
| | | | 195 | | | | | 200 | | | | | 205 | | |

| Pro | Ala | Ile | Met | Ala | Val | Gly | Val | Ile | Asp | Gly | Thr | Ser | Glu | Asp | Ile |
| | 210 | | | | | 215 | | | | | 220 | | | | |

| Phe | Asn | Thr | Leu | Met | Ser | Leu | Gly | Pro | Leu | Arg | Ser | Glu | Trp | Asp | Phe |
| 225 | | | | | 230 | | | | | 235 | | | | | 240 |

| Cys | Phe | Tyr | Lys | Gly | Asn | Val | Val | Glu | His | Leu | Asp | Gly | His | Thr | Asp |
| | | | | 245 | | | | | 250 | | | | | 255 | |

| Ile | Ile | His | Leu | Gln | Leu | Tyr | Ser | Asp | Trp | Leu | Pro | Trp | Gly | Met | Asn |
| | | | 260 | | | | | 265 | | | | | 270 | | |

| Arg | Arg | Asp | Leu | Leu | Arg | Arg | Tyr | Trp | Arg | Arg | Glu | Asp | Asp | Gly |
| | | | 275 | | | | | 280 | | | | | 285 | |

| Thr | Tyr | Val | Ile | Leu | Cys | His | Ser | Val | Tyr | His | Lys | Asn | Cys | Pro | Pro |
| | | | 290 | | | | | 295 | | | | | 300 | | |

| Lys | Lys | Gly | Tyr | Val | Arg | Ala | Cys | Val | Lys | Ser | Gly | Gly | Tyr | Val | Val |
| 305 | | | | | 310 | | | | | 315 | | | | | 320 |

| Thr | Pro | Ala | Asn | Asn | Gly | Lys | Gln | Ser | Leu | Val | Lys | His | Met | Val | Ala |
| | | | | 325 | | | | | 330 | | | | | 335 | |

| Ile | Asp | Trp | Arg | Ser | Trp | Asn | Leu | Tyr | Met | Arg | Pro | Ser | Ser | Ala | Arg |
| | | | 340 | | | | | 345 | | | | | 350 | | |

| Ser | Ile | Thr | Ile | Arg | Val | Val | Glu | Arg | Val | Ala | Ala | Leu | Arg | Glu | Met |
| | | | 355 | | | | | 360 | | | | | 365 | | |

| Phe | Lys | Ala | Lys | Gln | Gly | His | Gly | Phe | Thr | Glu | Phe | Val | Ser | Gly | Glu |
| | 370 | | | | | 375 | | | | | 380 | | | | |

```
Phe Leu Asp Thr Lys Pro Cys Leu Ser Lys Ile Asn Thr Met Pro Leu
385                 390                 395                 400

Lys Thr Glu Ala Lys Glu Val Asp Leu Glu Thr Met His Ala Glu Glu
            405                 410                 415

Met Asp Lys Pro Thr Ser Ala Arg Asn Ser Leu Met Asp Leu Asn Asp
        420                 425                 430

Ala Ser Asp Glu Phe Phe Asp Val Pro Glu Pro Asn Glu Ser Thr Glu
    435                 440                 445

Phe Asp Ser Phe Ile Asp Ser Pro Tyr Ser Gln Gly His Gln Leu
450                 455                 460

Lys Ile Pro Thr Pro Ala Gly Ile Val Lys Lys Leu Gln Asp Leu Ala
465                 470                 475                 480

Ile Asn Lys Lys Gly Tyr Met Asp Leu Gln Glu Val Gly Leu Glu Glu
            485                 490                 495

Asn Asn Thr Phe Phe Tyr Gly Ala Thr Leu Gln Lys Asp Pro Ser Leu
        500                 505                 510

Thr Leu Pro Cys Ser Trp Ser Thr Ala Asp Pro Ser Thr Phe Leu Ile
    515                 520                 525

Arg Gly Asn Asn Tyr Leu Lys Asn Gln Gln Lys Val Lys Ala Lys Gly
530                 535                 540

Thr Leu Met Gln Met Ile Gly Ala Asp Trp Ile Ser Ser Asp Lys Arg
545                 550                 555                 560

Glu Asp Asp Leu Gly Gly Arg Ile Gly Leu Val Gln Glu Tyr Ala
            565                 570                 575

Ala Lys Gly Ser Pro Glu Phe Phe Phe Ile Val Asn Ile Gln Val Pro
        580                 585                 590

Gly Ser Ala Met Tyr Ser Leu Ala Leu Tyr Tyr Met Leu Lys Thr Pro
    595                 600                 605

Leu Glu Glu His Pro Leu Leu Glu Ser Phe Val Asn Gly Asp Asp Ala
610                 615                 620

Tyr Arg Asn Ser Arg Phe Lys Leu Ile Pro His Ile Ser Lys Gly Ser
625                 630                 635                 640

Trp Ile Val Lys Gln Ser Val Gly Lys Lys Ala Cys Leu Val Gly Gln
            645                 650                 655

Val Leu Glu Val Cys Tyr Thr Arg Gly Lys Asn Tyr Leu Glu Leu Asp
        660                 665                 670

Ile Asp Val Gly Ser Ser Thr Val Ala Arg Gly Val Thr Asn Leu Val
    675                 680                 685

Leu Gly Tyr Leu Asn Asn Leu Val Ile Glu Met Ala Phe Leu Ile Gln
690                 695                 700

Ala Asn Thr Val Glu Glu Leu Pro Glu Leu Leu Leu Gly Thr Cys Arg
705                 710                 715                 720

Leu Asn Tyr Leu Asp Val Ser Lys Ser Val Lys Glu Arg
            725                 730
```

<210> SEQ ID NO 108
<211> LENGTH: 277
<212> TYPE: PRT
<213> ORGANISM: Arabidopsis thaliana

<400> SEQUENCE: 108

```
Met Leu Ala Val Asp Trp Lys Ser Trp Arg Ser Tyr Val Lys Pro Ser
1               5                   10                  15

Leu Ala Arg Ser Ile Thr Val Lys Met Leu Gly Arg Ile Ser Ala Leu
            20                  25                  30
```

```
Arg Glu Leu Phe Arg Ala Lys His Gly Ser Phe Pro Pro Asn Leu Ser
            35                  40                  45

Ser Gly Glu Leu Ser Arg Ser Ala Arg Leu Thr Gln Asn Glu Asp Gly
     50                  55                  60

Val Phe Gly Asp Ser Ser Leu Arg Glu Asn Glu Met Phe Lys Asp Thr
 65                  70                  75                  80

Ala Asn Glu Glu Arg Asp Lys Phe Pro Ser Glu Arg Ser Ser Leu Val
                 85                  90                  95

Asp Leu Asp Glu Phe Phe Asp Val Pro Glu Pro Ser Asp Asn Asp Asn
            100                 105                 110

Leu Asp Asp Ser Trp Thr Ser Asp Phe Asp Leu Asp Thr Cys Cys Gln
        115                 120                 125

Glu Ser Arg Gln Pro Lys Leu Asn Ser Ala Thr Ser Leu Val Lys Lys
130                 135                 140

Leu His Asp Leu Ala Val Gln Lys Arg Gly Tyr Val Asp Leu His Glu
145                 150                 155                 160

Arg Ala Lys Glu Glu Ser Ser Pro His Ala Thr Cys Asn Pro Pro Cys
                165                 170                 175

Cys Tyr Gly Thr Thr Leu Pro Thr Asp Pro Ser Cys Leu Pro Cys
            180                 185                 190

Ser Trp Thr Thr Thr Asp Pro Ser Thr Phe Leu Ile Arg Gly Lys Thr
        195                 200                 205

Tyr Leu Asp Asp Gln Lys Lys Val Lys Ala Lys Gly Thr Leu Met Glu
    210                 215                 220

Met Val Ala Ala Asp Trp Leu Lys Ser Asp Lys Arg Glu Asp Asp Leu
225                 230                 235                 240

Gly Ser Arg Pro Gly Gly Ile Val Gln Lys Tyr Ala Ala Lys Gly Gly
                245                 250                 255

Pro Glu Phe Phe Phe Ile Val Asn Ile Gln Pro Cys Ala Leu Leu His
            260                 265                 270

Asp Glu His Ser Tyr
        275

<210> SEQ ID NO 109
<211> LENGTH: 712
<212> TYPE: PRT
<213> ORGANISM: Physcomitrella patens

<400> SEQUENCE: 109

Met Gly Asp Ile Ala Gly Thr Arg Met Glu Gly Trp Val Tyr Tyr Leu
 1               5                  10                  15

Ser Ser Ser Lys Leu Arg Leu Asn His Pro Arg Lys Arg Tyr Leu Val
            20                  25                  30

Leu Glu Gly Ile Arg Ala Ser Ser Phe Lys Asp Lys Pro Arg Thr Gly
        35                  40                  45

Val Glu Ile Leu Val Arg Ser Gly Ile Ile Asp Pro Thr Arg Val
     50                  55                  60

Ile Asp His Gly Arg Glu Thr Val His Gly Arg Val Phe Phe Val Phe
 65                  70                  75                  80

Ser Ile Tyr Asp Pro Tyr Ala Pro Glu Ala Lys Leu Arg Ile Gly Val
                 85                  90                  95

Gln Asn Ala Glu Asp Ala Ala Lys Trp Met His Ala Phe Arg Glu Ala
            100                 105                 110

Ala Glu Arg Pro Pro Gly Thr Asn Lys Thr Phe Leu Pro Ser Pro Pro
```

-continued

```
            115                 120                 125
Gly Arg Arg Arg Leu Pro Asn Leu Arg Ser Asp Gln Thr Arg Ser Phe
        130                 135                 140

Cys Ile Asn His Trp Thr Gly Gly Leu Leu Thr Lys Asp Ala Ser Pro
145                 150                 155                 160

Asp Val Val Ala Ser Pro Trp Gln Ile Ile Gly Cys Lys Asn Gly
                165                 170                 175

Leu Arg Phe Phe Gln Glu Thr Ser Asp Gly Asp Glu Ser Leu Leu Glu
                180                 185                 190

Lys Ile Arg Gly Asp Asp Ile Pro Thr Leu Met Ala Val Gly Val Val
                195                 200                 205

Asp Ala Thr Pro Ala Ser Val Phe Glu Thr Ala Met Ala Leu Gly Arg
        210                 215                 220

Ser Arg Ala Glu Trp Asp Phe Cys Phe His Gln Gly Arg Val Ile Glu
225                 230                 235                 240

Asn Val His Gly His Thr Asp Ile Ile His Glu Gln Phe His Ser Arg
                245                 250                 255

Trp Leu Pro Trp Arg Met Lys Pro Arg Asp Leu Val Phe Gln Arg Tyr
                260                 265                 270

Trp Arg Arg Asp Asp Asp Gly Thr Tyr Val Ile Leu Tyr Asn Ser Ile
                275                 280                 285

Asn His Glu Lys Cys Pro Pro Gly Arg Lys Phe Thr Arg Ala Trp Leu
        290                 295                 300

His Ser Gly Gly Phe Val Ile Ser Pro Leu Lys Gly Arg Lys Asp Lys
305                 310                 315                 320

Val Lys Trp Cys Met Val Lys His Ile Met Lys Val Asp Trp Lys Gly
                325                 330                 335

Trp Glu Phe Leu Trp Arg Lys Ser Arg Asn Arg Asp Met Ser Leu Ile
                340                 345                 350

Met Leu Glu Arg Ile Ala Ala Ile Arg Glu Leu Tyr Lys Val Lys Glu
        355                 360                 365

Lys Pro Ile Ile Ser Met Lys Lys Glu His His Gln Arg His Glu Asp
        370                 375                 380

Ile Phe Tyr Glu Ser Ala Glu Pro Lys Pro Glu Ser Glu Asp Glu Ser
385                 390                 395                 400

Ser Asn Arg Asp Arg Val Ser Asn Gln Pro Ser Leu Lys Glu Ser Thr
                405                 410                 415

Ser Lys Phe Ile Glu Val Ala Asp Asp Glu Phe Phe Asp Ala Glu Glu
                420                 425                 430

Pro Thr Ser Trp Glu Arg Gly Glu Asp Pro Glu Leu Lys Phe Tyr Glu
        435                 440                 445

Glu Leu Glu Gly Ser Ser Met Asp Glu Val Glu Gln Lys Ala His Asn
        450                 455                 460

Leu Pro Val Trp Ser Leu Arg Lys Leu Ala Asp Glu Ala Asp Val Glu
465                 470                 475                 480

Phe Met Asn Arg Glu Ser Ser Leu Gly Ser Val Tyr Trp Glu Pro Ala
                485                 490                 495

Glu Pro Gly Thr Phe Leu Ile Arg Gly Lys His Phe Leu Arg Asp His
                500                 505                 510

Lys Lys Val Lys Ala Gly Thr Pro Leu Met Gln Leu Val Ala Ala Asp
                515                 520                 525

Trp Phe Lys Ser Asp Lys Arg Glu Asp His Ile Ala Ala His Asp Gly
530                 535                 540
```

```
Cys Val Ile Gln Lys Leu Phe Ala Lys Gln Val Ala Asp Ser Tyr Phe
545                 550                 555                 560

Val Ile Ile Asn Leu Gln Val Pro Gly Thr Pro Thr Tyr Ser Leu Val
                565                 570                 575

Leu Tyr Tyr Met Thr Asn Lys Arg Leu Gln Asp Ile Pro Leu Leu Glu
            580                 585                 590

Asn Phe Val Arg Gly Asp Asn Arg Tyr Arg Ala Cys Arg Phe Lys Leu
        595                 600                 605

Cys Pro Tyr Val Ala Lys Gly Pro Trp Ile Val Lys Gln Ser Val Gly
610                 615                 620

Lys Ser Ala Cys Leu Val Gly Glu Ala Leu Asp Ile Thr Tyr Phe Ser
625                 630                 635                 640

Ser Asp Asn Tyr Leu Glu Leu Asp Ile Asp Ile Gly Ser Ser Ser Val
                645                 650                 655

Ala Arg Gly Val Val Asn Leu Val Thr Gly Tyr Val Thr Lys Leu Val
            660                 665                 670

Ile Glu Met Ala Phe Leu Ile Gln Ala Asn Thr Glu Glu Leu Pro
        675                 680                 685

Glu Lys Leu Leu Gly Thr Val Arg Ile Ser Asn Leu Asp Met Gln Lys
690                 695                 700

Ala Val Leu Pro Pro Glu Tyr
705                 710

<210> SEQ ID NO 110
<211> LENGTH: 729
<212> TYPE: PRT
<213> ORGANISM: Physcomitrella patens

<400> SEQUENCE: 110

Met Arg Met Glu Gly Trp Val Tyr Ile Leu Asn Pro Ser Lys Leu Arg
1               5                   10                  15

Leu Asn His Pro Arg Lys Arg Tyr Leu Val Leu Val Gly Asn Arg Ala
            20                  25                  30

Ser Ala Phe Lys Asp Lys Ser Arg Ala Lys Asp Glu Ser Pro Leu Arg
        35                  40                  45

Ser Gly Ile Ile Asp Leu Gly Thr Arg Val Thr Asp His Gly Arg Glu
    50                  55                  60

Ile Val Leu Gly Arg Val Phe Phe Val Phe Ser Val His Asp Pro His
65                  70                  75                  80

Ala Ser Glu Ala Lys Leu Lys Phe Gly Val Gln Asn Ala Glu Asp Ala
                85                  90                  95

Ala Arg Trp Met Gln Ala Phe Arg Asn Ala Ala Glu Arg Val Arg Asn
            100                 105                 110

Phe Ser Ser Asn Trp Val Phe Phe Gln Val Ser Cys Arg His Ser His
        115                 120                 125

Leu Val Ser Ile Lys Leu Ser Phe Gln Leu Gln Asp Glu Asn Ala Val
    130                 135                 140

Gln Thr Leu Gly Glu Ala Ile Arg Asn Leu Lys Met Pro Asn Trp Thr
145                 150                 155                 160

Gly Ala Leu Leu Ala Lys Asp Ala Ser Pro Asp Val Val Ala Ser Ser
                165                 170                 175

Pro Trp Glu Ile Phe Gly Cys Lys Asn Gly Thr Gln Ile Ser Ser Leu
            180                 185                 190

Asp Leu Ala Met Ile Arg Gly Gly Thr Pro Pro Ala Leu Met Ala Val
```

```
                195                 200                 205
Gly Val Val Asp Ala Ile Pro Ala Thr Val Phe Asp Thr Val Met Ala
210                 215                 220
Leu Gly Pro Ser Arg Ala Glu Trp Asp Phe Cys Phe His Gln Gly Gln
225                 230                 235                 240
Ile Ile Asp His Val His Gly His Met Asp Ile Val His Lys Gln Phe
                    245                 250                 255
His Ser Lys Trp Leu Pro Trp Arg Met Lys Pro Arg Asp Leu Val Phe
                260                 265                 270
Glu Arg Tyr Trp Arg Arg Asp Asp Gly Thr Tyr Val Ile Leu Tyr
            275                 280                 285
Arg Ser Ile Lys His Pro Lys Cys Pro Pro Ser Lys Lys Phe Thr Arg
290                 295                 300
Ala Tyr Val Leu Ser Gly Gly Tyr Val Ile Ser Pro Leu Thr Gly Lys
305                 310                 315                 320
Asn Ala Glu Val Asn Arg Ser Met Val Lys His Ile Met Lys Val Asp
                325                 330                 335
Trp Arg Gly Tyr Phe Trp Arg Lys Ser Arg Asn Arg Asn Met Ser Leu
            340                 345                 350
Leu Met Leu Glu Arg Ile Ala Ala Ile Arg Glu Leu Phe Lys Val Lys
            355                 360                 365
Glu Arg Pro Pro Val Pro Leu Lys Thr Glu Arg Arg Glu Asn Glu Glu
370                 375                 380
Ser Ile Phe Glu Arg Ala Gln Ser Gln Gln Glu Phe Ala Asn Thr Leu
385                 390                 395                 400
Ser Asn Lys Leu Thr Asn Gln Ser Thr Leu Glu Glu Ser Glu Ser Lys
                405                 410                 415
Phe Leu Gln Val Ala Asp Asp Glu Phe Phe Asp Ala Glu Glu Pro Leu
                420                 425                 430
Ser Trp Lys Arg Glu Ser Gln Ser Glu Leu Met Ser Ser Asp Glu Val
            435                 440                 445
Glu Gly Ser Ser Met Asp Glu Glu Gln Tyr Glu Pro Arg Asn Tyr Ile
450                 455                 460
Ala Ser Phe Gln Phe Thr Cys Ser Asn Glu Lys Gln Tyr Ser Ser Phe
465                 470                 475                 480
Ala Ser Gln Gly Gly Thr Arg Asp Arg Thr Thr Glu Gly Asp Leu Glu
                485                 490                 495
Phe Met Lys Arg Glu Ser Ser Leu Gly Thr Met Thr Trp Asp Thr Ala
                500                 505                 510
Glu Ser Ser Thr Phe Leu Ile Arg Gly Lys His Tyr Leu Arg Asp His
            515                 520                 525
Lys Lys Val Lys Ala Gly Thr Pro Val Met Gln Leu Val Ala Ala Asp
            530                 535                 540
Trp Phe Lys Ser Asp Arg Ser Glu Glu His Leu Ala Ala Arg Ala Gly
545                 550                 555                 560
Cys Val Ile Gln Lys Leu Phe Thr Ser Ala Gln Arg Val Ala Glu Ser
                565                 570                 575
Tyr Phe Val Ile Ile Asn Leu Gln Val Pro Gly Thr Pro Ser Tyr Ser
                580                 585                 590
Leu Val Leu Tyr Tyr Met Ala Asn Lys Leu Leu Gln Asp Ile Pro Leu
            595                 600                 605
Leu Glu Gly Phe Val Arg Gly Asp Asp His Tyr Arg Asn Ser Arg Phe
            610                 615                 620
```

Lys Leu Cys Pro His Val Ala Lys Gly Ser Trp Ile Val Lys Gln Ser
625                 630                 635                 640

Val Gly Lys Ser Ala Cys Leu Val Gly Glu Ala Leu Asp Ile Asn Tyr
            645                 650                 655

Phe Ser Ser Asp Asn Tyr Leu Glu Met Asp Ile Asp Ile Gly Ser Ser
        660                 665                 670

Ser Val Ala Lys Gly Val Val Asn Leu Val Ala Asn Tyr Ala Ser Lys
            675                 680                 685

Leu Val Leu Glu Met Ala Phe Leu Ile Gln Ala Asn Thr Asp Glu Glu
        690                 695                 700

Leu Pro Glu Lys Leu Leu Gly Thr Val Arg Ile Ser Asn Leu Asp Met
705                 710                 715                 720

Ala Lys Ala Val Ile Pro Pro Ala Pro
                725

<210> SEQ ID NO 111
<211> LENGTH: 731
<212> TYPE: PRT
<213> ORGANISM: Physcomitrella patens

<400> SEQUENCE: 111

Met Glu Gly Trp Leu Tyr Leu Ile Gly Ser Asn Arg Leu Met Met Thr
1               5                   10                  15

Asn Pro Arg Lys Arg Tyr Val Leu Cys Gly Asn Gln Ala Arg Phe
            20                  25                  30

Tyr Lys Asp Lys Pro Ala His Arg Glu Glu Val Ala Ala Pro Ile Lys
        35                  40                  45

Ser Gly Thr Val Asp Pro Tyr Lys Arg Val Ala Asp His Gly Arg Glu
    50                  55                  60

Asn Ile Leu Gly Arg Thr Leu Phe Val Phe Thr Val Tyr Asp Ser Tyr
65                  70                  75                  80

Ile His Glu Asp Lys Leu Lys Phe Gly Ala Arg Ser Ser Glu Glu Ala
                85                  90                  95

Ala Lys Trp Met Glu Ala Phe Lys Glu Ala Ala Glu Gln Val Ser Phe
            100                 105                 110

Ala Glu Tyr Phe Ile Asn Leu Leu Val Arg Ile His Glu Asp Ser Thr
        115                 120                 125

Thr Leu Ala Gly Cys Thr Arg Thr Leu Thr Ala Ile Arg Phe Asp Ala
    130                 135                 140

His Met Phe Val Ser Leu Leu Pro Lys Asp Ala Ser Pro Asp Val Val
145                 150                 155                 160

Ala Asp Ser Pro Trp Gln Ile Phe Gly Cys Glu Asn Gly Leu Arg Leu
                165                 170                 175

Phe Lys Glu Ala Thr Asp His His Gly Leu Lys Ser Met Val Arg His
            180                 185                 190

Asp Pro Pro Ala Leu Met Ser Val Gly Val Val His Ala Thr Cys Glu
        195                 200                 205

Ser Val Phe Glu Thr Val Met Ala Leu Gly Ser Ser Arg Ala Glu Trp
    210                 215                 220

Asp Phe Cys Tyr Leu Lys Gly Arg Val Ile Glu His Ile Asp Gly His
225                 230                 235                 240

Ser Asp Ile Val His Lys His Phe His Lys Phe Trp Leu Ser Ser Arg
                245                 250                 255

Met Lys Pro Arg Asp Leu Val Val His Arg Tyr Trp Arg Arg Glu Asp

```
                260                 265                 270
Asp Gly Ser Tyr Val Ile Leu Tyr Thr Ser Val Asn His Glu Lys Cys
            275                 280                 285

Pro Pro Arg Arg Lys Phe Val Arg Ala Trp Leu Lys Ser Gly Gly Tyr
        290                 295                 300

Val Ile Ser Pro Leu Pro Thr Gln Gly Gly Tyr Pro Asn Arg Cys Met
305                 310                 315                 320

Val Lys His Ile Leu Thr Val Asp Trp Lys Asn Trp Lys Ser Cys Trp
            325                 330                 335

Ser Pro Cys Arg Asp Lys Asp Ile Thr Leu Lys Val Leu Glu Arg Val
        340                 345                 350

Ala Ala Leu Lys Glu Phe Tyr Lys Ile Lys Pro Ser Asp Tyr Met Pro
    355                 360                 365

Ser Ser Met Gly Pro Asn Val Arg Gln Pro Ala Arg Cys Lys Leu Pro
    370                 375                 380

Val Ala Gln Lys Glu Asn Ile Leu Pro Ile His Leu Asn Asp Asp Ala
385                 390                 395                 400

Ala Ala Phe Leu Leu Glu Glu Lys Asn Val Gly Lys Ser Met Phe Gln
            405                 410                 415

Gln Leu Ala Glu Asp Glu Phe Phe Asp Val Pro Glu Asp Ser Ala Trp
        420                 425                 430

Asp Leu Glu Leu Asp Arg Asp Leu Asp Gly Gln Gln Asn Thr Asp
        435                 440                 445

Leu Glu Glu Thr Ser Asp Glu Asp Lys Val Arg Gln Ser Gly Phe Gly
    450                 455                 460

Phe Asp Arg Leu Ile Ala Leu Asp Met Pro Phe Ala Ala Gln Lys Arg
465                 470                 475                 480

Thr Tyr Gln Asp Thr Asp Gln Asp Ile Asp Leu Leu Thr Arg Glu
            485                 490                 495

Gly Thr Leu Pro Lys Ile Ser Ser Ser Gly Thr Thr Ser Cys Tyr Gln
            500                 505                 510

Ser Ala Glu Ala Ser Thr Phe Leu Ile Arg Gly Lys His Tyr Leu Gln
        515                 520                 525

Asp Arg Lys Lys Val Val Ala Lys Asp Pro Val Met Gln Phe Val Ala
        530                 535                 540

Ala Asp Trp Leu Lys Ser Asn Lys Arg Glu Asp His Leu Ala Asn Arg
545                 550                 555                 560

Pro Ser Tyr Pro Val Gln Leu Phe Leu Ala Asn Gln Gly Arg Val Asp
            565                 570                 575

Asp Ala Phe Phe Phe Ile Ile Asn Ile Gln Val Pro Gly Ser Thr Thr
            580                 585                 590

Tyr Ser Leu Ala Leu Tyr Tyr Met Ile Thr Gln Pro Leu Ser Asp Phe
        595                 600                 605

Pro Leu Leu Glu Asn Phe Val His Gly Asp Asp Arg Tyr Arg Asn Ala
    610                 615                 620

Gly Phe Lys Leu Ile Pro His Ile Ala Lys Gly Ser Trp Ile Val Lys
625                 630                 635                 640

Gln Ser Val Gly Lys Thr Ala Cys Leu Ile Gly Glu Ala Leu Glu Ile
            645                 650                 655

Thr Tyr His Ser Gly Lys Asn Tyr Ile Glu Leu Asp Val Asp Ile Gly
        660                 665                 670

Ser Ser Ser Val Ala Lys Gly Val Val Asn Leu Val Leu Gly Tyr Leu
        675                 680                 685
```

```
Ser Thr Leu Val Ile Glu Leu Ala Phe Leu Ile Gln Ala Asn Thr Glu
690                 695                 700

Glu Glu Leu Pro Glu Tyr Leu Leu Gly Thr Cys Arg Leu Val Asn Leu
705                 710                 715                 720

Asp Ile Ala Lys Ala Ile Pro Ala Arg Pro Glu
                725                 730

<210> SEQ ID NO 112
<211> LENGTH: 730
<212> TYPE: PRT
<213> ORGANISM: Physcomitrella patens

<400> SEQUENCE: 112

Met Ala Ile Met Glu Gly Trp Leu Tyr Leu Ile Glu Ser Asn Lys Leu
1               5                   10                  15

Met Met Thr His Pro Arg Lys Arg Tyr Phe Val Leu Ser Gly Asn Gln
                20                  25                  30

Ala Arg Tyr Tyr Lys Glu Lys Pro Ala Tyr Arg Gln Glu Ala Pro Leu
            35                  40                  45

Lys Ser Gly Ser Phe Asp Pro Tyr Thr Arg Val Val Asp His Gly Arg
50                  55                  60

Glu Ser Ile His Gly Arg Thr Leu Phe Val Phe Glu Ile Tyr Asp Ser
65                  70                  75                  80

Tyr Thr His Gly Asp Lys Leu Lys Phe Gly Ala Arg Ser Ser Glu Glu
                85                  90                  95

Ala Ala Lys Trp Met Glu Ala Phe Lys Glu Ala Glu Gln Ser Cys
            100                 105                 110

Phe Ser Trp Asp Ala Glu Val Met Leu Ser Tyr His Ser Val Leu Leu
        115                 120                 125

Ser Cys Gln Ser Leu Ser Met Trp Asp Ala Ser Pro Asp Val Val Ala
130                 135                 140

Asp Ser Pro Trp Gln Ile Phe Gly Cys Val Asn Gly Leu Arg Leu Phe
145                 150                 155                 160

Arg Glu Thr Thr Asp His His Gly Phe Lys Ser Met Pro Cys Ser Arg
                165                 170                 175

Gly Phe Leu Ile Arg Gly Glu Asp Pro Pro Ala Leu Met Gly Val Gly
            180                 185                 190

Val Val Phe Ala Thr Cys Glu Ser Val Phe Gln Thr Val Met Thr Leu
        195                 200                 205

Gly Ser Ser Arg Ser Glu Trp Asp Phe Cys Tyr Ala Lys Gly Arg Val
210                 215                 220

Ile Glu His Ile Asp Gly His Ser Asp Ile Val His Lys Gln Phe His
225                 230                 235                 240

Thr His Trp Leu Pro Trp Arg Met Lys Pro Arg Asp Leu Val Val His
                245                 250                 255

Arg Tyr Trp Arg Arg Glu Asp Asp Gly Ser Tyr Val Ile Leu Tyr Lys
            260                 265                 270

Ser Val Lys His Glu Lys Cys Arg Pro Arg Lys Phe Val Arg Ala
        275                 280                 285

Trp Leu Lys Ser Gly Gly Tyr Val Ile Ser Pro Leu Pro Pro Gln Gly
    290                 295                 300

Gly Phe Gln His Arg Cys Ala Val Lys His Ile Leu Thr Val Asp Trp
305                 310                 315                 320

Lys His Phe Lys Thr Pro Trp Ser Ser Ser Lys Asp Arg Val Ile Thr
```

325                 330                 335
Leu Lys Val Leu Glu Arg Val Ala Ala Leu Arg Glu Phe Tyr Lys Val
                340                 345                 350
Lys Pro Ala Asp Tyr Met Pro Thr Ser Ile Ser Pro Asp Leu Arg Arg
            355                 360                 365
Leu Asp Val Ala Gly Cys Lys Pro Leu Leu Gln Lys Glu Asn Ile
        370                 375                 380
Pro Glu Val His Leu Cys Gly Ala Glu Val Ala Arg Ser Pro Glu Asp
385                 390                 395                 400
Asn Ile Ala Gly Gln Ser Met Phe Arg Gln Leu Ala Glu Glu Phe
                405                 410                 415
Phe Asp Val Pro Glu Asp Ser Ala Trp Asp Thr Glu Leu Glu Pro Asp
                420                 425                 430
Leu Asp Gly Arg Arg Glu Ser Thr Asp Pro Asp Glu Thr Ser Asp Glu
            435                 440                 445
Asp Gln Asn Gly Gly Val His Lys Leu Ser Ala Ala Thr Ile Val
        450                 455                 460
Lys Arg Phe Gln Gly Met Ala Ala Gln Lys Arg Thr His Gln Asp Asp
465                 470                 475                 480
Asp Glu Asp Gly Ile Glu Leu Leu Ala Arg Gly Thr Leu Pro Lys
                485                 490                 495
Ser Ser Gly Cys Cys Thr Thr Ser Cys Tyr Glu Ser Glu Ala Ser
            500                 505                 510
Ile Phe Leu Ile Arg Gly Lys His Tyr Leu Gln Asp Arg Lys Lys Val
        515                 520                 525
Val Ala Lys Asp Pro Val Met Gln Phe Val Ala Ala Asp Trp Leu Lys
    530                 535                 540
Ser Asn Lys Arg Glu Asp His Leu Ala Ser Arg Pro Ser Asn Pro Val
545                 550                 555                 560
Gln Gln Phe Leu Ala Asn Gln Arg Lys Ile Glu Gly Arg Val Gln Asp
                565                 570                 575
Pro Phe Phe Phe Ile Ile Asn Ile Gln Val Pro Gly Ser Thr Thr Tyr
            580                 585                 590
Ser Leu Ala Leu Tyr Tyr Met Ile Thr Gln Pro Leu Ser Asp Phe Leu
        595                 600                 605
Ile Leu Glu Asn Phe Val Arg Gly Asp Arg His Arg Asn Ala Ser
    610                 615                 620
Phe Lys Leu Ile Pro His Ile Ala Lys Gly Pro Trp Ile Val Lys Gln
625                 630                 635                 640
Ser Val Gly Lys Thr Ala Cys Leu Ile Gly Glu Ala Leu Glu Ile Thr
                645                 650                 655
Tyr His Thr Asp Lys Asn Tyr Ile Glu Leu Asp Val Asp Ile Gly Ser
            660                 665                 670
Ser Ser Val Ala Lys Gly Val Val Asn Leu Val Leu Gly Tyr Leu Ser
        675                 680                 685
Asn Leu Val Ile Glu Leu Ala Phe Leu Ile Gln Ala Asn Thr Glu Glu
    690                 695                 700
Glu Leu Pro Glu Tyr Leu Leu Gly Thr Cys Arg Leu Val Asn Leu Asp
705                 710                 715                 720
Ile Ala Lys Ala Ile Pro Ala Arg Pro Glu
                725                 730

<210> SEQ ID NO 113

-continued

```
<211> LENGTH: 707
<212> TYPE: PRT
<213> ORGANISM: Physcomitrella patens

<400> SEQUENCE: 113
```

| | | | | | | | | | | | | | | |
|---|---|---|---|---|---|---|---|---|---|---|---|---|---|---|
| Met | Glu | Gly | Trp | Leu | Tyr | Leu | Ile | Glu | Ser | Asn | Arg | Leu | Met | Met | Thr |
| 1 | | | | 5 | | | | | 10 | | | | | 15 | |
| Asn | Pro | Arg | Lys | Arg | Tyr | Phe | Val | Leu | Ala | Gly | Asn | Arg | Ala | Phe | Phe |
| | | | 20 | | | | | 25 | | | | | 30 | | |
| Tyr | Lys | Glu | Lys | Pro | Ala | His | Pro | Asp | Glu | Thr | Pro | Ile | Lys | Thr | Gly |
| | | 35 | | | | | 40 | | | | | 45 | | | |
| Ile | Ile | Asp | Pro | Ser | Thr | Arg | Val | Ala | Asp | His | Gly | Arg | Glu | Lys | Ile |
| 50 | | | | | 55 | | | | | 60 | | | | | |
| His | Gly | Trp | Thr | Leu | Phe | Val | Phe | Glu | Ile | Tyr | Asp | Ser | Tyr | Asn | His |
| 65 | | | | 70 | | | | | 75 | | | | | 80 | |
| Asp | Asp | Lys | Leu | Lys | Phe | Gly | Ala | Arg | Ser | Glu | Glu | Ala | Ala | Arg | |
| | | | 85 | | | | | 90 | | | | | 95 | | |
| Trp | Met | Ser | Ala | Leu | Lys | Glu | Ala | Ala | Glu | Gln | His | Lys | Arg | Pro | Ile |
| | | | 100 | | | | | 105 | | | | | 110 | | |
| Pro | Asn | Phe | Tyr | Val | Thr | Glu | Leu | Gly | Ile | Ser | Gln | Leu | Cys | Phe | Ile |
| | | | 115 | | | | | 120 | | | | | 125 | | |
| Asn | Arg | Lys | Arg | Arg | Val | Arg | Val | Thr | Phe | Ile | Asp | Ser | Gly | Thr | Cys |
| | 130 | | | | | 135 | | | | | 140 | | | | |
| Ser | Val | Asn | Leu | Val | Asn | Met | Met | Asp | Ala | Ser | Pro | Asp | Val | Ile | Ala |
| 145 | | | | | 150 | | | | | 155 | | | | | 160 |
| Asp | Ser | Pro | Trp | Gln | Ile | Phe | Gly | Cys | Arg | Asn | Gly | Leu | Arg | Leu | Phe |
| | | | | 165 | | | | | 170 | | | | | 175 | |
| Arg | Glu | Thr | Thr | Asp | His | His | Gly | Leu | Lys | Ser | Met | Asp | Pro | Pro | Ala |
| | | | 180 | | | | | 185 | | | | | 190 | | |
| Leu | Met | Ala | Val | Gly | Val | Val | Gln | Ala | Ser | Cys | Glu | Ser | Val | Phe | Glu |
| | | | 195 | | | | | 200 | | | | | 205 | | |
| Ser | Val | Met | Ser | Leu | Gly | Ser | Ser | Arg | Val | Glu | Trp | Asp | Phe | Cys | Tyr |
| | 210 | | | | | 215 | | | | | 220 | | | | |
| Ser | Lys | Gly | Arg | Val | Ile | Glu | His | Ile | Asp | Gly | His | Ser | Asp | Ile | Val |
| 225 | | | | | 230 | | | | | 235 | | | | | 240 |
| His | Lys | Gln | Leu | His | Lys | Tyr | Trp | Leu | Pro | Trp | Arg | Met | Lys | Pro | Arg |
| | | | | 245 | | | | | 250 | | | | | 255 | |
| Asp | Leu | Leu | Val | His | Arg | Tyr | Trp | Arg | Arg | Glu | Asp | Asp | Gly | Ser | Tyr |
| | | | 260 | | | | | 265 | | | | | 270 | | |
| Val | Ile | Leu | Tyr | Lys | Ser | Val | Asn | His | Glu | Arg | Cys | Pro | Pro | Arg | Arg |
| | | | 275 | | | | | 280 | | | | | 285 | | |
| Lys | Phe | Val | Arg | Ala | Trp | Ile | Lys | Ser | Gly | Gly | Tyr | Val | Ile | Ser | Pro |
| | 290 | | | | | 295 | | | | | 300 | | | | |
| Leu | Pro | Pro | Gln | Gly | Gly | Phe | Pro | Tyr | Arg | Cys | Ala | Val | Lys | His | Ile |
| 305 | | | | | 310 | | | | | 315 | | | | | 320 |
| Leu | Thr | Val | Asp | Trp | Lys | His | Phe | Asn | Met | Arg | Trp | Ser | His | Cys | Arg |
| | | | | 325 | | | | | 330 | | | | | 335 | |
| Asn | Arg | Asp | Ile | Thr | Leu | Arg | Val | Leu | Glu | Arg | Val | Ser | Ala | Leu | Ser |
| | | | 340 | | | | | 345 | | | | | 350 | | |
| Glu | Phe | Tyr | Lys | Val | Lys | Pro | Ala | Asp | Tyr | Met | Pro | Ile | Ser | Ile | Gly |
| | | | 355 | | | | | 360 | | | | | 365 | | |
| Gln | Asp | Leu | Arg | Arg | Leu | Asn | Leu | Thr | Gly | Cys | Lys | Phe | Gln | Val | Ser |
| | 370 | | | | | 375 | | | | | 380 | | | | |
| Gln | Lys | Gln | Asn | Ile | Ser | Ser | Val | His | Leu | Thr | Asp | Asp | Glu | Val | Ser |

```
            385                 390                 395                 400
    His Ser Gln Gly Asn Asn Thr Ala Gly Gln Ser Met Phe Arg Gln Leu
                        405                 410                 415

Ala Glu Asp Glu Phe Asp Val Pro Glu Asp Ser Ala Trp Asp Thr
                    420                 425                 430

Glu Leu Glu Pro Asp Leu Asp Gly Gln Arg Lys Ser Ala Asp Pro Glu
                    435                 440                 445

Glu Thr Ser Asp Glu Val Gln Arg Met His Gln Asp Thr Val Glu Asp
            450                 455                 460

Gly Ile Glu Leu Met Val Arg Ala Gly Thr Leu Pro Lys Ser Ser Cys
    465                 470                 475                 480

Ser Cys Thr Thr Ser Cys Tyr Glu Ser Ala Glu Ala Ser Val Phe Leu
                        485                 490                 495

Val Arg Gly Lys His Tyr Leu His Asp Arg Lys Val Val Ala Glu
                    500                 505                 510

Asp Pro Val Met Gln Phe Val Ala Ala Asp Trp Leu Lys Ser Asn Lys
                    515                 520                 525

Arg Glu Asp His Leu Ala Ser Arg Pro Ser His Pro Ile Gln Lys Phe
            530                 535                 540

Leu Ala Asn Gln Gly Arg Val Pro Asp Pro Phe Phe Ile Val Asn
    545                 550                 555                 560

Ile Gln Val Pro Gly Ser Thr Thr Tyr Ser Leu Ala Leu Tyr Tyr Met
                        565                 570                 575

Ile Thr Ser Pro Leu Ser Asp Phe Pro Ile Leu Glu Asn Phe Val Ser
                    580                 585                 590

Gly Asp Asp Arg His Arg Asn Ala Ser Phe Lys Leu Ile Pro His Ile
                    595                 600                 605

Ala Lys Gly Pro Trp Ile Val Lys Gln Ser Val Gly Lys Thr Ala Cys
            610                 615                 620

Leu Ile Gly Gln Ala Leu Glu Ile Thr Tyr His Ile Asp Lys Thr Tyr
    625                 630                 635                 640

Ile Glu Leu Asp Val Asp Ile Gly Ser Ser Val Ala Lys Gly Val
                        645                 650                 655

Val Asn Leu Val Leu Ser Tyr Leu Ser Asn Leu Val Ile Glu Leu Ala
                    660                 665                 670

Phe Leu Ile Gln Ala Asn Thr Glu Glu Glu Leu Pro Glu Cys Leu Leu
                    675                 680                 685

Gly Thr Cys Arg Leu Met Asn Leu Asp Ile Ala Lys Ala Ile Pro Ala
            690                 695                 700

Leu Leu Glu
    705

<210> SEQ ID NO 114
<211> LENGTH: 593
<212> TYPE: PRT
<213> ORGANISM: Arabidopsis thaliana

<400> SEQUENCE: 114

Met Thr Ser Pro Gly Ser Lys Lys Val Val Thr Thr Asp Asp Gly Ser
    1               5                   10                  15

Glu Lys Lys Val Ser Gly Asn Leu Gly Lys Val Ser Phe Ser Gly Asp
                    20                  25                  30

Leu Asn His Ser Gly Ser His Ser Gly Ser His Ser Arg Ser Ser Ser
            35                  40                  45
```

-continued

Ser Ala Gly Gly Gly Glu Gly Thr Phe Glu Tyr Phe Gly Trp Val
50              55                      60

Tyr His Leu Gly Val Asn Lys Ile Gly His Glu Tyr Cys Asn Leu Arg
65              70                      75              80

Phe Leu Phe Ile Arg Gly Lys Tyr Val Glu Met Tyr Lys Arg Asp Pro
                85                      90              95

His Glu Asn Pro Asp Ile Lys Pro Ile Arg Arg Gly Val Ile Gly Pro
                100             105                     110

Thr Met Val Ile Glu Glu Leu Gly Arg Arg Lys Val Asn His Gly Asp
                115             120                     125

Val Tyr Val Ile Arg Phe Tyr Asn Arg Leu Asp Glu Ser Arg Lys Gly
130             135                     140

Glu Ile Ala Cys Ala Thr Ala Gly Glu Ala Leu Lys Trp Val Glu Ala
145             150                     155                     160

Phe Glu Glu Ala Lys Gln Gln Ala Glu Tyr Ala Leu Ser Arg Gly Gly
                165                     170                     175

Ser Thr Arg Thr Lys Leu Ser Met Glu Ala Asn Ile Asp Leu Glu Gly
                180                     185                     190

His Arg Pro Arg Val Arg Arg Tyr Ala Tyr Gly Leu Lys Lys Leu Ile
                195                     200                     205

Arg Ile Gly Gln Gly Pro Glu Ser Leu Leu Arg Gln Ser Ser Thr Leu
210             215                     220

Val Asn Asp Val Arg Gly Asp Gly Phe Tyr Glu Gly Gly Asp Asn Gly
225             230                     235                     240

Asp Ala Ile Glu Ala His Glu Trp Lys Cys Val Arg Thr Ile Asn Gly
                245                     250                     255

Val Arg Ile Phe Glu Asp Val Ala Asn Phe Lys Ala Gly Arg Gly Val
                260                     265                     270

Leu Val Lys Ala Val Ala Val Glu Ala Ser Ala Asp Thr Val Phe
                275                     280                     285

Glu Val Leu Leu Asn Ile Asp Lys His Gln Arg Tyr Glu Trp Asp Ala
290             295                     300

Val Thr Gly Asp Ser Glu Lys Ile Asp Ser Tyr Glu Gly His Tyr Asp
305             310                     315                     320

Val Ile Tyr Cys Ile Tyr Asp Pro Lys Tyr Leu Ser Arg Trp Gln Ser
                325                     330                     335

Lys Arg Asp Phe Val Phe Ser Arg Gln Trp Val Arg Gly Gln Asp Gly
                340                     345                     350

Thr Tyr Thr Ile Leu Gln Phe Pro Ala Val His Lys Lys Arg Pro Ala
                355                     360                     365

Lys Ser Gly Tyr Arg Arg Thr Glu Ile Thr Pro Ser Thr Trp Glu Ile
370                     375                     380

Lys Ser Leu Lys Lys Arg Ser Asp Ala Glu Thr Pro Ser Cys Leu Val
385                     390                     395                     400

Thr His Met Leu Glu Ile His Ser Lys Arg Trp Cys Lys Trp Lys Arg
                405                     410                     415

Thr Ser Tyr Ser Lys Phe Glu Lys Thr Ile Pro Tyr Ala Leu Leu Leu
                420                     425                     430

Gln Val Ala Gly Leu Lys Glu Tyr Ile Gly Ala Asn Pro Ala Phe Lys
                435                     440                     445

Tyr Glu Thr Ser Ala Thr Val Val Gln Ser Lys Phe Gln Asp Val Pro
450                     455                     460

Asn Gly Glu Tyr Val Asp Glu Glu Met Glu Glu Gln Phe Tyr Asp Ala

```
                 465                 470                 475                 480
        Thr Asp Ser Ser Gly Glu Glu Asp Glu Glu Ser Asp Asp
                        485                 490                 495

Asp Glu Asn Gln Asp Asn Lys Glu Ile Lys Val Lys Leu Lys Asn Val
                        500                 505                 510

Ser Trp Ala Ile Ala Ser Leu Ser Leu Lys Arg Pro Lys Ala Pro Gly
                        515                 520                 525

Ala Ser Asn Val Leu Asp Ala Ser Val Asp Pro Val Ser Ile Asp Pro
                        530                 535                 540

Ser Gln Phe Gln Gly Ser Leu Arg Lys Gly Asn Gly Asp Lys Asp Ser
        545                 550                 555                 560

Asn Cys Trp Asn Ser Pro Ser Gly Met Gly Phe Met Ile Arg Gly Lys
                                565                 570                 575

Thr Tyr Leu Lys Asp Asn Ala Lys Val Ala Leu Glu Phe Leu His Leu
                        580                 585                 590

Leu

<210> SEQ ID NO 115
<211> LENGTH: 763
<212> TYPE: PRT
<213> ORGANISM: Oryza sativa

<400> SEQUENCE: 115

Met Ala Thr Ile Thr Leu Lys Pro Pro Ala Thr Ala Ala Ala Ala Gly
1               5                   10                  15

Gly Glu Val Ser Glu Val Glu Leu Ser Glu Ala Gly Ser Pro Asp Val
                20                  25                  30

Gly Ser Gln Ser Ser Gly Ser Gly Ser Gly Arg Ser Thr Ala Gly
            35                  40                  45

Ser Ser Gly Trp Val Tyr His Leu Gly Val Asn Ser Ile Gly His Glu
        50                  55                  60

Tyr Arg His Leu Arg Phe Leu Val Ile Arg Gly Lys Thr Val Ala Met
65                  70                  75                  80

Tyr Lys Arg Asp Pro Ser Lys Asn Pro Gly Ile Gln Pro Ile Arg Lys
                85                  90                  95

Gly Val Val Ser His Thr Leu Met Val Glu Glu Leu Gly Arg Arg Ile
                100                 105                 110

Thr Ser His Gly Glu Leu Tyr Val Leu Arg Phe Tyr Asn Arg Leu Asp
            115                 120                 125

Gln Thr Lys Lys Gly Glu Ile Ala Cys Gly Asp Pro Gly Glu Ala Arg
        130                 135                 140

Lys Trp Val Glu Ala Phe Glu Gln Ala Lys Gln Gln Ala Asp Tyr Asp
145                 150                 155                 160

Leu Met Thr Arg Gly Val Ser Trp Asn Arg Ser Gln Asn Glu Asn Glu
                165                 170                 175

Leu Asn Leu Asp Gly His Arg Pro Arg Val Arg Tyr Ala Gln Gly
                180                 185                 190

Leu Gly Lys Leu Val Arg Ile Gly Lys Gly Pro Glu Lys Leu Leu Arg
            195                 200                 205

Gln Ser Ser Asn Leu Gln Ser His Glu Ile Ile Asn Thr Asn Phe Gly
        210                 215                 220

Gly Asp Ser Gly Asp Ala Phe Glu Ala His Glu Trp Arg Tyr Val Arg
225                 230                 235                 240

Thr Phe Asn Gly Ile Arg Ile Phe Glu Asp Ile Ala Asn Thr Lys Gly
```

```
              245                 250                 255
Gly Lys Gly Val Leu Lys Ser Val Gly Val Gly Ala Asn Pro
            260                 265                 270

Asp Thr Val Phe Ala Val Val Leu Ser Ser Asp Lys His Lys Arg Tyr
            275                 280                 285

Glu Trp Asp Met Leu Thr Ala Asp Leu Glu Leu Val Glu Thr Ile Asp
            290                 295                 300

Gly Tyr Tyr Asp Val Val Tyr Gly Thr Tyr Glu Pro Arg Tyr Leu Ser
305                 310                 315                 320

Trp Trp Lys Thr Lys Lys Asp Phe Val Phe Ser Arg Gln Trp Phe Arg
                325                 330                 335

Gly Gln Asp Gly Ala Tyr Thr Ile Leu Gln Ile Pro Ala Cys His Lys
                340                 345                 350

Asn Lys Pro Pro Arg His Gly Tyr Glu Arg Thr Lys Ile Asn Ser Ser
                355                 360                 365

Thr Trp Glu Leu Arg Arg Leu Asn Pro Pro Gly Ser Ser Thr Pro Lys
            370                 375                 380

Cys Leu Val Thr His Met Leu Glu Met Ser Pro Ser Phe Trp Asp Arg
385                 390                 395                 400

Trp Lys Arg Arg His Asn Glu Asn Phe Asp Arg Ser Ile Ala Phe Ala
                405                 410                 415

Leu Leu Ser Gln Val Ala Gly Leu Arg Glu Tyr Phe Ala Ala Asn Pro
                420                 425                 430

Ala Leu Thr Ser Asp Leu Pro Ser Thr Val Val Lys Pro Lys Gln Ser
            435                 440                 445

Asp Ser Leu Ile Ile Gln Ser Glu Leu Glu Asp Ser Glu Leu Asn Asp
450                 455                 460

Glu Phe Tyr Asp Ala Leu Ala Arg Gly Glu Ser Phe Glu Asp Glu Asp
465                 470                 475                 480

Ser Asp Asp Asp Asp Met Ile Pro Lys Ala Gly Lys Val Lys Phe
                485                 490                 495

Lys Asn Ile Ser Trp Ala Ile Ala Gly Leu Ala Met Lys Pro Thr Lys
                500                 505                 510

Ala Ser Val Glu Lys Ser Glu Leu Val Thr Asn Ser Thr Pro Val Thr
            515                 520                 525

Ile Asp Ser Asn His Phe His Gly Thr Leu Arg Arg Ala Lys Ser Glu
            530                 535                 540

Asn Asp Pro Asn Ser Trp Ser Glu Pro Gly Gly Glu Lys Phe Met Ile
545                 550                 555                 560

Arg Gly Lys Thr Tyr Leu Thr Asp Tyr Thr Lys Val Val Gly Gly Asp
                565                 570                 575

Pro Leu Leu Lys Leu Ile Ala Val Asp Trp Phe Lys Ala Asp Glu Arg
            580                 585                 590

Phe Asp Ser Val Ala Leu His Pro Lys Ser Leu Val Gln Ser Glu Ala
            595                 600                 605

Ala Lys Lys Ile Pro Phe Ile Leu Val Ile Asn Leu Gln Val Pro Ala
            610                 615                 620

Lys Pro Asn Tyr Asn Leu Val Met Tyr Tyr Ala Ala Glu Arg Pro Val
625                 630                 635                 640

Asn Lys Asp Ser Leu Leu Gly Arg Phe Ile Asp Gly Thr Asp Ala Phe
                645                 650                 655

Arg Asp Ala Arg Phe Lys Leu Ile Pro Ser Ile Val Glu Gly Tyr Trp
                660                 665                 670
```

-continued

```
Met Val Lys Arg Ala Val Gly Thr Lys Ala Cys Leu Leu Gly Lys Ala
        675                 680                 685

Val Thr Cys Asn Tyr Leu Arg Gln Asp Asn Phe Leu Glu Ile Asp Val
    690                 695                 700

Asp Ile Gly Ser Ser Ser Val Ala Arg Ser Ile Ile Gly Leu Val Leu
705                 710                 715                 720

Gly Tyr Val Thr Gly Leu Val Val Asp Leu Ala Ile Leu Ile Glu Ala
                725                 730                 735

Lys Glu Glu Lys Glu Leu Pro Glu Tyr Ile Leu Gly Thr Val Arg Leu
            740                 745                 750

Asn Arg Ala Asn Pro Asp Ser Ala Val Pro Ile
        755                 760
```